United States Patent
Priepke et al.

(10) Patent No.: US 7,429,597 B2
(45) Date of Patent: Sep. 30, 2008

(54) SUBSTITUTED NITROGEN-CONTAINING HETEROBICYCLES, THE PREPARATION THEREOF AND THEIR USE AS PHARMACEUTICAL COMPOSITIONS

(75) Inventors: Henning Priepke, Warthausen (DE); Roland Pfau, Biberach (DE); Kai Gerlach, Ulm (DE); Uwe Ries, Biberach (DE); Wolfgang Wienen, Biberach-Rissegg (DE); Eckhart Bauer, Biberach (DE); Herbert Nar, Ochsenhausen (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 302 days.

(21) Appl. No.: 10/739,172

(22) Filed: Dec. 18, 2003

(65) Prior Publication Data
US 2004/0176603 A1    Sep. 9, 2004

Related U.S. Application Data

(60) Provisional application No. 60/437,431, filed on Dec. 30, 2002.

(30) Foreign Application Priority Data
Dec. 23, 2002    (DE) .............................. 102 60 730

(51) Int. Cl.
A61K 31/517 (2006.01)
C07D 239/94 (2006.01)
(52) U.S. Cl. .............................. 514/266.22; 514/266.2; 514/266.4; 544/284; 544/293
(58) Field of Classification Search .............. 514/228.2, 514/233.5, 218, 266.2, 266.22, 266.4; 540/492; 544/62, 116, 284, 293
See application file for complete search history.

(56) References Cited

U.S. PATENT DOCUMENTS

| | | | |
|---|---|---|---|
| 5,693,652 A * | 12/1997 | Takase et al. | 514/322 |
| 6,046,206 A * | 4/2000 | Pamukcu et al. | 514/266.21 |
| 6,087,380 A | 7/2000 | Hauel et al. | |
| 6,414,008 B1 | 7/2002 | Hauel et al. | |
| 6,469,039 B1 | 10/2002 | Hauel et al. | |
| 6,710,055 B2 | 3/2004 | Hauel et al. | |

FOREIGN PATENT DOCUMENTS

| | | |
|---|---|---|
| CA | 2 277 949 A1 | 8/1998 |
| WO | WO 97/03069 | 1/1997 |
| WO | WO 98/37075 | 8/1998 |

OTHER PUBLICATIONS

International Search Report for PCT/EP03/14378 mailed May 10, 2004.
Flavia Messina, et al; Stereoselective Synthesis of α-aryl-2-Benzofuranmethanamines and α-aryl-1 H-indole-2-methanamines Through Pallladium-Mediated Annulation of Chiral α-arylpropargylamines; Tetrahedron Asymmetry (2000) vol. 11 pp. 1681-1685.
R. Marshall Wilson, et al; Synthesis and Chemistry of a Stabilized Dehydrosecodine Model System; Journal of Organic Chemistry (1981) vol. 46 pp. 3293-3302.

* cited by examiner

*Primary Examiner*—James O. Wilson
*Assistant Examiner*—Tamthom N Truong
(74) *Attorney, Agent, or Firm*—Michael P. Morris; Edouard G. Lebel; Mary-Ellen M. Devlin

(57) ABSTRACT

The present invention relates to new substituted nitrogen-containing heterobicyclic compounds of general formula (I)

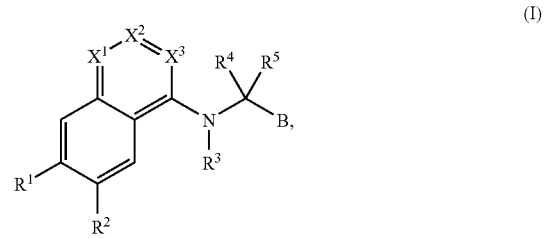

wherein B, $X^1$ to $X^3$ and $R^1$ to $R^5$ are defined as in claim 1, the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

4 Claims, No Drawings

SUBSTITUTED NITROGEN-CONTAINING HETEROBICYCLES, THE PREPARATION THEREOF AND THEIR USE AS PHARMACEUTICAL COMPOSITIONS

"This application claims the benefit of U.S. Provisional Application Ser. No. 60/437,431, filed on Dec. 30, 2002, and claims priority to German Application 102 60 730, filed on Dec. 23, 2002, each of which is incorporated herein in its entirety."

The present invention relates to new substituted nitrogen-containing heterobicyclic compounds of general formula

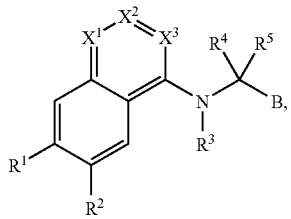

(I)

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

The present application thus relates to the new compounds of the above general formula I, the preparation thereof, the pharmaceutical compositions containing the pharmacologically effective compounds, the preparation thereof and their use.

In the above general formula in a 1st embodiment $R^1$ denotes an amino, $C_{1-5}$-alkylamino, $C_{3-7}$-cycloalkylamino or (phenyl-$C_{1-3}$-alkyl)-amino group which may in each case additionally be substituted at the amino nitrogen atom by a phenylcarbonyl or phenylsulphonyl group or by a $C_{1-5}$-alkyl or $C_{1-5}$-alkylcarbonyl group optionally substituted in the alkyl moiety by a hydroxy, $C_{1-3}$-alkoxy or carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the substitution of the previously mentioned $C_{1-5}$-alkyl group two heteroatoms are separated from one another by at least two carbon atoms, a 4- to 7-membered cycloalkyleneiminocarbonyl or cycloalkyleneiminosulphonyl group, while the cycloalkyleneimino moiety may be substituted in the carbon skeleton by one or two $C_{1-3}$-alkyl, $C_{2-3}$-alkenyl, $C_{2-3}$-alkynyl, phenyl-$C_{1-3}$-alkyl, 1,1-diphenyl-$C_{1-3}$-alkyl, hydroxy-$C_{1-3}$-alkyl, $C_{1-3}$-alkyloxy-$C_{1-3}$-alkyl, heteroaryl-$C_{1-3}$-alkyl, carboxy-$C_{1-3}$-alkyl, $C_{1-3}$-alkyloxycarbonyl-$C_{1-3}$-alkyl, amino-$C_{1-5}$-alkyl, $C_{1-5}$-alkylamino-$C_{1-5}$-alkyl, $C_{3-6}$-cycloalkylamino-$C_{1-3}$-alkyl, phenylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-5}$-alkyl, N—$C_{1-3}$-alkylpiperazin-4-yl-$C_{1-3}$-alkyl, N-(heteroaryl-$C_{1-3}$-alkyl)-$C_{1-3}$-alkylamino-$C_{1-3}$-alkyl, $C_{1-3}$-alkylcarbonylamino-$C_{1-3}$-alkyl, $C_{1-3}$-alkylsulphonylamino-$C_{1-3}$-alkyl, $C_{1-5}$-alkyloxycarbonylamino-$C_{1-3}$-alkyl, aminocarbonylamino-$C_{1-3}$-alkyl, $C_{1-3}$-alkylaminocarbonylamino-$C_{1-3}$-alkyl, di-($C_{1-3}$-alkyl)-amino-carbonylamino-$C_{1-3}$-alkyl, $C_{1-3}$-alkylcarbonyl, carboxy, $C_{1-5}$-alkyloxycarbonyl, benzyloxycarbonyl, aminocarbonyl, $C_{1-3}$-alkylaminocarbonyl, $C_{3-6}$-cycloalkyl-aminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, a phenyl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulphur atom, a sulphinyl or sulphonyl group or a methylene group in the 2 position of a 5-membered cycloalkyleneimino group may be replaced by an —NH— group or a methylene group in the 4 position of a 6- or 7-membered cycloalkyleneimino group may be replaced by an oxygen or sulphur atom, a methylidene, carbonyl, sulphinyl or sulphonyl group or by a —NH— group optionally substituted by a $C_{1-3}$-alkyl, hydroxy, formyl, $C_{1-3}$-alkylcarbonyl or phenylcarbonylamino group, while additionally a methylene group adjacent to a previously mentioned —NH— group may be replaced by a carbonyl or sulphonyl group, with the proviso that in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, a —$CH_2$—$CH_2$— group in a 5- to 7-membered cycloalkyleneimino group may be replaced by an —NH—CO—, —CO—NH—, —CO—N($CH_3$)— or a —N($CH_3$)—CO— group, with the proviso that a cycloalkyleneimino group as hereinbefore defined wherein two nitrogen atoms are separated from one another by precisely one —$CH_2$— group is excluded, a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, $C_{3-6}$-cycloalkyl, 5- to 7-membered cycloalkyleneimino, pyrrolidinyl, piperidinyl, morpholinyl, piperazinyl or N—$C_{1-3}$-alkyl-piperazinyl groups, while the substituents may be identical or different and in each case one of the previously mentioned $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, 4- to 7-membered cycloalkyleneimino, C-pyrrolidinyl, C-piperidinyl, C-morpholinyl, C-piperazinyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or 4- to 7-membered cycloalkyleneiminocarbonyl groups, while the cycloalkyleneimino groups previously mentioned in the groups may additionally be substituted by a carboxy or $C_{1-5}$-alkyloxycarbonyl group, a $C_{1-7}$-alkylcarbonyl or $C_{3-7}$-cycloalkylcarbonyl group, while the methylene group in the 2, 3 or 4 position in a $C_{3-7}$-cycloalkylcarbonyl group may be replaced by an oxygen or sulphur atom, a carbonyl, sulphinyl, sulphonyl or an —NH— group, wherein the hydrogen atom of the —NH— group may be replaced by a $C_{1-3}$-alkyl or $C_{1-3}$-alkyl-carbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{1-3}$-alkoxy group and/or a —$CH_2$—$CH_2$— group in a 5- to 7-membered cycloalkyleneimino group may be replaced by a —NH—CO—, —CO—NH—, —NH—$SO_2$—, —$SO_2$—NH—, —CO—N($CH_3$)— or a —N($CH_3$)—CO— group or a methylene group, which is adjacent to the nitrogen atom, in a 5- to 7-membered cycloalkyleneimino group may be replaced by a carbonyl group, or a group of formulae

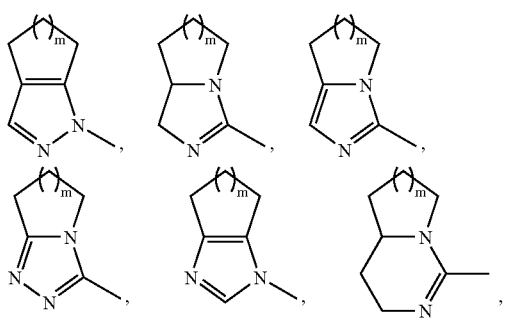

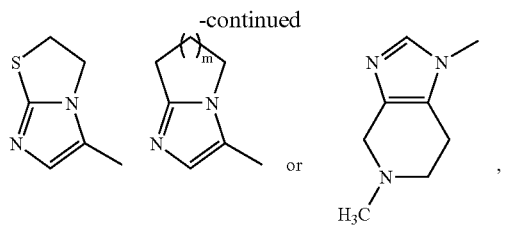

wherein in the heterocyclic moiety in each case a hydrogen atom may be replaced by a $C_{1-3}$-alkyloxycarbonyl, $C_{1-5}$-alkyloxycarbonylamino-$C_{1-3}$-alkyl, methylsulphonylmethyl, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylaminocarbonyl or di-($C_{1-3}$-alkyl)-aminocarbonyl group and m denotes the number 1, 2 or 3, $R^2$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, nitro, amino, $C_{1-3}$-alkoxy, a mono-, di- or trifluoromethoxy group, $R^3$ denotes a hydrogen atom or a $C_{1-3}$-alkyl group, $R^4$ denotes a hydrogen atom or a straight-chain or branched $C_{1-5}$-alkyl group which is optionally substituted by a fluorine atom, a $C_{2-3}$-alkenyl, $C_{2-3}$-alkynyl, mono-, di- or trifluoromethyl, a hydroxy, $C_{1-5}$-alkyloxy, allyloxy, propargyloxy, phenyloxy, heteroaryloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, mercapto, $C_{1-3}$-alkylsulphanyl, $C_{1-3}$-alkylsulphinyl, $C_{1-3}$-alkylsulphonyl, carboxy, $C_{1-5}$-alkyloxycarbonyl, allyloxycarbonyl, propargyloxycarbonyl, benzyloxycarbonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{1-3}$-alkylsulphonylamino, $C_{3-6}$-cycloalkylcarbonylamino, benzyloxycarbonylamino, phenylcarbonylamino or guanidino group, a group of general formula

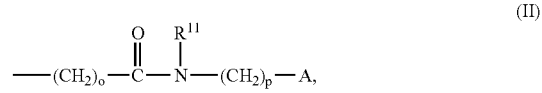

(II)

wherein o denotes one of the numbers 1, 2, 3, 4 or 5, p denotes one of the numbers 0, 1, 2 or 3, $R^{11}$ denotes a hydrogen atom or a $C_{1-3}$-alkyl group and A denotes a $C_{3-7}$-cycloalkyl group wherein the methyne group in the 1 position may be replaced by a nitrogen atom, if p denotes one of the numbers 2, 3, 4 or 5, and/or a methylene group of a previously mentioned cycloalkyl group may be replaced by an oxygen or sulphur atom, a —NH—, —N(OH)—, —N($C_{1-3}$-alkyl)-, —N($C_{1-3}$-alkylcarbonyl)- or —N(heteroaryl)- group with the proviso that in a group —N($R^{11}$)—$(CH_2)_p$-A- thus formed two heteroatoms are separated from one another by at least two carbon atoms, and/or a methylene group adjacent to an —NH—, —N(OH)—, —N($C_{1-3}$-alkyl)-, —N($C_{1-3}$-alkylcarbonyl)- or —N(heteroaryl)-group may be replaced by a carbonyl, sulphinyl or sulphonyl group, a 4- to 7-membered cycloalkyleneiminocarbonyl-$C_{1-5}$-alkyl group, while a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino, morpholino, piperazinyl, N—($C_{1-3}$-alkyl)-piperazinyl or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group and/or a methylene group in the 3 position of a 5-membered cycloalkyleneimino group may be replaced by a sulphur atom, a carbonyl, sulphinyl or sulphonyl group or a methylene group in the 4 position of a 6- or 7-membered cycloalkyleneimino group may be replaced by an oxygen or sulphur atom, by a carbonyl, sulphinyl, sulphonyl or by an —NH— group optionally substituted by a $C_{1-3}$-alkyl or heteroaryl group and additionally a methylene group adjacent to an above-mentioned —NH— or —N($C_{1-3}$-alkyl)- group may be replaced by a carbonyl group and/or two geminal hydrogen atoms of a methylene group in a previously mentioned cycloalkyleneimino group may be substituted by a 5- to 7-membered carbocyclic group forming a spiro compound, while one or two methylene groups of the previously mentioned carbocyclic group which are not adjacent to each other may independently of one another be replaced by an oxygen or sulphur atom or an —NH—, —N(OH)— or —N($C_{1-3}$-alkyl)- group and additionally a methylene group of the carbocyclic group adjacent to an —NH—, —N(OH)—, or —N($C_{1-3}$-alkyl)- group may be replaced by a carbonyl, sulphinyl or sulphonyl group, or a phenyl or heteroaryl group may be fused to two adjacent methylene groups in the 2 and 3 position of a previously mentioned 5-membered cycloalkyleneimino group or in the 3 and 4 position of a previously mentioned 6- to 7-membered cycloalkyleneimino group, an aminocarbonyl-$C_{1-5}$-alkyl, aminosulphonyl-$C_{1-3}$-alkyl, $C_{1-3}$-alkylaminocarbonyl-$C_{1-5}$-alkyl or $C_{1-3}$-alkylamino-sulphonyl-$C_{1-3}$-alkyl group, while the previously mentioned amino groups may additionally be substituted by a $C_{3-6}$-cycloalkyl-$C_{1-3}$-alkyl, phenyl-$C_{1-3}$-alkyl, heteroaryl-$C_{1-3}$-alkyl, heteroarylamino-$C_{2-3}$-alkyl, hydroxy-$C_{2-3}$-alkyl, $C_{1-3}$-alkyloxy-$C_{2-3}$-alkyl, carboxy-$C_{1-3}$-alkyl, $C_{1-5}$-alkyloxycarbonyl-$C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl group, a phenyl or heteroaryl, phenyl-$C_{1-3}$-alkyl or heteroaryl-$C_{1-3}$-alkyl group which is optionally substituted by a fluorine, chlorine or bromine atom, an amino, $C_{1-3}$-alkylamino, di-($C_{1-3}$-alkyl)-amino, hydroxy, $C_{1-4}$-alkyloxy, a mono-, di- or trifluoromethoxy, benzyloxy, carboxy-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4- to 7-membered cycloalkyleneiminocarbonyl-$C_{1-3}$-alkoxy, carboxy or $C_{1-3}$-alkyloxycarbonyl group, a 4- to 7-membered cycloalkyleneimino-$C_{1-5}$-alkyl group wherein a methylene group of the cycloalkyleneimino moiety may be replaced by an oxygen or sulphur atom, a carbonyl, sulphinyl or sulphonyl group, an —NH—, —N(OH)—, —N($C_{1-3}$-alkyl)- or —N($C_{1-3}$-alkylcarbonyl)- group, a 4- to 7-membered cycloalkyl-$C_{1-5}$-alkyl group wherein in the cyclic moiety a methylene group may be replaced by an —NH— or —N($C_{1-3}$-alkyl)- group and wherein a methylene group adjacent to the —NH— or —N($C_{1-3}$-alkyl)- group may be replaced in each case by a carbonyl group, with the proviso that a cycloalkyleneimino group as hereinbefore defined wherein two nitrogen atoms are separated from one another by precisely one —$CH_2$— group are excluded, $R^5$ denotes a hydrogen atom or a $C_{1-3}$-alkyl group or $R^4$ and $R^5$ together with the carbon atom to which they are bound denote a $C_{3-7}$-cycloalkyl group, while one of the methylene groups of the $C_{3-7}$-cycloalkyl group may be replaced by an imino, $C_{1-3}$-alkylimino, acylimino or sulphonylimino group, B denotes a group of formulae

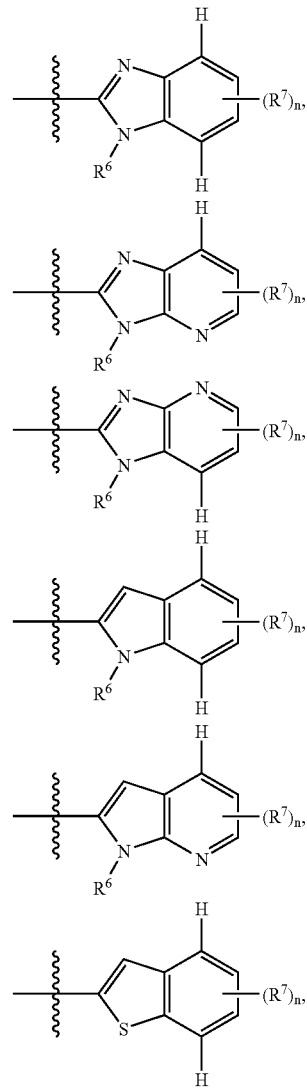

-continued

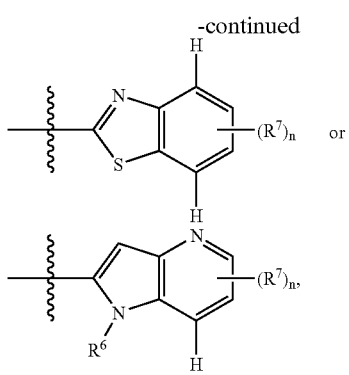

wherein
n denotes the number 1 or 2,
$R^6$ denotes a hydrogen atom or a $C_{1-3}$-alkyl, hydroxy, amino, $C_{1-3}$-alkylamino group,
$R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy or cyano group, and
$X^1$ to $X^3$ independently of one another each denote a nitrogen atom, an N-oxide or a CH group optionally substituted by a $C_{1-3}$-alkyl group,
while at least one and not more than two of the groups $X^1$ to $X^3$ denote a nitrogen atom,
while, unless otherwise stated, the expression "heteroaryl group" mentioned hereinbefore in the definitions denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxycarbonylamino group, while
the 6-membered heteroaryl group contains one, two or three nitrogen atoms and
the 5-membered heteroaryl group contains one or two imino groups optionally substituted by a $C_{1-3}$-alkyl or phenyl-$C_{1-3}$-alkyl group, or an oxygen or sulphur atom or
an imino group optionally substituted by a $C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group, or an oxygen or sulphur atom and additionally a nitrogen atom or
an imino group optionally substituted by a $C_{1-3}$-alkyl or phenyl-$C_{1-3}$-alkyl group and two or three nitrogen atoms,
and also a phenyl ring may be fused to the above-mentioned monocyclic heteroaryl groups via two adjacent carbon atoms
and the bond is effected via a nitrogen atom or via a carbon atom of the heterocyclic moiety or a fused-on phenyl ring,
while unless otherwise stated the alkyl and alkoxy groups contained in the above definitions which have more than two carbon atoms may be straight-chain or branched and the alkyl groups in the above-mentioned dialkylated groups, for example the dialkylamino groups, may be identical or different,
and the hydrogen atoms of the methyl or ethyl groups contained in the above-mentioned definitions may be wholly or partly replaced by fluorine atoms.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]iso-thiazolyl, benzo[d]isothiazolyl, benzoxazolyl, benzo[c]isoxazolyl, benzo[d]isoxazo-lyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-8}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, 1-hexyl, 2-hexyl, 3-hexyl, 1-heptyl, 2-heptyl, 3-heptyl, 4-heptyl, 1-octyl, 2-octyl, 3-octyl or 4-octyl group.

Examples of the $C_{1-8}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy, 1-hexyloxy, 2-hexyloxy, 3-hexyloxy, 1-heptyloxy, 2-heptyloxy, 3-heptyloxy, 4-heptyloxy, 1-octyloxy, 2-octyloxy, 3-octyloxy or 4-octyloxy group.

By a group which may be converted in vivo into a carboxy group is meant for example a carboxy group esterified with an alcohol wherein the alcohol moiety is preferably a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol or an alcohol of formula $$R^8-CO-O-(R^9CR^{10})-OH,$$

wherein
$R^8$ denotes a $C_{1-8}$-alkyl, $C_{5-7}$-cycloalkyl, phenyl or phenyl-$C_{1-3}$-alkyl group,
$R^9$ denotes a hydrogen atom, a $C_{1-3}$-alkyl, $C_{5-7}$-cycloalkyl or phenyl group and
$R^{10}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

Those compounds of general formula I wherein $R^1$ contains a group which may be converted in vivo into a carboxy group are prodrugs for those compounds of general formula I wherein $R^1$ contains a carboxy group.

A 2nd embodiment of the present invention comprises those compounds of general formula I, wherein
$R^1$ denotes an amino, $C_{1-5}$-alkylamino, $C_{3-7}$-cycloalkylamino or (phenyl-$C_{1-3}$-alkyl)-amino group which may in each case additionally be substituted at the amino nitrogen atom by a $C_{1-5}$-alkyl or $C_{1-5}$-alkylcarbonyl group, optionally substituted in the alkyl moiety by a hydroxy, $C_{1-3}$-alkoxy or carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the substitution of the previously mentioned $C_{1-5}$-alkyl group two heteroatoms are separated from one another by at least two carbon atoms, a 4- to 7-membered cycloalkyleneiminocarbonyl or cycloalkyleneiminosulphonyl group, while the cycloalkyleneimino moiety in the carbon skeleton may be substituted by one or two $C_{1-3}$-alkyl, phenyl-$C_{1-3}$-alkyl, 1,1-diphenyl-$C_{1-3}$-alkyl, hydroxy-$C_{1-3}$-alkyl, $C_{1-3}$-alkyloxy-$C_{1-3}$-alkyl, heteroaryl-$C_{1-3}$-alkyl, carboxy-$C_{1-3}$-alkyl, $C_{1-3}$-alkyloxycarbonyl-$C_{1-3}$-alkyl, amino-$C_{1-5}$-alkyl, $C_{1-5}$-alkylamino-$C_{1-5}$-alkyl, $C_{3-6}$-cycloalkylamino-$C_{1-3}$-alkyl, phenylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, 4- to 7-membered cycloalkyleneimino-$C_{1-3}$-alkyl, N—$C_{1-3}$-alkylpiperazin-4-yl-$C_{1-3}$-alkyl, N-(heteroaryl-$C_{1-3}$-alkyl)-$C_{1-3}$-alkylamino-$C_{1-3}$-alkyl, $C_{1-3}$-alkylcarbonylamino-$C_{1-3}$-alkyl, $C_{1-3}$-alkylsulphonylamino-$C_{1-3}$-alkyl, $C_{1-5}$-alkyloxycarbonylamino-$C_{1-3}$-alkyl, aminocarbonylamino-$C_{1-3}$-alkyl, $C_{1-3}$-alkylaminocarbonylamino-$C_{1-3}$-alkyl, di-($C_{1-3}$-alkyl)-aminocarbonylamino-$C_{1-3}$-alkyl, $C_{1-3}$-alkylcarbonyl, carboxy, $C_{1-5}$-alkyloxycarbonyl, benzyloxycarbonyl, aminocarbonyl, $C_{1-3}$-alkylaminocarbonyl, $C_{3-6}$-cycloalkylaminocarbonyl, di-($C_{1-3}$-alkyl)-amino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, a phenyl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulphur atom, a sulphinyl or sulphonyl group or a methylene group in the 2 position of a 5-membered cycloalkyleneimino group may be replaced by an —NH— group or a methylene group in the 4 position of a 6- or 7-membered cycloalkyleneimino group may be replaced by an oxygen or sulphur atom, a methylidene, carbonyl, sulphinyl or sulphonyl group or by an —NH— group optionally substituted by a $C_{1-3}$-alkyl, hydroxy, formyl, $C_{1-3}$-alkylcarbonyl or phenylcarbonylamino group, while additionally a methylene group adjacent to a previously mentioned —NH— group may be replaced by a carbonyl or sulphonyl group, with the proviso that in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group with the proviso that a cycloalkyleneimino group as hereinbefore defined wherein two nitrogen atoms are separated from one another by precisely one —$CH_2$— group is excluded, a 5- to 7-membered cycloalkenyleneiminocarbonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, 4- to 7-membered cycloalkyleneimino-$C_{1-3}$-alkyl or $C_{3-6}$-cycloalkylamino-$C_{1-3}$-alkyl groups, while the double bond is not bound to a nitrogen atom and may be fused to a 5- or 6-membered heteroaryl group, an aminocarbonyl group optionally substituted by one or two $C_{1-5}$-alkyl, $C_3$-cycloalkyl, 5- to 7-membered cycloalkyleneimino, pyrrolidinyl, piperidinyl, morpholinyl, piperazinyl or N—$C_{1-3}$-alkylpiperazinyl groups, while the substituents may be identical or different and in each case one of the previously mentioned $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, 4- to 7-membered cycloalkyleneimino-$C_{1-3}$-alkyl, C-pyrrolidinyl, C-piperidinyl, C-morpholinyl, C-piperazinyl, $C_{3-6}$-cycloalkylamino-$C_{1-3}$-alkyl or 4- to 7-membered cycloalkyleneiminocarbonyl groups, while the cycloalkyleneimino groups previously mentioned in the groups may additionally be substituted by a carboxy or $C_{1-5}$-alkyloxycarbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{1-3}$-alkoxy group, a $C_{1-3}$-alkyl group optionally monosubstituted by a di-($C_{1-3}$-alkyl)-amino, heteroaryl or a 4- to 7-membered cycloalkyleneimino group, while a —$CH_2$—$CH_2$— group in a 5- to 7-membered cycloalkyleneimino group may be replaced by a —NH—CO—, —CO—NH—, —NH—$SO_2$—, —$SO_2$—NH—, —CO—N($CH_3$)— or a —N($CH_3$)—CO— group or a methylene group, which is adjacent to the nitrogen atom, in a 5- to 7-membered cycloalkyleneimino group may be replaced by a carbonyl group, or a group of formulae

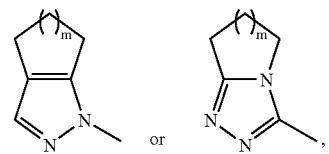

wherein in the heterocyclic moiety in each case a hydrogen atom may be replaced by a $C_{1-3}$-alkyloxycarbonyl, $C_{1-5}$-alkyloxycarbonylamino-$C_{1-3}$-alkyl, methylsulphonylmethyl, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylaminocarbonyl or di-($C_{1-3}$-alkyl)-aminocarbonyl group and m denotes the number 1, 2 or 3, $R^2$ denotes a chlorine or bromine atom, a $C_{1-3}$-alkyloxy or $C_{1-3}$-alkyl group wherein the hydrogen atoms may be wholly or partly replaced by fluorine atoms, or a $C_{2-3}$-alkenyl group, $R^3$ denotes a hydrogen atom, $R^4$ denotes a hydrogen atom or a straight-chain or branched $C_{1-5}$-alkyl group which is optionally substituted by a $C_{2-3}$-alkenyl, $C_{2-3}$-alkynyl, hydroxy, $C_{1-5}$-alkyloxy, phenyloxy, heteroaryloxy, benzyloxy, $C_{1-5}$-alkylcarbonyloxy, carboxy-$C_{1-3}$-alkyloxy, $C_{1-5}$-alkyloxycarbonyl-$C_{1-3}$-alkyloxy, $C_{1-5}$-alkyloxycarbonylamino, mercapto, $C_{1-3}$-alkylsulphanyl, $C_{1-3}$-alkylsulphinyl, $C_{1-3}$-alkylsulphonyl, carboxy, $C_{1-5}$-alkyloxycarbonyl, allyloxycarbonyl, propargyloxycarbonyl, benzyloxycarbonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{1-3}$-alkylsulphonylamino, $C_{3-6}$-cycloalkylcarbonylamino, benzyloxycarbonylamino or phenylcarbonylamino group, a group of general formula

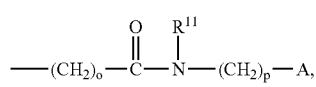

(II)

wherein
o denotes one of the numbers 1, 2 or 3,
p denotes one of the numbers 0, 1, 2 or 3,
$R^{11}$ denotes a hydrogen atom or a $C_{1-3}$-alkyl group and
A denotes a $C_{3-7}$-cycloalkyl group wherein
the methyne group in the 1 position may be replaced by a nitrogen atom, if p denotes one of the numbers 2 or 3, and/or
a methylene group of a previously mentioned cycloalkyl groups may be replaced by an oxygen or sulphur atom, a —NH—, —N(OH)—, —N($C_{1-3}$-alkyl)-, —N($C_{1-3}$-alkylcarbonyl)- or —N(heteroaryl)- group, with the proviso that in an —N($R^{11}$)-($CH_2$)$_p$-A- group thus formed two heteroatoms are separated from one another by at least two carbon atoms, and/or
a methylene group adjacent to a —NH—, —N(OH)—, —N($C_{1-3}$-alkyl)-, —N($C_{1-3}$-alkylcarbonyl)- or —N(heteroaryl)- group may be replaced by a carbonyl, sulphinyl or sulphonyl group,
a 4- to 7-membered cycloalkyleneiminocarbonyl-$C_{1-5}$-alkyl group, while
a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino, morpholino, piperazinyl-N—($C_{1-3}$-alkyl)-piperazinyl or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group and/or
a methylene group in the 3 position of a 5-membered cycloalkyleneimino group may be replaced by a sulphur atom, a carbonyl, sulphinyl or sulphonyl group or
a methylene group in the 4 position of a 6- or 7-membered cycloalkyleneimino group may be replaced by an oxygen or sulphur atom, by a carbonyl, sulphinyl, sulphonyl or by a —NH— group optionally substituted by a $C_{1-3}$-alkyl or heteroaryl group and additionally a methylene group adjacent to an above-mentioned —NH— or —N($C_{1-3}$-alkyl)- group may be replaced by a carbonyl group and/or
two geminal hydrogen atoms of a methylene group in a previously mentioned cycloalkyleneimino group may be substituted by a 5- to 7-membered carbocycle forming a spiro compound, while one or two methylene groups of the aforementioned carbocycle which are not adjacent to one another may independently of one another be replaced by an oxygen or sulphur atom or a —NH—, —N(OH)—, or —N($C_{1-3}$-alkyl)- group and additionally a methylene group of the carbocyclic group adjacent to an —NH—, —N(OH)—, or —N($C_{1-3}$-alkyl)- group may be replaced by a carbonyl, sulphinyl or sulphonyl group, or
a phenyl or heteroaryl group may be fused to two adjacent methylene groups in the 2 and 3 position of a previously mentioned 5-membered cycloalkyleneimino group or in the 3 and 4 position of a previously mentioned 6- to 7-membered cycloalkyleneimino group,
an aminocarbonyl-$C_{1-5}$-alkyl, aminosulphonyl-$C_{1-3}$-alkyl, $C_{1-3}$-alkylaminocarbonyl-$C_{1-5}$-alkyl or $C_{1-3}$-alkylaminosulphonyl-$C_{1-3}$-alkyl group, while
the previously mentioned amino groups may additionally be substituted by a $C_{3-6}$-cycloalkyl-$C_{1-3}$-alkyl, phenyl-$C_{1-3}$-alkyl, heteroaryl-$C_{1-3}$-alkyl, heteroarylamino-$C_{2-3}$-alkyl, hydroxy-$C_{2-3}$-alkyl, $C_{1-3}$-alkyloxy-$C_{2-3}$-alkyl, carboxy-$C_{1-3}$-alkyl, $C_{1-5}$-alkyloxycarbonyl-$C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl group,
a phenyl or heteroaryl, phenyl-$C_{1-3}$-alkyl or heteroaryl-$C_{1-3}$-alkyl group which is optionally substituted by a chlorine atom, a hydroxy, $C_{1-4}$-alkyloxy, trifluoromethoxy, carboxy or $C_{1-3}$-alkyloxycarbonyl group,
a 4- to 7-membered cycloalkyleneimino-$C_{1-5}$-alkyl group wherein
a methylene group of the cycloalkyleneimino moiety may be replaced by an oxygen or sulphur atom, a carbonyl or sulphonyl group, or
a 4- to 7-membered cycloalkyl-$C_{1-5}$-alkyl group wherein in the cyclic moiety a methylene group may be replaced by an —NH— or —N($C_{1-3}$-alkyl)- group and wherein a methylene group adjacent to the —NH— or —N($C_{1-3}$-alkyl)- group may be replaced by a carbonyl group in each case, with the proviso that a cycloalkyleneimino group as hereinbefore defined wherein two nitrogen atoms are separated from one another by precisely one —$CH_2$— group are excluded,
$R^5$ denotes a hydrogen atom,
B denotes a group of formulae

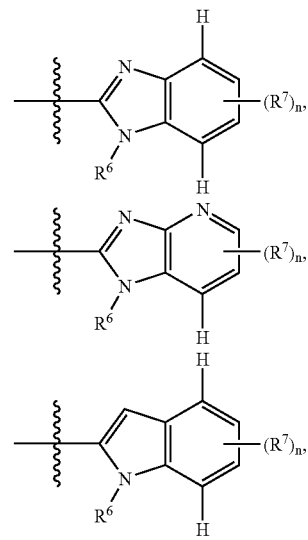

-continued

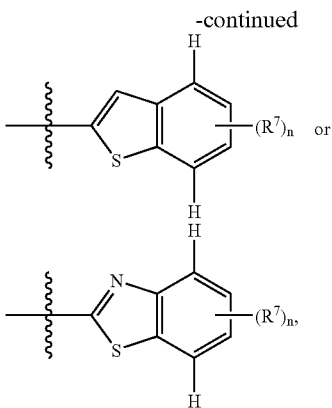

wherein
n denotes the number 1,
R⁶ denotes a hydrogen atom or a $C_{1-3}$-alkyl, hydroxy, amino, $C_{1-3}$-alkylamino group,
R⁷ denotes a hydrogen, fluorine, chlorine or bromine atom and
$X^1$ to $X^3$ independently of one another each denote a nitrogen atom or a CH group optionally substituted by a methyl group,
while at least one and not more than two of the groups $X^1$ to $X^3$ denote a nitrogen atom,
while, unless otherwise stated, the term "heteroaryl group" mentioned hereinbefore in the definitions denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while
the 6-membered heteroaryl group contains one, two or three nitrogen atoms and
the 5-membered heteroaryl group contains one or two imino groups optionally substituted by a $C_{1-3}$-alkyl or phenyl-$C_{1-3}$-alkyl group, an oxygen or sulphur atom or
an imino group optionally substituted by a $C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group or an oxygen or sulphur atom and additionally a nitrogen atom or
an imino group optionally substituted by a $C_{1-3}$-alkyl or phenyl-$C_{1-3}$-alkyl group and two or three nitrogen atoms,
and moreover a phenyl ring may be fused to the above-mentioned monocyclic heteroaryl groups via two adjacent carbon atoms
and the bond is effected via a nitrogen atom or a carbon atom of the heterocyclic moiety or a fused-on phenyl ring,
while the alkyl and alkoxy groups contained in the foregoing definitions, which have more than two carbon atoms, unless otherwise stated, may be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
the tautomers, the enantiomers, the diastereomers, the mixtures thereof and the salts thereof.

A 3rd embodiment of the present invention comprises those compounds of general formula I, wherein
R¹ denotes an amino, $C_{1-5}$-alkylamino, $C_{3-7}$-cycloalkylamino or (phenyl-$C_{1-3}$-alkyl)-amino group which may in each case additionally be substituted at the amino nitrogen atom by a $C_{1-5}$-alkyl or $C_{1-5}$-alkylcarbonyl group optionally substituted in the alkyl moiety by a hydroxy, $C_{1-3}$-alkoxy or carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the substitution of the previously mentioned $C_{1-5}$-alkyl group two heteroatoms are separated from one another by at least two carbon atoms,
a 4- to 7-membered cycloalkyleneiminocarbonyl or cycloalkyleneiminosulphonyl group, while
the cycloalkyleneimino moiety in the carbon skeleton may be substituted by one or two $C_{1-3}$-alkyl, phenyl-$C_{1-3}$-alkyl, 1,1-diphenyl-$C_{1-3}$-alkyl, hydroxy-$C_{1-3}$-alkyl, $C_{1-3}$-alkyloxy-$C_{1-3}$-alkyl, carboxy-$C_{1-3}$-alkyl, $C_{1-3}$-alkyloxycarbonyl-$C_{1-3}$-alkyl, amino-$C_{1-5}$-alkyl, $C_{1-5}$-alkylamino-$C_{1-5}$-alkyl, $C_{3-6}$-cycloalkylamino-$C_{1-3}$-alkyl, phenylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-5}$-alkyl, N—$C_{1-3}$-alkylpiperazin-4-yl-$C_{1-3}$-alkyl, N-(heteroaryl-$C_{1-3}$-alkyl)-$C_{1-3}$-alkylamino-$C_{1-3}$-alkyl, $C_{1-3}$-alkylcarbonylamino-$C_{1-3}$-alkyl, $C_{1-3}$-alkylsulphonylamino-$C_{1-3}$-alkyl, $C_{1-5}$-alkyloxycarbonylamino-$C_{1-3}$-alkyl, $C_{1-3}$-alkylcarbonyl, carboxy, $C_{1-3}$-alkyloxycarbonyl, benzyloxycarbonyl, aminocarbonyl, $C_{1-3}$-alkylaminocarbonyl, di-($C_{1-3}$-alkyl)-aminocarbonyl, hydroxy, $C_{1-3}$-alkyloxy, benzyloxy, amino, $C_{1-3}$-alkylamino, di-($C_{1-3}$-alkyl)-amino, a 4- to 7-membered cycloalkyleneimino, a phenyl or a 5- to 6-membered heteroaryl group, with the proviso that in the substitution of a methylene group adjacent to the imino group two heteroatoms are separated from each other by at least two carbon atoms, and/or
a methylene group in the 3 position of a 5-membered cycloalkyleneimino group may be replaced by a sulphur atom, a sulphinyl or sulphonyl group or a methylene group in the 2 position of a 5-membered cycloalkyleneimino group may be replaced by an —NH— group or
a methylene group in the 4 position of a 6- or 7-membered cycloalkyleneimino group may be replaced by an oxygen or sulphur atom, a methylidene, carbonyl, sulphinyl or sulphonyl group or by an —NH— group optionally substituted by a $C_{1-3}$-alkyl, hydroxy, formyl, $C_{1-3}$-alkylcarbonyl or phenylcarbonylamino group, while additionally a methylene group adjacent to a previously mentioned —NH— group may be replaced by a carbonyl or sulphonyl group, with the proviso that
in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, and/or
a —$CH_2$—$CH_2$— group in a 5- to 6-membered cycloalkyleneimino group may be replaced by a —NH—CO—, —CO—NH—, —CO—N($CH_3$)— or a —N($CH_3$)—CO— group with the proviso that
a cycloalkyleneimino group as hereinbefore defined wherein two nitrogen atoms are separated from one another by precisely one —$CH_2$— group is excluded,
a 5- to 7-membered cycloalkenyleneiminocarbonyl group optionally substituted by one or two $C_{1-3}$-alkyl, amino- $C_{1-3}$-alkyl, $C_{1-3}$-alkylamino-$C_{1-3}$-alkyl, di-($C_{1-3}$-alkyl)-amino-$C_{1-3}$-alkyl, 5- to 6-membered cycloalkyleneimino-$C_{1-3}$-alkyl or $C_{3-6}$-cycloalkylamino-$C_{1-3}$-alkyl groups, while the double bond is not bound to a nitrogen atom and may be fused to a 5- or 6-membered heteroaryl group, an aminocarbonyl group optionally substituted by one or two $C_{1-5}$-alkyl, $C_{3-6}$-cycloalkyl, 5- to 7-membered cycloalkyleneimino or piperidinyl groups, while the substituents may be identical or different and in each case one of the previously mentioned $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, 4- to 7-membered cycloalkyleneimino-$C_{1-3}$-alkyl, C-pyrrolidinyl, $C_{3-6}$-cycloalkylamino-$C_{1-3}$-alkyl or 4- to 7-membered cycloalkyleneiminocarbonyl groups, while the cycloalkyleneimino groups previously mentioned in the groups may additionally be substituted by a carboxy or $C_{1-5}$-alkyloxycarbonyl group, or a group of formula

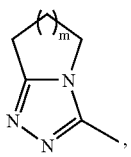

wherein m denotes the number 1, 2 or 3, $R^2$ denotes a chlorine or bromine atom, a $C_{1-3}$-alkyloxy or $C_{1-3}$-alkyl group wherein the hydrogen atoms may be wholly or partly replaced by fluorine atoms, $R^3$ denotes a hydrogen atom, $R^4$ denotes a hydrogen atom or a straight-chain or branched $C_{1-5}$-alkyl group which is optionally substituted by a $C_{2-3}$-alkenyl, $C_{2-3}$-alkynyl, hydroxy, $C_{1-5}$-alkyloxy, phenyloxy, heteroaryloxy, benzyloxy, $C_{1-5}$-alkylcarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, mercapto, $C_{1-3}$-alkylsulphanyl, $C_{1-3}$-alkylsulphinyl, $C_{1-3}$-alkylsulphonyl, carboxy, $C_{1-5}$-alkyloxycarbonyl, allyloxycarbonyl, propargyloxycarbonyl, benzyloxycarbonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{1-3}$-alkylsulphonylamino, $C_{3-6}$-cycloalkylcarbonylamino, benzyloxycarbonylamino or phenylcarbonylamino group, a group of general formula

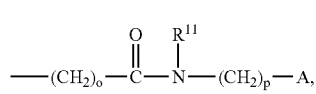   (II)

wherein o denotes one of the numbers 1, 2 or 3, p denotes one of the numbers 0, 1, 2 or 3, $R^{11}$ denotes a hydrogen atom or a $C_{1-3}$-alkyl group and A denotes a $C_{3-7}$-cycloalkyl group wherein the methyne group in the 1 position may be replaced by a nitrogen atom, if p denotes one of the numbers 2 or 3, and/or a methylene group of a previously mentioned cycloalkyl group may be replaced by an oxygen or sulphur atom, a —NH—, —N(OH)—, —N($C_{1-3}$-alkyl)-, —N($C_{1-3}$-alkylcarbonyl)- or —N(heteroaryl)- group, with the proviso that in a —N($R^{11}$)—$(CH_2)_p$-A- group thus formed two heteroatoms are separated from one another by at least two carbon atoms, and/or a methylene group adjacent to a —NH—, —N(OH)—, —N($C_{1-3}$-alkyl)-, —N($C_{1-3}$-alkylcarbonyl)- or —N(heteroaryl)- group may be replaced by a carbonyl, sulphinyl or sulphonyl group, a 4- to 7-membered cycloalkyleneiminocarbonyl-$C_{1-5}$-alkyl group, while a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino, morpholino, piperazinyl, N—($C_{1-3}$-alkyl)-piperazinyl or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group and/or a methylene group in the 3 position of a 5-membered cycloalkyleneimino group may be replaced by a sulphur atom, a carbonyl, sulphinyl or sulphonyl group or a methylene group in the 4 position of a 6- or 7-membered cycloalkyleneimino group may be replaced by an oxygen or sulphur atom, by a carbonyl, sulphinyl, sulphonyl or by an —NH— group optionally substituted by a $C_{1-3}$-alkyl or heteroaryl group and additionally a methylene group adjacent to an above-mentioned —NH— or —N($C_{1-3}$-alkyl)- group may be replaced by a carbonyl group and/or two geminal hydrogen atoms of a methylene group in a previously mentioned cycloalkyleneimino group may be substituted by a 5- to 7-membered carbocycle forming a spiro compound, while one or two methylene groups of the aforementioned carbocycle which are not adjacent to one another may be replaced independently of one another by an oxygen or sulphur atom or an —NH—, —N(OH)—, or —N($C_{1-3}$-alkyl)- group and additionally a methylene group of the carbocyclic group adjacent to an —NH—, —N(OH)—, or —N($C_{1-3}$-alkyl)- group may be replaced by a carbonyl, sulphinyl or sulphonyl group, or a phenyl or heteroaryl group may be fused to two adjacent methylene groups in the 2 and 3 position of a previously mentioned 5-membered cycloalkyleneimino group or in the 3 and 4 position of a previously mentioned 6- to 7-membered cycloalkyleneimino group, an aminocarbonyl-$C_{1-5}$-alkyl, aminosulphonyl-$C_{1-3}$-alkyl, $C_{1-3}$-alkylaminocarbonyl-$C_{1-5}$-alkyl or $C_{1-3}$-alkylaminosulphonyl-$C_{1-3}$-alkyl group, while the previously mentioned amino groups may additionally be substituted by a $C_{3-6}$-cycloalkyl-$C_{1-3}$-alkyl, phenyl-$C_{1-3}$-alkyl, heteroaryl-$C_{1-3}$-alkyl, heteroarylamino-$C_{2-3}$-alkyl, hydroxy-$C_{2-3}$-alkyl, $C_{1-3}$-alkyloxy-$C_{2-3}$-alkyl, carboxy-$C_{1-3}$-alkyl, $C_{1-5}$-alkyloxycarbonyl-$C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl group, a phenyl or heteroaryl, phenyl-$C_{1-3}$-alkyl or heteroaryl-$C_{1-3}$-alkyl group which is optionally substituted by a chlorine atom, a hydroxy, $C_{1-4}$-alkyloxy, carboxy or $C_{1-3}$-alkyloxycarbonyl group, a 4- to 7-membered cycloalkyleneimino-$C_{1-3}$-alkyl group wherein
  a methylene group of the cycloalkyleneimino moiety may be replaced by an oxygen or sulphur atom, a carbonyl or sulphonyl group, or a 4- to 7-membered cycloalkyl-$C_{1-3}$-alkyl group wherein in the cyclic moiety a methylene group may be replaced by an —NH— or —N($C_{1-3}$-alkyl)- group and wherein a methylene group adjacent to the —NH— or —N($C_{1-3}$-alkyl)- group may be replaced in each case by a carbonyl group, with the proviso that a cycloalkyleneimino group as hereinbefore defined wherein two nitrogen atoms are separated from one another by precisely one —$CH_2$— group are excluded, $R^5$ denotes a hydrogen atom, B denotes a group of formulae

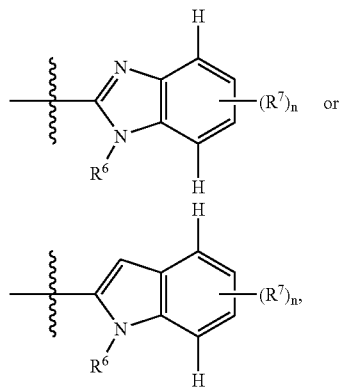

wherein
  n denotes the number 1,
  $R^6$ denotes a hydrogen atom,
  $R^7$ denotes a fluorine, chlorine or bromine atom, and
  $X^1$ to $X^3$ independently of one another each denote a nitrogen atom or a CH group,
    while at least one and not more than two of the groups $X^1$ to $X^3$ denote a nitrogen atom, while, unless otherwise stated, the term "heteroaryl group" mentioned hereinbefore in the definitions refers to a monocyclic 5- or 6-membered heteroaryl group optionally substituted in the carbon skeleton by a $C_{1-3}$-alkyl group, while
  the 6-membered heteroaryl group contains one, two or three nitrogen atoms and
  the 5-membered heteroaryl group contains one or two imino groups optionally substituted by a $C_{1-3}$-alkyl or phenyl-$C_{1-3}$-alkyl group or a sulphur atom or
  an imino group optionally substituted by a $C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl or phenyl-$C_{1-3}$-alkyl group or a sulphur atom and additionally a nitrogen atom or
  an imino group optionally substituted by a $C_{1-3}$-alkyl or phenyl-$C_{1-3}$-alkyl group and two or three nitrogen atoms,
  and moreover a phenyl ring may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, the alkyl and alkoxy groups contained in the foregoing definitions which have more than two carbon atoms may be straight-chain or branched and the alkyl groups in the previously mentioned dialkylated groups, for example the dialkylamino group, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 4th embodiment of the present invention comprises those compounds of the above general formula I wherein $R^1$ denotes a 4- to 7-membered cycloalkyleneiminocarbonyl group, while
  the cycloalkyleneimino moiety in the carbon skeleton may be substituted by one or two $C_{1-3}$-alkyl, phenyl-$C_{1-3}$-alkyl, 1,1-diphenyl-$C_{1-3}$-alkyl, hydroxy-$C_{1-3}$-alkyl, $C_{1-3}$-alkyloxy-$C_{1-3}$-alkyl, carboxy-$C_{1-3}$-alkyl, $C_{1-3}$-alkyloxycarbonyl-$C_{1-3}$-alkyl, amino-$C_{1-5}$-alkyl, $C_{1-5}$-alkylamino-$C_{1-5}$-alkyl, $C_{3-6}$-cycloalkylamino-$C_{1-3}$-alkyl, phenylamino-$C_{1-3}$-alkyl, di-($C_{1-5}$-alkyl)-amino-$C_{1-5}$-alkyl, N—($C_{3-6-cyc}$loalkyl )-$C$-$_{1-3}$-alkylamino-$C_{1-3}$-alkyl, a 4- to 7-membered cycloalkyleneimino-$C_{1-5}$-alkyl, N-$C_{1-3}$-alkylpiperazin-4-yl-$C_{1-3}$-alkyl, N-(piperidin-2-yl-$C_{1-3}$-alkyl)-$C_{1-3}$-alkylamino-$C_{1-3}$-alkyl, $C_{1-3}$-alkylcarbonylamino-$C_{1-3}$-alkyl, $C_{1-3}$-alkylsulphonylamino-$C_{1-3}$-alkyl, $C_{1-5}$-alkyloxycarbonylamino-$C_{1-3}$-alkyl, $C_{1-3}$-alkylcarbonyl, carboxy, $C_{1-5}$-alkyloxycarbonyl, benzyloxycarbonyl, aminocarbonyl, $C_{1-3}$-alkylamino-carbonyl, di-($C_{1-3}$-alkyl)-aminocarbonyl, hydroxy, $C_{1-3}$-alkyloxy, benzyloxy, amino, $C_{1-3}$-alkylamino, di-($C_{1-3}$-alkyl)-amino, a 4- to 7-membered cycloalkyleneimino, a phenyl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulphur atom, a sulphinyl or sulphonyl group or a methylene group in the 2 position of a 5-membered cycloalkyleneimino group may be replaced by an —NH— group or a methylene group in the 4 position of a 6- or 7-membered cycloalkyleneimino group may be replaced by an oxygen or sulphur atom, a methylidene, carbonyl, sulphinyl or sulphonyl group or by an —NH— group optionally substituted by a $C_{1-3}$-alkyl, hydroxy, formyl, $C_{1-3}$-alkylcarbonyl or phenylcarbonylamino group, while additionally a methylene group adjacent to a previously mentioned —NH— group may be replaced by a carbonyl or sulphonyl group, with the proviso that
  in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, and/or a —$CH_2$—$CH_2$— group in a 5- to 6-membered cycloalkyleneimino group may be replaced by an —NH—CO—, —CO—NH—, —CO—N($CH_3$)— or a —N($CH_3$)—CO— group, with the proviso that a cycloalkyleneimino group as hereinbefore defined wherein two nitrogen atoms are separated from one another by precisely one —CH$_2$— group is excluded, a 5- to 7-membered cycloalkenyleneiminocarbonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, 5- to 6-membered cycloalkyleneimino-$C_{1-3}$-alkyl or $C_{3-6}$-cycloalkylamino-$C_{1-3}$-alkyl groups, while the double bond is not bound to a nitrogen atom and may be fused to a 5- or 6-membered heteroaryl group, an aminocarbonyl group optionally substituted by one or two $C_{1-5}$-alkyl, $C_{3-6}$-cycloalkyl, 5- to 7-membered cycloalkyleneimino or piperidinyl groups, while the substituents may be identical or different and in each case one of the previously mentioned $C_{1-5}$-alkyl groups may be substituted by one or two amino-$C_{1-3}$-alkyl, $C_{1-3}$-alkylamino-$C_{1-3}$-alkyl, di-($C_{1-3}$-alkyl)-amino-$C_{1-3}$-alkyl, 4- to 7-membered cycloalkyleneimino-$C_{1-3}$-alkyl, C-pyrrolidinyl, $C_{3-6}$-cycloalkylamino-$C_{1-3}$-alkyl or 4- to 7-membered cycloalkyleneiminocarbonyl groups, while the cycloalkyleneimino groups previously mentioned in the groups may additionally be substituted by a carboxy or $C_{1-5}$-alkyloxycarbonyl group, or a group of formula

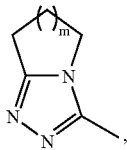

wherein m denotes the number 1, 2 or 3, $R^2$ denotes a chlorine or bromine atom, a $C_{1-3}$-alkyloxy or $C_{1-3}$-alkyl group wherein the hydrogen atoms may be wholly or partly replaced by fluorine atoms, $R^3$ denotes a hydrogen atom, $R^4$ denotes a hydrogen atom or a straight-chain or branched $C_{1-5}$-alkyl group which is optionally substituted by a $C_{2-3}$-alkynyl, hydroxy, $C_{1-5}$-alkyloxy, benzyloxy, $C_{1-5}$-alkylcarbonyloxy, carboxy-$C_{1-3}$-alkyloxy, $C_{1-5}$-alkyloxycarbonyl-$C_{1-3}$-alkyloxy, $C_{1-3}$-alkylsulphanyl, $C_{1-3}$-alkylsulphinyl, $C_{1-3}$-alkylsulphonyl, carboxy, $C_{1-5}$-alkyloxycarbonyl, allyloxycarbonyl, benzyloxycarbonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{1-3}$-alkylsulphonylamino, $C_{3-6}$-cycloalkylcarbonylamino, benzyloxycarbonylamino or phenylcarbonylamino group, a group of general formula

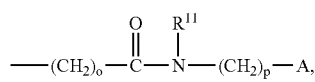

(II)

wherein o denotes one of the numbers 1, 2 or 3, p denotes one of the numbers 0, 1, 2 or 3, $R^{11}$ denotes a hydrogen atom or a $C_{1-3}$-alkyl group and A denotes a $C_{3-7}$-cycloalkyl group wherein the methyne group in the 1 position may be replaced by a nitrogen atom, if p denotes one of the numbers 2 or 3, and/or a methylene group of a previously mentioned cycloalkyl group may be replaced by an oxygen or sulphur atom, a —NH—, —N(OH)—, —N($C_{1-3}$-alkyl)-, —N($C_{1-3}$-alkylcarbonyl)- or —N(heteroaryl)- group, with the proviso that in a group —N($R^{11}$)—(CH$_2$)$_p$-A- thus formed two heteroatoms are separated from one another by at least two carbon atoms, and/or a methylene group adjacent to an —NH—, —N(OH)—, —N($C_{1-3}$-alkyl)-, —N($C_{1-3}$-alkylcarbonyl)- or —N(heteroaryl)- group may be replaced by a carbonyl, sulphinyl or sulphonyl group, a 5- to 6-membered cycloalkyleneiminocarbonyl-$C_{1-5}$-alkyl group, while a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino, morpholino, piperazinyl, N—($C_{1-3}$-alkyl)-piperazinyl or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group and/or a methylene group in the 3 position of a 5-membered cycloalkyleneimino group may be replaced by a sulphur atom, a carbonyl, sulphinyl or sulphonyl group or a methylene group in the 4 position of a 6- or 7-membered cycloalkyleneimino group may be replaced by an oxygen or sulphur atom, by a carbonyl, sulphinyl, sulphonyl or by a —NH— group optionally substituted by a $C_{1-3}$-alkyl or heteroaryl group and additionally a methylene group adjacent to an above-mentioned —NH— or —N($C_{1-3}$-alkyl)- group may be replaced by a carbonyl group and/or two geminal hydrogen atoms of a methylene group in a previously mentioned cycloalkyleneimino group may be substituted by a 5- to 7-membered carbocycle forming a spiro compound, while one or two methylene groups of the aforementioned carbocycle which are not adjacent to one another may be replaced independently of one another by an oxygen or sulphur atom or an —NH—, —N(OH)—, or —N($C_{1-3}$-alkyl)- group and additionally a methylene group of the carbocyclic group adjacent to an —NH—, —N(OH)—, or —N($C_{1-3}$-alkyl)- group may be replaced by a carbonyl, sulphinyl or sulphonyl group, or a phenyl or heteroaryl group may be fused to two adjacent methylene groups in the 2 and 3 position of a previously mentioned 5-membered cycloalkyleneimino group or in the 3 and 4 position of a previously mentioned 6- to 7-membered cycloalkyleneimino group, an aminocarbonyl-$C_{1-5}$-alkyl or $C_{1-3}$-alkylaminocarbonyl-$C_{1-5}$-alkyl group, while the previously mentioned amino groups may additionally be substituted by a $C_{3-6}$-cycloalkyl-$C_{1-3}$-alkyl, phenyl-$C_{1-3}$-alkyl, heteroaryl-$C_{1-3}$-alkyl, heteroarylamino-$C_{2-3}$-alkyl, hydroxy-$C_{2-3}$-alkyl, $C_{1-3}$-alkyloxy-$C_{2-3}$-alkyl, carboxy-$C_{1-3}$-alkyl, $C_{1-5}$-alkyloxycarbonyl-$C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl group, a phenyl or heteroaryl, phenyl-$C_{1-3}$-alkyl or heteroaryl-$C_{1-3}$-alkyl group which is optionally substituted by a chlorine atom, a hydroxy, $C_{1-4}$-alkyloxy, trifluoromethoxy, carboxy or $C_{1-3}$-alkyloxycarbonyl group, a 4- to 7-membered cycloalkyleneimino-$C_{1-5}$-alkyl group wherein a methylene group of the cycloalkyleneimino moiety may be replaced by an oxygen or sulphur atom, a carbonyl or sulphonyl group, $R^5$ denotes a hydrogen atom, B denotes a group of formulae

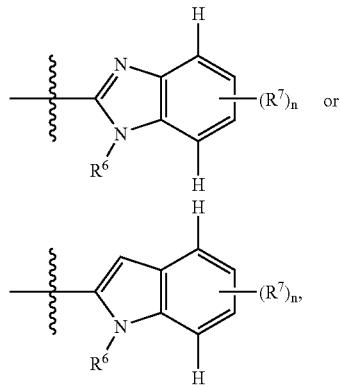

wherein n denotes the number 1, $R^6$ denotes a hydrogen atom, $R^7$ denotes a chlorine or bromine atom and $X^1$ to $X^3$ independently of one another each denote a nitrogen atom or a CH group, while at least one and not more than two of the groups $X^1$ to $X^3$ denote a nitrogen atom, while, unless otherwise stated, the term "heteroaryl group" mentioned hereinbefore in the definitions denotes a monocyclic 5- or 6-membered heteroaryl group optionally substituted in the carbon skeleton by a $C_{1-3}$-alkyl group, while the 6-membered heteroaryl group contains one, two or three nitrogen atoms and the 5-membered heteroaryl group contains one or two imino groups optionally substituted by a $C_{1-3}$-alkyl or phenyl-$C_{1-3}$-alkyl group or a sulphur atom or an imino group optionally substituted by a $C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl or phenyl-$C_{1-3}$-alkyl group or a sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, the alkyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 5th embodiment of the present invention comprises those compounds of the above general formula I, wherein $R^1$ denotes a 2,5-dihydro-1H-pyrrol-1-yl-carbonyl, pyrrolidin-1-yl-carbonyl, 2-(aminomethyl)-pyrrolidin-1-yl-carbonyl, 2-(N-tert.-butyloxycarbonylaminomethyl)-pyrrolidin-1-yl-carbonyl, 3-oxo-piperazin-1-yl-carbonyl, morpholin-4-yl-carbonyl, carboxy, 3-aminomethyl-pyrrolidin-1-yl-carbonyl, thiazolidin-3-yl-carbonyl, 3-aminomethyl-pyrrolidin-1-yl-carbonyl, pyrazolidin-3-on-1-yl-carbonyl, pyrrolidin-2-ylmethylamino-carbonyl, 1-tert.-butyloxycarbonyl-pyrrolidin-2-yl-methylamino-carbonyl, 2-(acetylamino-methyl)-pyrrolidin-1-yl-carbonyl, 2-(pyrrolidin-1-yl-methyl)-pyrrolidin-1-yl- carbonyl, 2-(tert.-butyloxycarbonyl-aminomethyl)-thiazolidin-1-yl-carbonyl, 2-(pyridin-4-yl)-pyrrolidin-1-yl-carbonyl, 2-aminomethyl-thiazolidinyl-carbonyl, 2-(methanesulphonyl-aminomethyl)-pyrrolidin-1-yl-carbonyl, 2-acetaminomethyl-thiazolidin-1-yl-carbonyl, 5,6,7,8-tetrahydro-[1,2,4]triazolo[4,3a]pyridin-4-yl, 2-(pyridin-4-yl)-thiazolidin-3-yl-carbonyl, 2-(2,2,2-trifluorethyl)-thiazolidin-3-yl-carbonyl, 2-(2-aminoethyl )-pyrrolidin-1-yl-carbonyl, 2-ethoxycarbonyl-piperidin-1-yl-carbonyl, 4,5,6,7-tetrahydro-thieno[3,2-c]pyridin-5-yl-carbonyl, 2-benzhydryl-pyrrolidin-1-yl-carbonyl, [1,4]diazepan-1-yl-carbonyl, 2-(2-ethoxycarbonyl-ethyl)-piperidin-1-yl-carbonyl, 2-methylaminocarbonyl-pyrrolidin-1-yl-carbonyl, 3-(3-diethylamino-propyl)-piperidin-1-yl-carbonyl, 4-methyl-piperidin-1-yl-carbonyl, 2-(phenylaminomethyl)-pyrrolidin-1-yl-carbonyl, 2-benzyl-pyrrolidin-1-yl-carbonyl, 3-hydroxy-piperidin-1-yl-carbonyl, 2-dimethylaminocarbonyl-pyrrolidin-1-yl-carbonyl, piperidin-1-yl-carbonyl, 4-oxo-piperidin-1-yl-carbonyl, 4-methylene-piperidin-1-yl-carbonyl, 2-methyl-piperidin-1-yl-carbonyl, 2-benzyloxycarbonyl-pyrrolidin-1-yl-carbonyl, N-(3-amino-propyl )-N-ethyl-amino-carbonyl, N-cyclopropyl-N-methylamino-carbonyl, 2-methoxymethyl-pyrrolidin-1-yl-carbonyl,3-(1H-benzimidazol-2-yl)-piperidin-1-yl]-carbonyl, 3-dimethylamino-pyrrolidin-1-yl-carbonyl, 2,5-dimethyl-2,5-dihydro-1H-pyrrol-1-yl)-carbonyl, 2-isopropyl-pyrrolidin-1-yl-carbonyl, 2-aminomethyl-piperidin-1-yl-carbonyl], 3-aminomethyl-piperidin-1-yl-carbonyl, 2-ethoxycarbonyl-pyrrolidin-1-yl-carbonyl, 3-(dimethylamino-methyl)-piperidin-1-yl-carbonyl, 2-(2-phenyl-ethyl)-pyrrolidin-1-yl-carbonyl, 2-(pyridin-2-yl)-pyrrolidin-1-yl-carbonyl, 2-(2-aminoethyl )-piperidin-1-yl-carbonyl, 4-acetyl-piperazin-1-yl-carbonyl, N-(2-amino-ethyl )-N-ethyl-amino-carbonyl, 2-(pyridin-3-yl)-piperidin-1-yl-carbonyl, 2,5-dimethyl-pyrrolidin-1-yl-carbonyl, 4-aminocarbonyl-piperidin-1-yl-carbonyl, 4-hydroxy-piperidin-1-yl-carbonyl, 2-ethoxycarbonyl- piperidin-1-yl-carbonyl, 1-(1,4,6,7-tetrahydro-pyrazolo[4,3]pyridin-5-yl )-carbonyl, 2,5-dimethoxymethyl-pyrrolidin-1-yl-carbonyl, 2-methoxycarbonyl-pyrrolidin-1-yl-carbonyl, pyrazolidin-1-yl-carbonyl, 1-oxo-thiomorpholin-4-yl-carbonyl, 2-[(N-butyl-N-ethyl-amino)-methyl]-piperidin-1-yl-carbonyl, N-ethyl-N-(piperidin-4-yl)-aminocarbonyl, 4-formyl-piperazin-1-yl-carbonyl, 2-(2-dimethylamino-ethyl)-piperidin-1-yl-carbonyl, 2-(2-diethylamino-ethyl)-piperidin-1-yl-carbonyl, 1,4,6,7-tetrahydro-imidazo[4,5-c]pyridin-5-yl-carbonyl, 3,6-dihydro-2H-pyridin-1-yl-carbonyl, 2-[(N-butyl-N-methyl-amino)-methyl]-piperidin-1-ylcarbonyl, 2-methyl-morpholin-4-yl-carbonyl, thiomorpholin-4-yl-carbonyl, 2-(2-amino-ethyl)-piperidin-1-yl-carbonyl, 2-ethyl-piperidin-1-yl-carbonyl, 3-amino-pyrrolidin-1-yl-carbonyl, 4-trifluoromethyl-piperidin-1-yl-carbonyl, 3-[4-(pyrrolidin-1-yl)-butyl]-pyrrolidin-1-yl-carbonyl, 2-[(N-methyl-N-(pyridin-2-ylmethyl)-amino)-methyl]-piperidin-1-yl-carbonyl, 4-hydroxy-piperazin-1-yl-carbonyl, 3-(pyrrolidin-1-ylmethyl)-piperidin-1-yl-carbonyl, 2-diethylaminomethyl-piperidin-1-yl-carbonyl, 2-(4-diethylamino-butyl)-piperidin-1-yl-carbonyl, 2-hydroxymethyl-pyrrolidin-1-yl-carbonyl, 2-(N-ethyl-N-methyl-aminomethyl)-piperidin-1-yl-carbonyl, 2-aminocarbonyl-pyrrolidin-1-yl-carbonyl, 2-(4-methyl-piperazin-1-ylmethyl)-piperidin-1-yl-carbonyl, 2-methoxymethyl-pyrrolidin-1-yl-carbonyl, 2-(3-dimethylamino-propyl)-piperidin-1-yl-carbonyl, 2-diethylaminocarbonyl-piperidin-1-yl-carbonyl, 2-[(N-cyclohexyl-N-methyl-amino)-methyl]-piperidin-1-yl-carbonyl, 2-piperidin-1-ylmethyl-piperidin-1-yl-carbonyl, 2-(1-methyl-1H-pyrazol-4-yl)-thiazolidinyl-carbonyl or 6,7,8,9-tetrahydro-[1,2,4]triazolo[4,3-a]pyridin-4-yl-group, $R^2$ denotes a hydrogen, chlorine or bromine atom, a $C_{1-3}$-alkyloxy or a $C_{1-3}$-alkyl group wherein the hydrogen atoms may be wholly or partly replaced by fluorine atoms, $R^3$ denotes a hydrogen atom, $R^4$ denotes a hydrogen atom, a methyl, propyl, 2-methylsulphanyl-ethyl, 2-methylsulphonyl-ethyl, hydroxymethyl, 2-carboxyethyl, 2-benzyloxycarbonyl-ethyl, 2-methoxy-ethyl, 2-methylsulphinyl-ethyl, tert.-butyloxycarbonyl-methoxy-methyl, 2-ethoxycarbonyl-ethyl, carboxymethoxy-methyl, o-chlorophenyl, p-chlorophenyl, methoxymethyl, 2-diethylaminocarbonyl-ethyl, 2-propargyloxycarbonyl-ethyl, 2-(pyrrolidin-1-yl-carbonyl)-ethyl, 2-[N-methyl-N-piperidin-4-yl-amino]-carbonyl-ethyl, 2-[4-methyl-piperazin-1-yl]-carbonyl-ethyl, 2-(C-piperidin-4-yl-methylamino)-carbonyl-ethyl, 2-(N-benzyl-N-methyl-amino)-carbonyl-ethyl, 3-tert.-butyloxycarbonyl-propyl, 2-benzyloxycarbonylamino-ethyl, 2-[(1,2,3,4-tetrahydroisoquinolin-1-yl)-carbonyl-ethyl, 2-(benzylamino-carbonyl)-ethyl, 2-[(N-methyl-N-phenethyl-amino-carbonyl)-ethyl, 2-(hydroxyethylamino-carbonyl)-ethyl, 2-[(C-pyridin-3-yl-methylamino-carbonyl)-propyl, 2-[(1-oxa-3,8-diaza-spiro[4,5]decan-2-on-8-yl)-carbonyl]-ethyl, 2-(morpholin-4-yl-carbonyl)-ethyl, 2-(C-cyclohexyl-methylamino-carbonyl)-ethyl, 2-(methoxyethylamino-carbonyl)-ethyl, 2-(dimethylaminoethyl-amino-carbonyl)-ethyl, 2-(cyclopropylamino-carbonyl)-ethyl, 2-[C-2-tetrahydrofuran-2-yl-methylamino-carbonyl)-ethyl, 2-(dimethylaminopropylamino-carbonyl)-ethyl, 2-(aminoethylamino-carbonyl)-ethyl, 2-(hydroxycarbonylmethyl-methyl-amino-carbonyl)-ethyl, 2-((3-(pyrrolidin-2-on-1-yl)-propyl)-amino-carbonyl)-ethyl, 2-[(1-[1,3,5]triazin-2-yl-piperidin-4-ylamino)-carbonyl]-ethyl, 2-[(2-imidazol-1-yl-ethylamino)-carbonyl)-ethyl, 2-[C-(1H-imidazol-2-yl)-methylamino-carbonyl)-ethyl, 2-(2,2,2-trifluoroethylamino-carbonyl)-ethyl, 2-[N-(2-dimethylamino-ethyl)-N-methyl-amino-carbonyl]-ethyl, 2-[1-phenyl-ethylamino-carbonyl]-ethyl, 2-[2-(4-methyl-piperazin-1-ylmethyl)-piperidin-1-yl-carbonyl]-ethyl, 2-(N-aminocarbonylmethyl-N-methyl-amino-carbonyl)-ethyl, 2-(4,5,6,7-tetrahydro-1H-imidazo[4,5-c]pyridin-5-yl-carbonyl)-ethyl, 2-(1-oxo-thiomorpholin-4-yl-carbonyl)-ethyl, 2-(N-dimethylaminocarbonylmethyl-N-methyl-amino-carbonyl)-ethyl, 2-(N-hydroxycarbonylethyl-N-methyl-amino-carbonyl)-ethyl, 2-[C-(1-methyl-1H-imidazol-2-yl)-methylamino-carbonyl)-ethyl, 2-(N-piperidin-2-yl-aminocarbonyl)-ethyl, 2-[C-(tetrahydropyran-4-yl)-methylamino-carbonyl]-ethyl, 2-(4-hydroxypiperidin-1-yl-carbonyl)-ethyl, 2-[C-(pyridin-4-yl)-methylamino-carbonyl]-ethyl, 2-(N-methylaminocarbonylmethyl-N-methyl-amino-carbonyl)-ethyl, 2-[N-(2-(1H)-imidazol-4-yl)-ethyl)-N-methyl-amino-carbonyl]-ethyl, 2-(1-thiazolidin-3-yl-carbonyl)-ethyl, 2-(N-cyclopropyl-N-methyl-amino-carbonyl)-ethyl, 2-(cyclopentylamino-carbonyl)-ethyl, 2-(N-piperidin-4-yl-aminocarbonyl)-ethyl, 2-[C-(pyridin-2-yl)-methylamino-carbonyl]-ethyl, 2-(4-thiazol-2-yl-piperazin-1-yl-carbonyl)-ethyl, 2-(piperidin-1-yl-carbonyl)-ethyl, 2-amino-ethyl, thiophen-3-yl, 2-(2-oxo-pyrrolidin-1-yl)-ethyl, 2-(1,1-dioxo-isothiazolidin-2-yl)-ethyl, isopropylcarbonyloxy-methyl, 3-carboxypropyl, 2-methylsulphonylamino-ethyl, methylsulphanyl-methyl, benzyloxy-methyl, 2-[2-(pyridin-4-yl-amino)-ethylamino-carbonyl]-ethyl, but-3-yn-1-yl, 1-methoxy-ethyl, 1-tert.-butyloxy-ethyl or 1-hydroxy-ethyl group, $R^5$ denotes a hydrogen atom, B denotes a group of formulae

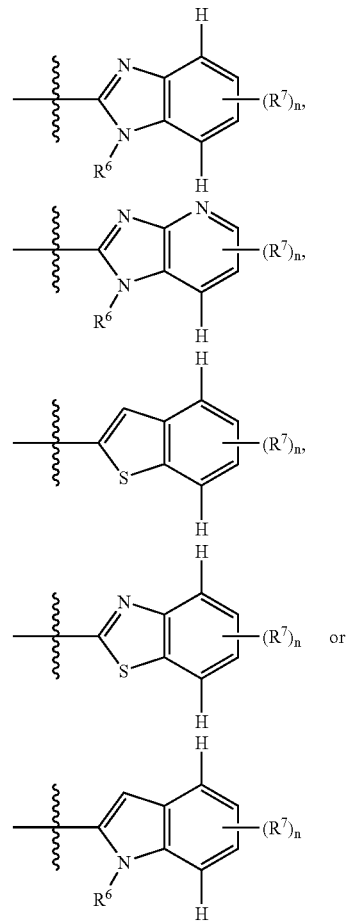

wherein $R^6$ denotes a hydrogen atom, $R^7$ denotes a chlorine or bromine atom, and $X^1$ to $X^3$ independently of one another each denote a nitrogen atom or a CH group, while at least one and not more than two of the groups $X^1$ to $X^3$ denote a nitrogen atom, the tautomers, the enantiomers, the diastereomers, the mixtures thereof and the salts thereof.

The following preferred compounds of general formula I will now be mentioned by way of example:

(1) 4-[(5-chloro-1H-benzimidazol-2-yl)-methylamino]-7-(pyrrolidin-1-yl-carbonyl)-quinoline,
(2) 6-chloro-4-[C-(5-chloro-1H-benzimidazol-2-yl)-methylamino]-7-(pyrrolidin-1-yl-carbonyl)-quinazoline,
(3) 4-[C-(5-chloro-1H-benzimidazol-2-yl)methylamino]-7-(pyrrolidin-1-yl-carbonyl)-quinazoline,
(4) 6-chloro-4-[1-(5-chloro-1H-benzimidazol-2-yl)-ethylamino]-7-(2,5-dihydropyrrol-1-yl-carbonyl)-quinazoline,
(5) 6-chloro-4-[1-(5-chloro-1H-benzimidazol-2-yl)-ethylamino]-7-(2-tert.-butyloxycarbonyl-aminomethyl-pyrrolidin-1-yl-carbonyl)-quinazoline,
(6) 6-chloro-4-[1-(5-chloro-1H-benzimidazol-2-yl)-ethylamino]-7-(2-aminomethyl-pyrrolidin-1-yl-carbonyl)-quinazoline,
(7) 6-chloro-4-[1-(5-chloro-1H-benzimidazol-2-yl)-ethylamino]-7-(morpholin-4-yl-carbonyl)-quinazoline,
(8) 6-chloro-4-[1-(S)-(5-chloro-1H-benzimidazol-2-yl)-ethylamino]-7-(piperazin-3-on-1-yl-carbonyl)-quinazoline,
(9) 6-chloro-4-[1-(S)-(5-chloro-1H-benzimidazol-2-yl)-ethylamino]-7-(2,5-dihydropyrrol-1-yl-carbonyl)-quinazoline,
(10) 6-chloro-4-[1-(S)-(5-chloro-1H-benzimidazol-2-yl)-ethylamino]-7-(pyrrolidin-1-yl-carbonyl)-quinazoline,
(11) 4-[1-(5-chloro-1H-benzimidazol-2-yl)-ethylamino]-7-(pyrrolidin-1-yl-carbonyl)-quinoline,
(12) 4-[1-(5-chloro-1H-benzimidazol-2-yl)-3-methylsulphanyl-propylamino]-6-methyl-7-(pyrrolidin-1-yl-carbonyl)-quinoline,
(13) 4-[1-(5-chloro-1H-benzimidazol-2-yl)-ethylamino]-6-methyl-7-(pyrrolidin-1 -yl-carbonyl)-quinoline,
(14) 4-[1-(5-chloro-1H-benzimidazol-2-yl)-ethylamino]-6-methyl-7-(3-oxo-piperazin-1-yl-carbonyl)-quinoline,
(15) 4-[(1R/S)-1-(5-chloro-1H-benzimidazol-2-yl)-ethylamino]-6-methyl-7-[(2R)-2-aminomethyl-pyrrolidin-1-yl-carbonyl]-quinoline,
(16) 4-[1-(5-chloro-1H-benzimidazol-2-yl)-3-methylsulphanyl-propylamino]-6-methyl-7-(3-oxo-piperazin-1-yl-carbonyl)-quinoline,
(17) 4-[1-(5-chloro-1H-benzimidazol-2-yl)-3-methanesulphonyl-propylamino]-6-methyl-7-(pyrrolidin-1-yl-carbonyl)-quinoline,
(18) 6-chloro-4-[(1S)-1-(5-chloro-1H-benzimidazol-2-yl)-ethylamino]-7-[(2R)-2-tert.-butyloxycarbonyl-aminomethyl-pyrrolidin-1-yl-carbonyl]-quinazoline,
(19) 6-chloro-4-[(1S)-1-(5-chloro-1H-benzimidazol-2-yl)-ethylamino]-7-[(2R)-2-aminomethyl-pyrrolidin-1-yl-carbonyl]-quinazoline,
(20) 6-chloro-4-[(1S)-1-(5-chloro-1H-benzimidazol-2-yl)-2-hydroxy-ethylamino]-7-(2,5-dihydropyrrol-1-yl-carbonyl)-quinazoline,
(21) 6-chloro-4-[(1S)-1-(5-chloro-1H-benzimidazol-2-yl)-2-hydroxy-ethylamino]-7-[(2R)-2-tert.-butyloxycarbonyl-aminomethyl-pyrrolidin-1-yl-carbonyl]-quinazoline,
(22) 6-chloro-4-[(1S)-1-(5-chloro-1H-benzimidazol-2-yl)-2-hydroxy-ethylamino]-7-[(2R)-2-aminomethyl-pyrrolidin-1-yl-carbonyl]-quinazoline,
(23) 6-chloro-4-[(1S)-1-(5-chloro-1H-benzimidazol-2-yl)-ethylamino]-7-[(2S)-2-tert.-butyloxycarbonyl-aminomethyl-pyrrolidin-1-yl-carbonyl]-quinazoline,
(24) 6-chloro-4-[(1S)-1-(5-chloro-1H-benzimidazol-2-yl)-ethylamino]-7-[(2S)-2-aminomethyl-pyrrolidin-1-yl-carbonyl]-quinazoline,
(25) 6-chloro-4-[1-(5-chloro-1H-benzimidazol-2-yl)-3-hydroxycarbonylpropylamino]-7-(pyrrolidin-1-yl-carbonyl)-quinazoline,
(26) 6-chloro-4-[1-(5-chloro-1H-benzimidazol-2-yl)-3-benzyloxycarbonylpropylamino]-7-(pyrrolidin-1-yl-carbonyl)-quinazoline,
(27) 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline,
(28) 6-chloro-4-[(1S)-1-(5-chloro-1H-benzimidazol-2-yl)-3-methylsulphanyl-propylamino]-7-(pyrrolidin-1-yl-carbonyl)-quinazoline,
(29) 6-chloro-4-[(1S)-1-(5-chloro-1H-benzimidazol-2-yl)-3-methoxy-propylamino]-7-(2,5-dihydropyrrol-1-yl-carbonyl)-quinazoline,
(30) 6-chloro-4-[(1S)-1-(5-chloro-1H-benzimidazol-2-yl)-3-methanesulphonyl-propylamino]-7-(pyrrolidin-1-yl-carbonyl)-quinazoline,
(31) 6-chloro-4-[(1S)-1-(5-chloro-1H-benzimidazol-2-yl)-3-methylsulphanyl-propylamino]-7-[(2R)-2-aminomethyl-pyrrolidin-1-yl-carbonyl]-quinazoline,
(32) 6-chloro-4-[(1S)-1-(5-chloro-1H-benzimidazol-2-yl)-3-methanesulphinyl-propylamino]-7-(pyrrolidin-1-yl-carbonyl)-quinazoline,
(33) 6-chloro-4-[(1S)-1-(5-chloro-1H-benzimidazol-2-yl)-3-benzyloxycarbonylpropylamino]-7-(pyrrolidin-1-yl-carbonyl)-quinazoline,
(34) 6-chloro-4-[(1S)-1-(5-chloro-1H-benzimidazol-2-yl)-2-hydroxy-ethylamino]-7-(piperazin-3-on-1-yl-carbonyl)-quinazoline,
(35) 6-chloro-4-[(1S)-1-(5-chloro-1H-benzimidazol-2-yl)-3-methanesulphinyl-propylamino]-7-[(2R)-2-tert.-butyloxycarbonyl-aminomethyl-pyrrolidin-1-yl-carbonyl]-quinazoline,
(36) 6-chloro-4-[(1S)-1-(5-chloro-1H-benzimidazol-2-yl)-ethylamino]-7-hydroxycarbonyl-quinazoline,
(37) 6-chloro-4-[(1S)-1-(5-chloro-1H-benzimidazol-2-yl)-ethylamino]-7-[(3-aminomethyl-pyrrolidin-1-yl-carbonyl]-quinazoline,
(38) 6-chloro-4-[(1S)-1-(5-chloro-1H-benzimidazol-2-yl)-3-benzyloxycarbonylpropylamino]-7-[(2S)-2-tert.-butyloxycarbonyl-aminomethyl-pyrrolidin-1-yl-carbonyl]-quinazoline,
(39) 6-chloro-4-[(1S)-1-(5-chloro-1H-benzimidazol-2-yl)-3-hydroxycarbonylpropyl-amino]-7-[(2S)-2-tert.-butyloxycarbonyl-aminomethyl-pyrrolidin-1-yl-carbonyl]-quinazoline,
(40) 6-chloro-4-[(1S)-1-(5-chloro-1H-benzimidazol-2-yl)-3-hydroxycarbonylpropyl-amino]-7-[(2S)-2-aminomethyl-pyrrolidin-1-yl-carbonyl]-quinazoline,
(41) 6-chloro-4-[(1S)-1-(5-chloro-1H-benzimidazol-2-yl)-3-methanesulphonyl-propylamino]-7-[(2R)-2-tert.-butyloxycarbonyl-aminomethyl-pyrrolidin-1-yl-carbonyl]-quinazoline,
(42) 6-chloro-4-[(1S)-I -(5-chloro-1H-benzimidazol-2-yl)-3-methanesulphonyl-propylamino]-7-[(2R)-2-aminomethyl-pyrrolidin-1-yl-carbonyl]-quinazoline,
(43) 6-chloro-4-[(1S)-1-(5-chloro-1H-benzimidazol-2-yl)-ethylamino]-7-(thiazolidin-3-yl-carbonyl)-quinazoline,
(44) 6-chloro-4-[(1S)-1-(5-chloro-1H-benzimidazol-2-yl)-2-(tert.-butyloxycarbonyl-methoxy)-ethylamino]--(pyrrolidin-1-yl-carbonyl)-quinazoline,

(45) 6-chloro-4-[(1S)-1-(5-chloro-1H-benzimidazol-2-yl)-3-ethoxycarbonylpropylamino]-7-(pyrrolidin-1-yl-carbonyl)-quinazoline,
(46) 4-[(1S)-1-(5-chloro-1H-benzimidazol-2-yl)-ethylamino]-6-methyl-7-(pyrrolidin-1-yl-carbonyl)-quinazoline,
(47) 4-[(1S)-1-(5-chloro-1H-benzimidazol-2-yl)-ethylamino]-6-methyl-7-(pyrrolidin-1-yl-carbonyl)-quinazoline,
(48) 6-chloro-4-[(1S)-1-(5-chloro-1H-benzimidazol-2-yl)-ethylamino]-7-[(3S)-3-aminomethyl-pyrrolidin-1-yl-carbonyl]-quinazoline,
(49) 6-chloro-4-[(1S)-1-(5-chloro-1H-benzimidazol-2-yl)-2-(hydroxycarbonylmethoxy)-ethylamino]-7-(pyrrolidin-1-yl-carbonyl)-quinazoline,
(50) 6-chloro-4-[(1S)-1-(5-chloro-1H-benzimidazol-2-yl)-3-methanesulphinyl-propylamino]-7-[(2R)-2-aminomethyl-pyrrolidin-1-yl-carbonyl]-quinazoline,
(51) 4-[(1S)-1-(5-chloro-1H-benzimidazol-2-yl)-3-methylsulphanyl-propylamino]-6-methyl-7-(2,5-dihydropyrrol-1-yl-carbonyl)-quinazoline,
(52) 6-bromo-4-[(1S)-1-(5-chloro-1H-benzimidazol-2-yl)-ethylamino]-7-(2,5-dihydropyrrol-1-yl-carbonyl)-quinazoline,
(53) 6-chloro-4-[(1S)-1-(5-chloro-1H-benzimidazol-2-yl)-3-ethoxycarbonylpropyl-amino]-7-(2,5-dihydropyrrol-1-yl-carbonyl)-quinazoline,
(54) 6-chloro-4-[(1S)-1-(5-chloro-1H-benzimidazol-2-yl)-ethylamino]-7-(pyrazolidin-3-on-1-yl-carbonyl)-quinazoline,
(55) 6-chloro-4-[(1S)-1-(5-chloro-1H-benzimidazol-2-yl)-3-methylsulphanyl-propylamino]-7-(2,5-dihydropyrrol-1-yl-carbonyl)-quinazoline,
(56) 6-chloro-4-[1-(5-chloro-1H-benzimidazol-2-yl)-1-(2-chloro-phenyl)-methylamino]-7-(pyrrolidin-1-yl-carbonyl)-quinazoline,
(57) 6-chloro-4-[1-(5-chloro-1H-benzimidazol-2-yl)-1-(3-chloro-phenyl)-methylamino]-7-(pyrrolidin-1-yl-carbonyl)-quinazoline,
(58) 6-chloro-4-[(1S)-1-(5-chloro-1H-benzimidazol-2-yl)-butylamino]-7-(2,5-dihydropyrrol-1-yl-carbonyl)-quinazoline,
(59) 6-chloro-4-[(1S)-1-(5-chloro-1H-benzimidazol-2-yl)-3-methylsulphanyl-propylamino]-7-(2,5-dihydropyrrol-1-yl-carbonyl)-quinazoline,
(60) 6-chloro-4-[(1S)-1-(5-chloro-1H-benzimidazol-2-yl)-2-methoxy-ethylamino]-7-(2,5-dihydropyrrol-1-yl-carbonyl)-quinazoline,
(61) 6-chloro-4-[1-(5-chloro-1H-benzimidazol-2-yl)-3-diethylaminocarbonyl-propyl-amino]-7 -(pyrrolidin-1-yl-carbonyl)-quinazoline,
(62) 6-chloro-4-[(1S)-1-(5-chloro-1H-benzimidazol-2-yl)-3-(pyrrolidin-1-ylcarbonyl)-propylamino]-7-[(2R)-pyrrolidin-2-ylmethylamino-carbonyl]-quinazoline,
(63) 6-chloro-4-[1-(5-chloro-1H-benzimidazol-2-yl)-3-[N-methyl-N-piperidin-4-yl-amino]-carbonyl-propyl-amino]-7-(pyrrolidin-1-yl-carbonyl)-quinazoline,
(64) 6-chloro-4-[1-(5-chloro-1H-benzimidazol-2-yl)-3-[4-methyl-piperazin-1-yl]-carbonyl-propyl-amino]-7-(pyrrolidin-1-yl-carbonyl)-quinazoline,
(65) 6-chloro-4-[1-(5-chloro-1H-benzimidazol-2-yl)-3-(C-piperidin-4-yl-methylamino)-carbonyl-propyl-amino]-7-(pyrrolidin-1-yl-carbonyl)-quinazoline,
(66) 6-chloro-4-[1-(5-chloro-1H-benzimidazol-2-yl)-3-(N-benzyl-N-methyl-amino)-carbonyl-propyl-amino]-7-(pyrrolidin-1-yl-carbonyl)-quinazoline,
(67) 6-chloro-4-[(1S)-1-(5-chloro-1H-benzimidazol-2-yl)-3-methanesulphonyl-propylamino]-1-oxy-7-[(2R)-2-tert.-butyloxycarbonyl-aminomethyl-pyrrolidin-1-yl-carbonyl]-quinazoline,
(68) 4-[(1S)-1-(5-chloro-1H-benzimidazol-2-yl)-3-allyloxycarbonylpropyl-amino]-6-methyl-7-(2,5-dihydropyrrol-1-yl-carbonyl)-quinazoline,
(69) 6-bromo-4-[(1S)-1-(5-chloro-1H-benzimidazol-2-yl)-3-allyloxycarbonylpropyl-amino]-7-(2,5-dihydropyrrol-1-yl-carbonyl)-quinazoline,
(70) 6-chloro-4-[(1S)-1-(5-chloro-1H-benzimidazol-2-yl)-2-methoxy-ethylamino]-7-(pyrrolidin-1-yl-carbonyl)-quinazoline,
(71) 6-chloro-4-[(1S)-1-(5-chloro-1H-benzimidazol-2-yl)-4-(tert.-butyloxycarbonyl)-butyl-amino]-7-(pyrrolidin-1-yl-carbonyl)-quinazoline,
(72) 6-chloro-4-[(1S)-1-(5-chloro-1H-benzimidazol-2-yl)-4-(tert.-butyloxycarbonyl)-butyl-amino]-7-(2,5-dihydropyrrol-1-yl-carbonyl)-quinazoline,
(73) 6-chloro-4-[(1S)-1-(5-chloro-1H-benzimidazol-2-yl)-3-benzyloxycarbonyl-propylamino]-7-[(2R)-(1-tert.-butyloxycarbonyl-pyrrolidin-2-yl-methylamino)-carbonyl]-quinazoline,
(74) 6-chloro-4-[(1S)-1-(5-chloro-1H-benzimidazol-2-yl)-3-methanesulphonyl-propylamino]-1-oxy-7-[(2R)-2-aminomethyl-pyrrolidin-1-yl-carbonyl]-quinazoline,
(75) 6-chloro-4-[(1S)-1-(5-chloro-1H-benzimidazol-2-yl)-ethylamino]-7-[(2R)-2-(acetylamino-methyl)-pyrrolidin-1-yl-carbonyl]-quinazoline,
(76) 6-chloro-4-[(1S)-1-(5-chloro-1H-benzimidazol-2-yl)-ethylamino]-7-[(2-(pyrrolidin-1-yl-methyl)-pyrrolidin-1-yl-carbonyl]-quinazoline,
(77) 6-chloro-4-[(1S)-1-(5-chloro-1H-benzimidazol-2-yl)-ethylamino]-7-[(2R/S)-2-(tert.-butyloxycarbonyl-aminomethyl)-thiazolidin-1-yl-carbonyl]-quinazoline,
(78) 6-chloro-4-[(1S)-1-(5-chloro-1H-benzimidazol-2-yl)-ethylamino]-7-[(2R/S)-2-(pyridin-4-yl)-pyrrolidin-1-yl-carbonyl]-quinazoline,
(79) 6-chloro-4-[(1S)-1-(5-chloro-1H-benzimidazol-2-yl)-ethylamino]-7-[(2R/S)-2-aminomethyl-thiazolidinyl-carbonyl]-quinazoline,
(80) 6-chloro-4-[(1S)-1-(5-chloro-1H-benzimidazol-2-yl)-3-methanesulphonyl-propylamino]-7-[(2R)-2-(methanesulphonyl-aminomethyl)-pyrrolidin-1-yl-carbonyl]-quinazoline,
(81) 6-chloro-4-[(1S)-3-(benzyloxycarbonyl-amino)-1 -(5-chloro-1H-benzimidazol-2-yl)-propyl-amino]-7-(2,5-dihydropyrrol-1-yl-carbonyl)-quinazoline,
(82) 7-(2-acetaminomethyl-thiazolidin-1-yl-carbonyl)-6-chloro-4-[(1S)-1-(5-chloro-1H-benzimidazol-2-yl)-ethylamino]-quinazoline,
(83) 6-chloro-4-{1-(5-chloro-1H-benzimidazol-2-yl)-3-[(1,2,3,4-tetrahydroisoquinolin-1-yl)-carbonyl-propyl-amino]}-7-(pyrrolidin-1-yl-carbonyl)-quinazoline,
(84) 6-chloro-4-[1-(5-chloro-1H-benzimidazol-2-yl)-3-(benzylamino-carbonyl)-propyl-amino]-7-(pyrrolidin-1-yl-carbonyl)-quinazoline,
(85) 6-chloro-4-{ I -(5-chloro-1H-benzimidazol-2-yl)-3-[(N-methyl-N-phenethyl-amino-carbonyl)-propyl-amino]}--(pyrrolidin-1-yl-carbonyl)-quinazoline,
(86) 6-chloro-4-[l -(5-chloro-1H-benzimidazol-2-yl)-3-(hydroxyethylamino-carbonyl)-propyl-amino]-7-(pyrrolidin-1-yl-carbonyl)-quinazoline,
(87) 6-chloro-4-{1-(5-chloro-1H-benzimidazol-2-yl)-3-[(C-pyridin-3-yl-methylamino-carbonyl)-propyl-amino]}-7-(pyrrolidin-1-yl-carbonyl)-quinazoline,

(88) 6-chloro-4-{1-(5-chloro-1H-benzimidazol-2-yl)-3-[(1-oxa-3,8-diaza-spiro[4.5]decan-2-on-8-yl)-carbonyl]-propyl-amino}-7-(pyrrolidin-1-yl-carbonyl)-quinazoline,

(89) 6-chloro-4-[1-(5-chloro-1H-benzimidazol-2-yl)-3-(morpholin-4-yl-carbonyl)-propyl-amino]-7-(pyrrolidin-1-yl-carbonyl)-quinazoline,

(90) 6-chloro-4-[1-(5-chloro-1H-benzimidazol-2-yl)-3-(C-cyclohexyl-methylamino-carbonyl)-propyl-amino]-7-(pyrrolidin-1-yl-carbonyl)-quinazoline,

(91) 6-chloro-4-[1-(5-chloro-1H-benzimidazol-2-yl)-3-(methoxyethylamino-carbonyl)-propyl-amino]-7-(pyrrolidin-1-yl-carbonyl)-quinazoline,

(92) 6-chloro-4-[1-(5-chloro-1H-benzimidazol-2-yl)-3-(dimethylaminoethyl-amino-carbonyl)-propyl-amino]-7-(pyrrolidin-1-yl-carbonyl)-quinazoline,

(93) 6-chloro-4-[1-(5-chloro-1H-benzimidazol-2-yl)-3-(cyclopropylamino-carbonyl)-propyl-amino]-7-(pyrrolidin-1-yl-carbonyl)-quinazoline,

(94) 6-chloro-4-{(1R/S)-1-(5-chloro-1H-benzimidazol-2-yl)-3-[C-(2R/S)-tetrahydrofuran-2-yl-methylamino-carbonyl)-propyl-amino])-7-(pyrrolidin-1-yl-carbonyl)-quinazoline,

(95) 6-chloro-4-[1 -(5-chloro-1H-benzimidazol-2-yl)-3-(dimethylaminopropylamino-carbonyl)-propyl-amino]-7-(pyrrolidin-1-yl-carbonyl)-quinazoline,

(96) 6-chloro-4-[1-(5-chloro-1H-benzimidazol-2-yl)-3-(aminoethylamino-carbonyl)-propyl-amino]-7-(pyrrolidin-1-yl-carbonyl)-quinazoline,

(97) 6-chloro-4-[1-(5-chloro-1H-benzimidazol-2-yl)-3-(hydroxycarbonylmethyl-methyl-amino-carbonyl)-propyl-amino]-7-(pyrrolidin-1-yl-carbonyl)-quinazoline,

(98) 6-chloro-4-{[1-(5-chloro-1H-benzimidazol-2-yl)-3-((3-(pyrrolidin-2-on-1-yl)-propyl)-amino-carbonyl)-propyl-amino]}-7-(pyrrolidin-1-yl-carbonyl)-quinazoline,

(99) 6-chloro-4-{1-(5-chloro-1H-benzimidazol-2-yl)-3-[(1-[1,3,5]triazin-2-yl-piperidin-4-ylamino)-carbonyl]-propyl-amino}-7-(pyrrolidin-1-yl-carbonyl)-quinazoline, (100) 6-chloro-4-{1-(5-chloro-1H-benzimidazol-2-yl)-3-[(2-imidazol-1-yl-ethylamino)-carbonyl)-propyl-amino]}-7-(pyrrolidin-1-yl-carbonyl)-quinazoline, (101) 6-chloro-4-{1-(5-chloro-1H-benzimidazol-2-yl)-3-[C-(1H-imidazol-2-yl-methylamino-carbonyl)-propyl-amino]}-7-(pyrrolidin-1-yl-carbonyl)-quinazoline, (102) 6-chloro-4-[1-(5-chloro-1H-benzimidazol-2-yl)-3-(2,2,2-trifluoroethylamino-carbonyl)-propyl-amino]-7-(pyrrolidin-1-yl-carbonyl)-quinazoline, (103) 6-chloro-4-{1-(5-chloro-1H-benzimidazol-2-yl)-3-[N-(2-dimethylamino-ethyl)-N-methyl-amino-carbonyl]-propyl-amino}-7-(pyrrolidin-1-yl-carbonyl)-quinazoline, (104) 6-chloro-4-{(1R/S)-1-(5-chloro-1H-benzimidazol-2-yl)-3-[(1R/S)-1-phenyl-ethylamino-carbonyl]-propyl-amino}-7-(pyrrolidin-1-yl-carbonyl)-quinazoline, (105) 6-chloro-4-{1-(5-chloro-1H-benzimidazol-2-yl)-3-[2-(4-methyl-piperazin-1-ylmethyl)-piperidin-1-yl-carbonyl]-propyl-amino}-7-(pyrrolidin-1-yl-carbonyl)-quinazoline, (106) 6-chloro-4-[1-(5-chloro-1H-benzimidazol-2-yl)-3-(N-aminocarbonylmethyl-N-methyl-amino-carbonyl)-propyl-amino]-7-(pyrrolidin-1-yl-carbonyl)-quinazoline, (107) 6-chloro-4-[1 -(5-chloro-1H-benzimidazol-2-yl)-3-(4,5,6,7-tetrahydro-1H-imidazo[4,5-c]pyridin-5-yl-carbonyl)-propyl-amino]-7-(pyrrolidin-1-yl-carbonyl)-quinazoline, (108) 6-chloro-4-[1-(5-chloro-1H-benzimidazol-2-yl)-3-(1-oxo-thiomorpholin-4-yl-carbonyl)-propyl-amino]-7-(pyrrolidin-1-yl-carbonyl)-quinazoline, (109) 6-chloro-4-[1-(5-chloro-1H-benzimidazol-2-yl)-3-(N-dimethylaminocarbonylmethyl-N-methyl-amino-carbonyl)-propyl-amino]-7-(pyrrolidin-1-yl-carbonyl)-quinazoline, (110) 6-chloro-4-[1-(5-chloro-1H-benzimidazol-2-yl)-3-(N-hydroxycarbonylethyl-N-methyl-amino-carbonyl)-propyl-amino]-7-(pyrrolidin-1-yl-carbonyl)-quinazoline, (111) 6-chloro-4-{1-(5-chloro-1H-benzimidazol-2-yl)-3-[C-(1-methyl-1H-imidazol-2-yl)-methylamino-carbonyl)-propyl-amino]}-7-(pyrrolidin-1-yl-carbonyl)-quinazoline, (112) 6-chloro-4-[1-(5-chloro-1H-benzimidazol-2-yl)-3-(N-piperidin-2-yl-aminocarbonyl)-propyl-amino]-7-(pyrrolidin-1-yl-carbonyl)-quinazoline, (113) 6-chloro-4-{1-(5-chloro-1H-benzimidazol-2-yl)-3-[C-(tetrahydropyran-4-yl)-methylamino-carbonyl]-propyl-amino}-7-(pyrrolidin-1-yl-carbonyl)-quinazoline, (114) 6-chloro-4-[1-(5-chloro-1H-benzimidazol-2-yl)-3-(4-hydroxypiperidin-1-yl-carbonyl)-propyl-amino]-7-(pyrrolidin-1-yl-carbonyl)-quinazoline, (115) 6-chloro-4-{1-(5-chloro-1H-benzimidazol-2-yl)-3-[C-(pyridin-4-yl)-methylamino-carbonyl]-propyl-amino}-7-(pyrrolidin-1-yl-carbonyl)-quinazoline, (116) 6-chloro-4-[1-(5-chloro-1H-benzimidazol-2-yl)-3-(N-methylaminocarbonylmethyl-N-methyl-amino-carbonyl)-propyl-amino]-7-(pyrrolidin-1-yl-carbonyl)-quinazoline, (117) 6-chloro-4-{1-(5-chloro-1H-benzimidazol-2-yl)-3-[N-(2-(1H)-imidazol-4ethyl)-N-methyl-amino-carbonyl]-propyl-amino}-7-(pyrrolidin-1-yl-carbonyl)-quinazoline, (118) 6-chloro-4-[1-(5-chloro-1H-benzimidazol-2-yl)-3-(1-thiazolidin-3-yl-propyl-amino]-7-(pyrrolidin-1-yl-carbonyl)-quinazoline, (119) 6-chloro-4-[1-(5-chloro-1H-benzimidazol-2-yl)-3-(N-cyclopropyl-N-methyl-amino-carbonyl)-propyl-amino]-7-(pyrrolidin-1-yl-carbonyl)-quinazoline, (120) 6-chloro-4-[1-(5-chloro-1H-benzimidazol-2-yl)-3-(N-cyclopropylmethyl-N-methyl-amino-carbonyl)-propyl-amino]-7-(pyrrolidin-1-yl-carbonyl)-quinazoline, (121) 6-chloro-4-[1-(5-chloro-1H-benzimidazol-2-yl)-3-(cyclopentylamino-carbonyl)-propyl-amino]-7-(pyrrolidin-1-yl-carbonyl)-quinazoline, (122) 6-chloro-4-[1-(5-chloro-1H-benzimidazol-2-yl)-3-(N-piperidin-4-yl-aminocarbonyl)-propyl-amino]-7-(pyrrolidin-1-yl-carbonyl)-quinazoline, (123) 6-chloro-4-{1-(5-chloro-1H-benzimidazol-2-yl)-3-[C-(pyridin-2-yl)-methylamino-carbonyl]-propyl-amino}-7-(pyrrolidin-1-yl-carbonyl)-quinazoline, (124) 6-chloro-4-[1-(5-chloro-1H-benzimidazol-2-yl)-3-(4-thiazol-2-yl-piperazin-1-yl-carbonyl)-propyl-amino]-7-(pyrrolidin-1-yl-carbonyl)-quinazoline, (125) 6-chloro-4-[1-(5-chloro-1H-benzimidazol-2-yl)-3-(piperidin-1-yl-carbonyl)-propyl-amino]-7-(pyrrolidin-1-yl-carbonyl)-quinazoline, (126) 6-chloro-4-[(1S)-1-(5-chloro-1H-benzimidazol-2-yl)-3-amino-propyl-amino]-7-(2,5-dihydropyrrol-1-yl-carbonyl)-quinazoline, (127) 6-chloro-4-[(1S)-1-(5-chloro-1H-benzimidazol-2-yl)-3-hydroxycarbonyl-propylamino]-7-(pyrrolidin-1-yl-carbonyl)-quinazoline, (128) 6-chloro-4-[(1S)-1-(5-chloro-1H-benzimidazol-2-yl)-ethylamino]-7-(5,6,7,8-tetrahydro-[1,2,4]triazolo[4,3a]pyridin-4-yl)-quinazoline, (129) 6-chloro-4-[1-(5-chloro-1H-benzimidazol-2-yl)-1-(thiophen-3-yl)-methylamino]-7-(2,5-dihydropyrrol-1-yl-carbonyl)-quinazoline, (130) 6-chloro-4-[(1S)-1-(5-chloro-1H-benzimidazol-2-yl)-3-(2-oxo-pyrrolidin-1-yl-propyl-amino]-7-(2,5-dihydropyrrol-1-yl-carbonyl)-quinazoline,
(131) 6-chloro-4-[(1S)-1-(5-chloro-1H-benzimidazol-2-yl)-3-(1,1-dioxo-isothiazolidin-2-yl)-propyl-amino]-7-(2,5-dihydropyrrol-1-yl-carbonyl)-quinazoline,
(132) 6-chloro-4-[(1S)-1-(5-chloro-1H-benzimidazol-2-yl)-2-isopropylcarbonyloxy-ethylamino]-7-(2,5-dihydropyrrol-1-yl-carbonyl)-quinazoline,
(133) 6-chloro-4-[(1S)-1-(5-chloro-1H-benzimidazol-2-yl)-4-(hydroxycarbonyl)-butylamino]-7-(2,5-dihydropyrrol-1-yl-carbonyl)-quinazoline,
(134) 6-chloro-4-[(1S)-1-(5-chloro-1H-benzimidazol-2-yl)-ethylamino]-7-[(2R/S)-2-(pyridin-4-yl)-thiazolidin-3-yl-carbonyl]-quinazoline,
(135) 6-chloro-4-[(1S)-1-(5-chloro-1H-benzimidazol-2-yl)-ethylamino]-7-[(2R/S)-2-(2,2,2-trifluorethyl)-thiazolidin-3-yl-carbonyl]-quinazoline,
(136) 6-chloro-4-[(1S)-1-(5-chloro-1H-benzimidazol-2-yl)-3-methanesulphonylamino-propyl-amino]-7-(2,5-dihydropyrrol-1-yl-carbonyl)-quinazoline,
(137) 6-chloro-4-[(1S)-1-(5-chloro-1H-benzimidazol-2-yl)-2-methylsulphanyl-ethylamino]-7-(2,5-dihydropyrrol-1-yl-carbonyl)-quinazoline,
(138) 4-[(1S)-1-(5-chloro-1H-benzimidazol-2-yl)-ethylamino]-7-(2,5-dihydropyrrol-1-yl-carbonyl)-6-methoxy-quinazoline,
(139) 7-[(2S)-2-(2-aminoethyl)-pyrrolidin-1-yl-carbonyl]-6-chloro-4-[(1R/S)-1-(5-chloro-1H-benzimidazol-2-yl)-ethylamino]-quinazoline,
(140) 6-chloro-4-[(1R/S)-1-(5-chloro-1H-benzimidazol-2-yl)-ethylamino]-7-[(2R/S)-2-ethoxycarbonyl-piperidin-1-yl-carbonyl]-quinazoline,
(141) 6-chloro-4-[1-(5-chloro-1H-benzimidazol-2-yl)-ethylamino]-7-(4,5,6,7-tetrahydro-thieno[3,2-c]pyridin-5-yl-carbonyl)-quinazoline,
(142) 7-[(2S)-2-benzhydryl-pyrrolidin-1-yl-carbonyl]-6-chloro-4-[(1R/S)-1-(5-chloro-1H-benzimidazol-2-yl)-ethylamino]-quinazoline,
(143) 6-chloro-4-[1-(5-chloro-1H-benzimidazol-2-yl)-ethylamino]-7-([1,4]diazepan-1-yl-carbonyl)-quinazoline,
(144) 6-chloro-4-[(1R/S)-1-(5-chloro-1H-benzimidazol-2-yl)-ethylamino]-7-[(2R/S)-2-(2-ethoxycarbonyl-ethyl)-piperidin-1-yl-carbonyl]-quinazoline,
(145) 6-chloro-4-[(1R/S)-1-(5-chloro-1H-benzimidazol-2-yl)-ethylamino]-7-[(2S)-2-methylaminocarbonyl-pyrrolidin-1-yl-carbonyl]-quinazoline,
(146) 6-chloro-4-[(1R/S)-1-(5-chloro-1H-benzimidazol-2-yl)-ethylamino]-7-[(3R/S)-3-(3-diethylamino-propyl)-piperidin-1-yl-carbonyl]-quinazoline,
(147) 6-chloro-4-[1-(5-chloro-1H-benzimidazol-2-yl)-ethylamino]-7-(4-methyl-piperidin-1-yl-carbonyl)-quinazoline,
(148) 6-chloro-4-[(1R/S)-1-(5-chloro-1H-benzimidazol-2-yl)-ethylamino]-7-[(2S)-2-(phenylaminomethyl)-pyrrolidin-1-yl-carbonyl]-quinazoline,
(149) 6-chloro-4-[(1R/S)-1-(5-chloro-1H-benzimidazol-2-yl)-ethylamino]-7-[(2R/S)-2-benzyl-pyrrolidin-1-yl-carbonyl]-quinazoline,
(150) 6-chloro-4-[(1R/S)-1-(5-chloro-1H-benzimidazol-2-yl)-ethylamino]-7-[(3R/S)-3-hydroxy-piperidin-1-yl-carbonyl]-quinazoline,
(151) 6-chloro-4-[(1R/S)-1-(5-chloro-1H-benzimidazol-2-yl)-ethylamino]-7-[(2S)-2-dimethylaminocarbonyl-pyrrolidin-1-yl-carbonyl]-quinazoline,
(152) 6-chloro-4-[1-(5-chloro-1H-benzimidazol-2-yl)-ethylamino]-7-(piperidin-1-yl-carbonyl)-quinazoline,
(153) 6-chloro-4-[1-(5-chloro-1H-benzimidazol-2-yl)-ethylamino]-7-(4-oxo-piperidin-1-yl-carbonyl)-quinazoline,
(154) 6-chloro-4-[1-(5-chloro-1H-benzimidazol-2-yl)-ethylamino]-7-(4-methylene-piperidin-1-yl-carbonyl)-quinazoline,
(155) 6-chloro-4-[(1R/S)-1-(5-chloro-1H-benzimidazol-2-yl)-ethylamino]-7-[(2R/S)-2-methyl-piperidin-1-yl-carbonyl]-quinazoline,
(156) 6-chloro-4-[(1R/S)-1-(5-chloro-1H-benzimidazol-2-yl)-ethylaminol-7-[(2R/S)-2-benzyloxycarbonyl-pyrrolidin-1-yl-carbonyl]-quinazoline,
(157) 6-chloro-4-[1-(5-chloro-1H-benzimidazol-2-yl)-ethylamino]-7-[N-(3-amino-propyl)-N-ethyl-amino-carbonyl]-quinazoline,
(158) 6-chloro-4-[1-(5-chloro-1H-benzimidazol-2-yl)-ethylamino]-7-(N-cyclopropyl-N-methylamino-carbonyl)-quinazoline,
(159) 6-chloro-4-[1-(5-chloro-1H-benzimidazol-2-yl)-ethylamino]-7-(2-oxo-piperazin-4-yl-carbonyl)-quinazoline,
(160) 6-chloro-4-[(1R/S)-1-(5-chloro-1H-benzimidazol-2-yl)-ethylamino]-7-[(2R/S)-2-methoxymethyl-pyrrolidin-1-yl-carbonyl]-quinazoline,
(161) 6-chloro-4-[(1R/S)-1-(5-chloro-1H-benzimidazol-2-yl)-ethylamino]-7-[(2R)-2-(phenylaminomethyl)-pyrrolidin-1-yl-carbonyl]-quinazoline,
(162) 6-chloro-4-[(1R/S)-1-(5-chloro-1H-benzimidazol-2-yl)-ethylamino]-7-{1-[(3R/S)-3-(1H-benzimidazol-2-yl)-piperidin-1-yl]-carbonyl}-quinazoline,
(163) 6-chloro-4-[(1R/S)-1-(5-chloro-1H-benzimidazol-2-yl)-ethylamino]-7-[(3R/S)-3-dimethylamino-pyrrolidin-1-yl-carbonyl]-quinazoline,
(164) 6-chloro-4-[1-(5-chloro-1H-benzimidazol-2-yl)-ethylamino]-7-[(2,5-dimethyl-2,5-dihydro-1H-pyrrol-1-yl)-carbonyl]-quinazoline,
(165) 6-chloro-4-[(1R/S)-1-(5-chloro-1H-benzimidazol-2-yl)-ethylamino]-7-[(2R/S)-2-isopropyl-pyrrolidin-1-yl-carbonyl]-quinazoline,
(166) 6-chloro-4-[(1R/S)-1-(5-chloro-1H-benzimidazol-2-yl)-ethylamino]-7-[(2R/S)-2-aminomethyl-piperidin-1-yl-carbonyl]-quinazoline,
(167) 6-chloro-4-[(1R/S)-1-(5-chloro-1H-benzimidazol-2-yl)-ethylamino]-7-[(3R/S)-3-aminomethyl-piperidin-1-yl-carbonyl]-quinazoline,
(168) 6-chloro-4-[(1R/S)-1-(5-chloro-1H-benzimidazol-2-yl)-ethylamino]-7-[(2R)-2-ethoxycarbonyl-pyrrolidin-1-yl-carbonyl]-quinazoline,
(169) 6-chloro-4-[1-(5-chloro-1H-benzimidazol-2-yl)-ethylamino]-7-[3-(dimethylamino-methyl)-piperidin-1-yl-carbonyl]-quinazoline,
(170) 6-chloro-4-[(1R/S)-1-(5-chloro-1H-benzimidazol-2-yl)-ethylamino]-7-[(2R/S)-2-(2-phenyl-ethyl)-pyrrolidin-1-yl-carbonyl]-quinazoline,
(171) 6-chloro-4-[(1R/S)-1-(5-chloro-1H-benzimidazol-2-yl)-ethylamino]-7-[(2R/S)-2-(pyridin-2-yl)-pyrrolidin-1-yl-carbonyl]-quinazoline,
(172) 6-chloro-4-[(1R/S)-1-(5-chloro-1H-benzimidazol-2-yl)-ethylamino]-7-[(2R/S)-2-(2-amino-ethyl)-piperidin-1-yl-carbonyl]-quinazoline,
(173) 6-chloro-4-[1-(5-chloro-1H-benzimidazol-2-yl)-ethylamino]-7-(4-acetyl-piperazin-1-yl-carbonyl)-quinazoline,
(174) 6-chloro-4-[1-(5-chloro-1H-benzimidazol-2-yl)-ethylamino]-7-[N-(2-amino-ethyl)-N-ethyl-amino-carbonyl]-quinazoline,
(175) 6-chloro-4-[(1R/S)-1-(5-chloro-1H-benzimidazol-2-yl)-ethylamino]-7-[(2R/S)-2-(pyridin-3-yl)-piperidin-1-yl-carbonyl]-quinazoline, (176) 6-chloro-4-[(1R/S)-1-(5-chloro-1H-benzimidazol-2-yl)-ethylamino]-7-[(2R/S), (5R/S)-2,5-dimethyl-pyrrolidin-1-yl-carbonyl]-quinazoline,
(177) 6-chloro-4-[1-(5-chloro-1H-benzimidazol-2-yl)-ethylamino]-7-(4-aminocarbonyl-piperidin-1-yl-carbonyl)-quinazoline,
(178) 6-chloro-4-[1-(5-chloro-1H-benzimidazol-2-yl)-ethylamino]-7-(4-hydroxy-piperidin-1-yl-carbonyl)-quinazoline,
(179) 6-chloro-4-[(1R/S)-1-(5-chloro-1H-benzimidazol-2-yl)-ethylamino]-7-[(2R/S)-2-ethoxycarbonyl-piperidin-1-yl-carbonyl]-quinazoline,
(180) 6-chloro-4-[1-(5-chloro-1H-benzimidazol-2-yl)-ethylamino]-7-[1-(1,4,6,7-tetrahydro-pyrazolo[4,3]pyridin-5-yl)-carbonyl]-quinazoline,
(181) 6-chloro-4-[(1R/S)-1-(5-chloro-1H-benzimidazol-2-yl)-ethylamino]-7-(2R, 5S-dimethoxymethyl-pyrrolidin-1-yl-carbonyl)-quinazoline,
(182) 6-chloro-4-[(1R/S)-1-(5-chloro-1H-benzimidazol-2-yl)-ethylamino]-7-[(2R/S)-2-methoxycarbonyl-pyrrolidin-1-yl-carbonyl]-quinazoline,
(183) 6-chloro-4-[1-(5-chloro-1H-benzimidazol-2-yl)-ethylamino]-7-(pyrazolidin-1-yl-carbonyl)-quinazoline,
(184) 6-chloro-4-[1-(5-chloro-1H-benzimidazol-2-yl)-ethylamino]-7-(1-oxo-thiomorpholin-4-yl-carbonyl)-quinazoline,
(185) 6-chloro-4-[(1R/S)-1-(5-chloro-1H-benzimidazol-2-yl)-ethylamino]-7-{(2R/S)-2-[(N-butyl-N-ethyl-amino)-methyl]-piperidin-1-yl-carbonyl}-quinazoline,
(186) 6-chloro-4-[1-(5-chloro-1H-benzimidazol-2-yl)-ethylamino]-7-[N-ethyl-N-(piperidin-4-yl)-aminocarbonyl]-quinazoline,
(187) 6-chloro-4-[(1R/S)-1-(5-chloro-1H-benzimidazol-2-yl)-ethylamino]-7-[(2S)-2-ethoxycarbonyl-pyrrolidin-1-yl-carbonyl]-quinazoline,
(188) 6-chloro-4-[1-(5-chloro-1H-benzimidazol-2-yl)-ethylamino]-7-(4-formyl-piperazin-1-yl-carbonyl)-quinazoline,
(189) 6-chloro-4-[(1R/S)-1-(5-chloro-1H-benzimidazol-2-yl)-ethylamino]-7-[(2R/S)-2-(2-dimethylamino-ethyl)-piperidin-1-yl-carbonyl]-quinazoline,
(190) 6-chloro-4-[(1R/S)-1-(5-chloro-1H-benzimidazol-2-yl)-ethylamino]-7-[(2R/S)-2-(2-diethylamino-ethyl)-piperidin-1-yl-carbonyl]-quinazoline,
(191) 6-chloro-4-[1-(5-chloro-1H-benzimidazol-2-yl)-ethylamino]-7-(1,4,6,7-tetrahydro-imidazo[4,5-c]pyridin-5-yl-carbonyl)-quinazoline,
(192) 6-chloro-4-[1-(5-chloro-1H-benzimidazol-2-yl)-ethylamino]-7-(3,6-dihydro-2H-pyridin-1-yl-carbonyl)-quinazoline,
(193) 6-chloro-4-[(1R/S)-1-(5-chloro-1H-benzimidazol-2-yl)-ethylamino]-7-{(2R/S)-2-[(N-butyl-N-methyl-amino)-methyl]-piperidin-1-yl-carbonyl}-quinazoline,
(194) 6-chloro-4-[(1R/S)-1-(5-chloro-1H-benzimidazol-2-yl)-ethylamino]-7-[(2R/S)-2-methyl-morpholin-4-yl-carbonyl]-quinazoline,
(195) 6-chloro-4-[1-(5-chloro-1H-benzimidazol-2-yl)-ethylamino]-7-(thiomorpholin-4-yl-carbonyl)-quinazoline,
(196) 6-chloro-4-[(1R/S)-1-(5-chloro-1H-benzimidazol-2-yl)-ethylamino]-7-[(2R/S)-2-(2-amino-ethyl)-piperidin-1-yl-carbonyl]-quinazoline,
(197) 6-chloro-4-[(1R/S)-1-(5-chloro-1H-benzimidazol-2-yl)-ethylamino]-7-[(2R/S)-2-ethyl-piperidin-1-yl-carbonyl]-quinazoline,
(198) 6-chloro-4-[(1R/S)-1-(5-chloro-1H-benzimidazol-2-yl)-ethylamino]-7-[(3R/S)-3-amino-pyrrolidin-1-yl-carbonyl]-quinazoline,
(199) 6-chloro-4-[1-(5-chloro-1H-benzimidazol-2-yl)-ethylamino]-7-(4-trifluoromethyl-piperidin-1-yl-carbonyl)-quinazoline,
(200) 6-chloro-4-[(1R/S)-1-(5-chloro-1H-benzimidazol-2-yl)-ethylamino]-7-{(3R/S)-3-[4-(pyrrolidin-1-yl)-butyl]-pyrrolidin-1-yl-carbonyl}-quinazoline,
(201) 6-chloro-4-[(1R/S)-1-(5-chloro-1H-benzimidazol-2-yl)-ethylamino]-7-{(2R/S)-2-[(N-methyl-N-(pyridin-2-ylmethyl)-amino)-methyl]-piperidin-1-yl-carbonyl}-quinazoline,
(202) 6-chloro-4-[1-(5-chloro-1H-benzimidazol-2-yl)-ethylamino]-7-(4-hydroxy-piperazin-1-yl-carbonyl)-quinazoline,
(203) 6-chloro-4-[(1R/S)-1-(5-chloro-1H-benzimidazol-2-yl)-ethylamino]-7-[(3R/S)-3-(pyrrolidin-1-ylmethyl)-piperidin-1-yl-carbonyl]-quinazoline,
(204) 6-chloro-4-[(1R/S)-1-(5-chloro-1H-benzimidazol-2-yl)-ethylamino]-7-[(2R/S)-2-diethylaminomethyl-piperidin-1-yl-carbonyl]-quinazoline,
(205) 6-chloro-4-[(1R/S)-1-(5-chloro-1H-benzimidazol-2-yl)-ethylamino]-7-[(2R/S)-2-(4-diethylamino-butyl)-piperidin-1-yl-carbonyl]-quinazoline,
(206) 6-chloro-4-[(1R/S)-1-(5-chloro-1H-benzimidazol-2-yl)-ethylamino]-7-[(2R)-2-hydroxymethyl-pyrrolidin-1-yl-carbonyl]-quinazoline,
(207) 6-chloro-4-[(1R/S)-1-(5-chloro-1H-benzimidazol-2-yl)-ethylamino]-7-[(2R/S)-2-(N-ethyl-N-methyl-aminomethyl)-piperidin-1-yl-carbonyl]-quinazoline,
(208) 6-chloro-4-[(1R/S)-1-(5-chloro-I H-benzimidazol-2-yl)-ethylamino]-7-[(2R)-2-aminocarbonyl-pyrrolidin-1-yl-carbonyl]-quinazoline,
(209) 6-chloro-4-[(1R/S)-1-(5-chloro-1H-benzimidazol-2-yl)-ethylamino]-7-[(2S)-2-hydroxymethyl-pyrrolidin-1-yl-carbonyl]-quinazoline,
(210) 6-chloro-4-[(1R/S)-1-(5-chloro-1H-benzimidazol-2-yl)-ethylamino]-7-[(2R/S)-2-(4-methyl-piperazin-1-ylmethyl)-piperidin-1-yl-carbonyl]-quinazoline,
(211) 6-chloro-4-[(1R/S)-1-(5-chloro-1H-benzimidazol-2-yl)-ethylamino]-7-[(2R)-2-methoxymethyl-pyrrolidin-1-yl-carbonyl]-quinazoline,
(212) 6-chloro-4-[(1R/S)-1-(5-chloro-1H-benzimidazol-2-yl)-ethylamino]-7-[(2R/S)-2-(3-dimethylamino-propyl)-piperidin-1-yl-carbonyl]-quinazoline,
(213) 6-chloro-4-[(1R/S)-1-(5-chloro-1H-benzimidazol-2-yl)-ethylamino]-7-[(2R/S)-2-diethylaminocarbonyl-piperidin-1-yl-carbonyl]-quinazoline,
(214) 6-chloro-4-[(1R/S)-1-(5-chloro-1H-benzimidazol-2-yl)-ethylamino]-7-{(2R/S)-2-[(N-cyclohexyl-N-methyl-amino)-methyl]-piperidin-1-yl-carbonyl}-quinazoline,
(215) 6-chloro-4-[(1R/S)-1-(5-chloro-1H-benzimidazol-2-yl)-ethylamino]-7-[(2R/S)-2-piperidin-1-ylmethyl-piperidin-1-yl-carbonyl]-quinazoline,
(216) 4-[(1S)-1-(5-chloro-1H-benzimidazol-2-yl)-3-(methylsulphanyl)-propylamino]-6-methoxy-7-(2,5-dihydropyrrol-1-yl-carbonyl)-quinazoline,
(217) 4-[(1S)-1-(5-chloro-1H-benzimidazol-2-yl)-2-methoxy-ethylamino]-6-methoxy-7-(2,5-dihydropyrrol-1-yl-carbonyl)-quinazoline,
(218) 6-chloro-4-[(1S)-1-(5-chloro-1H-benzimidazol-2-yl)-ethylamino]-7-[(2R/S)-2-(1-methyl-1H-pyrazol-4-yl)-thiazolidinyl-carbonyl]-quinazoline,
(219) 6-chloro-4-[(1S)-1-(5-chloro-1H-benzimidazol-2-yl)-2-methoxy-ethylamino]-7-(thiazolidinyl-carbonyl)-quinazoline,
(220) 4-[(1S)-1-(5-chloro-1H-benzimidazol-2-yl)-2-methoxy-ethylamino]-6-methyl-7-(2,5-dihydropyrrol-1-yl-carbonyl)-quinazoline, (221) 4-[(1S)-1-(5-chloro-1H-benzimidazol-2-yl)-2-methoxy-ethylamino]-6-methyl-7-(thiazolidinyl-carbonyl)-quinazoline,
(222) 6-bromo-4-[(1S)-1-(5-chloro-1H-benzimidazol-2-yl)-2-methoxy-ethylamino]-7-(2,5-dihydropyrrol-1-yl-carbonyl)-quinazoline,
(223) 6-bromo-4-[(1S)-1-(5-chloro-1H-benzimidazol-2-yl)-2-methoxy-ethylamino]-7-(thiazolidinyl-carbonyl)-quinazoline,
(224) 6-chloro-4-[(1S)-1-(5-chloro-1H-benzimidazol-2-yl)-ethylamino]-7-(6,7,8,9-tetrahydro-[1,2,4]triazolo[4,3-a]pyridin-4-yl)-quinazoline,
(225) 6-chloro-4-[(1S)-1-(5-chloro-1-methyl-i H-benzimidazol-2-yl)-3-methylsulphonylamino-propylamino]-7-(2,5-dihydropyrrolyl-carbonyl)-quinazoline,
(226) 6-chloro-4-[(1S)-1-(5-chloro-1H-benzimidazol-2-yl)-2-benzyloxy-ethylamino]-7-(2,5-dihydropyrrol-1-yl-carbonyl)-quinazoline,
(227) 6-chloro-4-{1-(5-chloro-1H-benzimidazol-2-yl)-3-[2-(pyridin-4-yl-ethylamino-carbonyl]-propylamino}-7-(pyrrolidin-1-yl-carbonyl)-quinazoline,
(228) 4-[(1S)-1-(5-bromo-1H-benzimidazol-2-yl)-2-methoxy-ethylamino]-6-chloro-7-(2,5-dihydropyrrolyl-carbonyl)-quinazoline,
(229) 4-[(1S)-1-(5-bromo-1H-benzimidazol-2-yl)-ethylamino]-6-chloro-7-(2,5-dihydropyrrolyl-carbonyl)-quinazoline,
(230) 6-bromo-4-[(1S)-1-(5-chloro-1H-benzimidazol-2-yl)-but-3-yl-1-yl-amino]-7-(2,5-dihydropyrrol-1-yl-carbonyl)-quinazoline,
(231) 4-[(1S,2R)-1-(5-chloro-1H-benzimidazol-2-yl)-2-methoxy-propylamino]-6-chloro-7-(2,5-dihydropyrrolyl-carbonyl)-quinazoline,
(232) 4-[(1S,2S)-1-(5-chloro-1H-benzimidazol-2-yl)-2-tert.-butyloxy-propylamino]-6-chloro-7-(2,5-dihydropyrrolyl-carbonyl)-quinazoline,
(233) 4-[(1S,2S)-1-(5-chloro-1H-benzimidazol-2-yl)-2-hydroxy-propylamino]-6-chloro-7-(2,5-dihydropyrrolyl-carbonyl)-quinazoline,
(234) 6-chloro-4-[1-(benzo[b]thiophen-2-yl)-ethylamino]-7-(pyrrolidin-1-yl-carbonyl)-quinazoline,
(235) 6-chloro-4-[(1R/S)-1-(5-chloro-1H-imidazo[4,5-b]pyridin-2-yl)-ethylamino]-7-[(2S)-2-(N-tert.-butyloxycarbonyl-aminomethyl)-pyrrolidin-1-yl-carbonyl]-quinazoline,
(236) 6-chloro-4-[(1R/S)-1-(5-chloro-1H-imidazo[4,5-b]pyridin-2-yl)-ethylamino]-7-[(2S)-2-aminomethyl-pyrrolidin-1-yl-carbonyl]-quinazoline,
(237) 6-chloro-4-[1-(5-chloro-benzothiazol-2-yl)-ethylamino]-7-(pyrrolidin-1-yl-carbonyl)-quinazoline,
(238) 6-bromo-4-[1-(5-chloro-1H-indol-2-yl)-methylamino]-7-(2,5-dihydropyrrol-1-yl-carbonyl)-quinazoline, the tautomers, stereoisomers and salts thereof.

According to the invention the following compounds of general formula I are of particular significance:
(1) 4-[1-(5-chloro-1H-benzimidazol-2-yl)-3-methylsulphanyl-propylamino]-6-methyl-7-(pyrrolidin-1-yl-carbonyl)-quinoline,
(2) 4-[1-(5-chloro-1H-benzimidazol-2-yl)-ethylamino]-6-methyl-7-(pyrrolidin-1-yl-carbonyl)-quinoline,
(3) 4-[1-(5-chloro-1H-benzimidazol-2-yl)-ethylamino]-6-methyl-7-(3-oxo-piperazin-1-yl-carbonyl)-quinoline,
(4) 4-[(1R/S)-1-(5-chloro-1H-benzimidazol-2-yl)-ethylamino]-6-methyl-7-[(2-aminomethyl-pyrrolidin-1-yl-carbonyl]-quinoline,
(5) 4-[1-(5-chloro-1H-benzimidazol-2-yl)-3-methylsulphanyl-propylamino]-6-methyl-7-(3-oxo-piperazin-1-yl-carbonyl)-quinoline,
(6) 4-[1-(5-chloro-1H-benzimidazol-2-yl)-3-methanesulphonyl-propylamino]-6-methyl-7-(pyrrolidin-1-yl-carbonyl)-quinoline,
(7) 6-chloro-4-[(1S)-1-(5-chloro-1H-benzimidazol-2-yl)-ethylamino]-7-[(2R)-2-aminomethyl-pyrrolidin-1-yl-carbonyl]-quinazoline,
(8) 6-chloro-4-[(1S)-1-(5-chloro-1H-benzimidazol-2-yl)-2-hydroxy-ethylamino]-7-2,5-dihydropyrrol-1-yl-carbonyl)-quinazoline,
(9) 6-chloro-4-[(1S)-1-(5-chloro-1H-benzimidazol-2-yl)-2-hydroxy-ethylamino]-7-[(2R)-2-aminomethyl-pyrrolidin-1-yl-carbonyl]-quinazoline,
(10) 6-chloro-4-[(1S)-1-(5-chloro-1H-benzimidazol-2-yl)-ethylamino]-7-[(2-aminomethyl-pyrrolidin-1-yl-carbonyl]-quinazoline,
(11) 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline,
(12) 6-chloro-4-[(1S)-1-(5-chloro-1H-benzimidazol-2-yl)-3-methylsulphanyl-propylamino]-7-(pyrrolidin-1-yl-carbonyl)-quinazoline,
(13) 6-chloro-4-[(1S)-1-(5-chloro-1H-benzimidazol-2-yl)-3-methoxy-propylamino]-7-(2,5-dihydropyrrol-1-yl-carbonyl)-quinazoline,
(14) 6-chloro-4-[(1S)-1-(5-chloro-1H-benzimidazol-2-yl)-3-methanesulphonyl-propylamino]-7-(pyrrolidin-1-yl-carbonyl)-quinazoline,
(15) 6-chloro-4-[(1S)-1-(5-chloro-1H-benzimidazol-2-yl)-3-methylsulphanyl-propylamino]-7-[(2R)-2-aminomethyl-pyrrolidin-1-yl-carbonyl]-quinazoline,
(16) 6-chloro-4-[(1S)-1-(5-chloro-1H-benzimidazol-2-yl)-3-methanesulphinyl-propylamino]-7-(pyrrolidin-1-yl-carbonyl)-quinazoline,
(17) 6-chloro-4-[(1S)-1-(5-chloro-1H-benzimidazol-2-yl)-3-benzyloxycarbonylpropylamino]-7-(pyrrolidin-1-yl-carbonyl)-quinazoline,
(18) 6-chloro-4-[(1S)-1-(5-chloro-1H-benzimidazol-2-yl)-2-hydroxy-ethylamino]-7-(piperazin-3-on-1-yl-carbonyl)-quinazoline,
(19) 6-chloro-4-[(1S)-1-(5-chloro-1H-benzimidazol-2-yl)-3-methanesulphinyl-propylamino]-7-[(2R)-2-tert.-butyloxycarbonyl-aminomethyl-pyrrolidin-1-yl-carbonyl]-quinazoline,
(20) 6-chloro-4-[(1S)-1-(5-chloro-1H-benzimidazol-2-yl)-3-hydroxycarbonylpropyl-amino]-7-[(2S)-2-aminomethyl-pyrrolidin-1-yl-carbonyl]-quinazoline,
(21) 6-chloro-4-[(1S)-1-(5-chloro-1H-benzimidazol-2-yl)-3-methanesulphonyl-propylamino]-7-[(2R)-2-tert.-butyloxycarbonyl-aminomethyl-pyrrolidin-1-yl-carbonyl]-quinazoline,
(22) 6-chloro-4-[(1S)-1-(5-chloro-1H-benzimidazol-2-yl)-3-methanesulphonyl-propylamino]-7-[(2R)-2-aminomethyl-pyrrolidin-1-yl-carbonyl]-quinazoline,
(23) 6-chloro-4-[(1S)-1-(5-chloro-1H-benzimidazol-2-yl)-ethylamino]-7-(thiazolidin-3-yl-carbonyl)-quinazoline,
(24) 6-chloro-4-[(1S)-1-(5-chloro-1H-benzimidazol-2-yl)-3-ethoxycarbonylpropylamino]-7-(pyrrolidin-1-yl-carbonyl)-quinazoline,
(25) 4-[(1S)-1-(5-chloro-1H-benzimidazol-2-yl)-ethylamino]-6-methyl-7-(pyrrolidin-1-yl-carbonyl)-quinazoline,

(26) 4-[(1S)-1-(5-chloro-1H-benzimidazol-2-yl)-ethylamino]-6-methyl-7-(pyrrolidin-1-yl-carbonyl)-quinazoline,
(27) 6-chloro-4-[(1S)-1-(5-chloro-1H-benzimidazol-2-yl)-3-methanesulphinyl-propylamino]-7-[(2R)-2-aminomethyl-pyrrolidin-1-yl-carbonyl]-quinazoline,
(28) 4-[(1S)-1-(5-chloro-1H-benzimidazol-2-yl)-3-methylsulphanyl-propylamino]-6-methyl-7-(2,5-dihydropyrrol-1-yl-carbonyl)-quinazoline,
(29) 6-bromo-4-[(1S)-1-(5-chloro-1H-benzimidazol-2-yl)-ethylamino]-7-(2,5-dihydropyrrol-1-yl-carbonyl)-quinazoline,
(30) 6-chloro-4-[(1S)-1-(5-chloro-1H-benzimidazol-2-yl)-3-ethoxycarbonylpropyl-amino]-7-(2,5-dihydropyrrol-1-yl-carbonyl)-quinazoline,
(31) 6-chloro-4-[(1S)-1-(5-chloro-1H-benzimidazol-2-yl)-3-methylsulphanyl-propylamino]-7-(2,5-dihydropyrrol-1-yl-carbonyl)-quinazoline,
(32) 6-chloro-4-[(1S)-1-(5-chloro-1H-benzimidazol-2-yl)-butylamino]-7-(2,5-dihydropyrrol-1-yl-carbonyl)-quinazoline,
(33) 6-chloro-4-[(1S)-1-(5-chloro-1H-benzimidazol-2-yl)-3-methylsulphanyl-propylamino]-7-(2,5-dihydropyrrol-1-yl-carbonyl)-quinazoline,
(34) 6-chloro-4-[(1S)-1-(5-chloro-1H-benzimidazol-2-yl)-2-methoxy-ethylamino]-7-(2,5-dihydropyrrol-1-yl-carbonyl)-quinazoline,
(35) 6-chloro-4-[1-(5-chloro-1H-benzimidazol-2-yl)-3-diethylaminocarbonyl-propyl-amino]-7-(pyrrolidin-1-yl-carbonyl)-quinazoline,
(36) 6-chloro-4-[1-(5-chloro-1H-benzimidazol-2-yl)-3-[4-methyl-piperazin-1-yl]-carbonyl-propyl-amino]-7-(pyrrolidin-1-yl-carbonyl)-quinazoline,
(37) 6-chloro-4-[1-(5-chloro-1H-benzimidazol-2-yl)-3-(C-piperidin-4-yl-methylamino)-carbonyl-propyl-amino]-7-(pyrrolidin-1-yl-carbonyl)-quinazoline,
(38) 4-[(1S)-1-(5-chloro-1H-benzimidazol-2-yl)-3-allyloxycarbonylpropyl-amino]-6-methyl-7-(2,5-dihydropyrrol-1-yl-carbonyl)-quinazoline,
(39) 6-bromo-4-[(1S)-1-(5-chloro-1H-benzimidazol-2-yl)-3-allyloxycarbonylpropyl-amino]-7-(2,5-dihydropyrrol-1-yl-carbonyl)-quinazoline,
(40) 6-chloro-4-[(1S)-1-(5-chloro-1H-benzimidazol-2-yl)-2-methoxy-ethylamino]-7-(pyrrolidin-1-yl-carbonyl)-quinazoline,
(41) 6-chloro-4-[(1S)-1-(5-chloro-1H-benzimidazol-2-yl)-3-methanesulphonyl-propylamino]-1-oxy-7-[(2R)-2-aminomethyl-pyrrolidin-1-yl-carbonyl]-quinazoline,
(42) 6-chloro-4-[(1S)-1-(5-chloro-1H-benzimidazol-2-yl)-ethylamino]-7-[(2R)-2-(acetylamino-methyl)-pyrrolidin-1-yl-carbonyl]-quinazoline,
(43) 6-chloro-4-[(1S)-1-(5-chloro-1H-benzimidazol-2-yl)-ethylamino]-7-[(2S)-2-(pyrrolidin-1-yl-methyl)-pyrrolidin-1-yl-carbonyl]-quinazoline,
(44) 6-chloro-4-[(1S)-1-(5-chloro-1H-benzimidazol-2-yl)-ethylamino]-7-[(2R/S)-2-(pyridin-4-yl)-pyrrolidin-1-yl-carbonyl]-quinazoline,
(45) 6-chloro-4-[(1S)-1-(5-chloro-1H-benzimidazol-2-yl)-ethylamino]-7-[(2R/S)-2-aminomethyl-thiazolidinyl-carbonyl]-quinazoline,
(46) 6-chloro-4-[(1S)-1-(5-chloro-1H-benzimidazol-2-yl)-3-methanesulphonyl-propylamino]-7-[(2R)-2-(methanesulphonyl-aminomethyl)-pyrrolidin-1-yl-carbonyl]-quinazoline,
(47) 6-chloro-4-[(1S)-3-(benzyloxycarbonyl-amino)-1-(5-chloro-1H-benzimidazol-2-yl)-propyl-amino]-7-(2,5-dihydropyrrol-1-yl-carbonyl)-quinazoline,
(48) 7-(2-acetaminomethyl-thiazolidin-1-yl-carbonyl)-6-chloro-4-[(1S)-1-(5-chloro-1H-benzimidazol-2-yl)-ethylamino]-quinazoline,
(49) 6-chloro-4-{1-(5-chloro-1H-benzimidazol-2-yl)-3-[(1,2,3,4-tetrahydroisoquinolin-1-yl)-carbonyl-propyl-amino]}-7-(pyrrolidin-1-yl-carbonyl)-quinazoline,
(50) 6-chloro-4-{1-(5-chloro-1H-benzimidazol-2-yl)-3-[(N-methyl-N-phenethyl-amino-carbonyl)-propyl-amino]}-7-(pyrrolidin-1-yl-carbonyl)-quinazoline,
(51) 6-chloro-4-[1-(5-chloro-1H-benzimidazol-2-yl)-3-(hydroxyethylamino-carbonyl)-propyl-amino]-7-(pyrrolidin-1-yl-carbonyl)-quinazoline,
(52) 6-chloro-4-{1-(5-chloro-1H-benzimidazol-2-yl)-3-[(1-oxa-3,8-diaza-spiro[4,5]decan-2-on-8-yl)-carbonyl]-propyl-amino}-7-(pyrrolidin-1-yl-carbonyl)-quinazoline,
(53) 6-chloro-4-[1-(5-chloro-1H-benzimidazol-2-yl)-3-(morpholin-4-yl-carbonyl)-propyl-amino]-7-(pyrrolidin-1-yl-carbonyl)-quinazoline,
(54) 6-chloro-4-[1-(5-chloro-1H-benzimidazol-2-yl)-3-(dimethylaminopropylamino-carbonyl)-propyl-amino]-7-(pyrrolidin-1-yl-carbonyl)-quinazoline,
(55) 6-chloro-4-[1-(5-chloro-1H-benzimidazol-2-yl)-3-(hydroxycarbonylmethyl-methyl-amino-carbonyl)-propyl-amino]-7-(pyrrolidin-1-yl-carbonyl)-quinazoline,
(56) 6-chloro-4-{[1-(5-chloro-1H-benzimidazol-2-yl)-3-((3-(pyrrolidin-2-on-1-yl)-propyl)-amino-carbonyl)-propyl-amino]}-7-(pyrrolidin-1-yl-carbonyl)-quinazoline,
(57) 6-chloro-4-[1-(5-chloro-1H-benzimidazol-2-yl)-3-(2,2,2-trifluoroethylamino-carbonyl)-propyl-amino]-7-(pyrrolidin-1-yl-carbonyl)-quinazoline,
(58) 6-chloro-4-[1-(5-chloro-1H-benzimidazol-2-yl)-3-(4,5,6,7-tetrahydro-1H-imidazo[4,5-c]pyridin-5-yl-carbonyl)-propyl-amino]-7-(pyrrolidin-1-yl-carbonyl)-quinazoline,
(59) 6-chloro-4-[1-(5-chloro-1H-benzimidazol-2-yl)-3-(1-oxo-thiomorpholin-4-yl-carbonyl)-propyl-amino]-7-(pyrrolidin-1-yl-carbonyl)-quinazoline,
(60) 6-chloro-4-[1-(5-chloro-1H-benzimidazol-2-yl)-3-(1-thiazolidin-3-yl-carbonyl)-propyl-amino]-7-(pyrrolidin-1-yl-carbonyl)-quinazoline,
(61) 6-chloro-4-[1-(5-chloro-1H-benzimidazol-2-yl)-3-(N-cyclopropylmethyl-N-methyl-amino-carbonyl)-propyl-amino]-7-(pyrrolidin-1-yl-carbonyl)-quinazoline,
(62) 6-chloro-4-[1-(5-chloro-1H-benzimidazol-2-yl)-3-(cyclopentylamino-carbonyl)-propyl-amino]-7-(pyrrolidin-1-yl-carbonyl)-quinazoline,
(63) 6-chloro-4-[1-(5-chloro-1H-benzimidazol-2-yl)-3-(piperidin-1-yl-carbonyl)-propyl-amino]-7-(pyrrolidin-1-yl-carbonyl)-quinazoline,
(64) 6-chloro-4-[(1S)-1-(5-chloro-1H-benzimidazol-2-yl)-3-hydroxycarbonyl-propylamino]-7-(pyrrolidin-1-yl-carbonyl)-quinazoline,
(65) 6-chloro-4-[1-(5-chloro-1H-benzimidazol-2-yl)-1-(thiophen-3-yl)-methylamino]-7-(2,5-dihydropyrrol-1-yl-carbonyl)-quinazoline,
(66) 6-chloro-4-[(1S)-1-(5-chloro-1H-benzimidazol-2-yl)-3-2-oxo-pyrrolidin-1-yl-propyl-amino]-7-(2,5-dihydropyrrol-1-yl-carbonyl)-quinazoline,
(67) 6-chloro-4-[(1S)-1-(5-chloro-1H-benzimidazol-2-yl)-3-(1,1-dioxo-isothiazolidin-2-yl)-propyl-amino]-7-(2,5-dihydropyrrol-1-yl-carbonyl)-quinazoline,
(68) 6-chloro-4-[(1S)-1-(5-chloro-1H-benzimidazol-2-yl)-2-isopropylcarbonyloxy-ethylamino]-7-(2,5-dihydropyrrol-1-yl-carbonyl)-quinazoline,
(69) 6-chloro-4-[(1S)-1-(5-chloro-1H-benzimidazol-2-yl)-3-methanesulphonylamino-propyl-amino]-7-(2,5-dihydropyrrol-1-yl-carbonyl)-quinazoline,

(70) 4-[(1S)-1-(5-chloro-1H-benzimidazol-2-yl)-ethylamino]-7-(2,5-dihydropyrrol-1-yl-carbonyl)-6-methoxy-quinazoline,

(71) 7-[(2S)-2-(2-aminoethyl)-pyrrolidin-1-yl-carbonyl]-6-chloro-4-[(1R/S)-1-(5-chloro-1H-benzimidazol-2-yl)-ethylamino]-quinazoline,

(72) 6-chloro-4-[(1R/S)-1-(5-chloro-1H-benzimidazol-2-yl)-ethylamino]-7-[(2R/S)-2-aminomethyl-piperidin-1-yl-carbonyl]-quinazoline,

(73) 6-chloro-4-[1-(5-chloro-1H-benzimidazol-2-yl)-ethylamino]-7-(4-acetyl-piperazin-1-yl-carbonyl)-quinazoline,

(74) 4-[(1S)-1-(5-chloro-1H-benzimidazol-2-yl)-3-(methylsulphanyl)-propylamino]-6-methoxy-7-(2,5-dihydropyrrol-1-yl-carbonyl)-quinazoline,

(75) 4-[(1S)-1-(5-chloro-1H-benzimidazol-2-yl)-2-methoxy-ethylamino]-6-methoxy-7-(2,5-dihydropyrrol-1-yl-carbonyl)-quinazoline,

(76) 6-chloro-4-[(1S)-1-(5-chloro-1H-benzimidazol-2-yl)-2-methoxy-ethylamino]-7-(thiazolidinyl-carbonyl)-quinazoline,

(77) 4-[(1S)-1-(5-chloro-1H-benzimidazol-2-yl)-2-methoxy-ethylamino]-6-methyl-7-(2,5-dihydropyrrol-1-yl-carbonyl)-quinazoline,

(78) 4-[(1S)-1-(5-chloro-1H-benzimidazol-2-yl)-2-methoxy-ethylamino]-6-methyl-7-(thiazolidinyl-carbonyl)-quinazoline,

(79) 6-bromo-4-[(1S)-1-(5-chloro-1H-benzimidazol-2-yl)-2-methoxy-ethylamino]-7-(2,5-dihydropyrrol-1-yl-carbonyl)-quinazoline,

(80) 6-bromo-4-[(1S)-1-(5-chloro-1H-benzimidazol-2-yl)-2-methoxy-ethylamino]-7-(thiazolidinyl-carbonyl)-quinazoline,

(81) 4-[(1S)-1-(5-bromo-1H-benzimidazol-2-yl)-2-methoxy-ethylamino]-6-chloro-7-(2,5-dihydropyrrolyl-carbonyl)-quinazoline,

(82) 4-[(1S)-1-(5-bromo-1H-benzimidazol-2-yl)-ethylamino]-6-chloro-7-(2,5-dihydropyrrolyl-carbonyl)-quinazoline,

(83) 6-bromo-4-[(1S)-1-(5-chloro-1H-benzimidazol-2-yl)-but-3-yn-1-yl-amino]-7-(2,5-dihydropyrrol-1-yl-carbonyl)-quinazoline,

(84) 4-[(1S,2S)-1-(5-chloro-1H-benzimidazol-2-yl)-2-hydroxy-propylamino]-6-chloro-7-(2,5-dihydropyrrolyl-carbonyl)-quinazoline, the tautomers, the stereoisomers and the salts thereof.

The present invention also relates to the following embodiments:

In the above general formula I in a 6th embodiment $R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulphonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety with the exception of the 1-position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulphonyl group, while the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl or di-($C_{1-3}$-alkyl)-aminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group and/or a methylene group in the 3 position of a 5-membered cycloalkyleneimino group may be replaced by a sulphur atom, a sulphinyl or sulphonyl group or a methylene group in the 4 position of a 6- or 7-membered cycloalkyleneimino group may be replaced by an oxygen or sulphur atom or by an —NH—, —N—$C_{1-3}$-alkyl-, —N($C_{2-3}$-alkanoyl)-, sulphinyl or sulphonyl group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group, a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-($C_{1-3}$-alkyl)-aminocarbonyl or $C_{3-6}$-cycloalkyleneiminocarbonyl groups, while the double bond is not bound to a nitrogen atom, an aminocarbonyl or aminosulphonyl group optionally substituted by one or two $C_{1-5}$-alkyl groups, while the substituents may be identical or different and in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group, a $C_{1-7}$-alkylcarbonyl or $C_{3-7}$-cycloalkylcarbonyl group, while the methylene group in the 2, 3 or 4 position in a $C_{3-7}$-cycloalkylcarbonyl group may be replaced by an oxygen or sulphur atom, a carbonyl, sulphinyl, sulphonyl or an —NH— group, wherein the hydrogen atom of the —NH— group may be replaced by a $C_{1-3}$-alkyl or $C_{1-3}$-alkyl-carbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while
  the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or
a —$CH_2$—$CH_2$— group in a 5- to 7-membered cycloalkyleneimino group may be replaced by an —NH—CO—, —CO—NH—, —CO—N($CH_3$)— or a —N($CH_3$)—CO— group or
a methylene group, which is adjacent to the nitrogen atom, in a 5- to 7-membered cycloalkyleneimino group may be replaced by a carbonyl group,
or a group of formulae

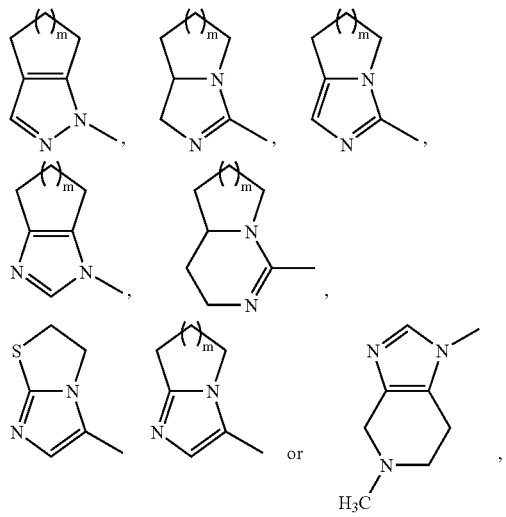

wherein in the heterocyclic moiety in each case a hydrogen atom may be replaced by a methylsulphonylmethyl, amino-$C_{1-3}$-alkyl or aminocarbonyl group and
  m denotes the number 1 or 2,
$R^2$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, $C_{1-3}$-alkoxy or trifluoromethoxy group,
$R^3$ denotes a hydrogen atom or a $C_{1-3}$-alkyl group,
$R^4$ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulphanyl, $C_{1-3}$-alkylsulphinyl, $C_{1-3}$-alkylsulphonyl, carboxy, aminocarbonyl, $C_{1-3}$-alkylamino-carbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonyl-amino, $C_{3-6}$-cycloalkylcarbonylamino, benzyloxycarbonylamino or guanidino group,
a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkoxy, carboxy, $C_{1-3}$-alkyloxycarbonyl group,
a 4- to 7-membered cycloalkyleneimino-$C_{1-3}$-alkyl group or
a 4- to 7-membered cycloalkyl-$C_{1-3}$-alkyl group wherein one or two methylene groups may be replaced by an —NH— or —N($C_{1-3}$-alkyl)- group and wherein one or two methylene groups adjacent to the —NH— or —N($C_{1-3}$-alkyl)- group may each be replaced by a carbonyl group, with the proviso that a cycloalkyl group as hereinbefore defined wherein two —NH— or —N($C_{1-3}$-alkyl)- groups are separated from one another by precisely one —$CH_2$— group are excluded,
$R^5$ denotes a hydrogen atom or a $C_{1-3}$-alkyl group or
$R^4$ and $R^5$ together with the carbon atom to which they are bound denote a $C_{3-7}$-cycloalkyl group, while
  one of the methylene groups of the $C_{3-7}$-cycloalkyl group may be replaced by an imino, $C_{1-3}$-alkylimino, acylimino or sulphonylimino group,
B denotes a group of formulae

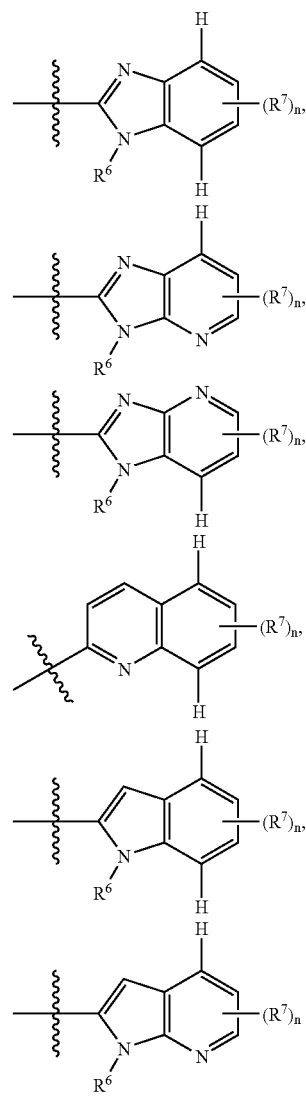

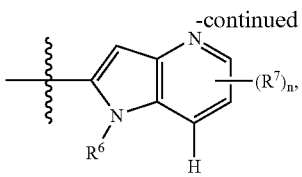

wherein
n denotes the number 1 or 2,
$R^6$ denotes a hydrogen atom or a $C_{1-3}$-alkyl, hydroxy, amino, $C_{1-3}$-alkylamino group,
$R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy or cyano group, and
$X^1$ to $X^3$ independently of one another each denote a nitrogen atom or a CH group,
while at least one and not more than two of the groups $X^1$ to $X^3$ denote a nitrogen atom,
while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while
the 6-membered heteroaryl group contains one, two or three nitrogen atoms and
the 5-membered heteroaryl group contains an imino group optionally substituted by a $C_{1-3}$-alkyl or phenyl-$C_{1-3}$-alkyl group, an oxygen or sulphur atom or
an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or phenyl-$C_{1-3}$-alkyl group or an oxygen or sulphur atom and additionally a nitrogen atom or
an imino group optionally substituted by a $C_{1-3}$-alkyl or phenyl-$C_{1-3}$-alkyl group and two or three nitrogen atoms,
and moreover a phenyl ring may be fused to the above-mentioned monocyclic heteroaryl groups via two adjacent carbon atoms
and the bond is effected via a nitrogen atom or a carbon atom of the heterocyclic moiety or a fused-on phenyl ring,
while, unless otherwise stated, the alkyl and alkoxy groups contained in the definitions which have more than two carbon atoms may be straight-chain or branched,
and the hydrogen atoms of the methyl or ethyl groups contained in the definitions may be wholly or partly replaced by fluorine atoms.

A 7th embodiment of the present invention comprises those compounds of the above general formula I, wherein $R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulphonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety with the exception of the 1-position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulphonyl group, while
the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or
a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group and/or
a methylene group in the 3 position of a 5-membered cycloalkyleneimino group may be replaced by a sulphur atom, a sulphinyl or sulphonyl group or
a methylene group in the 4 position of a 6- or 7-membered cycloalkyleneimino group may be replaced by an oxygen or sulphur atom or by a —NH—, —N—$C_{1-3}$-alkyl-, —N($C_{2-3}$-alkanoyl)-, sulphinyl or sulphonyl group and/or
a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group, a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-($C_{1-3}$-alkyl)-aminocarbonyl or $C_{3-6}$-cycloalkyleneiminocarbonyl groups, while the double bond is not bound to a nitrogen atom, an aminocarbonyl or aminosulphonyl group optionally substituted by one or two $C_{1-5}$-alkyl groups,
while the substituents may be identical or different and
in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or
a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group, a $C_{1-7}$-alkylcarbonyl or $C_{3-7}$-cycloalkylcarbonyl group, while
the methylene group in the 2, 3 or 4 position in a $C_{3-7}$-cycloalkylcarbonyl group may be replaced by an oxygen or sulphur atom, a carbonyl, sulphinyl, sulphonyl or an —NH— group wherein
the hydrogen atom of the —NH— group may be replaced by a $C_{1-3}$-alkyl or $C_{1-3}$-alkyl-carbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group or a methylene group, which is adjacent to the nitrogen atom, in a 5- to 7-membered cycloalkyleneimino group may be replaced by a carbonyl group, or a group of formulae

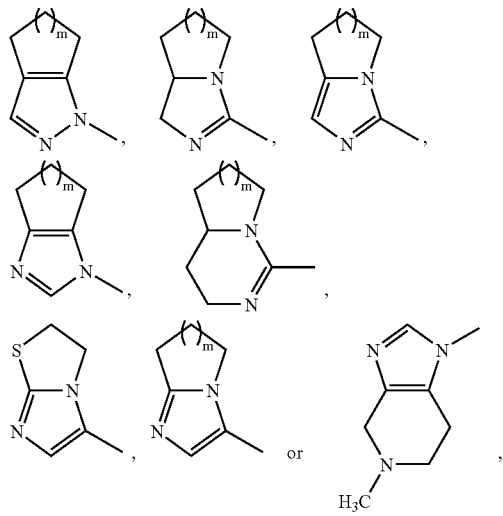

wherein in the heterocyclic moiety in each case a hydrogen atom may be replaced by a methylsulphonylmethyl, amino-$C_{1-3}$-alkyl or aminocarbonyl group and m denotes the number 1 or 2, $R^2$ denotes a chlorine or bromine atom, a $C_{1-3}$-alkyl group wherein the hydrogen atoms may be wholly or partly replaced by fluorine atoms, or a $C_{2-3}$-alkenyl group, $R^3$ denotes a hydrogen atom or a $C_{1-3}$-alkyl group, $R^4$ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulphanyl, $C_{1-3}$-alkylsulphinyl, $C_{1-3}$-alkylsulphonyl, carboxy, aminocarbonyl, $C_{1-3}$-alkylamino-carbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonyl-amino, $C_{3-6}$-cycloalkylcarbonylamino, benzyloxycarbonylamino or guanidino group, a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkoxy, carboxy, $C_{1-3}$-alkyloxycarbonyl group, a 4- to 7-membered cycloalkyleneimino-$C_{1-3}$-alkyl group or a 4- to 7-membered cycloalkyl-$C_{1-3}$-alkyl group wherein one or two methylene groups may be replaced by an —NH— or —N($C_{1-3}$-alkyl)- group and wherein one or two methylene groups adjacent to the —NH— or —N($C_{1-3}$-alkyl)- group may each be replaced by a carbonyl group, with the proviso that a cycloalkyl group as hereinbefore defined wherein two —NH— or —N($C_{1-3}$-alkyl)- groups are separated from one another by precisely one —$CH_2$— group are excluded, $R^5$ denotes a hydrogen atom or a $C_{1-3}$-alkyl group or $R^4$ and $R^5$ together with the carbon atom to which they are bound denote a $C_{3-7}$-cycloalkyl group, while one of the methylene groups of the $C_{3-7}$-cycloalkyl group may be replaced by an imino, $C_{1-3}$-alkylimino, acylimino or sulphonylimino group, B denotes a group of formulae

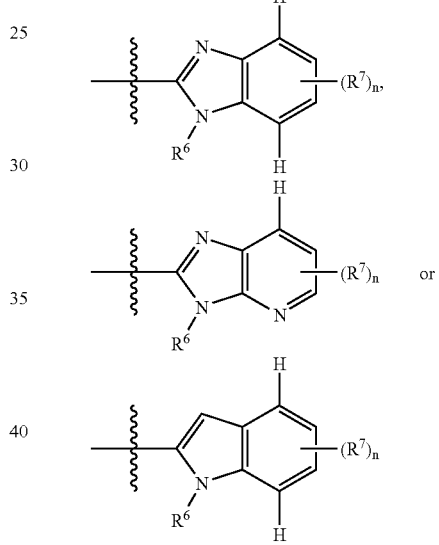

wherein n denotes the number 1, $R^6$ denotes a hydrogen atom or a $C_{1-3}$-alkyl, hydroxy, amino, $C_{1-3}$-alkylamino group, $R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy or cyano group, and $X^1$ to $X^3$ independently of one another each denote a nitrogen atom or a CH group, while at least one and not more than two of the groups $X^1$ to $X^3$ denote a nitrogen atom, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

An 8th embodiment of the present invention comprises those compounds of the above general formula I wherein $R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulphonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety with the exception of the 1-position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulphonyl group, while
the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group and/or a methylene group in the 3 position of a 5-membered cycloalkyleneimino group may be replaced by a sulphur atom, a sulphinyl or sulphonyl group or a methylene group in the 4 position of a 6- or 7-membered cycloalkyleneimino group may be replaced by an oxygen or sulphur atom or by an —NH—, —N—$C_{1-3}$-alkyl-, —N($C_{2-3}$-alkanoyl)-, sulphinyl or sulphonyl group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group, a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-($C_{1-3}$-alkyl)-aminocarbonyl or $C_{3-6}$-cycloalkyleneiminocarbonyl groups, while the double bond is not bound to a nitrogen atom, an aminocarbonyl or aminosulphonyl group optionally substituted by one or two $C_{1-5}$-alkyl groups,
while the substituents may be identical or different and
in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while
the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group or a methylene group, which is adjacent to the nitrogen atom, in a 5- to 7-membered cycloalkyleneimino group may be replaced by a carbonyl group, or a group of formulae

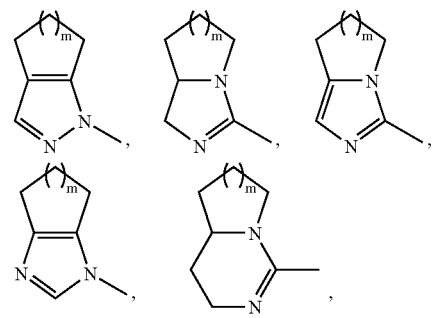

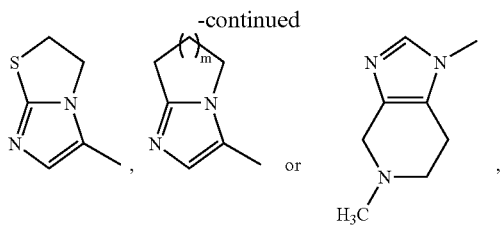 or 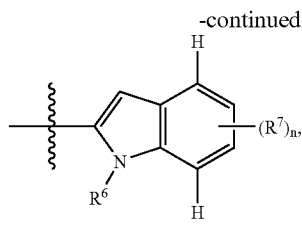,

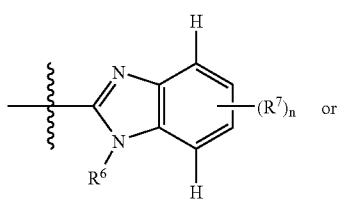

wherein in the heterocyclic moiety in each case a hydrogen atom may be replaced by a methylsulphonylmethyl, amino-$C_{1-3}$-alkyl or aminocarbonyl group and m denotes the number 1 or 2, $R^2$ denotes a chlorine or bromine atom, a $C_{1-3}$-alkyl group wherein the hydrogen atoms may be wholly or partly replaced by fluorine atoms, or a $C_{2-3}$-alkenyl group, $R^3$ denotes a hydrogen atom, $R^4$ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulphanyl, $C_{1-3}$-alkylsulphinyl, $C_{1-3}$-alkylsulphonyl, carboxy, aminocarbonyl, $C_{1-3}$-alkylamino-carbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonyl-amino, $C_{3-6}$-cycloalkylcarbonylamino, benzyloxycarbonylamino or guanidino group, a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkyloxy, carboxy, $C_{1-3}$-alkyloxycarbonyl group, a 4- to 7-membered cycloalkyleneimino-$C_{1-3}$-alkyl group or a 4- to 7-membered cycloalkyl-$C_{1-3}$-alkyl group wherein one or two methylene groups may be replaced by an —NH— or —N($C_{1-3}$-alkyl)- group and wherein one or two methylene groups adjacent to the —NH— or —N($C_{1-3}$-alkyl)- group may each be replaced by a carbonyl group, with the proviso that a cycloalkyl group as hereinbefore defined wherein two —NH— or —N($C_{1-3}$-alkyl)- groups are separated from one another by precisely one —$CH_2$— group are excluded, $R^5$ denotes a hydrogen atom or $R^4$ and $R^5$ together with the carbon atom to which they are bound denotes a $C_{3-7}$-cycloalkyl group, while one of the methylene groups of the $C_{3-7}$-cycloalkyl group may be replaced by an imino, $C_{1-3}$-alkylimino, acylimino or sulphonylimino group, B denotes a group of formulae wherein n denotes the number 1, $R^6$ denotes a hydrogen atom or a $C_{1-3}$-alkyl, hydroxy, amino, $C_{1-3}$-alkylamino group, $R^7$ denotes a fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl or a hydroxy group, and $X^1$ to $X^3$ independently of one another each denote a nitrogen atom or a CH group, while at least one and not more than two of the groups $X^1$ to $X^3$ denote a nitrogen atom, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, the alkyl and alkoxy groups contained in the definitions, which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

A 9th embodiment of the present invention comprises those compounds of the above general formula I wherein $R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulphonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety with the exception of the 1-position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulphonyl group, while the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group and/or a methylene group in the 3 position of a 5-membered cycloalkyleneimino group may be replaced by a sulphur atom, a sulphinyl or sulphonyl group or a methylene group in the 4 position of a 6- or 7-membered cycloalkyleneimino group may be replaced by an oxygen or sulphur atom or by a —NH—, —N—$C_{1-3}$-alkyl-, —N($C_{2-3}$-alkanoyl)-, sulphinyl or sulphonyl group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group, a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$V_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-($C_{1-3}$-alkyl)-aminocarbonyl or $C_{3-6}$-cycloalkyleneiminocarbonyl groups, while the double bond is not bound to a nitrogen atom, an aminocarbonyl or aminosulphonyl group optionally substituted by one or two $C_{1-5}$-alkyl groups, while the substituents may be identical or different and in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO-group or a methylene group, which is adjacent to the nitrogen atom, in a 5- to 7-membered cycloalkyleneimino group may be replaced by a carbonyl group, or a group of formulae

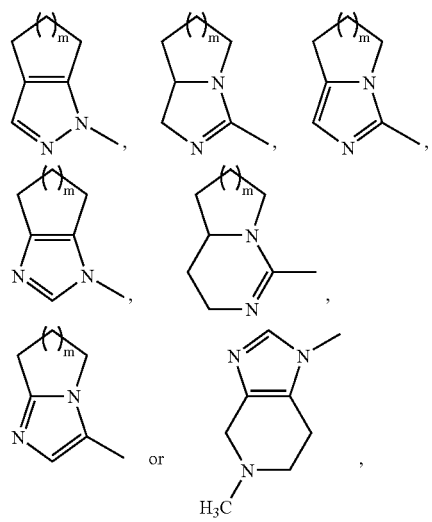

wherein in the heterocyclic moiety in each case a hydrogen atom may be replaced by a methylsulphonylmethyl, amino-$C_{1-3}$-alkyl or aminocarbonyl group and m denotes the number 1 or 2, $R^2$ denotes a chlorine or bromine atom, a $C_{1-3}$-alkyl group wherein the hydrogen atoms may be wholly or partly replaced by fluorine atoms, or a $C_{2-3}$-alkenyl group, $R^3$ denotes a hydrogen atom, $R^4$ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulphanyl, $C_{1-3}$-alkylsulphinyl, $C_{1-3}$-alkylsulphonyl, carboxy, aminocarbonyl, $C_{1-3}$-alkylamino-carbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonyl-amino, $C_{3-6}$-cycloalkylcarbonylamino, benzyloxycarbonylamino or guanidino group, a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkyloxy, carboxy, $C_{1-3}$-alkyloxycarbonyl group, a 4- to 7-membered cycloalkyleneimino-$C_{1-3}$-alkyl group or a 4- to 7-membered cycloalkyl-$C_{1-3}$-alkyl group wherein one or two methylene groups may be replaced by an —NH— or —N($C_{1-3}$-alkyl)-group and wherein one or two methylene groups adjacent to the —NH— or —N($C_{1-3}$-alkyl)-group may each be replaced by a carbonyl group, with the proviso that a cycloalkyl group as hereinbefore defined wherein two —NH— or —N($C_{1-3}$-alkyl)-groups are separated from one another by precisely one —$CH_2$— group are excluded, $R^5$ denotes a hydrogen atom, B denotes a group of formulae

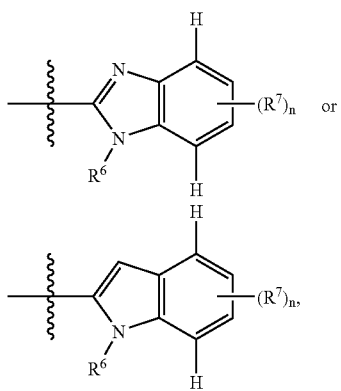

wherein n denotes the number 1, $R^6$ denotes a hydrogen atom or a $C_{1-3}$-alkyl, hydroxy, amino, $C_{1-3}$-alkylamino group, $R^7$ denotes a fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl or a hydroxy group, and $X^1$ to $X^3$ independently of one another each denote a nitrogen atom or a CH group, while at least one and not more than two of the groups $X^1$ to $X^3$ denote a nitrogen atom, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkylene-imino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

A 10th embodiment of the present invention comprises those compounds of the above general formula I, wherein $R^1$ denotes a 2,5-dihydro-1H-pyrrol-1-yl-carbonyl, pyrrolidin-1-yl-carbonyl, 2-(aminomethyl)-pyrrolidin-1-yl-carbonyl, 2-(N-tert.-butyloxycarbonylaminomethyl)-pyrrolidin-1-yl-carbonyl, 3-oxo-piperazin-1-yl-carbonyl or morpholin-4-yl-carbonyl group, $R^2$ denotes a hydrogen, chlorine or bromine atom or a $C_{1-3}$-alkyl group wherein the hydrogen atoms may be wholly or partly replaced by fluorine atoms, $R^3$ denotes a hydrogen atom, $R^4$ denotes a hydrogen atom or the methyl group, $R^5$ denotes a hydrogen atom, B denotes a group of formulae

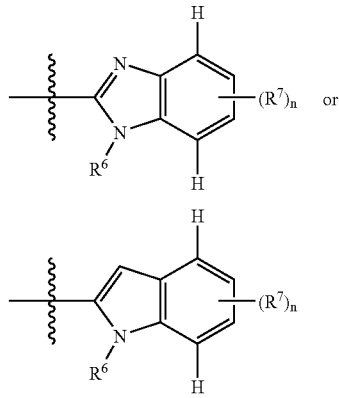

wherein $R^6$ denotes a hydrogen atom, $R^7$ denotes a chlorine atom, and $X^1$ to $X^3$ independently of one another each denote a nitrogen atom or a CH group, while at least one and not more than two of the groups $X^1$ to $X^3$ denote a nitrogen atom, the tautomers, the enantiomers, the diastereomers, the mixtures thereof and the salts thereof.

According to the invention the compounds of general formula I are obtained by methods known per se, for example by the following methods:

(a) In order to prepare a compound of general formula

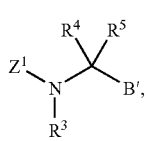

(III)

wherein $R^3$ to $R^5$ are as hereinbefore defined and $Z^1$ denotes the hydrogen atom or a protective group and B' denotes a group of formula

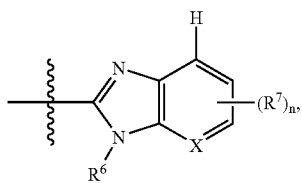

(IV)

wherein $R^6$ and $R^7$ are as hereinbefore defined and X denotes the nitrogen atom or the CH group:

cyclising a compound of general formula

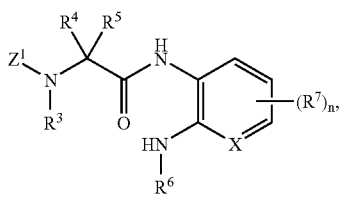

(V)

optionally formed in the reaction mixture, wherein $R^3$ to $R^7$ are as hereinbefore defined, X denotes the nitrogen atom or the CH group and $Z^1$ denotes the hydrogen atom or a protective group, any protective group present then being cleaved.

The cyclisation is conveniently carried out in a solvent or mixture of solvents such as ethanol, isopropanol, glacial acetic acid, benzene, chlorobenzene, toluene, xylene, glycol, glycolmonomethylether, diethyleneglycoldimethylether, sulpholane, dimethylformamide or tetraline, dimethylsulphoxide, methylene chloride, chloroform, tetrachloromethane, for example at temperatures between 0 and 250° C., but preferably between 20 and 100° C., optionally in the presence of a condensing agent such as phosphorus oxychloride, thionyl chloride, sulphurylchloride, sulphuric acid, p-toluenesulphonic acid, methanesulphonic acid, hydrochloric acid, phosphoric acid, polyphosphoric acid, acetic acid, acetic anhydride, N,N-dicyclohexylcarbodiimide or optionally also in the presence of a base such as potassium ethoxide or potassium-tert.-butoxide. The cyclisation may, however, also be carried out with a solvent and/or condensing agent.

(b) In order to prepare a compound of general formula

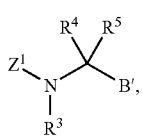

(III)

wherein $R^3$ to $R^5$ are as hereinbefore defined, $Z^1$ denotes the hydrogen atom or a protective group and B' denotes a group of formula

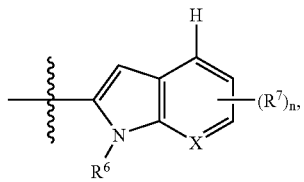

(VI)

wherein $R^6$ and $R^7$ are as hereinbefore defined and X denotes the nitrogen atom or the CH group:

i) transition metal-catalysed coupling and cyclisation of a compound of general formula

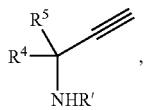

(VII)

wherein $R^4$ denotes a phenyl or heteroaryl group and $R^5$ denotes a hydrogen atom and R' denotes a hydrogen atom or a $C_{1-3}$-alkyl group, with a compound of general formula

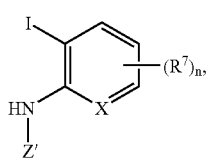

(VIII)

wherein $R^7$ is as hereinbefore defined, X denotes the nitrogen atom or the CH group and $Z^1$ denotes a protective group, for example an acetyl or methylsulphonyl group, this protective group then being cleaved.

The reaction sequence is conveniently carried out in a solvent or mixture of solvents such as ethanol, isopropanol, glacial acetic acid, benzene, chlorobenzene, toluene, xylene, glycol, glycolmonomethylether, diethyleneglycoldimethylether, sulpholane, dimethylformamide, N-methylpyrrolidinone, tetraline, dimethylsulphoxide, methylene chloride, chloroform or tetrachloromethane, for example at temperatures between 0 and 250° C., but preferably between 20 and 120° C., conveniently in the presence of transition metal catalysts such as bis-(triphenylphosphine)-palladium(II)-chloride, bis-(tricyclohexylphosphine)-palladium(II)-chloride, bis-(triethylphosphine)-palladium(II)-chloride, or bis-(tri-o-tolylphosphine)-palladium(II)-chloride and optionally in the presence of a transition metal catalyst such as copper (I)-iodide, copper(I)-bromide or copper(I)-acetate and conveniently in the presence of a base such as tetramethylguanidine, tetramethylethylenediamine or N,N'-dimethylethylenediamine as well as optionally using an inert gas atmosphere (for example nitrogen or argon).

ii) alkylation of a compound of general formula (IX)

wherein $R^6$ and $R^7$ are as hereinbefore defined, X denotes the nitrogen atom or the CH group and Y denotes a hydroxy, $C_{1-4}$-alkyloxy, hydroxylamino, $C_{1-4}$-alkyloxyamino or a $C_{1-4}$-alkyloxy-$C_{1-4}$-alkylamino group, with a compound of general formula $$R^4\text{---}M, \qquad (X)$$

wherein $R^4$ is as hereinbefore defined, with the proviso that a phenyl or heteroaryl group is excluded, and M denotes a metal, such as for example lithium, sodium or potassium, or a metal such as for example magnesium, cadmium, copper or zinc, with a suitable counter-ion, such as for example chloride, bromide or iodide, or also a combination of two metals, such as for example magnesium and copper, lithium and copper or zinc and copper, with suitable counter-ions, such as for example cyanide, chloride, bromide or iodide, and groups containing combinations thereof, followed by reductive amination of the compounds thus obtained.

The alkylation is conveniently carried out in a solvent or mixture of solvents such as benzene, chlorobenzene, toluene, xylene, glycoldimethylether, diethyleneglycoldimethylether, sulpholane, dimethylformamide, N-methylpyrrolidinone, tetraline, dimethylsulphoxide, methylene chloride, chloroform, tetrachloromethane, diethyl ether, tert.-butyl-methylether or tetrahydrofuran, for example, at temperatures between −100 and +100° C., but preferably between −100 and 30° C., with alkylating reagents such as Grignard reagents, organolithium reagents, Gilman or Knochel cuprates, which may be produced by methods known from the literature, optionally under an inert gas atmosphere (nitrogen or argon). The subsequent reductive amination of the ketones formed after alkylation is carried out by reacting for example with ammonia, hydroxylamine, alkoxylamines, primary amines, hydroxyl-alkylamines or alkoxy-alkylamines followed by or accompanied by reduction for example with hydride donors such as sodium borohydride, lithium aluminium hydride, sodium cyanoborohydride, sodium triacetoxyborohydride or diisobutyl aluminium hydride in a solvent or mixture of solvents such as ethanol, isopropanol, benzene, toluene, pyridine, ethyleneglycoldimethylether, diethyleneglycoldimethylether, N-alkylmorpholine, diethyl ether, tert.-butyl-methylether, tetrahydrofuran, hexane or cyclohexane or by hydrogenation optionally under pressure and conveniently in the presence of a catalyst such as Raney nickel, palladium, palladium charcoal, platinum or platinum oxide, in a solvent or mixture of solvents such as ethyl acetate, ethanol, isopropanol, benzene, toluene, pyridine, ethyleneglycoldimethylether, diethyleneglycoldimethylether, N-alkylmorpholine, diethyl ether, tert.-butyl-methylether, tetrahydrofuran, hexane or cyclohexane.

(c) In order to prepare a compound of general formula (I)

wherein
B, $X^1$ to $X^3$ and $R^1$ to $R^5$ are as hereinbefore defined:
coupling a compound of general formula (XI)

wherein
$R^1$, $R^2$ and $X^1$ to $X^3$ are as hereinbefore defined and Z denotes a leaving group such as a halogen atom, a sulphonyloxy or aryloxy group, e.g. a chlorine, bromine or iodine atom, a trifluoromethylsulphonyloxy, phenoxy or p-nitrophenoxy group,
with a compound of general formula (XII)

wherein B and $R^3$ to $R^5$ are as hereinbefore defined.

The coupling reaction is conveniently carried out in a solvent such as toluene, dioxane, dimethoxyethane, dimethylformamide or tetrahydrofuran preferably in the presence of a base such as sodium-tert.-butoxide, bis-(trimethylsilyl)-lithiumamide, potassium carbonate, caesium carbonate or triethylamine at a temperature between 0° C. and 150° C., preferably between 0° C. and 100° C., optionally using a suitable catalyst, for example bis-(tri-otolylphosphine)-palladium-(II)-chloride, tris-(dibenzylideneacetone)-dipalladium(0)/tris-o-tolylphosphine, tris-(dibenzyli-deneacetone)-dipalladium (0)/tris-(2-furyl )phosphane, tris-(dibenzylideneacetone)-dipalladium(0)/2,2'-bis-(diphenylphosphino)-1,1'-binaphthyl, tetrakis-(triphenylphosphine)-palladium(0), 1,1'-bis-(diphenylphosphi no)-ferrocene-palladium-dichloride or palladium-II-acetate/1,3-bis-(triphenylphosphino)-propane.

The coupling reaction may, however, also be carried out without the addition of solvent in substance by melting the compounds of general formulae V and VI at temperatures between ambient temperature and 150° C., optionally in the presence of one of the above-mentioned bases and/or optionally using one of the above-mentioned catalysts.

(d) In order to prepare a compound of general formula

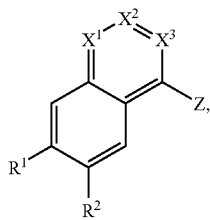

(XIII)

wherein
R$^1$ and R$^2$ are as hereinbefore defined, X$^1$ and X$^3$ in each case denote a nitrogen atom, X$^2$ denotes a CH group optionally substituted by a C$_{1-3}$-alkyl group, and Z denotes a leaving group such as a halogen atom, for example a chlorine or bromine atom:
cyclising a compound of general formula

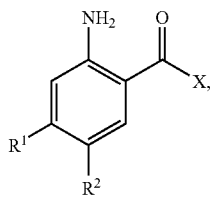

(XIV)

wherein
R$^1$ and R$^2$ are as hereinbefore defined and X denotes a hydroxy or C$_{1-4}$-alkoxy group or a halogen atom, with formamide or C$_{1-3}$-alkylcarbonylamide and subsequently reacting the resulting compound of general formula

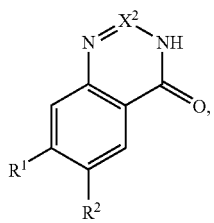

(XV)

wherein
R$^1$ and R$^2$ are as hereinbefore defined and X$^2$ denotes a CH group optionally substituted by a C$_{1-3}$-alkyl group, with a halogenating agent, for example with thionyl chloride, thionylbromide or oxalyl chloride.

The cyclisation is carried out for example in a high-boiling solvent such as chlorobenzene, xylene, dimethylformamide, dimethylsulphoxide, sulpholane or also without any other solvent in the presence of excess formamide at temperatures between 100 and 200° C., preferably between 130 and 170° C.

The subsequent reaction with a halogenating agent, for example with thionyl chloride, thionylbromide or oxalyl chloride, is conveniently carried out either without solvent in substance in the presence of dimethylformamide as catalyst or by the addition of a solvent such as dimethylformamide, pyridine, benzene, carbon tetrachloride, 1,2-dichloroethane or chloroform at temperatures between 20 and 120° C.

(e) In order to prepare a compound of general formula

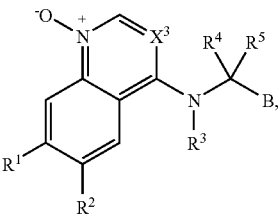

(XVI)

wherein R$^1$ to R$^5$ and B are as hereinbefore defined and X$^3$ denotes a nitrogen atom or a CH group:
Oxidation of a compound of general formula

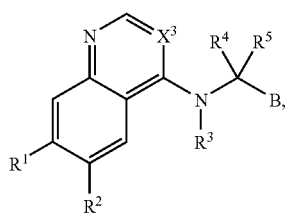

(XVII)

wherein R$^1$ to R$^5$ and B are as hereinbefore defined and X$^3$ denotes a nitrogen atom or a CH group, with an oxidising agent, for example with H$_2$O$_2$, m-chloroperbenzoic acid or monoperoxyphthalic acid.

The oxidation is carried out for example in a solvent which is inert under the oxidation conditions used, such as acetic acid, trifluoroacetic acid, water or chloroform, at temperatures between –10° C. and 100° C.

The compounds of general formula XVI may also be prepared for example analogously to methods described in E. Müller, O. Bayer (Eds.): Methoden der Organischen Chemie (Houben-Weyl), volume E9b, Hetarenes IV (ed. E. Schaumann), supplementary and follow-up volumes to the 4th edition, Verlag Thieme, Stuttgart 1998, p. 98-99 or in E. Müller, O. Bayer (Eds.): Methoden der Organischen Chemie (Houben-Weyl), volume E7a, Hetarenes II (ed. R. P. Kreher), supplementary and follow-up volumes to the 4th edition, Verlag Thieme, Stuttgart 1991, p. 511-515.

The compounds of general formulae III to XV used as starting materials, some of which are known from the literature, may be obtained by methods known from the literature. Their preparation is also described in the Examples.

The compounds of general formulae III and V may for example be prepared analogously to K. Maekawa, J. Ohtani, Agr. *Biol. Chem.* 1976, 40, 791-799.

Methods of amide coupling are described for example in P. D. Bailey, I. D. Collier, K. M. Morgan in "Comprehensive Functional Group Interconversions", Vol. 5, page 257ff., Pergamon 1995.

In the reactions described above any reactive groups present such as hydroxy, carboxy, amino, alkylamino or imino groups may be protected during the reaction by conventional protective groups which are cleaved again after the reaction.

For example a suitable protective group for a hydroxy group is the methoxy, benzyloxy, trimethylsilyl, acetyl, benzoyl, tert.-butyl, trityl, benzyl or tetrahydro-pyranyl group, a suitable protective group for a carboxyl group is the trimethylsilyl, methyl, ethyl, tert.-butyl, benzyl or tetrahydropyranyl group and a suitable protective group for an amino, alkylamino or imino group is the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally a suitable protective group for the amino group is the phthalyl group.

Other protective groups and their cleaving are described in T. W. Greene, P. G. M. Wuts, "Protective Groups in Organic Synthesis", Wiley, 1991 and 1999.

Any protective group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by means of ether splitting, e.g. in the presence of iodotrimethylsilane, at temperatures between 0 and 100° C., preferably at temperatures between 10 and 50° C.

A benzyl, methoxybenzyl or benzyloxycarbonyl group, however, is cleaved by hydrogenolysis, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and under a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.-butyl or tert.-butyloxycarbonyl group is preferably cleaved by treatment with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Compounds of general formulae IV with structure VII may be prepared for example analogously to F. Messina, M. Botta, F. Corelli, C. Villani, *Tetrahedron Asymm.* 2000, 11, 1681-1685 or R. M. Wilson, R. A. Farr, D. J. Burlett, *J. Org. Chem.* 1981, 46, 3293-3302.

Compounds of general formulae IV and XI in each case with structure VII may also be prepared for example analogously to methods described in E. Müller, O. Bayer (Eds.): Methoden der Organischen Chemie (Houben-Weyl), volume E6b, Hetarene I (ed. R. P. Kreher), supplementary and follow-up volumes to the 4th edition, Verlag Thieme, Stuttgart 1994, p. 546-1336.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the. activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula I and the tautomers, enantiomers, diastereomers and physiologically acceptable salts thereof have valuable pharmacological properties, particularly an antithrombotic activity which is preferably based on an effect on thrombin or factor Xa, for example on a thrombin-inhibiting or factor Xa-inhibiting activity, on a prolonging effect on the aPTT time and on an inhibitory effect on related serine proteases such as e.g. urokinase, factor VIIa, factor IX, factor XI and factor XII.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free Factor Xa (Calbiochem), spec. activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 µMol/l Procedure:

10 µl of a 23.5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation, for preventing and treating coronary thrombosis, for preventing stroke and the occlusion of shunts. In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic incidents in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention without restricting its scope:

Experimental Section

As a rule, melting points, IR, UV, $^1$H-NMR and/or mass spectra have been obtained for the compounds prepared. Unless otherwise stated, $R_f$ values were determined using ready-made silica gel 60 $F_{254}$ TLC plates (E. Merck, Darmstadt, Item no. 1.05714) without chamber saturation. The $R_f$ values given under the heading Alox were determined using ready-made aluminium oxide 60 $F_{254}$ TLC plates (E. Merck, Darmstadt, Item no. 1.05713) without chamber saturation. The $R_f$ values given under the heading Reversed-phase-8 were determined using ready-made RP-8 $F_{254s}$ TLC plates (E. Merck, Darmstadt, Item no. 1.15684) without chamber saturation. The ratios given for the eluants refer to units by volume of the solvents in question. For chromatographic purification silica gel made by Messrs Millipore (MATREX™, 35-70 my) was used. Unless more detailed information is provided as to the configuration, it is not clear whether the products are pure stereoisomers or mixtures of enantiomers and diastereomers.

The following abbreviations are used in the descriptions of the experiments:

| | |
|---|---|
| Boc | tert-butyloxycarbonyl |
| DMSO | dimethylsulphoxide |
| DMF | dimethylformamide |
| o | ortho |
| rac. | racemic |
| TBTU: | O-(benzotriazol-1-yl)-N,N,N',N'-tetramethyluronium tetrafluoroborate |
| tert. | tertiary |

The HPLC/MS data were obtained using the following system:

Waters ZMD, Alliance 2690 HPLC, Waters 2700 Autosampler, Waters 996 diode array detector The following was used as the mobile phase:
A: water with 0.1% trifluoroacetic acid
B: acetonitrile with 0.1% trifluoroacetic acid

| time in min | % A | % B | flow rate in ml/min |
|---|---|---|---|
| 0.0 | 95 | 5 | 1.00 |
| 0.1 | 95 | 5 | 1.00 |
| 5.1 | 2 | 98 | 1.00 |
| 6.5 | 2 | 98 | 1.00 |
| 7.0 | 95 | 5 | 1.00 |

The stationary phase used was a Waters column X-Terra™ MS $C_{18}$ 3.5 μm, 4.6 mm×50 mm (column temperature: constant at 25° C.)

The diode array detection took place in a wavelength range from 210-500 nm

Range of mass-spectrometric detection: m/z 120 to m/z 950

The HPLC/MS data for Examples 49, 83-125 and 227 were obtained using the following system:

Waters ZQ, Alliance 2690 HPLC, Waters 2700 Autosampler, Waters 996 diode array detector.

The following was used as the mobile phase:
A: water with 0.1% trifluoroacetic acid
B: acetonitrile with 0.1% trifluoroacetic acid

| time in min | % A | % B | flow rate in ml/min |
|---|---|---|---|
| 0.0 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

The stationary phase used was a Waters column X-Terra™ MS $C_{18}$ 2.5 μm, 4.6 mm×30 mm (column temperature: constant at 25° C.)

The diode array detection took place in a wavelength range from 210-500 nm

Range of mass-spectrometric detection: m/z 120 to m/z 950

The HPLC/MS Data for Examples 139-215 were obtained using the following system:

Waters ZQ 2000, Agilent HP1100, Gilson Autosampler, Agilent HP1100 diode array detector.

The following was used as the mobile phase:
A: water with 0.1% trifluoroacetic acid
B: acetonitrile with 0.1% trifluoroacetic acid

| time in min | % A | % B | flow rate in ml/min |
|---|---|---|---|
| 0.0 | 95 | 5 | 0.4 |
| 0.15 | 2 | 98 | 0.4 |
| 4.65 | 2 | 98 | 0.4 |
| 6.0 | 95 | 5 | 0.4 |
| 6.5 | 95 | 5 | 0.4 |

The stationary phase used was a Waters column X-Terra™ MS $C_{18}$ 3.5 μm, 2.1 mm×50 mm (column temperature: constant at 30° C.)

The diode array detection took place in a wavelength range from 210-550 nm

Range of mass-spectrometric detection: m/z 120 to m/z 1000.

EXAMPLE 1

4-[(5-chloro-1H-benzimidazol-2-yl)-methylamino]-7-(pyrrolidin-1-yl-carbonyl)-quinoline

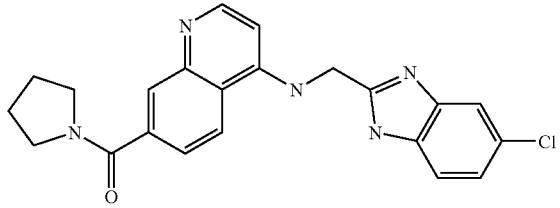

(a) N'-tert.-butyloxycarbonyl-N-(2-amino-4-chloro) phenyl-glycinamide and N'-tert.-butoxycarbonyl-N-(2-amino-5-chloro)phenyl-glycinamide 14.3 g (0.100 mol) 4-chloro-o-phenylenediamine together with 17.5 g (0.100 mol) N-tert.-butoxycarbonyl-glycine in 250 ml of tetrahydrofuran are combined with 20.6 g (0.100 mol) N,N'-dicyclohexylcarbodiimide while cooling with ice and under a nitrogen atmosphere within 15 minutes and then stirred for 16 hours at ambient temperature. The mixture is poured into 750 ml ice water, the precipitate is filtered off, washed with a little water and taken up in 500 ml of ethyl acetate. Insoluble constituents are filtered off and washed again with ethyl acetate and tetrahydrofuran. The filtrate is dried over magnesium sulphate and filtered through silica gel. Then the solvent is eliminated in vacuo.

Yield: 16.6 g (55%)

$R_f$ value: 0.41 (silica gel; dichloromethane/ethyl acetate=1:1+0.5% ammonia solution)

(b) N-tert.-butoxycarbonyl-C-(5-chloro-1H-benzimidazol-2-yl)methylamine 16.6 g (55.4 mmol) of a mixture of N'-tert.-butoxycarbonyl-N-(2-amino-4-chloro)-phenyl-glycinamide and N'-tert.-butoxycarbonyl-N-(2-amino-5-chloro)phenyl-glycinamide are placed in 160 ml glacial acetic acid and the mixture is refluxed for 1.5 hours. Then the majority of the glacial acetic acid is distilled off and the residue is poured into a mixture of crushed ice and concentrated ammonia solution. Insoluble constituents are filtered off, extracted with 500 ml of ethyl acetate, the organic phase is washed with saturated sodium chloride solution and dried over magnesium sulphate. After the solvent has been eliminated in vacuo the residue is purified by chromatography on silica gel (gradient: methylene chloride/methanol=98:2->95:5+0.2% ammonia solution).

Yield: 6.70 g (43%)

$R_f$ value: 0.45 (silica gel; petroleum ether/ethyl acetate=8:2)

$C_{13}H_{16}ClN_3O_2$ (281.74)

Mass spectrum: $(M+H)^+=282/284$ (chlorine isotope)

(c) C-(5-chloro-1H-benzimidazol-2-yl)-methylamine 4.62 g (16.4 mmol) N'-tert.-butoxycarbonyl-C-(5-chloro-1H-benzimidazol-2-yl)methylamine are dissolved in 100 ml saturated ethanolic hydrogen chloride solution and stirred for 2 hours at ambient temperature. Then all the volatile constituents are eliminated under reduced pressure and the crude product is further reacted.

Yield: quantitative $R_f$ value: 0.35 (silica gel; petroleum ether/ethyl acetate=8:2)

(d) 4-chloro-quinoline-7-carboxylic acid 10.0 g (43.2 mmol) 4-chloro-7-trifluoromethyl-quinoline are irradiated in 200 ml of conc. sulphuric acid for 2 hours at 550 Watt in the microwave. The reaction solution is poured onto ice water and adjusted to pH 3-4 with sodium hydroxide solution. The precipitated product is suction filtered, washed with water and dried.

Yield: 8.9 g (99%)

$R_f$ value: 0.45 (silica gel; toluene/ethanol=4:1)

$C_{10}H_6ClNO_2$ (207.62)

Mass spectrum: $(M+H)^+$=208/10 (chlorine isotope)

(e) 4-chloro-7-(pyrrolidin-1-ylcarbonyl)-guinoline 5.2 g (25 mmol) 4-chloro-quinoline-7-carboxylic acid and 2.1 ml (25 mmol) pyrrolidine are suspended in 125 ml of ethyl acetate, 14.0 ml (128 mmol) N-methylmorpholine is added and then 29.2 ml (50.8 mmol) propanephosphonic anhydride is added dropwise. After 40 hours the mixture is washed with 20 ml sodium hydrogen carbonate solution and extracted with ethyl acetate. The combined organic extracts are dried over sodium sulphate and concentrated by evaporation. The residue is chromatographed on silica gel (eluant: toluene/ethanol=95:5).

Yield: 4.7 g (72%)

$R_f$ value: 0.18 (silica gel; toluene/ethanol=9:1)

$C_{14}H_{13}ClN_2O$ (260.72)

Mass spectrum: $(M+H)^+$=261/63 (chlorine isotope)

(f) 4-[C-(5-chloro-1H-benzimidazol-2-yl)methylamino]-7-(pyrrolidin-1-yl-carbonyl)-guinoline 260 mg (1.00 mmol) 4-chloro-7-(pyrrolidin-1-yl-carbonyl)-quinoline are heated to 100° C. together with 330 mg (1.51 mmol) (5-chloro-1H-benzimidazol-2-yl)-methylamine with stirring for 20 hours. The resulting mixture is taken up in dichloromethane/methanol. After the addition of silica gel the solvent is eliminated in vacuo. Then the product is purified by chromatography on silica gel (eluant: dichloromethane/ethanol=20:1).

Yield: 66 mg (15%)

$R_f$ value: 0.85 (silica gel; dichloromethane/ethanol=95:5)

$C_{22}H_{20}ClN_5O$ (405.89)

Mass spectrum: $(M+H)^+$=406/408 (chlorine isotope)

EXAMPLE 2

6-chloro-4-[C-(5-chloro-1H-benzimidazol-2-yl)-methylamino]-7-(pyrrolidin-1-yl-carbonyl)-quinazoline

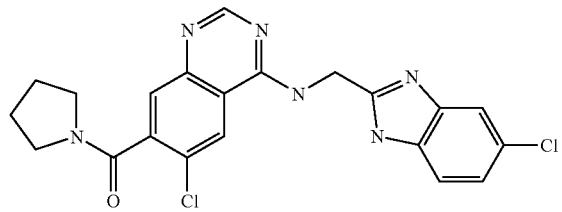

(a) 6-chloro-4-oxo-3.4-dihydro-quinazoline-7-carboxylic acid-hydrochloride 20.0 g (92.8 mmol) 2-amino-5-chloro-terephthalic acid are added batchwise to 35 ml (0.80 mol) formamide under a nitrogen atmosphere at 160° C. and the mixture is kept at 160° C. for 4 hours with stirring. The mixture is then poured into 500 ml ice water and adjusted to pH 3-4 with 2-molar hydrochloric acid solution. The mixture is diluted with a further 500 ml of water and stirred for 15 minutes at ambient temperature. Then the precipitate is filtered off, washed with water until neutral and dried at 40° C. The solid obtained is stirred in ether for another 30 minutes at ambient temperature, filtered off and dried.

Yield: 15.15 g (73%)

$R_f$ value: 0.30 (silica gel; dichloromethane/ethanol=4:1+1% acetic acid)

$C_9H_5ClN_2O_3 \times HCl$ (224.60/261.07)

Mass spectrum: $(M+H)^+$=225/227 (chlorine isotope)

(b) 4,6-dichloro-quinazoline-7-carboxylic acid chloride 2.50 g (11.1 mmol) 6-chloro-4-oxo-3,4-dihydro-quinazoline-7-carboxylic acid are refluxed for 15 hours in 50 ml of thionyl chloride and 0.3 ml of dimethylformamide. Then volatile constituents are eliminated in vacuo and the product is further reacted immediately without any more purification.

Yield: 2.91 g (98%)

$C_9H_3Cl_3N_2O$ (261.50)

Mass spectrum: $(M-H)^-$=260/262/264 (chlorine isotope)

(c) 4.6-dichloro-7-(pyrrolidin-1-yl-carbonyl)-quinazoline 0.56 ml (6.3 mmol) pyrrolidine are dissolved in 10 ml dichloromethane, within 20 minutes a solution of 1.65 g (6.3 mmol) 4,6-dichloro-quinazoline-7-carboxylic acid chloride in 70 ml dichloromethane is added dropwise at −65° C. and the mixture is stirred for 5 minutes. Then at −65° C. 0.31 ml (3.1 mmol) 10 molar sodium hydroxide solution are added dropwise and then the mixture is stirred for a further 2 hours without cooling. The solvent is distilled off and the residue is purified by chromatography on silica gel (eluant: dichloromethane->dichloromethane/isopropanol=9:1).

Yield: 0.59 g (32%)

$R_f$ value: 0.45 (silica gel; dichloromethane)

$C_{13}H_{11}Cl_2N_3O$ (296.16)

Mass spectrum: $(M+H)^+$=296/298/300 (chlorine isotope)

(d) 6-chloro-4-[(5-chloro-1H-benzimidazol-2-yl)-methylamino]-7-(pyrrolidin-1-yl-carbonyl)-quinazoline 114 mg (0.53 mmol) (5-chloro-1H-benzimidazol-2-yl)-methylamine-hydrochloride together with 150 mg (0.51 mmol) 4,6-dichloro-7-(pyrrolidin-1-yl-carbonyl)-quinazoline are dissolved in 5 ml of N,N-dimethylformamide under a nitrogen atmosphere and combined with 77 μl (0.55 mmol) triethylamine. The mixture is stirred for 3 hours at ambient temperature. Then it is poured into ice water and extracted three times with ethyl acetate. The combined organic phases are washed with saturated sodium chloride solution, dried over sodium sulphate and the solvent eliminated in vacuo. The residue is purified by chromatography on silica gel (eluant: dichloromethane/ethanol=1:0->25:1>19:1>9:1).

Yield: 42 mg (29%)
$R_f$ value: 0.45 (silica gel; dichloromethane/ethanol=1:1)
$C_{21}H_{18}Cl_2N_6O$ (441.32)
Mass spectrum: $(M-H)^-=439/441/443$ (chlorine isotope)

EXAMPLE 3

4-[C-(5-chloro-1H-benzimidazol-2-yl)methylamino]-7-(pyrrolidin-1-yl-carbonyl)-quinazoline

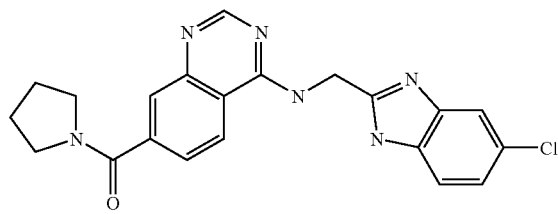

Prepared analogously to Example 2d from 4-chloro-7-(pyrrolidin-1-yl-carbonyl)-quinazoline, C-(5-chloro-1H-benzimidazol-2-yl)-methylamine-hydrochloride and triethylamine in N,N-dimethylformamide with subsequent purification by the addition of ethyl acetate and water, filtration of the precipitate formed and drying at 50° C.

Yield: 60%
$R_f$ value: 0.37 (silica gel; dichloromethane/ethanol=9:1)
$C_{21}H_{19}ClN_6O$ (406.88)
Mass spectrum: $(M+H)^+=407/409$ (chlorine isotope)

EXAMPLE 4

6-chloro-4-[1-(5-chloro-1H-benzimidazol-2-yl)-ethylamino]-7-(2,5-dihydropyrrol-1-yl-carbonyl)-quinazoline

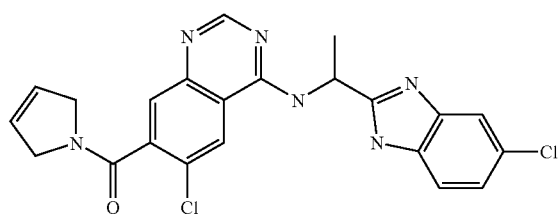

(a) N'-benzyloxycarbonyl-N-(2-amino-4-chloro)phenyl-alaninamide and N'-benzyloxycarbonyl-N-(2-amino-5-chloro)phenyl-alaninamide 4.50 g (20.2 mmol) N-benzyloxycarbonylalanine and 3.60 g (22.2 mmol) N,N'-carbonyldiimidazole are stirred in 25 ml of dimethylformamide for 10 minutes and then slowly combined with a solution of 4-chloro-o-phenylenediamine (6.00 g, 42.1 mmol) and 4.88 ml (44.4 mmol) N-methylmorpholine in 25 ml of dimethylformamide and stirred for 16 hours at ambient temperature. Then the mixture is combined with water and extracted three times with methylene chloride. The combined organic phases are dried with sodium sulphate and evaporated down. The residue is purified by chromatography with silica gel (gradient: methylene chloride/ethanol=100:0->95:5). The title compounds are contaminated with amounts of diacylated phenylenediamine.

Yield: 6.0 g (mixture)
$R_f$ value: 0.35 (silica gel; dichloromethane/ethanol=19:1)

(b) N-benzyloxycarbonyl-1-(5-chloro-1H-benzimidazol-2-yl)ethylamine

The mixture prepared in Example 4a (6.0 g) is dissolved in 30 ml glacial acetic acid and heated to boiling for 8 hours and stirred for a further 16 hours at ambient temperature. The acetic acid is distilled off and the crude product purified by chromatography on silica gel (gradient: methylene chloride/ethanol=100:0->98:2).

Yield: 5.00 g (contaminated, approx. 80% title compound)
$R_f$ value: 0.40 (silica gel; dichloromethane/ethanol=19:1)

(c) 1-(5-chloro-1H-benzimidazol-2-yl)ethylamine 5.00 g (contaminated) N-benzyloxycarbonyl-1-(5-chloro-1H-benzimidazol-2-yl)ethylamine are dissolved in a mixture of 100 ml of methanol and 40 ml methylene chloride, combined with 1.0 g palladium on charcoal and treated for 1 hour with hydrogen at 3.4 bars pressure. The solvents are distilled off and the crude product is purified by chromatography with silica gel (eluant: methylene chloride/ethanol=95:5+0.2% ammonia).

Yield: 1.08 g (25% over 3 steps)
$R_f$ value: 0.37 (silica gel; dichloromethane/ethanol=4:1+2% ammonia)
$C_9H_{10}ClN_3$ (195.65)
Mass spectrum: $(M+H)^+=196/198$ (chlorine isotope)

(d) 6-chloro-4-[1-(5-chloro-1H-benzimidazol-2-yl)-ethylamino]-7-(2,5-dihydropyrrol-1-yl-carbonvi)-quinazoline Prepared analogously to Example 2d from 4,6-dichloro-7-(dihydropyrrol-1-yl-carbonyl)-quinazoline, 1-(5-chloro-1H-benzimidazol-2-yl)ethylamine and triethylamine in N,N-dimethylformamide.

Yield: 46%
$R_f$ value: 0.55 (silica gel; dichloromethane/ethanol=9:1)
$C_{22}H_{18}Cl_2N_6O$ (453.33)
Mass spectrum: $(M+H)^+=453/455/457$ (chlorine isotope)

EXAMPLE 5

6-chloro-4-[1-(5-chloro-1H-benzimidazol-2-yl)-ethylamino]-7-(2-tert.-butyloxycarbonyl-aminomethyl-pyrrolidin-1-yl-carbonyl)-quinazoline

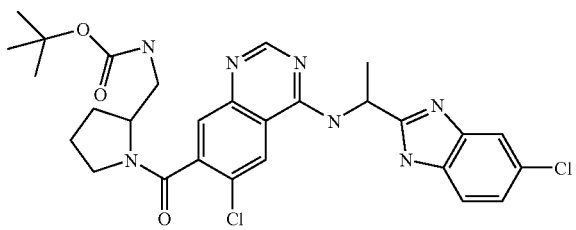

Prepared analogously to Example 2c from 4,6-dichloro-quinazoline-7-carboxylic acid chloride, 2-tert.-butoxycarbonylaminomethyl-pyrrolidine and sodium hydroxide solution in dichloromethane and subsequent reaction analogously to Example 2d with 1-(5-chloro-1H-benzimidazol-2-yl)ethylamine and triethylamine in N,N-dimethylformamide.

Yield: 23% (over 2 steps)

$R_f$ value: 0.65 (silica gel; dichloromethane/isopropanol=9:1)

$C_{28}H_{31}Cl_2N_7O_3$ (584.51)

Mass spectrum: $(M+H)^+$=584/586/588 (chlorine isotope)

EXAMPLE 6

6-chloro-4-[1-(5-chloro-1H-benzimidazol-2-yl)-ethylamino]-7-(2-aminomethyl-pyrrolidin-1-yl-carbonyl)-quinazoline

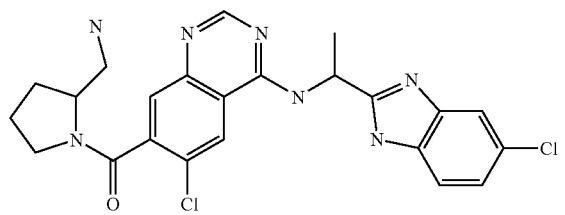

300 mg (0.51 mmol) 6-chloro-4-[1-(5-chloro-1H-benzimidazol-2-yl)-ethylamino]-7-(2-tert.-butoxycarbonylaminomethyl-pyrrolidin-1-yl-carbonyl)-quinazoline are dissolved in 5 ml dioxane and combined with 5 ml 6-molar hydrochloric acid solution with stirring at ambient temperature. The mixture is heated to 40° C. for 2 hours. The mixture is then stirred into ice water and adjusted to pH 8 with ammonia solution. Then it is extracted three times with ethyl acetate, the combined organic phases are washed with sodium chloride solution, dried over sodium sulphate and the solvent eliminated in vacuo. The residue is treated with ether, filtered off and dried.

Yield: 46%

$R_f$ value: 0.10 (silica gel; dichloromethane/ethanol=4:1 + 1% acetic acid)

$C_{23}H_{23}Cl_2N_7O$ (484.39)

Mass spectrum: $(M-H)^-$=482/484/486 (chlorine isotope)

EXAMPLE 7

6-chloro-4-[1-(5-chloro-1H-benzimidazol-2-yl)-ethylamino]-7-(morpholin-4-yl-carbonyl)-quinazoline

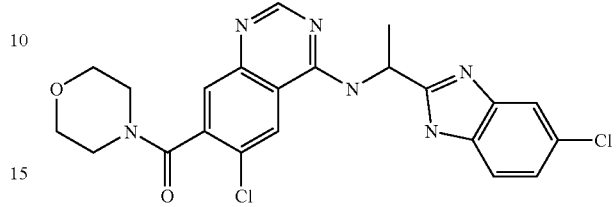

Prepared analogously to Example 2c from 4,6-dichloro-quinazoline-7-carboxylic acid chloride, morpholine and sodium hydroxide solution in dichloromethane and subsequent reaction analogously to Example 2d with 1-(5-chloro-1H-benzimidazol-2-yl)ethylamine and triethylamine in N,N-dimethylformamide.

Yield:. 10.8% (over 2 steps)

$R_f$ value: 0.60 (silica gel; dichloromethane/ethanol=9:1)

$C_{22}H_{20}Cl_2N_6O_2$ (471.35)

Mass spectrum: $(M+H)^+$=471/473/475 (chlorine isotope)

EXAMPLE 8

6-chloro-4-[1-(S)-(5-chloro-1H-benzimidazol-2-yl)-ethylamino]-7-(piperazin-3-on-1-yl-carbonyl)-quinazoline

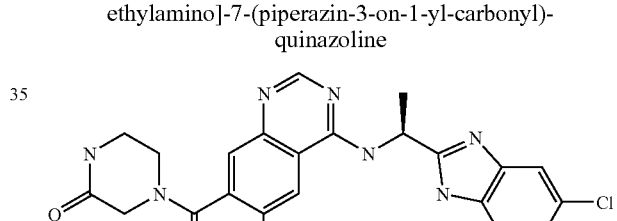

(a) (S)-N'-tert.-butoxycarbonyl-N-(2-amino-4-chloro)phenyl-alaninamide and (S)-N'-tert.-butoxycarbonyl-N-(2-amino-5-chloro)phenyl-alaninamide 6.64 g (35.1 mmol) (S)-N-tert.-butoxycarbonylalanine and 5.00 g (35.1 mmol) 4-chloro-o-phenylenediamine are dissolved in 150 ml of tetrahydrofuran, and 7.24 g (35.1 mmol) N,N'-dicyclohexylcarbodiimide are slowly added at 0° C. with stirring. After stirring for 16 hours at ambient temperature the mixture is filtered and the solvent eliminated in vacuo. The residue is recrystallised from 50 ml of ethyl acetate and dried at 50° C.

Yield: 6.35 g (58%) (mixture of the two title compounds)

$R_f$ value: 0.66 (silica gel; dichloromethane/ethanol=9:1)

$C_{14}H_{20}ClN_3O_3$ (313.79)

Mass spectrum: $(M+H)^+$=314/316 (chlorine isotope)

(b) (S)-N-tert.-butoxycarbonyl-1-(5-chloro-1H-benzimidazol-2-yl)ethylamine

The mixture prepared in Example 8a (6.35 g) is combined with 75 ml glacial acetic acid under an argon atmosphere and heated to 55° C. for 4 h. The acetic acid is distilled off in vacuo.

Yield: 6.80 g (94%)
$R_f$ value: 0.70 (silica gel; dichloromethane/ethanol=9:1+ 1% ammonia solution)
Mass spectrum: $(M-H)^-=294/296$ (chlorine isotope)

(c) (S)-1-(5-chloro-1H-benzimidazol-2-yl)ethylamine-ditrifluoroacetate 1.50 g (5.07 mmol) (S)-N-tert.-butoxycarbonyl-1-(5-chloro-1H-benzimidazol-2-yl)ethylamine are combined with a solution of 7 ml (92 mmol) trifluoroacetic acid in 50 ml dichloromethane and stirred for 70 minutes at ambient temperature. Volatile constituents are eliminated in vacuo, the residue is taken up twice in ethanol and twice in dichloromethane.
Yield: 2.05 g (95%)
$R_f$ value: 0.25 (silica gel; dichloromethane/ethanol=9:1+ 1% ammonia solution)
$C_9H_{10}ClN_3 \times 2\ C_2HF_3O_2$ (195.65/423.70)
Mass spectrum: $(M+H)^+=196/198$ (chlorine isotope)

(d) 6-chloro-4-[1-(S)-(5-chloro-1H-benzimidazol-2-yl)-ethylamino]7-(piperazin-3-on-1-yl-carbonyl)-quinazoline Prepared analogously to Example 2d from 4,6-dichloro-7-(piperazin-3-on-1-yl-carbonyl)-quinazoline, (S)-1-(5-chloro-1H-benzimidazol-2-yl)ethylamine -ditrifluoroacetate and triethylamine in N,N-dimethylformamide.
Yield: 22%
$R_f$ value: 0.30 (silica gel; dichloromethane/isopropanol=9:1)
$C_{22}H_{19}Cl_2N_7O_2$ (484.35)
Mass spectrum: $(M+H)^+=484/486/488$ (chlorine isotope)

EXAMPLE 9

6-chloro-4-[1-(S)-(5-chloro-1H-benzimidazol-2-yl)-ethylamino]-7-(2,5-dihydropyrrol-1-yl-carbonyl)-quinazoline

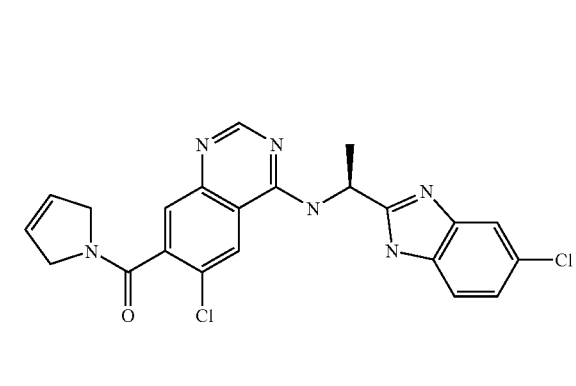

Prepared analogously to Example 2c from 4,6-dichloro-quinazoline-7-carboxylic acid chloride, 2,5-dihydropyrrole and sodium hydroxide solution in dichloromethane and subsequent reaction analogously to Example 2d with (S)-1-(5-chloro-1H-benzimidazol-2-yl)ethylamine and triethylamine in N,N-dimethylformamide.

Yield: 22% (over 2 steps)
$R_f$ value: 0.55 (silica gel; dichloromethane/ethanol=9:1)
$C_{22}H_{18}Cl_2N_6O$ (453.33)
Mass spectrum: $(M+H)^+=453/455/457$ (chlorine isotope)

EXAMPLE 10

6-chloro-4-[1-(S)-(5-chloro-1H-benzimidazol-2-yl)-ethylamino]-7-(pyrrolidin-1-yl-carbonyl)-quinazoline

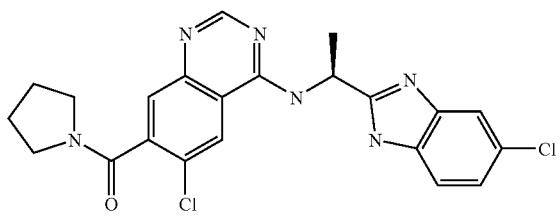

125 mg (0.28 mmol) 6-chloro-4-[1-(S)-(5-chloro-1H-benzimidazol-2-yl)-ethylamino]-7-(2,5-dihydropyrrol-1-yl-carbonyl)-quinazoline are dissolved in 20 ml of methanol, combined with 100 mg Raney nickel and treated with hydrogen at 5 bars pressure for 5 hours at ambient temperature. Then the mixture is filtered and the filtrate evaporated down in vacuo. The residue is treated with 20 ml of a mixture of ethyl acetate and diethyl ether in the ratio 1:1, filtered off and dried.
Yield: 82 mg (65%)
$R_f$ value: 0.50 (silica gel; dichloromethane/ethanol=9:1+ 1% acetic acid)
$C_{22}H_{20}Cl_2N_6O$ (455.35)
Mass spectrum: $(M+H)^+=455/457/459$ (chlorine isotope)

EXAMPLE 11

4-[1-(5-chloro-1H-benzimidazol-2-yl)-ethylamino]-7-(pyrrolidin-1-yl-carbonyl)-quinoline Prepared analogously to Example 1f from 4-chloro-7-(pyrrolidin-1-yl-carbonyl)-quinoline and 1-(5-chloro-1H-benzimidazol-2-yl)ethylamine.
Yield: 33%
$R_f$ value: 0.55 (silica gel; dichloromethane/methanol=9:1)
$C_{22}H_{22}ClN_5O$ (419.914)
Mass spectrum: $(M+H)^+=420/422$ (chlorine isotope)

EXAMPLE 12

4-[1-(5-chloro-1H-benzimidazol-2-yl)-3-methylsulphanyl-propylamino]-6-methyl-7-(pyrrolidin-1-yl-carbonyl)-quinoline

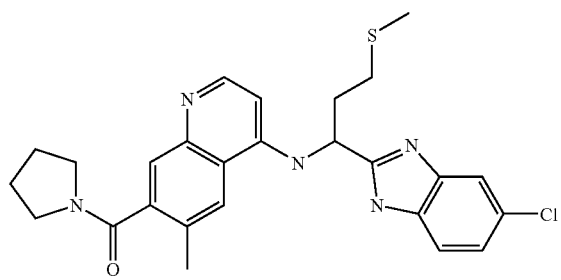

(a) 2,2-dimethyl-5-[(4-methyl-3-trifluoromethyl-phenylamino)-methylene]-[1,3]-dioxan-4,6-dione 56.5 g (0.392 mol) 2,2-dimethyl-[1,3]-dioxan-4,6-dione are stirred in 375 ml (3.43 mol) trimethyl orthoformate at reflux temperature. The mixture is cooled, 47.5 g (0.27 mol) 4-methyl-3-trifluoromethyl-aniline is added and the mixture is stirred for 6 hours at reflux temperature and two days at ambient temperature. The mixture is cooled, the precipitated solid is suction filtered, washed with petroleum ether and dried.

Yield: 38.6 g (30%)
$R_f$ value: 0.36 (silica gel; dichloromethane)
$C_{15}H_{14}F_3NO_4$ (329.278)
Mass spectrum: $(M+H)^+=330$ $(M-H)^-=328$

(b) 6-methyl-7-trifluoromethyl-1H-luinolin-4-one 5 g (15.2 mmol) 2,2-dimethyl-5-[(4-methyl-3-trifluoromethyl-phenylamino)-methylene]-[1,3]-dioxan-4,6-dione are stirred in 165 g diphenylether for 30 minutes at 245° C. The mixture is cooled, the precipitated solid is suction filtered and washed with plenty of petroleum ether.

Yield: 2.84 g (82%)
$R_f$ value: 0.41 (silica gel; dichloromethane/methanol=95:5)
$C_{11}H_8F_3NO$ (227.188)
Mass spectrum: $(M+H)^+=228$

(c) 4-chloro-6-methyl-7-trifluoromethyl-quinoline 1.14 g (5 mmol) 6-methyl-7-trifluoromethyl-1H-quinolin-4-one are stirred in 15 ml phosphorus oxychloride for 3 hours at 80° C. The solution is carefully added to ice water, stirred for 15 minutes and the solution is made basic with 33% ammonia solution while cooling with ice (pH=8). The precipitated solid is suction filtered and dried.

Yield: 0.79 g (64%)
$R_f$ value: 0.76 (silica gel; dichloromethane/methanol=95:5)
$C_{11}H_7ClF_3N$ (245.633)
Mass spectrum: $(M+H)^+=246/248$ (chlorine isotope)

(d) 4-chloro-6-methyl-quinoline-7-carboxylic acid

Prepared analogously to Example 1d from 4-chloro-6-methyl-7-trifluoromethyl-quinoline.
Yield: 76% (87%)
$C_{11}H_8ClNO_2$ (221.645)
Mass spectrum: $(M-H)^-=220/222$ (chlorine isotope)

(e) 4-chloro-6-methyl-7-(pyrrolidin-1-vicarbonyl)-quinoline 1.28 g (87%, 5 mmol) 4-chloro-6-methyl-quinoline-7-carboxylic acid are suspended in 20 ml of thionyl chloride and stirred for 2 hours at reflux temperature.

The solvent is distilled off, combined with toluene and evaporated to dryness. The crude product is combined with 3 ml triethylamine and then with 1 ml (12.1 mmol) pyrrolidine and stirred for three days at ambient temperature. The suspension is concentrated and combined with water and ethyl acetate. The aqueous phase is extracted three times with ethyl acetate. The organic phases are combined, dried over sodium sulphate and evaporated to dryness. The crude product is purified by chromatography (silica gel; eluant: dichloromethane/methanol 95:5).

Yield: 0.85 g (62% over 2 steps)
$R_f$ value: 0.57 (silica gel; dichloromethane/methanol=95:5)
$C_{15}H_{15}ClN_2O$ (274.753)
Mass spectrum: $(M+H)^+=275$

(f) 4-[1-(5-chloro-1H-benzimidazol-2-yl)-3-methyl-sulphanyl-propylamino]-6-methyl-7-(Pyrrolidin-1-yl-carbonyl)-guinoline Prepared analogously to Example 1f from 4-chloro-6-methyl-7-(pyrrolidin-1-yl-carbonyl)-quinoline and 1-(5-chloro-1H-benzimidazol-2-yl)-3-methylsulphanyl-propylamine.

Yield: 66%
$R_f$ value: 0.21 (silica gel; dichloromethane/methanol=100:5)
$C_{26}H_{28}ClN_5OS$ (496.06)
Mass spectrum: $(M+H)^+=494/496$ (chlorine isotope) $(M-H)^-=492/494$ (chlorine isotope)

EXAMPLE 13

4-[1-(5-chloro-1H-benzimidazol-2-yl)-ethylamino]-6-methyl-7-(pyrrolidin-1-yl-carbonyl)-quinoline

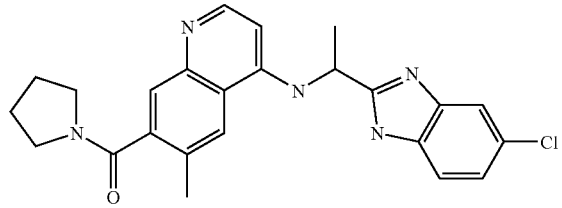

Prepared analogously to Example 1f from 4-chloro-6-methyl-7-(pyrrolidin-1-yl-carbonyl)-quinoline and 1-(5-chloro-1H-benzimidazol-2-yl)ethylamine.

Yield: 11%
$R_f$ value: 0.40 (silica gel; dichloromethane/methanol=9:1)
$C_{24}H_{24}ClN_5O$ (433.94)
Mass spectrum: $(M+H)^+=434/436$ (chlorine isotope) $(M-H)^-=432/434$ (chlorine isotope)

EXAMPLE 14

4-[1-(5-chloro-1H-benzimidazol-2-yl)-ethylamino]-6-methyl-7-(3-oxo-piperazin-1-yl-carbonyl)-quinoline

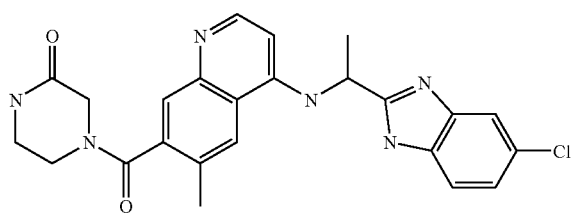

(a) 4-chloro-6-methyl-7-(3-oxo-piperazin-1-ylcarbonyl)-guinoline

Prepared analogously to Example 12e from 4-chloro-6-methyl-quinoline-7-carboxylic acid and piperazin-2-one.
Yield: 38% over two steps
$R_f$ value: 0.42 (silica gel; dichloromethane/methanol=9:1)
$C_{15}H_{14}ClN_3O_2$ (303.75)
Mass spectrum: $(M+H)^+$=304/306 (chlorine isotope)

(b) 4-[1-(5-chloro-1H-benzimidazol-2-yl)-ethylamino]-6-methyl-7-(3-oxo-piperazin-1-yl-carbonyl)-guinoline Prepared analogously to Example 1f from 4-chloro-6-methyl-7-(3-oxo-piperazin-1-ylcarbonyl)-quinoline and 1-(5-chloro-1H-benzimidazol-2-yl)ethylamine.
Yield: 48%
$R_f$ value: 0.17 (silica gel; dichloromethane/methanol=85:15)
$C_{24}H_{23}ClN_6O_2$ (463.94)
Mass spectrum: $(M+H)^+$=463/465 (chlorine isotope) $(M-H)^-$=461/463 (chlorine isotope)

EXAMPLE 15

4-[(1R/S)-1-(5-chloro-1H-benzimidazol-2-yl)-ethylamino]-6-methyl-7-[(2R)-2-aminomethyl-pyrrolidin-1-yl-carbonyl]-quinoline

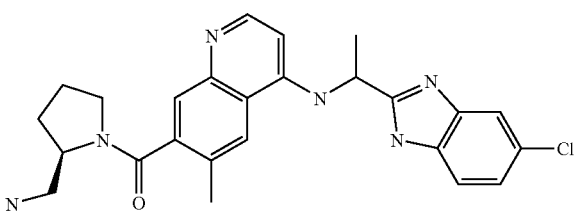

(a) 4-chloro-6-methyl-7-[(2R)-2-(N-benzyloxycarbonyl-aminomethyl)-pyrrolidin-1-yl-carbonyl]-quinoline Prepared analogously to Example 12e from 4-chloro-6-methyl-quinoline-7-carboxylic acid and (2R)-2-(N-benzyloxycarbonyl-aminomethyl)-pyrrolidine.
Yield: 14%
$R_f$ value: 0.47 (silica gel; dichloromethane/methanol=95:5)
$C_{24}H_{24}ClN_3O_3$ (437.93)
Mass spectrum: $(M+H)^+$=438/440 (chlorine isotope)

(b) 4-[(1R/S)-1-(5-chloro-1H-benzimidazol-2-yl)-ethylamino]-6-methyl-7-[(2R)-2-(N-benzyloxycarbonyl-aminomethyl)-pyrrolidin-1-yl-carbony-]-quinoline Prepared analogously to Example if from 4-chloro-6-methyl-7-[(2R)-2-(N-benzyloxycarbonyl-aminomethyl)-pyrrolidin-1-yl-carbonyl]-quinoline and 1-(5-chloro-1H-benzimidazol-2-yl)ethylamine.
Yield: 62%
$R_f$ value: 0.48 (silica gel; dichloromethane/methanol=90:10)
$C_{33}H_{33}ClN_6O_3$ (597.12)
Mass spectrum: $(M+H)^+$=597/599 (chlorine isotope) $(M-H)^-$=595/597 (chlorine isotope)

(c) 4-[(1R/S)-1-(5-chloro-1H-benzimidazol-2-yl)-ethylamino]-6-methyl-7-[(2R)-2-aminomethyl-pyrrolidin-1-yl-carbony-]-quinoline An ice-cooled solution of 75 mg (0.13 mmol) 4-[(1R/S)-1-(5-chloro-1H-benzimidazol-2-yl)-ethylamino]-6-methyl-7-[(2R)-2-(N-benzyloxycarbonyl-aminomethyl)-pyrrolidin-1-yl-carbonyl]-quinoline in 1.5 ml dichloromethane is combined with 90 µl (0.63 mmol) trimethylsilyl iodide and stirred for two hours. It is combined with 1 M HCl solution and extracted with ethyl acetate. The aqueous phase is made alkaline and extracted three times with ethyl acetate. The combined organic phases are dried over sodium sulphate and evaporated down.
Yield: 20 mg (34%)
$C_{25}H_{27}ClN_6O$ (462.99)
Mass spectrum: $(M+H)^+$=463/465 (chlorine isotope) $(M-H)^-$=461/463 (chlorine isotope)

EXAMPLE 16

4-[1-(5-chloro-1H-benzimidazol-2-yl)-3-methylsulphanyl-propylamino]-6-methyl-7-(3-oxo-piperazin-1-yl-carbonyl)-quinoline

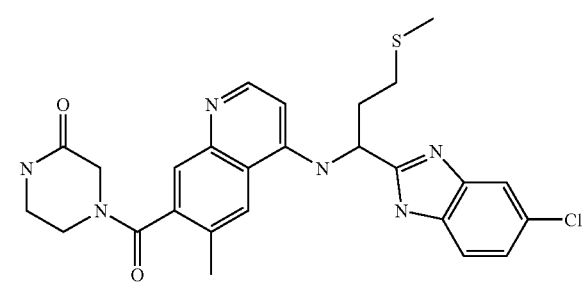

Prepared analogously to Example 1f from 4-chloro-6-methyl-7-(3-oxo-piperazin-1-ylcarbonyl)-quinoline and 1-(5-chloro-1H-benzimidazol-2-yl)-3-methylsulphanyl-propylamine.

Yield: 71%

$R_f$ value: 0.13 (silica gel; dichloromethane/methanol=90:10)

$C_{26}H_{27}ClN_6O_2S$ (523.06)

Mass spectrum: $(M+H)^+=523/525$ (chlorine isotope) $(M-H)^-=521/523$ (chlorine isotope)

EXAMPLE 17

4-[1-(5-chloro-1H-benzimidazol-2-yl)-3-methanesulphonyl-propylamino]-6-methyl-7-(pyrrolidin-1-yl-carbonyl)-quinoline

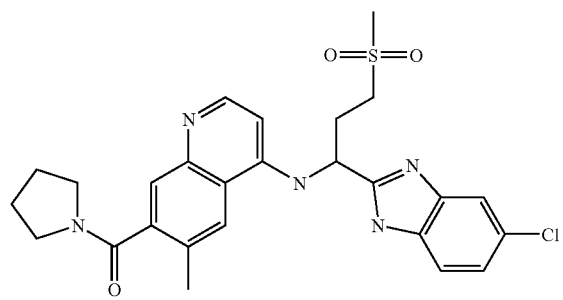

(a) N-tert.-butyloxycarbonyl-1-(5-chloro-1H-benzimidazol-2-yl)-3-methanesulphonyl-propylamine 1 g (2.8 mmol) N-tert.-butyloxycarbonyl-1-(5-chloro-1H-benzimidazol-2-yl)-3-methylsulphanyl-propylamine are dissolved in 40 ml dichloromethane and 5 ml glacial acetic acid and at −15° C. combined with 1.35 g (5.5 mmol) meta-chloroperbenzoic acid. The mixture is stirred for 30 minutes at −15° C. and for two hours at ambient temperature. It is combined with water and the aqueous phase is extracted twice with dichloromethane. The crude product is purified by chromatography (silica gel; eluant: dichloromethane/methanol 95:5).

Yield: 0.55 g (51%)

$R_f$ value: 0.49 (silica gel; dichloromethane/methanol=95:5)

$C_{16}H_{22}ClN_3O_4S$ (387.89)

Mass spectrum: $(M+H)^+=388/390$ (chlorine isotope)

(b) 1-(5-chloro-1H-benzimidazol-2-yl)-3-methanesulphonyl-propylamine

Prepared analogously to Example 8c from N-tert.-butyloxycarbonyl-1-(5-chloro-1H-benzimidazol-2-yl)-3-methanesulphonyl-propylamine.

Yield: 48%

$R_f$ value: 0.24 (silica gel; dichloromethane/methanol=90:10)

$C_{11}H_{14}ClN_3O_2S$ (288.77)

Mass spectrum: $(M+H)^+=288/290$ (chlorine isotope)

(c) 4-[1-(5-chloro-1H-benzimidazol-2-yl)-3-methanesulphonyl-propylamino]-6-methyl-7-(pyrrolidin-1-yl-carbonvy)-guinoline Prepared analogously to Example 1f from 4-chloro-6-methyl-7-(pyrrolidin-1-yl-carbonyl)-quinoline and 1-(5-chloro-1H-benzimidazol-2-yl)-3-methanesulphonyl-propylamine.

Yield: 24%

$R_f$ value: 0.26 (silica gel; dichloromethane/methanol=90:10)

$C_{26}H_{28}ClN_5O_3S$ (526.06)

Mass spectrum: $(M+H)^+=526/528$ (chlorine isotope)

EXAMPLE 18

6-chloro-4-[(1 S)-1-(5-chloro-1H-benzimidazol-2-yl)-ethylamino]-7-[(2R)-2-tert.-butyloxycarbonyl-aminomethyl-pyrrolidin-1-yl-carbonyl]-quinazoline

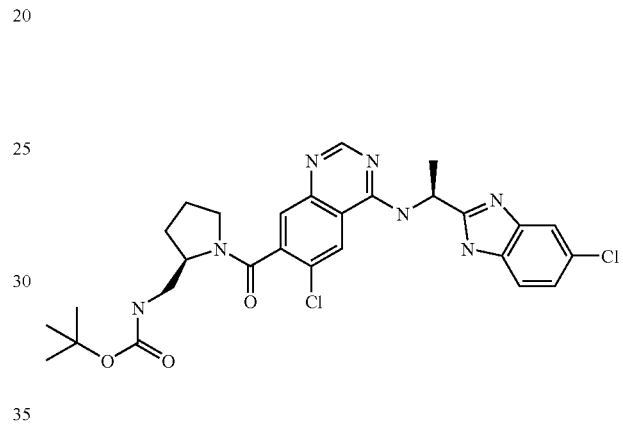

(a) 4,6-dichloro-7-[(2R)-2-tert.-butyloxycarbonyl-aminomethyl-pyrrolidin-1-yl-carbonyl]-quinazoline Prepared analogously to Example 2c from 4,6-dichloroquinazoline-7-carboxylic acid chloride, (2R)-tert.-butyloxycarbonylaminomethyl-pyrrolidine and sodium hydroxide solution in dichloromethane Yield: 55%

$R_f$ value: 0.80 (silica gel; dichloromethane/isopropanol=9:1)

$C_{19}H_{22}Cl_2N_4O_3$ (425.32)

Mass spectrum: $(M+H)^+=425/427/429$ (chlorine isotope)

(b) 6-chloro-4-[(1S)-1-(5-chloro-1H-benzimidazol-2-yl)-ethylamino]-7-[(2R)-2-tert.-butyloxycarbonyl-aminomethyl-pyrrolidin-1-yl-carbonyl]-quinazoline Prepared analogously to Example 2d from 4,6-dichloro-7-[(2R)-2-tert.-butyloxycarbonyl-aminomethyl-pyrrolidin-1-yl-carbonyl]-quinazoline, (S)-1-(5-chloro-1H-benzimidazol-2-yl)ethylamine and triethylamine in N,N-dimethylformamide.

Yield: 64%

$R_f$ value: 0.65 (silica gel; dichloromethane/isopropanol=9:1)

$C_{28}H_{31}Cl_2N_7O_3$ (584.51)

Mass spectrum: $(M+H)^+=584/586/588$ (chlorine isotope)

EXAMPLE 19

6-chloro-4-[(1S)-1-(5-chloro-1H-benzimidazol-2-yl)-ethylamino]-7-[(2R)-2-aminomethyl-pyrrolidin-1-yl-carbonyl]-quinazoline

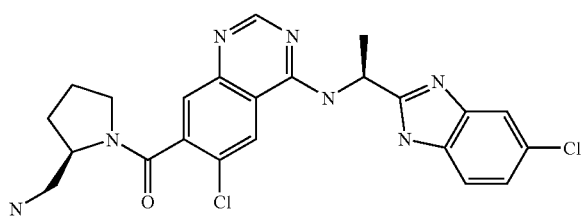

Prepared analogously to Example 8c from 6-chloro-4-[(1S)-1-(5-chloro-1H-benzimidazol-2-yl)-ethylamino]-7-[(2R)-2-tert.-butyloxycarbonyl-aminomethyl-pyrrolidin-1-yl-carbonyl]-quinazoline and trifluoroacetic acid.

Yield: 82%

$R_f$ value: 0.10 (silica gel; dichloromethane/ethanol 9:1+1% acetic acid)

$C_{23}H_{23}Cl_2N_7O$ (484.39)

Mass spectrum: $(M+H)^+=484/486/488$ (chlorine isotope)

EXAMPLE 20

6-chloro-4-[(1S)-1-(5-chloro-1H-benzimidazol-2-yl)-2-hydroxy-ethylamino]-7-(2,5-dihydropyrrol-1-yl-carbonyl)-quinazoline

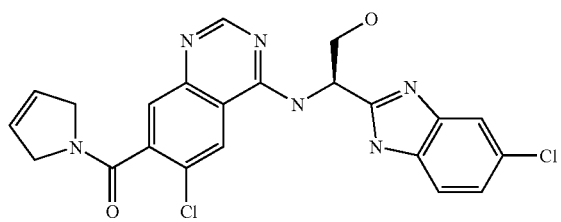

(a) 4,6-dichloro-7-(2.5-dihydropyrrol-1-yl-carbonyl)-quinazoline

Prepared analogously to Example 2c from 4,6-dichloro-quinazoline-7-carboxylic acid chloride, pyrroline and sodium hydroxide solution in dichloromethane Yield: 77%

$R_f$ value: 0.24 (silica gel; ethyl acetate/petroleum ether 1:1)

$C_{13}H_9Cl_2N_3O$ (294.14)

Mass spectrum: $(M+H)^+=294/296/298$ (chlorine isotope)

(b) 6-chloro-4-[(1S)-1-(5-chloro-1H-benzimidazol-2-yl)-2-hydroxy-ethylamino]-7-(2,5-dihydropyrrol-1-yl-carbonyl)-quinazoline Prepared analogously to Example 2d from 4,6-dichloro-7-(2,5-dihydropyrrol-1-yl-carbonyl)-quinazoline, (S)-1-(5-chloro-1H-benzimidazol-2-yl)-2-hydroxy-ethylamine and triethylamine in N,N-dimethylformamide.

Yield: 51%

$R_f$ value: 0.60 (silica gel; dichloromethane/methanol=95:5)

$C_{22}H_{18}Cl_2N_6O_2$ (469.33)

Mass spectrum: $(M+H)^+=469/471/473$ (chlorine isotope)

EXAMPLE 21

6-chloro-4-[(1S)-1-(5-chloro-1H-benzimidazol-2-yl)-2-hydroxy-ethylamino]-7-[(2R)-2-tert.-butyloxy-carbonyl-aminomethyl-pyrrolidin-1-yl-carbonyl]-quinazoline

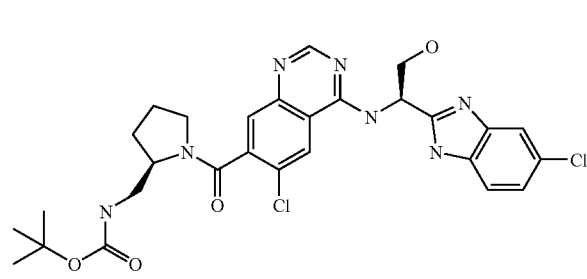

Prepared analogously to Example 2d from 4,6-dichloro-7-[(2R)-2-tert.-butyloxycarbonyl-aminomethyl-pyrrolidin-1-yl-carbonyl]-quinazoline, (S)-1-(5-chloro-1H-benzimidazol-2-yl)-2-hydroxy-ethylamine and triethylamine in N,N-dimethylformamide.

Yield: 26%

$R_f$ value: 0.35 (silica gel; dichloromethane/isopropanol 9:1)

$C_{28}H_{31}Cl_2N_7O_4$ (600.51)

Mass spectrum: $(M+H)^+=600/602/604$ (chlorine isotope)

EXAMPLE 22

6-chloro-4-[(1S)-1-(5-chloro-1H-benzimidazol-2-yl)-2-hydroxy-ethylamino]-7-[(2R)-2-aminomethyl-pyrrolidin-1-yl-carbonyl]-quinazoline

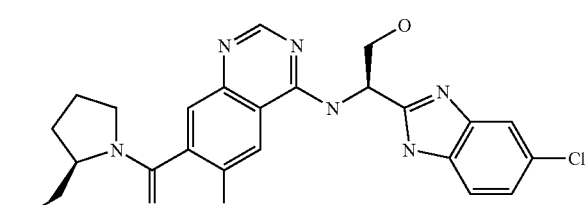

Prepared analogously to Example 8c from 6-chloro-4-[(1S)-1-(5-chloro-1H-benzimidazol-2-yl)-2-hydroxyethylamino]-7-[(2R)-2-tert.-butyloxycarbonyl-aminomethyl-pyrrolidin-1-yl-carbonyl]-quinazoline and trifluoroacetic acid.

Yield: 61%

$R_f$ value: 0.10 (silica gel; dichloromethane/ethanol 8:2+1% acetic acid)

$C_{23}H_{23}Cl_2N_7O_2$ (500.39)

Mass spectrum: $(M+H)^+=502/504/506$ (chlorine isotope)
$(M-H)^-=498/500/502$ (chlorine isotope)

EXAMPLE 23

6-chloro-4-[(1S)-1-(5-chloro-1H-benzimidazol-2-yl)-ethylamino]-7-[(2S)-2-tert.-butyloxycarbonyl-aminomethyl-pyrrolidin-1-yl-carbonyl]-quinazoline

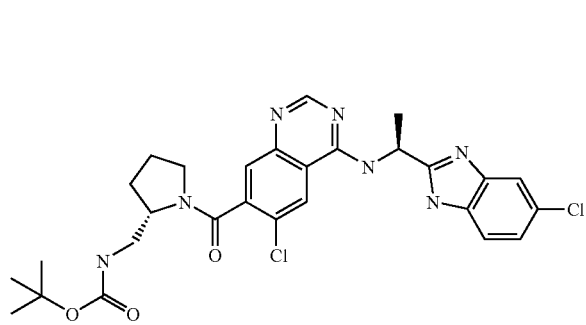

Prepared analogously to Example 2d from 4,6-dichloro-7-[(2S)-2-tert.-butyloxycarbonyl-aminomethyl-pyrrolidin-1-yl-carbonyl]-quinazoline, (S)-1-(5-chloro-1H-benzimidazol-2-yl)ethylamine and triethylamine in N,N-dimethylformamide.

Yield: 19%

$R_f$ value: 0.65 (silica gel; dichloromethane/isopropanol=9:1)

$C_{28}H_{31}Cl_2N_7O_3$ (584.51)

Mass spectrum: $(M+H)^+=584/586/588$ (chlorine isotope)

EXAMPLE 24

6-chloro-4-[(1S)-1-(5-chloro-1H-benzimidazol-2-yl)-ethylamino]-7-[(2S)-2-aminomethyl-pyrrolidin-1-yl-carbonyl]-quinazoline

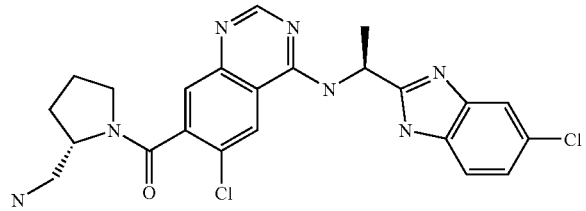

Prepared analogously to Example 8c from 6-chloro-4-[(1S)-1-(5-chloro-1H-benzimidazol-2-yl)-ethylamino]-7-[(2S)-2-teff.-butyloxycarbonyl-aminomethyl-pyrrolidin-1-yl-carbonyl]-quinazoline and trifluoroacetic acid.

Yield: 65%

$R_f$ value: 0.10 (silica gel; dichloromethane/ethanol 9:1+1% acetic acid)

$C_{23}H_{23}Cl_2N_7O$ (484.39)

Mass spectrum: $(M+H)^+=484/486/488$ (chlorine isotope)

EXAMPLE 25

6-chloro-4-[1-(5-chloro-1H-benzimidazol-2-yl)-3-hydroxycarbonylpropylamino]-7-(pyrrolidin-1-yl-carbonyl)-quinazoline

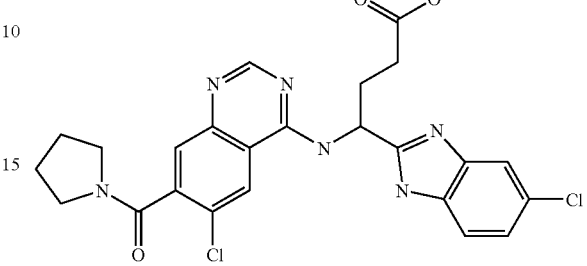

0.54 ml 1-molar sodium hydroxide solution are added to a solution of 162 mg (0.268 mmol) 6-chloro-4-[1-(5-chloro-1H-benzimidazol-2-yl)-3-benzyloxycarbonylpropylamino]-7-(pyrrolidin-1-yl-carbonyl)-quinazoline in 3 ml of tetrahydrofuran. The mixture is stirred for 18 hours at ambient temperature and then acidified by the addition of 40 ml of water and 50 µl glacial acetic acid. It is extracted three times with ethyl acetate, the combined organic phases dried over sodium sulphate and evaporated to dryness. The crude product is triturated with a mixture of tert.-butylmethylether, petroleum ether and ethyl acetate. A white solid is obtained.

Yield: 105 mg (76%)

$R_f$ value: 0.68 (silica gel; ethyl acetate/ethanol/acetic acid 80:15:5)

$C_{24}H_{22}Cl_2N_6O_3$ (513.39)

Mass spectrum: $(M+H)^+=513/515/517$ (chlorine isotope)

EXAMPLE 26

6-chloro-4-[1-(5-chloro-1H-benzimidazol-2-yl)-3-benzyloxycarbonylpropylamino]-7-(pyrrolidin-1-yl-carbonyl)-quinazoline

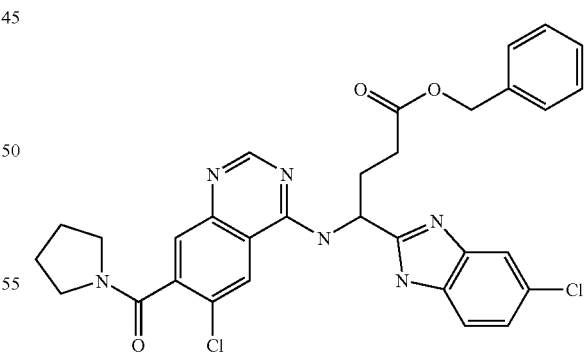

Prepared analogously to Example 2d from 4,6-dichloro-7-(pyrrolidin-1-yl-carbonyl)-quinazoline, 1-(5-chloro-1H-benzimidazol-2-yl)-3-benzyloxycarbonylpropylamine-ditrifluoroacetate and triethylamine in N,N-dimethylformamide.

Yield: 86%

$R_f$ value: 0.38 (silica gel; dichloromethane/isopropanol=95:5)

$C_{31}H_{28}Cl_2N_6O_3$ (603.51)

Mass spectrum: $(M+H)^+=601/603/605$ (chlorine isotope)

EXAMPLE 27

6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline

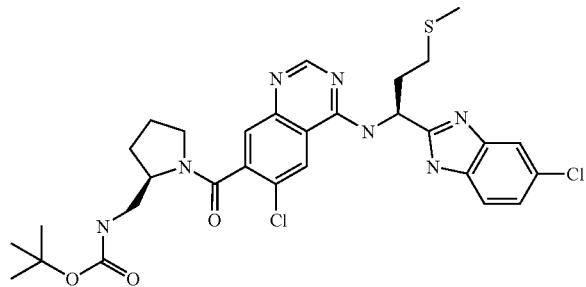

Prepared analogously to Example 2d from 4,6-dichloro-7-[(2R)-2-tert.-butyloxycarbonyl-aminomethyl-pyrrolidin-1-yl-carbonyl]-quinazoline, (S)-1-(5-chloro-1H-benzimidazol-2-yl)-3-methylsulphanyl-ethylamine-ditrifluoroacetate and triethylamine in N,N-dimethylformamide.

Yield: 59%

$R_f$ value: 0.50 (silica gel; dichloromethane/ethanol=9:1)

$C_{30}H_{35}Cl_2N_7O_3S$ (644.63)

Mass spectrum: $(M+H)^+$=644/646/648 (chlorine isotope)

EXAMPLE 28

6-chloro-4-[(1S)-1-(5-chloro-1H-benzimidazol-2-yl)-3-methylsulphanyl-propylamino]-7-(pyrrolidin-1-yl-carbonyl)-quinazoline

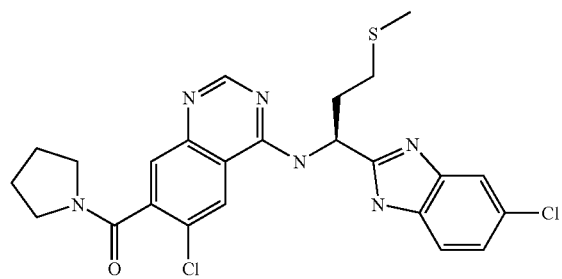

Prepared analogously to Example 2d from 4,6-dichloro-7-(pyrrolidin-1-yl-carbonyl)-quinazoline, (S)-1-(5-chloro-1H-benzimidazol-2-yl)-3-methylsul phanyl-ethylamine-ditrifluoroacetate and triethylamine in N,N-dimethylformamide.

Yield: 46%

$R_f$ value: 0.40 (silica gel; dichloromethane/ethanol=9:1)

$C_{24}H_{24}Cl_2N_6OS$ (515.47)

Mass spectrum: $(M+H)^+$=515/517/519 (chlorine isotope)

EXAMPLE 29

6-chloro-4-[(1S)-1-(5-chloro-1H-benzimidazol-2-yl)-3-methoxy-propylamino]-7-(2,5-dihydropyrrol-1-yl-carbonyl)-quinazoline

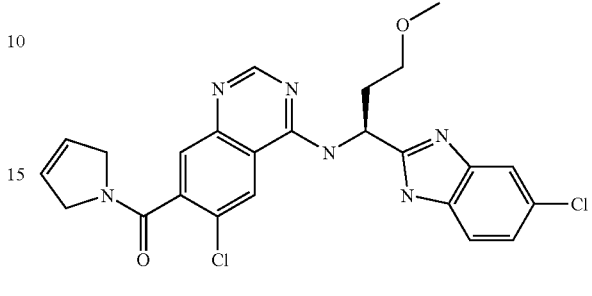

Prepared analogously to Example 2d from 4,6-dichloro-7-(2,5-dihydropyrrol-1-yl-carbonyl)-quinazoline, (S)-1-(5-chloro-1H-benzimidazol-2-yl)-3-methoxy-propylamine-ditrifluoroacetate and triethylamine in N,N-dimethylformamide.

Yield: 79%

$R_f$ value: 0.16 (silica gel; dichloromethane/isopropanol=19:1)

$C_{24}H_{22}Cl_2N_6O_2$ (497.39)

Mass spectrum: $(M+H)^+$=497/499/501 (chlorine isotope) $(M-H)^-$=495/497/499 (chlorine isotope)

EXAMPLE 30

6-chloro-4-[(1S)-1-(5-chloro-1H-benzimidazol-2-yl)-3-methanesulphonyl-propylamino]-7-(pyrrolidin-1-yl-carbonyl)-quinazoline

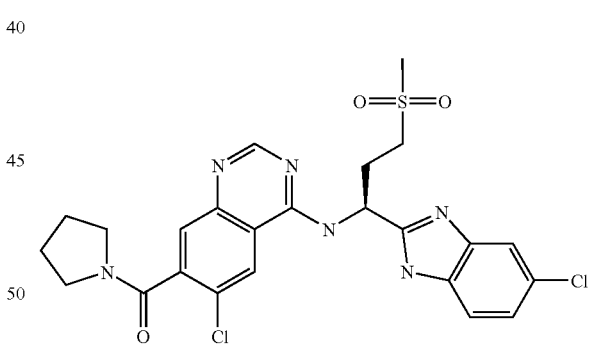

0.25 g (1.1 mmol) meta-chloroperbenzoic acid are added at −10° C. to a solution of 0.2 g (0.39 mmol) 6-chloro-4-[(1S)-1-(5-chloro-1H-benzimidazol-2-yl)-3-methylsulphanyl-propylamino]-7-(pyrrolidin-1-yl-carbonyl)-quinazoline in 10 ml dichloromethane and 1 ml glacial acetic acid and stirred for 30 minutes. Then the mixture is stirred for 4 hours at ambient temperature and washed with 5% sodium hydrogen carbonate solution. The combined organic phases are dried with sodium sulphate and concentrated.

Yield: 0.18 g (85%)

$R_f$ value: 0.40 (silica gel; dichloromethane/methanol=9:1)

$C_{24}H_{24}Cl_2N_6O_3S$ (547.47)

Mass spectrum: $(M+H)^+$=547/549/551 (chlorine isotope)

EXAMPLE 31

6-chloro-4-[(1S)-1-(5-chloro-1H-benzimidazol-2-yl)-3-methylsulphanyl-propylamino]-7-[(2R)-2-aminomethyl-pyrrolidin-1-yl-carbonyl]-quinazoline

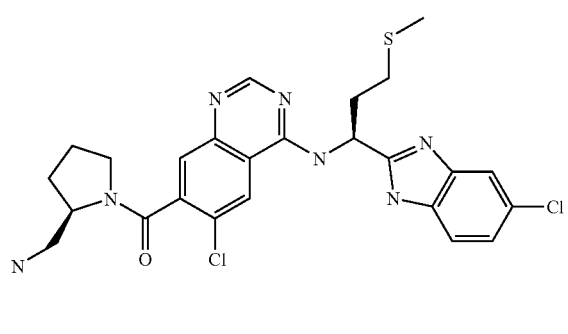

Prepared analogously to Example 8c from 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline and trifluoroacetic acid.

Yield: quantitative $R_f$ value: 0.15 (silica gel; dichloromethane/ethanol 9:1+1% ammonia solution)

$C_{25}H_{27}Cl_2N_7OS$ (544.51)

Mass spectrum: $(M+H)^+$=544/546/548 (chlorine isotope)

EXAMPLE 32

6-chloro-4-[(1S)-1-(5-chloro-1H-benzimidazol-2-yl)-3-methanesulphinyl-propylamino]-7-(pyrrolidin-1-yl-carbonyl)-quinazoline

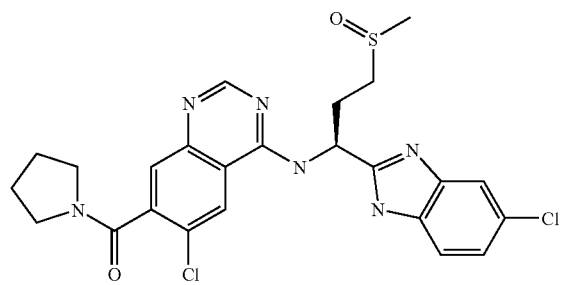

Prepared analogously to Example 30 from 6-chloro-4-[(1S)-1-(5-chloro-1H-benzimidazol-2-yl)-3-methylsulphanyl-propylamino]-7-(pyrrolidin-1-yl-carbonyl)-quinazoline with 1 equivalent of meta-chloroperbenzoic acid.

Yield: 68%

$R_f$ value: 0.25 (silica gel; dichloromethane/methanol=9:1)

$C_{24}H_{24}Cl_2N_6O_2S$ (531.47)

Mass spectrum: $(M+H)^+$=531/533/535 (chlorine isotope)

EXAMPLE 33

6-chloro-4-[(1S)-1-(5-chloro-1H-benzimidazol-2-yl)-3-benzyloxycarbonylpropylamino]-7-(pyrrolidin-1-yl-carbonyl)-quinazoline

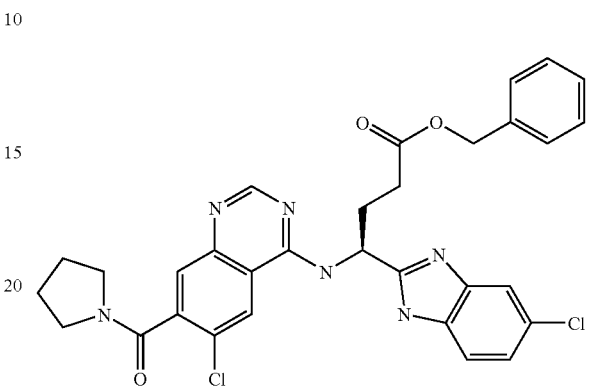

Prepared analogously to Example 2d from 4,6-dichloro-7-(pyrrolidin-1-yl-carbonyl)-quinazoline, (S)-1-(5-chloro-1H-benzimidazol-2-yl)-3-benzyloxycarbonylpropylamine-ditrifluoroacetate and triethylamine in N,N-dimethylformamide.

Yield: 11%

$R_f$ value: 0.38 (silica gel; dichloromethane/isopropanol=95:5)

$C_{31}H_{28}Cl_2N_6O_3$ (603.51)

Mass spectrum: $(M+H)^+$=601/603/605 (chlorine isotope)

EXAMPLE 34

6-chloro-4-[(1S)-1-(5-chloro-1H-benzimidazol-2-yl)-2-hydroxy-ethylamino]-7-(piperazin-3-on-1-yl-carbonyl)-quinazoline

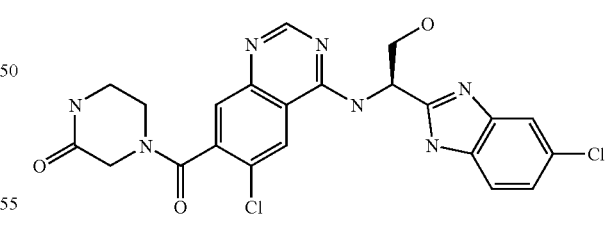

Prepared analogously to Example 2d from 4,6-dichloro-7-(piperazin-3-on-1-yl-carbonyl)-quinazoline, (S)-1-(5-chloro-1H-benzimidazol-2-yl)-2-hydroxy-ethylamine and triethylamine in N,N-dimethylformamide.

Yield: 2%

$R_f$ value: 0.05 (silica gel; dichloromethane/isopropanol=17:3)

$C_{22}H_{19}Cl_2N_7O_3$ (500.35)

Mass spectrum: $(M+H)^+$=500/502/504 (chlorine isotope)

EXAMPLE 35

6-chloro-4-[(1S)-1-(5-chloro-1H-benzimidazol-2-yl)-3-methanesulphinyl-propylamino]-7-[(2R)-2-tert.-butyloxycarbonyl-aminomethyl-pyrrolidin-1-yl-carbonyl]-quinazoline

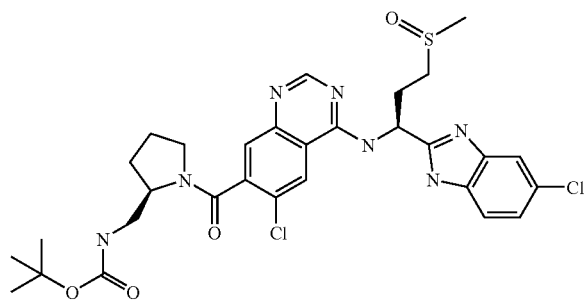

Prepared analogously to Example 30 from 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline with 1 equivalent of meta-chloroperbenzoic acid.

Yield: 70%
$R_f$ value: 0.18 (silica gel; dichloromethane/ethanol=9:1)
$C_{30}H_{35}Cl_2N_7O_4S$ (660.63)
Mass spectrum: $(M+H)^+=660/662/664$ (chlorine isotope)

EXAMPLE 36

6-chloro-4-[(1S)-1-(5-chloro-1H-benzimidazol-2-yl)-ethylamino]-7-hydroxycarbonyl-quinazoline

(a) 6-chloro-4-[(1S)-1-(5-chloro-1H-benzimidazol-2-yl)-ethylamino]-7-methoxycarbonyl-quinazoline

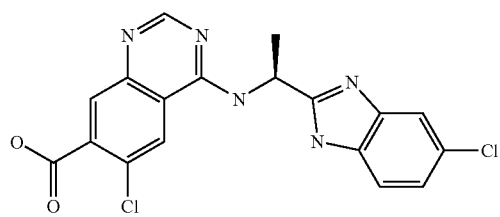

2.88 g (6.8 mmol) (S)-1-(5-chloro-1H-benzimidazol-2-yl)-ethylamine-ditrifluoroacetate are combined with 2.1 ml (15 mmol) triethylamine in 10 ml N,N-dimethylformamide. The mixture is stirred for 5 minutes, then 1.75 g (6.8 mmol) 4,6-dichloro-7-methoxycarbonyl-quinazoline are added and stirred for three hours at ambient temperature. Then the mixture is poured onto ice water and the precipitated solid is suction filtered. It is washed with water and dried.

Yield: 1.9 g (67%)
$R_f$ value: 0.45 (silica gel; dichloromethane/ethanol=19:1)
$C_{19}H_{15}Cl_2N_5O_2$ (416.27)
Mass spectrum: $(M+H)^+=416/418/420$ (chlorine isotope)

(b) 6-chloro-4-[(1S)-1-(5-chloro-1H-benzimidazol-2-yl)-ethylamino]-7-hydroxycarbonyl-quinazoline 1.85 g (4.44 mmol) 6-chloro-4-[(1S)-1-(5-chloro-1H-benzimidazol-2-yl)-ethylamino]-7-methoxycarbonyl-quinazoline are dissolved in 50 ml of tetrahydrofuran/methanol mixture (v/v=1:1) and combined with 294 mg (7 mmol) lithium hydroxide hydrate and stirred for one day at ambient temperature. Then the solvents are distilled off and the residue is combined with 50 ml of water. It is acidified with 2N acetic acid to pH=4, the precipitated solid is suction filtered, washed with water until neutral and dried until a constant weight is obtained.

Yield: 1.35 g (76%)
$R_f$ value: 0.40 (Reversed phase RP8; methanol/5% sodium chloride solution=7:3)
$C_{18}H_{13}Cl_2N_5O_2$ (402.24)
Mass spectrum: $(M-H)^-=400/402/404$ (chlorine isotope)

EXAMPLE 37

6-chloro-4-[(1S)-1-(5-chloro-1H-benzimidazol-2-yl)-ethylamino]-7-[(3R)-3-aminomethyl-pyrrolidin-1-yl-carbonyl]-quinazoline

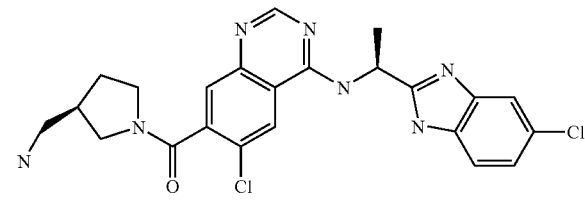

(a) 6-chloro-4-[(1S)-1-(5-chloro-1H-benzimidazol-2-yl)-ethylamino]-7-[(3R)-3-(9H-fluoren-9-yl-methoxycarbonyl)aminomethyl-pyrrolidin-1-yl-carbony-]-quinazoline 402 mg (1 mmol) 6-chloro-4-[(1S)-1-(5-chloro-1H-benzimidazol-2-yl)-ethylamino]-7-hydroxycarbonyl-quinazoline are dissolved in 5 ml N,N-dimethylformamide and combined with 321 mg (1 mmol) TBTU and 0.33 ml (3 mmol) N-methylmorpholine. After 5 minutes 359 mg (1 mmol) (3R)-3-[(9H-fluoren-9-ylmethoxycarbonyl)aminomethyl]-pyrrolidine-hydrochloride are added and stirred for three hours at ambient temperature. The mixture is poured onto ice water and the precipitated solid is suction filtered. It is dissolved in methanol/ethyl acetate, combined with activated charcoal and then filtered through kieselguhr. The solution thus obtained is evaporated to dryness, the residue is triturated with a little diethyl ether and dried.

Yield: 660 mg (93%)
$R_f$ value: 0.45 (silica gel; dichloromethane/ethanol=9:1)
$C_{38}H_{33}Cl_2N_7O_3$ (706.64)
Mass spectrum: $(M+H)^+=706/708/710$ (chlorine isotope)

(b) 6-chloro-4-[(1S)-1-(5-chloro-1H-benzimidazol-2-yl)-ethylamino]-7-[(3R)-3-aminomethyl-pyrrolidin-1-yl-carbonyl]-quinazoline 1 ml diethylamine are added to a solution of 0.65 g (0.92 mmol) 6-chloro-4-[(1S)-1-(5-chloro-1H-benzimidazol-2-yl)-ethylamino]-7-[(3R)-3-(9H-fluoren-9-ylmethoxycarbonyl)aminomethyl-pyrrolidin-1-yl-carbonyl]-quinazoline in 15 ml of tetrahydrofuran. After two days' stirring at ambient temperature the mixture is concentrated and combined with water. The aqueous phase is extracted three times with ethyl acetate. The combined organic phases are dried over sodium sulphate and evaporated down.

Yield: 40 mg (9%)

$R_f$ value: 0.35 (Reversed phase RP8; methanol/5% sodium chloride solution=7:3)

$C_{23}H_{23}Cl_2N_7O$ (484.39)

Mass spectrum: $(M+H)^+$=484/486/488 (chlorine isotope)

EXAMPLE 38

6-chloro-4-[(1S)-1-(5-chloro-1H-benzimidazol-2-yl)-3-benzyloxycarbonylpropylamino]-7-[(2S)-2-tert.-butyloxycarbonyl-aminomethyl-pyrrolidin-1-yl-carbonyl]-quinazoline

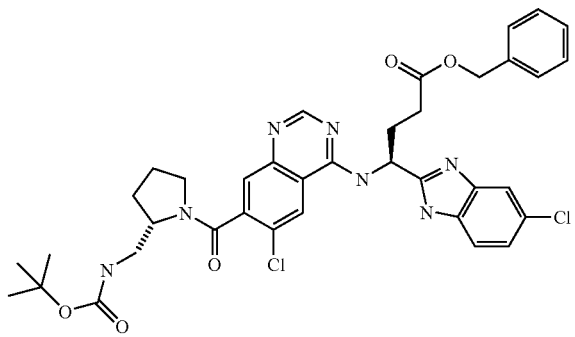

Prepared analogously to Example 2d from 4,6-dichloro-7-[(2S)-2-tert.-butyloxycarbonyl-aminomethyl-pyrrolidin-1-yl-carbonyl]-quinazoline, (S)-1-(5-chloro-1H-benzimidazol-2-yl)-3-benzyloxycarbonylpropyl-amine-trifluoroacetate and triethylamine in N,N-dimethylformamide.

Yield: 26%

$R_f$ value: 0.75 (silica gel; dichloromethane/isopropanol=9:1)

$C_{37}H_{39}Cl_2N_7O_5$ (732.67)

Mass spectrum: $(M+H)^+$=732/734/736 (chlorine isotope)

EXAMPLE 39

6-chloro-4-[(1S)-1-(5-chloro-1H-benzimidazol-2-yl)-3-hydroxycarbonylpropyl-amino]-7-[(2S)-2-tert.-butyloxycarbonyl-aminomethyl-pyrrolidin-1-yl-carbonyl]-quinazoline

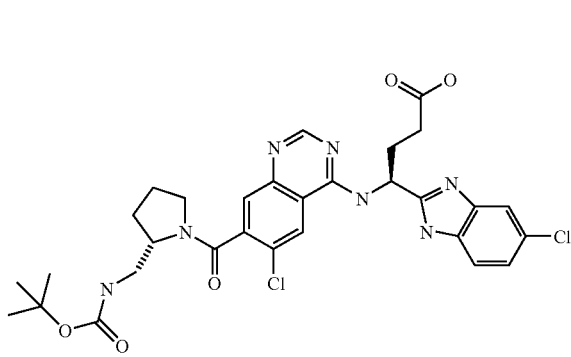

Prepared analogously to Example 4c from 6-chloro-4-[(1S)-1-(5-chloro-1H-benzimidazol-2-yl)-3-benzyloxycarbonyl propylamino]-7-[(2S)-2-tert.-butyloxycarbonyl-aminomethyl-pyrrolidin-1-yl-carbonyl]-quinazoline in methanol.

Yield: 82%

$R_f$ value: 0.15 (silica gel; dichloromethane/ethanol=9:1)

$C_{30}H_{33}Cl_2N_7O_5$ (642.55)

Mass spectrum: $(M+H)^+$=642/644/646 (chlorine isotope)

EXAMPLE 40

6-chloro-4-[(1S)-1-(5-chloro-1H-benzimidazol-2-yl)-3-hydroxycarbonylpropyl-amino]-7-[(2S)-2-aminomethyl-pyrrolidin-1-yl-carbonyl]-quinazoline

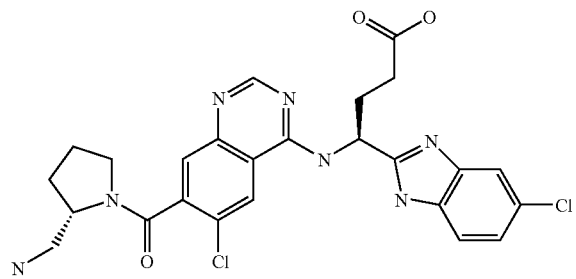

Prepared analogously to Example 8c from 6-chloro-4-[(1S)-1-(5-chloro-1H-benzimidazol-2-yl)-3-hydroxycarbonylpropylamino]-7-[(2S)-2-tert.-butyloxycarbonyl-aminomethyl-pyrrolidin-1-yl-carbonyl]-quinazoline and trifluoroacetic acid.

Yield: 87%

$R_f$ value: 0.15 (Reversed phase RP8; methanol/5% sodium chloride solution=7:3)

$C_{25}H_{25}Cl_2N_7O_3$ (542.43)

Mass spectrum: $(M+H)^+$=542/544/546 (chlorine isotope) $(M-H)^-$=540/542/544 (chlorine isotope)

EXAMPLE 41

6-chloro-4-[(1S)-1-(5-chloro-1H-benzimidazol-2-yl)-3-methanesulphonyl-propylamino]-7-[(2R)-2-tert.-butyloxycarbonyl-aminomethyl-pyrrolidin-1-yl-carbonyl]-quinazoline

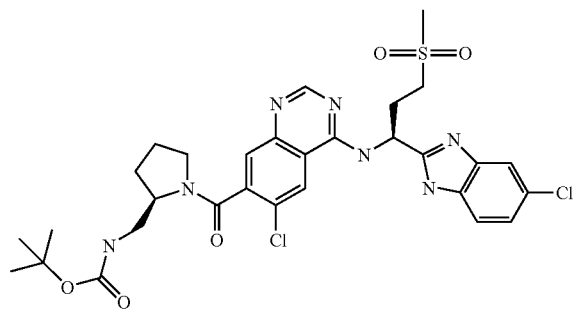

Prepared analogously to Example 30 from 6-chloro-4-[(1S)-1-(5-chloro-1H-benzimidazol-2-yl)-3-methylsul phanyl-propylamino]-7-[(2R)-2-tert.-butyloxycarbonyl-aminomethyl-pyrrolidin-1-yl-carbonyl]-quinazoline with meta-chloroperbenzoic acid.

Yield: 46%

R$_f$ value: 0.40 (silica gel; dichloromethane/ethanol=9:1)

C$_{30}$H$_{35}$Cl$_2$N$_7$O$_5$S (676.63)

Mass spectrum: (M+H)$^+$=676/678/680 (chlorine isotope)

EXAMPLE 42

6-chloro-4-[(1S)-1-(5-chloro-1H-benzimidazol-2-yl)-3-methanesulphonyl-propylamino]-7-[(2R)-2-aminomethyl-pyrrolidin-1-yl-carbonyl]-quinazoline

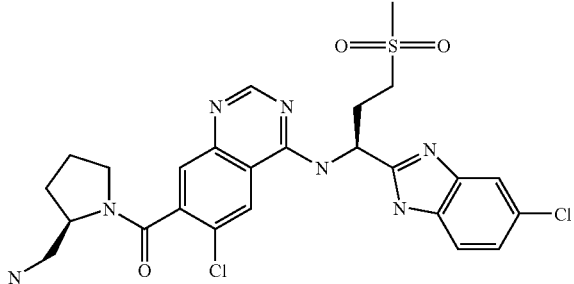

Prepared analogously to Example 8c from 6-chloro-4-[(1S)-1-(5-chloro-1H-benzimidazol-2-yl)-3-methanesulphonyl-propylamino]-7-[(2R)-2-(N-tert.-butyloxycarbonyl-aminomethyl)-pyrrolidin-1-yl-carbonyl]-quinazoline and trifluoroacetic acid.

Yield: 95%

R$_f$ value: 0.30 (silica gel; dichloromethane/ethanol=8:2+ 2% ammonia solution)

C$_{25}$H$_{27}$Cl$_2$N$_7$O$_3$S (576.51)

Mass spectrum: (M+H)$^+$=576/578/580 (chlorine isotope)

EXAMPLE 43

6-chloro-4-[(1S)-1-(5-chloro-1H-benzimidazol-2-yl)-ethylamino]-7-(thiazolidin-3-yl-carbonyl)-quinazoline

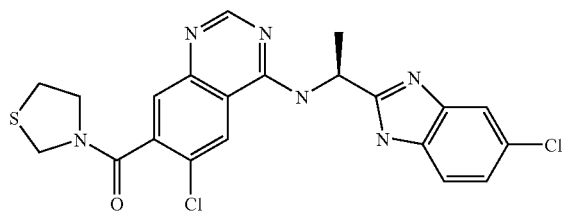

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and thiazolidine in N,N-dimethylformamide.

Yield: 10%

R$_f$ value: 0.60 (silica gel; dichloromethane/ethanol=9:1)

C$_{21}$H$_{18}$Cl$_2$N$_6$OS (473.39)

Mass spectrum: (M−H)$^-$=471/4731475 (chlorine isotope)

EXAMPLE 44

6-chloro-4-[(1S)-1-(5-chloro-1H-benzimidazol-2-yl)-2-(tert.-butyloxycarbonylmethoxy)-ethylamino]-7-(pyrrolidin-1-yl-carbonyl)-quinazoline

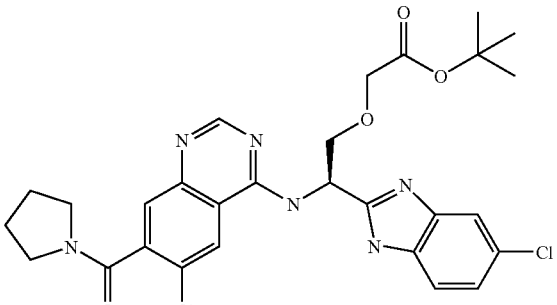

Prepared analogously to Example 2d from 4,6-dichloro-7-(pyrrolidin-1-yl-carbonyl]-quinazoline, (S)-1-(5-chloro-1H-benzimidazol-2-yl)-2-(tert.-butyloxycarbonylmethoxy)-ethylamine and triethylamine in N,N-dimethylformamide.

Yield: 52%

R$_f$ value: 0.30 (silica gel; dichloromethane/methanol=95:5)

C$_{28}$H$_{30}$Cl$_2$N$_6$O$_4$ (585.49)

Mass spectrum: (M+H)$^+$=585/587/589 (chlorine isotope) (M−H)$^-$=583/585/587 (chlorine isotope)

EXAMPLE 45

6-chloro-4-[(1S)-1-(5-chloro-1H-benzimidazol-2-yl)-3-ethoxycarbonylpropylamino]-7-(pyrrolidin-1-yl-carbonyl)-quinazoline

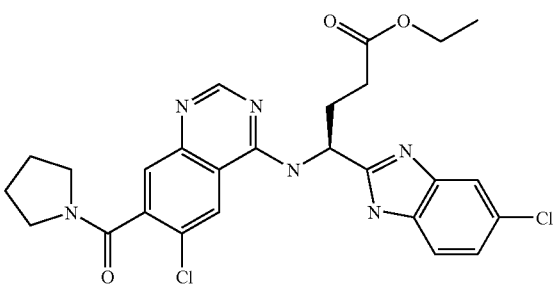

Prepared analogously to Example 2d from 4,6-dichloro-7-(pyrrolidin-1-yl-carbonyl)-quinazoline, (S)-1-(5-chloro-1H-benzimidazol-2-yl)-3-ethoxycarbonylpropylamine and triethylamine in N,N-dimethylformamide.

Yield: 18%

R$_f$ value: 0.65 (silica gel; dichloromethane/methanol=95:5)

C$_{26}$H$_{26}$Cl$_2$N$_6$O$_3$ (541.44)

Mass spectrum: (M+H)$^+$=541/543/545 (chlorine isotope)

EXAMPLE 46

4-[(1S)-1-(5-chloro-1H-benzimidazol-2-yl)-ethylamino]-6-methyl-7-(pyrrolidin-1-yl-carbonyl)-quinazoline

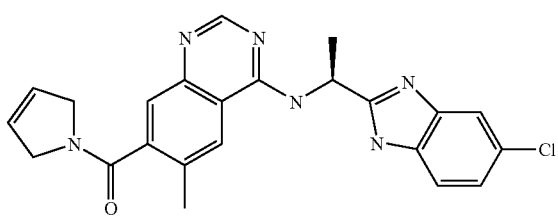

(a) 2-fluoro-5-methyl-terephthalic acid dinitrile 13.4 g (50 mmol) 2,5-dibromo-4-fluoro-toluene, 7.04 g (60 mmol) zinc cyanide and 4.62 g (4 mmol) tetrakisphenylphosphine-palladium(0) are heated to 150° C. in 50 ml of 1-methyl-pyrrolidin-2-one for 1.5 hours. After cooling the mixture is taken up in 400 ml of ethyl acetate, washed five times with 100 ml of 2N ammonia solution and then filtered through Celite. The organic phase is washed with water and saturated sodium chloride solution, dried over sodium sulphate and evaporated down. The residue is purified by chromatography (silica gel; eluant: ethyl acetate/petroleum ether 1:19->1:4).

Yield: 6.35 g (79%)

$R_f$ value: 0.20 (silica gel; ethyl acetate/petroleum ether=1:9)

$C_9H_5FN_2$ (160.15)

Mass spectrum: $(M)^+=160$ (b) 4-amino-6-methyl-7-cyano-quinazoline 4.7 g (29.4 mmol) 2-fluoro-5-methyl-terephthalic acid dinitrile, 15.2 g (0.11 mol) potassium carbonate and 10.41 g (0.1 mol) formamidine-acetate are heated to 100° C. in 25 ml of 1-methyl-pyrrolidin-2-one for 2.5 hours. The mixture is cooled, combined with ice water, adjusted to pH=7 with glacial acetic acid and the precipitate is removed by suction filtering. The precipitate is washed with water and after drying purified by chromatography (silica gel; eluant: dichloromethane/methanol 0-10%).

Yield: 2.3 g (43%)

$R_f$ value: 0.01 (silica gel; ethyl acetate/petroleum ether=1:2)

$C_{14}H_{12}ClN_3O$ (184.20)

Mass spectrum: $(M+H)^+=185$ $(M-H)^-=183$ (c) 6-methyl-4-oxo-3,4-dihydro-quinazoline-7-carboxylic acid 0.5 g (2.7 mmol) 4-amino-6-methyl-7-cyano-quinazoline are suspended in 15 ml of ethanol and combined with 20 ml of 2.5-molar lithium hydroxide solution and heated to 100° C. After one day the ethanol is distilled off and stirred for another day at 100° C. The reaction mixture is cooled and the precipitate is filtered off. The filtrate is evaporated down to ⅔ of its volume and acidified with glacial acetic acid. The precipitated product is washed with water until neutral and dried.

Yield: 0.35 g (63%)

$R_f$ value: 0.55 (Reversed phase RP8; methanol/5% sodium chloride solution=1:1)

$C_{10}H_8N_2O_3$ (204.19)

Mass spectrum: $(M+H)^+=205$ $(M-H)^-=203$ (d) 4-chloro-6-methyl-7-(2,5-dihydropyrrol-1-yl-carbonyl)-quinazoline Prepared analogously to Example 2b or 2c from 6-methyl-4-oxo-3,4-dihydro-quinazoline-7-carboxylic acid, thionyl chloride, 2,5-dihydropyrrole, sodium hydroxide solution and dichloromethane.

Yield: 68% (over two steps)

$R_f$ value: 0.19 (silica gel; ethyl acetate/petroleum ether=9:1)

$C_{14}H_{12}ClN_3O$ (273.724)

Mass spectrum: $(M+H)^+=274/276$ (chlorine isotope)

(e) 4-[(1S)-1-(5-chloro-1H-benzimidazol-2-yl)-ethylamino]-6-methyl-(2,5-dihydropyrrol-1-yl-carbonyl)-guinazoline Prepared analogously to Example 2d from 4-chloro-6-methyl-7-(2,5-dihydropyrrol-1-yl-carbonyl)-quinazoline, (S)-1-(5-chloro-1H-benzimidazol-2-yl)-ethylamine and triethylamine in N,N-dimethylformamide.

Yield: 55%

$R_f$ value: 0.30 (silica gel; ethyl acetate/diethyl ether=9:1+1% ammonia solution)

$C_{23}H_{21}ClN_6O$ (432.92)

Mass spectrum: $(M+H)^+=433/435$ (chlorine isotope)

EXAMPLE 47

4-[(1S)-1-(5-chloro-1H-benzimidazol-2-yl)-ethylamino]-6-methyl-7-(pyrrolidin-1-yl-carbonyl)-quinazoline

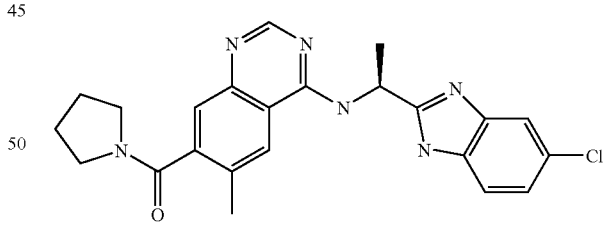

Prepared analogously to Example 10 from 4-[(1S)-1-(5-chloro-1H-benzimidazol-2-yl)-ethylamino]-6-methyl-(2,5-dihydropyrrol-1-yl-carbonyl)-quinazoline with 5% palladium on charcoal in methanol at 5 bar hydrogen pressure.

Yield: 75%

$R_f$ value: 0.20 (silica gel; ethyl acetate/petroleum ether=9:1+1% ammonia solution)

$C_{23}H_{23}ClN_6O$ (434.93)

Mass spectrum: $(M+H)^+=435/437$ (chlorine isotope) $(M-H)^-=433/435$ (chlorine isotope)

EXAMPLE 48

6-chloro-4-[(1S)-1-(5-chloro-1H-benzimidazol-2-yl)-ethylamino]-7-[(3S)-3-aminomethyl-pyrrolidin-1-yl-carbonyl]-quinazoline

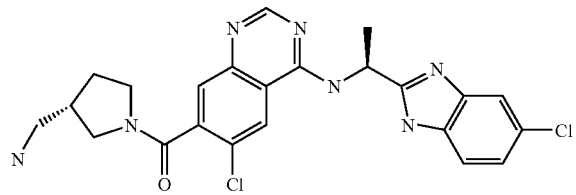

Prepared analogously to Example 37 from 6-chloro-4-[(1S)-1-(5-chloro-1H-benzimidazol-2-yl)-ethylamino]-7-[(3S)-3-(9H-fluoren-9-ylmethoxycarbonyl)aminomethyl-pyrrolidin-1-yl-carbonyl]-quinazoline with diethylamine in tetrahydrofuran.

Yield: 23%

$R_f$ value: 0.35 (Reversed phase RP8; methanol/5% sodium chloride solution=7:3)

$C_{23}H_{23}Cl_2N_7O$ (484.39)

Mass spectrum: $(M+H)^+$=484/486/488 (chlorine isotope)

EXAMPLE 49

6-chloro-4-[(1S)-1-(5-chloro-1H-benzimidazol-2-yl)-2-(hydroxycarbonylmethoxy)-ethylamino]-7-(pyrrolidin-1-yl-carbonyl)-quinazoline

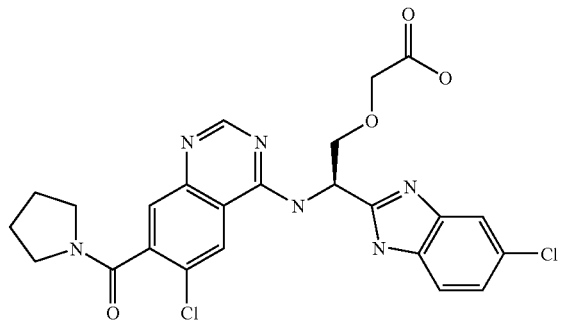

Prepared analogously to Example 8c from 6-chloro-4-[(1S)-1-(5-chloro-1H-benzimidazol-2-yl)-2-(tert.-butyloxycarbonylmethoxy)-ethylamino]-7-(pyrrolidin-1-yl-carbonyl)-quinazoline and trifluoroacetic acid.

Yield: quantitative

HPLC-retention time: 3.80 minutes $C_{24}H_{22}Cl_2N_6O_4$ (529.38)

Mass spectrum: $(M+H)^+$=529/531/533 (chlorine isotope)

EXAMPLE 50

6-chloro-4-[(1S)-1-(5-chloro-1H-benzimidazol-2-yl)-3-methanesulphinyl-propylamino]-7-[(2R)-2-aminomethyl-pyrrolidin-1-yl-carbonyl]-quinazoline

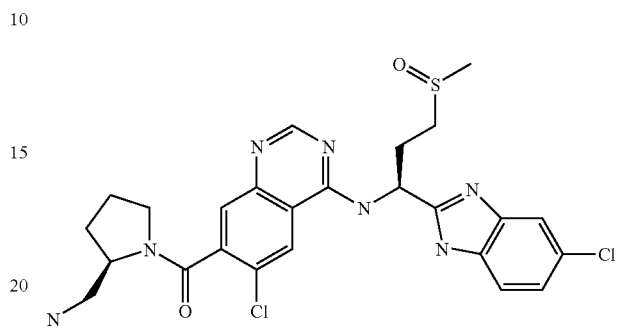

Prepared analogously to Example 8c from 6-chloro-4-[(1S)-1-(5-chloro-1H-benzimidazol-2-yl)-3-methanesulphinyl-propylamino]-7-[(2R)-2-aminomethyl-pyrrolidin-1-yl-carbonyl]-quinazoline and trifluoroacetic acid.

Yield: quantitative $R_f$ value: 0.20 (silica gel; dichloromethane/ethanol=8:2+2% ammonia solution)

$C_{25}H_{27}Cl_2N_7O_2S$ (560.51)

Mass spectrum: $(M+H)^+$=560/562/564 (chlorine isotope)

EXAMPLE 51

4-[(1S)-1-(5-chloro-1H-benzimidazol-2-yl)-3-methylsulphanyl-propylamino]-6-methyl-7-(2,5-dihydropyrrol-1-yl-carbonyl)-quinazoline

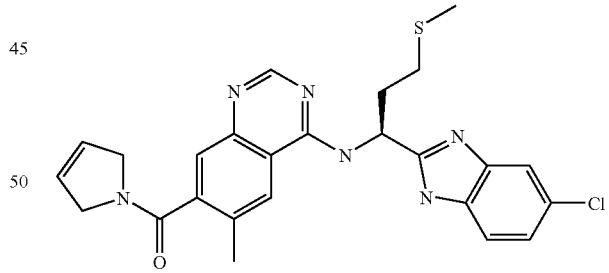

Prepared analogously to Example 2d from 4-chloro-6-methyl-7-(2,5-dihydropyrrol-1-yl-carbonyl)-quinazoline, (S)-1-(5-chloro-1H-benzimidazol-2-yl)-3-methylsulphanyl-ethylamine-ditrifluoroacetate and triethylamine in N,N-dimethylformamide.

Yield: 37%

$R_f$ value: 0.53 (silica gel; dichloromethane/methanol=9:1+1% ammonia solution)

$C_{25}H_{25}ClN_6OS$ (493.03)

Mass spectrum: $(M+H)^+$=493/495 (chlorine isotope) $(M-H)^-$=491/493 (chlorine isotope)

EXAMPLE 52

6-bromo-4-[(1S)-1-(5-chloro-1H-benzimidazol-2-yl)-ethylamino]-7-(2,5-dihydropyrrol-1-yl-carbonyl)-quinazoline

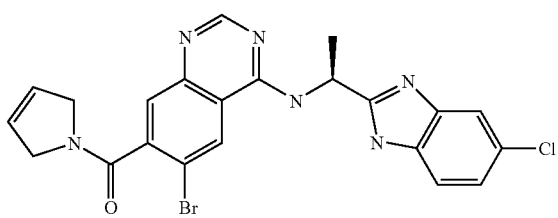

(a) dimethyl 6-amino-4-bromo-terephthalate 10.5 g (50 mmol) dimethyl amino-terephthalate and 8.1 ml (100 mmol) pyridine are dissolved in 175 ml dichloromethane and at −16° C. a solution of 2.7 ml (52.5 mmol) bromine in 25 ml dichloromethane is added dropwise. It is stirred for 4 hours at 0° C. and then heated overnight to ambient temperature. The mixture is added to ice water, washed three times with water and then dried over magnesium sulphate and evaporated down. The crude product is recrystallised from ethanol.

Yield: 11.6 g (81%)
$R_f$ value: 0.20 (silica gel; petroleum ether/ethyl acetate=4:1)
$C_{10}H_{10}BrNO_4$ (288.10)
Mass spectrum: $(M+H)^+$=288/290 (bromine isotope)

(b) 6-bromo-4-oxo-3,4-dihydro-quinazoline-7-carboxylic acid

Prepared analogously to Example 2a from dimethyl 6-amino-4-bromo-terephthalate and formamidine-acetate and subsequently saponified analogously to EXAMPLE 36b with lithium hydroxide at 85° C.

Yield: 43% (over two steps)
$R_f$ value: 0.40 (silica gel; dichloromethane/methanol=4:1)
$C_9H_5BrN_2O_3$ (269.06)
Mass spectrum: $(M-H)^-$=267/269 (bromine isotope)

(c) 6-bromo-4-chloro-7-(2,5-dihydropyrrol-1-yl-carbonyl)-quinazoline

Prepared analogously to Example 2b or 2c from 6-bromo-4-oxo-3,4-dihydro-quinazoline-7-carboxylic acid, thionyl chloride, 2,5-dihydropyrrole, sodium hydroxide solution and dichloromethane.

Yield: 39% (over two steps)
$R_f$ value: 0.50 (silica gel; dichloromethane/methanol=19:1)
$C_{13}H_9BrClN_3O$ (338.59)
Mass spectrum: $(M+H)^+$=338/340/342 (chlorine, bromine isotope)

(d) 6-bromo-4-[(1S)-1-(5-chloro-1H-benzimidazol-2-yl)-ethylamino]-7-(2,5-dihydropyrrol-1-yl-carbonyl)-quinazoline Prepared analogously to Example 2d from 6-bromo-4-chloro-7-(2,5-dihydropyrrol-1-yl-carbonyl)-quinazoline, (S)-1-(5-chloro-1H-benzimidazol-2-yl)-ethylamine-ditrifluoroacetate and triethylamine in N,N-dimethylformamide.

Yield: 52%
$R_f$ value: 0.40 (silica gel; dichloromethane/methanol=9:1+1% ammonia solution)
$C_{22}H_{18}BrClN_6O$ (497.78)
Mass spectrum: $(M+H)^+$=497/499/501 (chlorine, bromine isotope) $(M-H)^-$=495/497/499 (chlorine, bromine isotope)

EXAMPLE 53

6-chloro-4-[(1S)-1-(5-chloro-1H-benzimidazol-2-yl)-3-ethoxycarbonylpropyl-amino]-7-(2,5-dihydropyrrol-1-yl-carbonyl)-quinazoline

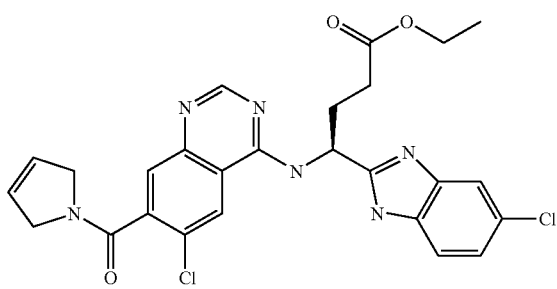

Prepared analogously to Example 2d from 4,6-dichloro-7-(2,5-dihydropyrrol-1-yl-carbonyl)-quinazoline, (S)-1-(5-chloro-1H-benzimidazol-2-yl)-3-ethoxycarbonylpropyl-amine and triethylamine in N,N-dimethylformamide.

Yield: 11%
$R_f$ value: 0.43 (silica gel; dichloromethane/methanol=95:5)
$C_{26}H_{24}Cl_2N_6O_3$ (539.43)
Mass spectrum: $(M+H)^+$=539/541/543 (chlorine isotope)

EXAMPLE 54

6-chloro-4-[(1S)-1-(5-chloro-1H-benzimidazol-2-yl)-ethylamino]-7-(pyrazolidin-3-on-1-yl-carbonyl)-quinazoline

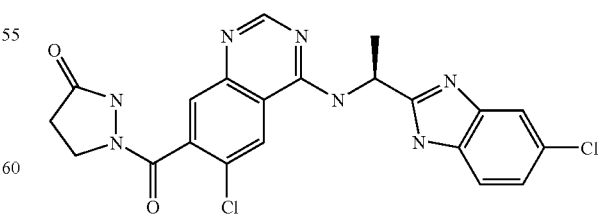

Prepared analogously to Example 2d from 4,6-dichloro-7-(pyrazolidin-3-on-1-yl-carbonyl)-quinazoline, (S)-1-(5-chloro-1H-benzimidazol-2-yl)-ethylamine-ditrifluoroacetate and triethylamine in N,N-dimethylformamide.

Yield: 17%
R$_f$ value: 0.07 (silica gel; dichloromethane/methanol=8:2)
C$_{21}$H$_{17}$Cl$_2$N$_7$O$_2$ (470.32)
Mass spectrum: (M+H)$^+$=470/472/474 (chlorine isotope)

EXAMPLE 55

6-chloro-4-[(1S)-1-(5-chloro-1H-benzimidazol-2-yl)-3-methylsulphanyl-propylamino]-7-(2,5-dihydro-pyrrol-1-yl-carbonyl)-quinazoline

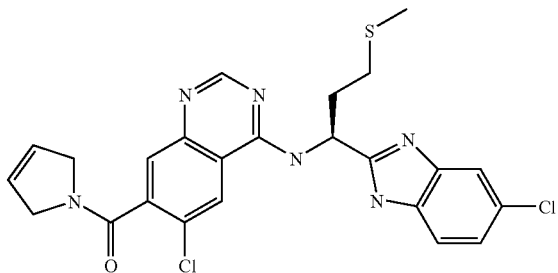

Prepared analogously to Example 2d from 4,6-dichloro-7-(2,5-dihydropyrrol-1-yl-carbonyl)-quinazoline, (S)-1-(5-chloro-1H-benzimidazol-2-yl)-3-methylsulphanyl-ethylamine-ditrifluoroacetate and triethylamine in N,N-dimethylformamide.
Yield: 44%
R$_f$ value: 0.4 (silica gel; dichloromethane/methanol=9:1)
C$_{24}$H$_{22}$Cl$_2$N$_6$OS (513.45)
Mass spectrum: (M+H)$^+$=513/515/517 (chlorine isotope)

EXAMPLE 56

6-chloro-4-[1-(5-chloro-1H-benzimidazol-2-yl)-1-(2-chloro-phenyl)-methylamino]-7-(pyrrolidin-1-yl-carbonyl)-quinazoline

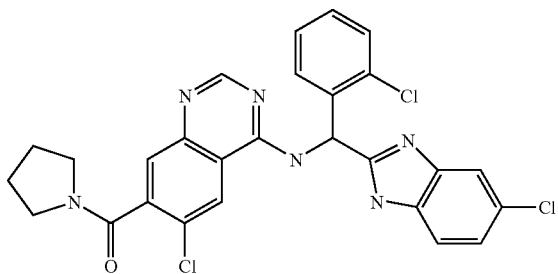

Prepared analogously to Example 2d from 4,6-dichloro-7-(pyrrolidin-1-yl-carbonyl)-quinazoline, C-(5-chloro-1H-benzimidazol-2-yl)-C-(2-chloro-phenyl)-methylamine and triethylamine in N,N-dimethylformamide.
Yield: 9%
R$_f$ value: 0.65 (silica gel; dichloromethane/methanol=95:5)
C$_{27}$H$_{21}$Cl$_3$N$_6$O (551.86)
Mass spectrum: (M+H)$^+$=551/553/555/557 (chlorine isotope)

EXAMPLE 57

6-chloro-4-[1-(5-chloro-1H-benzimidazol-2-yl)-1-(3-chloro-phenyl)-methylamino]-7-(pyrrolidin-1-yl-carbonyl)-quinazoline

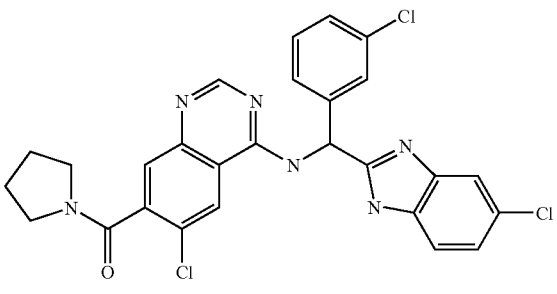

Prepared analogously to Example 2d from 4,6-dichloro-7-(pyrrolidin-1-yl-carbonyl)-quinazoline, C-(5-chloro-1H-benzimidazol-2-yl)-C-(3-chloro-phenyl)-methylamine and triethylamine in N,N-dimethylformamide.
Yield: 9%
R$_f$ value: 0.20 (silica gel; dichloromethane/methanol=95:5)
C$_{27}$H$_{21}$Cl$_3$N$_6$O (551.86)
Mass spectrum: (M+H)$^+$=551/553/555/557 (chlorine isotope)

EXAMPLE 58

6-chloro-4-[(1S)-1-(5-chloro-1H-benzimidazol-2-yl)-butylamino]-7-(2,5-dihydropyrrol-1-yl-carbonyl)-quinazoline

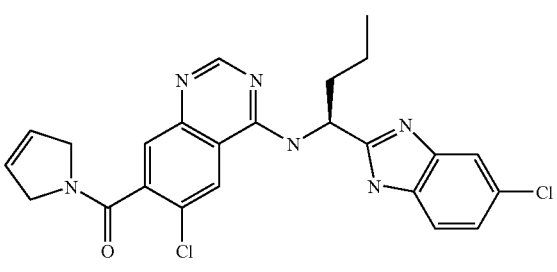

Prepared analogously to Example 2d from 4,6-dichloro-7-(2,5-dihydropyrrol-1-yl-carbonyl)-quinazoline, (S)-1-(5-chloro-1H-benzimidazol-2-yl)-butylamine-ditrifluoroacetate and triethylamine in N,N-dimethylformamide.
Yield: 28%
R$_f$ value: 0.35 (silica gel; dichloromethane/ethanol=9:1)
C$_{24}$H$_{22}$Cl$_2$N$_6$O (481.39)
Mass spectrum: (M+H)$^+$=481/483/485 (chlorine isotope)

EXAMPLE 59

6-chloro-4-[(1S)-1-(5-chloro-1H-benzimidazol-2-yl)-3-methylsulphanyl-propylamino]-7-(2,5-dihydropyrrol-1-yl-carbonyl)-quinazoline

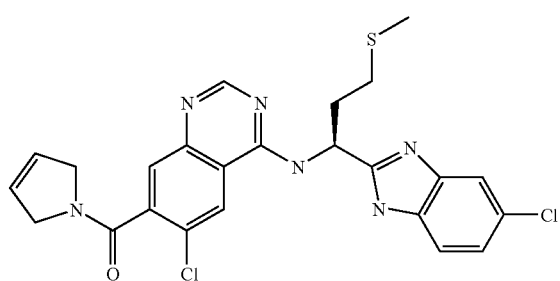

Prepared analogously to Example 2d from 4,6-dichloro-7-(2,5-dihydropyrrol-1-yl-carbonyl)-quinazoline, (S)-1-(5-chloro-1H-benzimidazol-2-yl)-3-methylsulphanyl-ethylamine-ditrifluoroacetate and triethylamine in N,N-dimethylformamide.
Yield: 18%
$R_f$ value: 0.30 (silica gel; dichloromethane/methanol=9:1)
$C_{24}H_{22}Cl_2N_6O_3S$ (545.45)
Mass spectrum: $(M+H)^+$=545/547/549 (chlorine isotope)

EXAMPLE 60

6-chloro-4-[(1S)-1-(5-chloro-1H-benzimidazol-2-yl)-2-methoxy-ethylamino]-7-(2,5-dihydropyrrol-1-yl-carbonyl)-quinazoline

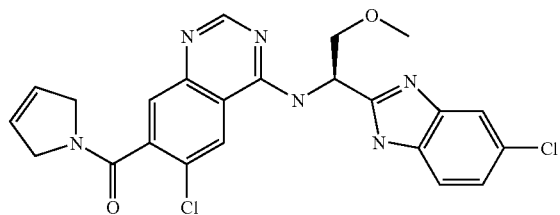

Prepared analogously to Example 2d from 4,6-dichloro-7-(2,5-dihydropyrrol-1-yl-carbonyl)-quinazoline, (S)-1-(5-chloro-1H-benzimidazol-2-yl)-2-methoxy-ethylamine and triethylamine in N,N-dimethylformamide.
Yield: 49%
$R_f$ value: 0.66 (silica gel; dichloromethane/methanol=9:1)
$C_{23}H_{20}Cl_2N_6O_2$ (483.36)
Mass spectrum: $(M+H)^+$=483/485/487 (chlorine isotope)

EXAMPLE 61

6-chloro-4-[1-(5-chloro-1H-benzimidazol-2-yl)-3-diethylaminocarbonyl-propyl-amino]-7-(pyrrolidin-1-yl-carbonyl)-quinazoline

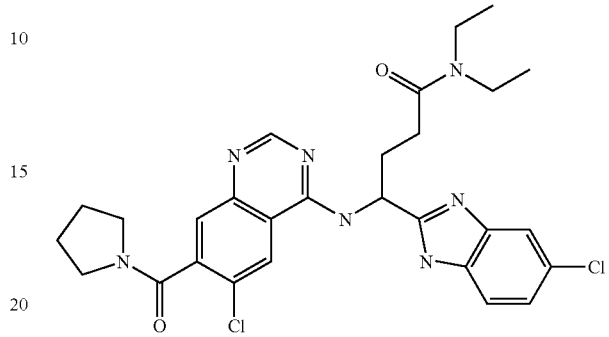

A solution of 118 mg (0.37 mmol) TBTU in acetonitrile and then a solution of 178 mg (2.4 mmol) diethylamine in 0.5 ml acetonitrile are added successively to a suspension of 150 mg (0.24 mmol) 6-chloro-4-[1-(1-tert.-butyloxycarbonyl-5-chloro-1H-benzimidazol-2-yl)-3-hydroxycarbony-propyl-amino]-7-(pyrrolidin-1-yl-carbonyl)-quinazoline in 1.5 ml acetonitrile. The mixture is stirred for two hours at ambient temperature, 1 ml trifluoroacetic acid are added and the mixture is stirred for a further 20 hours. 4.5 ml of water are added and the mixture is purified directly by RP-HPLC with an acetonitrile/water gradient with 0.1% trifluoroacetic acid buffer.
Yield: 78%
$R_f$ value: 0.57 (silica gel; ethyl acetate/ethanol=7:3)
$C_{28}H_{31}Cl_2N_7O_2$ (568.51)
Mass spectrum: $(M+H)^+$=568/570/572 (chlorine isotope)

EXAMPLE 62

6-chloro-4-[(1S)-1-(5-chloro-1H-benzimidazol-2-yl)-3-(pyrrolidin-1-ylcarbonyl)-propylamino]-7-[(2R)-pyrrolidin-2-ylmethylamino-carbonyl]-quinazoline

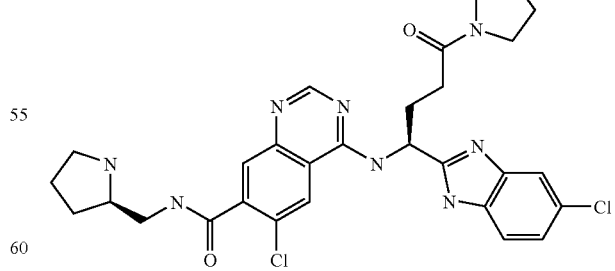

Prepared analogously to Example 8c from 6-chloro-4-[(1S)-1-(5-chloro-1H-benzimidazol-2-yl)-3-methanesulphinyl-propylamino]-7-[(2R)-(1-tert.-butyloxycarbonyl-pyrrolidin-2-yl-methylamino)-carbonyl]-quinazoline and trifluoroacetic acid.

Yield: quantitative
R$_f$ value: 0.20 (silica gel; dichloromethane/ethanol=8:2+2% ammonia solution)
C$_{29}$H$_{32}$Cl$_2$N$_8$O$_2$ (595.53)
Mass spectrum: (M+H)$^+$=560/562/564 (chlorine isotope)

EXAMPLE 63

6-chloro-4-[1-(5-chloro-1H-benzimidazol-2-yl)-3-[N-methyl-N-piperidin-4-yl-amino]-carbonyl-propyl-amino]-7-(pyrrolidin-1-yl-carbonyl)-quinazoline

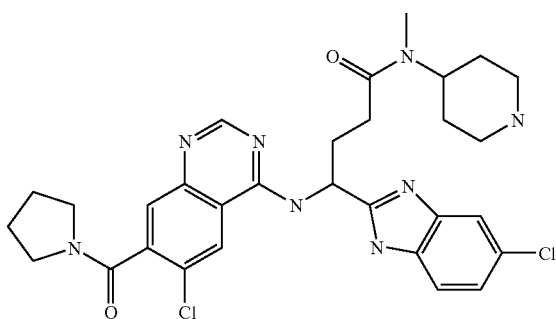

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and (1-tert.-butyloxycarbonyl-piperidin-4-yl)-methyl-amine with TBTU in acetonitrile/tetrahydrofuran and subsequent reaction with trifluoroacetic acid.
Yield: 79%
R$_f$ value: 0.10 (silica gel; ethyl acetate/ethanol=70:25+5% triethylamine)
C$_{30}$H$_{34}$Cl$_2$N$_8$O$_2$ (609.56)
Mass spectrum: (M+H)$^+$=609/611/613 (chlorine isotope)

EXAMPLE 64

6-chloro-4-[1-(5-chloro-1H-benzimidazol-2-yl)-3-[4-methyl-piperazin-1-yl]-carbonyl-propyl-amino]-7-(pyrrolidin-1-yl-carbonyl)-quinazoline

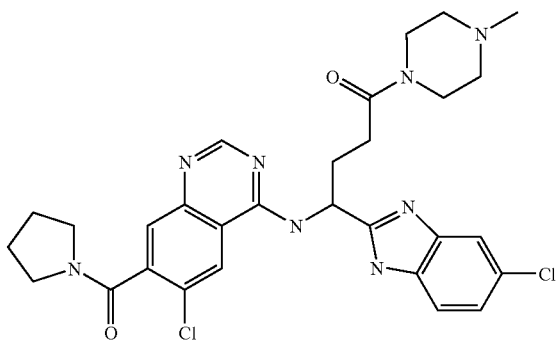

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and N-methylpiperazine with TBTU in acetonitrile/tetrahydrofuran and subsequent reaction with trifluoroacetic acid.
Yield: 87%
R$_f$ value: 0.25 (silica gel; ethyl acetate/ethanol=7:3)
C$_{29}$H$_{32}$Cl$_2$N$_8$O$_2$ (595.54)
Mass spectrum: (M+H)$^+$=595/597/599 (chlorine isotope)

EXAMPLE 65

6-chloro-4-[1-(5-chloro-1H-benzimidazol-2-yl)-3-(C-piperidin-4-yl-methylamino)-carbonyl-propyl-amino]-7-(pyrrolidin-1-yl-carbonyl)-quinazoline

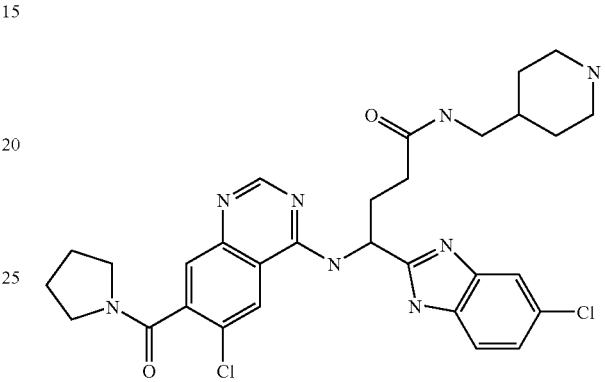

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(1-tert.-butyloxycarbonyl-piperidin-4-yl)-methylamine with TBTU in acetonitrile/tetrahydrofuran and subsequent reaction with trifluoroacetic acid.
Yield: 82%
R$_f$ value: 0.10 (silica gel; ethyl acetate/ethanol=70:25+5% triethylamine)
C$_{30}$H$_{34}$Cl$_2$N$_8$O$_2$ (609.56)
Mass spectrum: (M+H)$^+$=609/611/613 (chlorine isotope)

EXAMPLE 66

6-chloro-4-[1-(5-chloro-1H-benzimidazol-2-yl)-3-(N-benzyl-N-methyl-amino)-carbonyl-propyl-amino]-7-(pyrrolidin-1-yl-carbonyl)-quinazoline

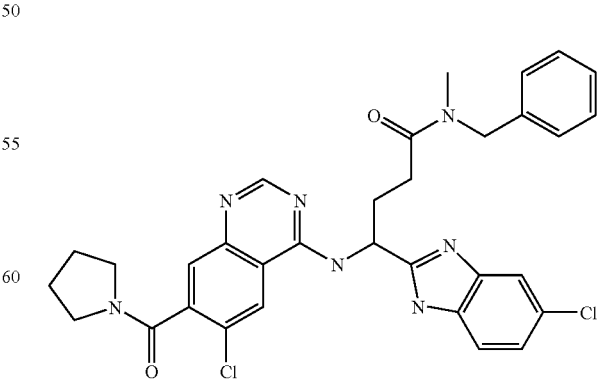

Prepared analogously to Example 61 from 6-chloro-4-[1-(1-tert.-butyloxycarbonyl-5-chloro-1H-benzimidazol-2-yl)-

3-hydroxycarbonyl-propyl-amino]-7-(pyrrolidin-1-yl-carbonyl)-quinazoline and benzylmethylamine with TBTU in acetonitrile/tetrahydrofuran and subsequent reaction with trifluoroacetic acid.

Yield: 82%
$R_f$ value: 0.80 (silica gel; ethyl acetate/ethanol=7:3)
$C_{32}H_{31}Cl_2N_7O_2$ (615.56)
Mass spectrum: $(M+H)^+$=618/620/622 (chlorine isotope)

EXAMPLE 67

6-chloro-4-[(1S)-1-(5-chloro-1H-benzimidazol-2-yl)-3-methanesulphonyl-propylamino]-1-oxy-7-[(2R)-2-tert.-butyloxycarbonyl-aminomethyl-pyrrolidin-1-yl-carbonyl]-quinazoline

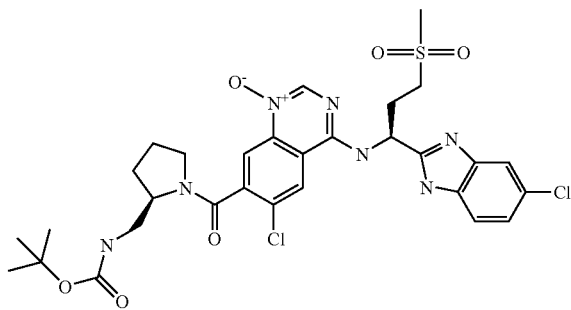

Prepared analogously to Example 61 from 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline with meta-chloroperbenzoic acid.

Yield: 21%
$R_f$ value: 0.10 (silica gel; dichloromethane/ethanol=9:1)
$C_{30}H_{35}Cl_2N_7O_6S$ (692.63)
Mass spectrum: $(M+H)^+$=692/694/696 (chlorine isotope)

EXAMPLE 68

4-[(1S)-1-(5-chloro-1H-benzimidazol-2-yl)-3-allyloxycarbonylpropyl-amino]-6-methyl-7-(2,5-dihydropyrrol-1-yl-carbonyl)-quinazoline

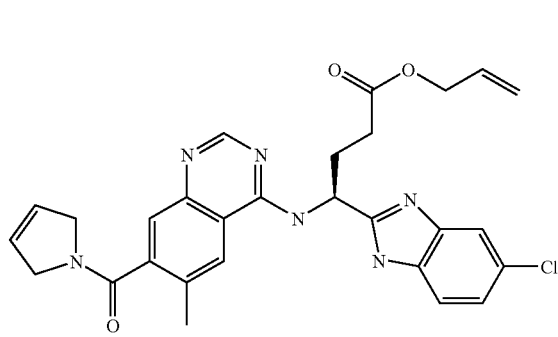

Prepared analogously to Example 2d from 4-chloro-6-methyl-7-(2,5-dihydropyrrol-1-yl-carbonyl)-quinazoline, (S)-1-(5-chloro-1H-benzimidazol-2-yl)-3-allyloxycarbonylpropyl-amine-trifluoroacetate and triethylamine in N,N-dimethylformamide.

Yield: 31%
$R_f$ value: 0.40 (silica gel; ethyl acetate/ethanol=9:1+1% ammonia solution)
$C_{28}H_{27}ClN_6O_3$ (531.02)
Mass spectrum: $(M+H)^+$=531/533 (chlorine isotope)

EXAMPLE 69

6-bromo-4-[(1S)-1-(5-chloro-1H-benzimidazol-2-yl)-3-allyloxycarbonylpropyl-amino]-7-(2,5-dihydropyrrol-1-yl-carbonyl)-quinazoline

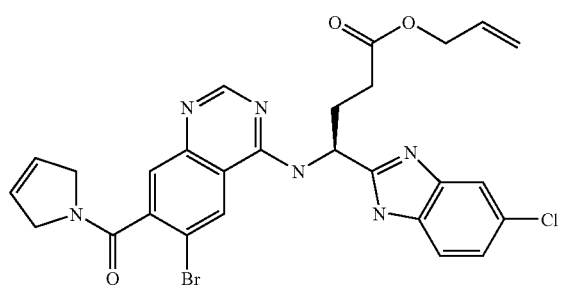

Prepared analogously to Example 2d from 6-bromo-4-chloro-7-(2,5-dihydropyrrol-1-yl-carbonyl)-quinazoline, (S)-1-(5-chloro-1H-benzimidazol-2-yl)-3-allyloxycarbonyl-propyl-amine-ditrifluoroacetate and triethylamine in N,N-dimethylformamide.

Yield: 65%
$R_f$ value: 0.70 (silica gel; ethyl acetate/ethanol=9:1+1% ammonia solution)
$C_{27}H_{24}BrClN_6O_3$ (595.89)
Mass spectrum: $(M+H)^+$=595/597/599 (chlorine, bromine isotope)

EXAMPLE 70

6-chloro-4-[(1S)-1-(5-chloro-1H-benzimidazol-2-yl)-2-methoxy-ethylamino]-7-(pyrrolidin-1-yl-carbonyl)-quinazoline

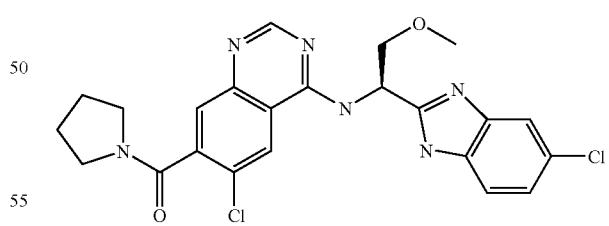

Prepared analogously to Example 2d from 4,6-dichloro-7-(pyrrolidin-1-yl-carbonyl)-quinazoline, (S)-1-(5-chloro-1H-benzimidazol-2-yl)-2-methoxy-ethylamine and triethylamine in N,N-dimethylformamide.

Yield: 44%
$R_f$ value: 0.45 (silica gel; dichloromethane/methanol=95:5)
$C_{23}H_{22}Cl_2N_6O_2$ (485.38)
Mass spectrum: $(M+H)^+$=485/487/489 (chlorine isotope)

EXAMPLE 71

6-chloro-4-[(1S)-1-(5-chloro-1H-benzimidazol-2-yl)-4-(tert.-butyloxycarbonyl)-butyl-amino]-7-(pyrrolidin-1-yl-carbonyl)-quinazoline

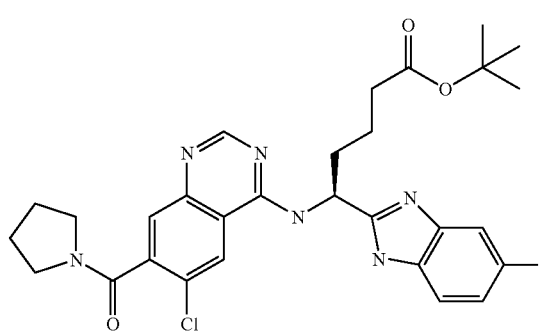

Prepared analogously to Example 2d from 4,6-dichloro-7-(pyrrolidin-1-yl-carbonyl)-quinazoline, (S)-1-(5-chloro-1H-benzimidazol-2-yl)-4-(tert.-butyloxycarbonyl)-butylamine and triethylamine in N,N-dimethylformamide.

Yield: 19% retention time: 2.83 minutes $C_{29}H_{32}Cl_2N_6O_3$ (583.52)

Mass spectrum: $(M+H)^+$=583/585/587 (chlorine isotope) $(M-H)^-$=581/583/585 (chlorine isotope)

EXAMPLE 72

6-chloro-4-[(1S)-1-(5-chloro-1H-benzimidazol-2-yl)-4-(tert.-butyloxycarbonyl)-butyl-amino]-7-(2,5-dihydropyrrol-1-yl-carbonyl)-quinazoline

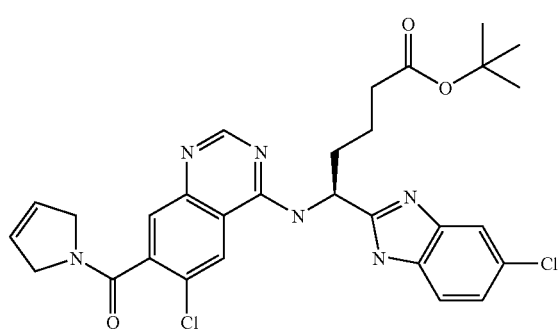

Prepared analogously to Example 2d from 4,6-dichloro-7-(2,5-dihydropyrrol-1-yl-carbonyl)-quinazoline, (S)-1-(5-chloro-1H-benzimidazol-2-yl)-4-(tert.-butyloxycarbonyl)-butylamine and triethylamine in N,N-dimethylformamide.

Yield: 14% retention time: 2.79 minutes $C_{29}H_{30}Cl_2N_6O_3$ (581.51)

Mass spectrum: $(M+H)^+$=581/583/585 (chlorine isotope) $(M-H)^-$=579/581/583 (chlorine isotope)

EXAMPLE 73

6-chloro-4-[(1S)-1-(5-chloro-1H-benzimidazol-2-yl)-3-benzyloxycarbonyl-propylamino]-7-[(2R)-(1-tert.-butyloxycarbonyl-pyrrolidin-2-yl-methylamino)-carbonyl]-quinazoline

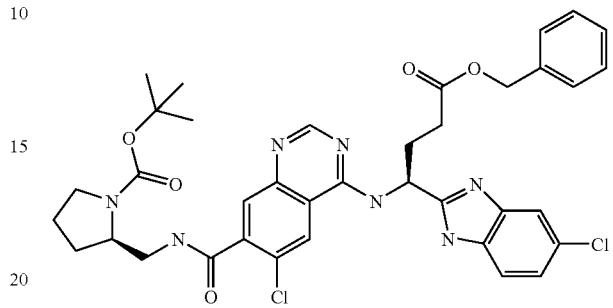

Prepared analogously to Example 2d from 4,6-dichloro-3-benzyloxycarbonyl-propylamino]-7-[(2R)-(1-tert.-butyloxycarbonyl-pyrrolidin-2-yl-methylamino)-carbonyl]-quinazoline and (S)-1-(5-chloro-1H-benzimidazol-2-yl)-3-benzyloxycarbonyl-propylamine-trifluoroacetate.

Yield: 19%

$R_f$ value: 0.70 (silica gel; dichloromethane/isopropanol=9:1)

$C_{37}H_{39}Cl_2N_7O_5$ (732.67)

Mass spectrum: $(M+H)^+$=732/734/736 (chlorine isotope)

EXAMPLE 74

6-chloro-4-[(1S)-1-(5-chloro-1H-benzimidazol-2-yl)-3-methanesulphonyl-propylamino]-1-oxy-7-[(2R)-2-aminomethyl-pyrrolidin-1-yl-carbonyl]-quinazoline

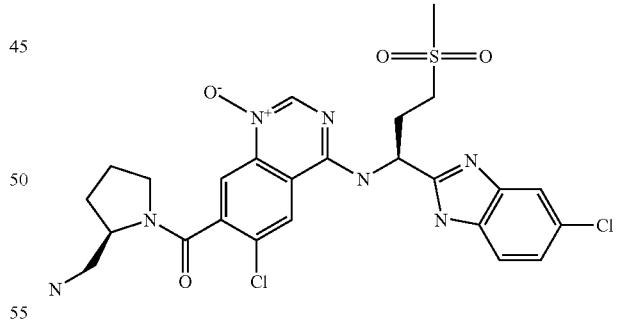

Prepared analogously to Example 8c from 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline with trifluoroacetic acid.

Yield: 85%

$R_f$ value: 0.20 (silica gel; dichloromethane/ethanol=8:2+2% ammonia solution)

$C_{25}H_{27}Cl_2N_7O_4S$ (592.51)

Mass spectrum: $(M+H)^+$=592/594/596 (chlorine isotope)

EXAMPLE 75

6-chloro-4-[(1S)-1-(5-chloro-1H-benzimidazol-2-yl)-ethylamino]-7-[(2R)-2-(acetylamino-methyl)-pyrrolidin-1-yl-carbonyl]-quinazoline

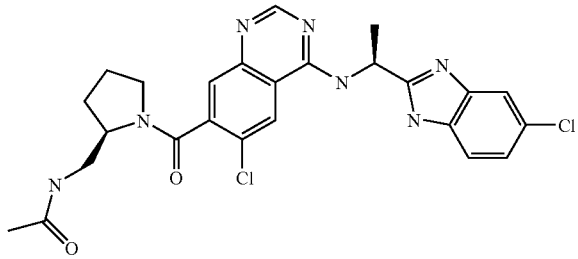

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and (R)-2-(acetylamino-methyl)-pyrrolidine in N,N-dimethylformamide.

Yield: 34%

$R_f$ value: 0.55 (silica gel; dichloromethane/ethanol=9:1+1% acetic acid)

$C_{25}H_{25}Cl_2N_7O_2$ (526.43)

Mass spectrum: $(M-H)^-$=524/526/528 (chlorine isotope)

EXAMPLE 76

6-chloro-4-[(1S)-1-(5-chloro-1H-benzimidazol-2-yl)-ethylamino]-7-[(2S)-2-(pyrrolidin-1-yl-methyl)-pyrrolidin-1-yl-carbonyl]-quinazoline

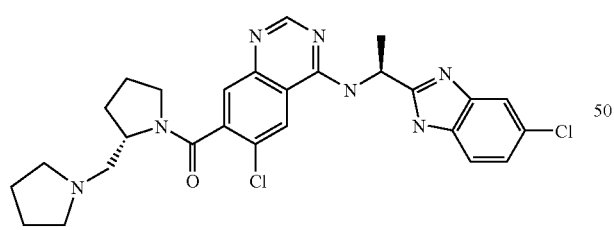

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and (S)-2-(pyrrolidin-1-ylmethyl)-pyrrolidine in N,N-dimethylformamide.

Yield: 50%

$R_f$ value: 0.1 (silica gel; dichloromethane/ethanol=9:1+1% acetic acid)

$C_{27}H_{29}Cl_2N_7O$ (538.43)

Mass spectrum: $(M+H)^+$=538/540/542 (chlorine isotope)

EXAMPLE 77

6-chloro-4-[(1S)-1-(5-chloro-1H-benzimidazol-2-yl)-ethylamino]-7-[(2R/S)-2-(tert.-butyloxycarbonyl-aminomethyl)-thiazolidin-1-yl-carbonyl]-quinazoline

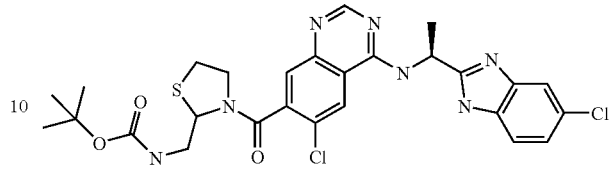

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and 2-(tert.-butyloxycarbonyl-aminomethyl)-thiazolidine in N,N-dimethylformamide.

Yield: 24%

$R_f$ value: 0.75 (silica gel; dichloromethane/ethanol=9:1)

$C_{27}H_{29}Cl_2N_7O_3S$ (602.54)

Mass spectrum: $(M-H)^-$=600/602/604 (chlorine isotope)

EXAMPLE 78

6-chloro-4-[(1S)-1-(5-chloro-1H-benzimidazol-2-yl)-ethylamino]-7-[(2R/S)-2-(pyridin-4-yl)-pyrrolidin-1-yl-carbonyl]-quinazoline

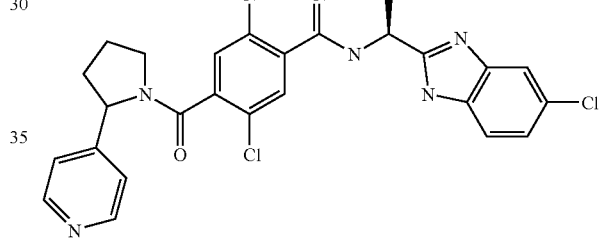

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and 2-(pyridin-4-yl)-pyrrolidine in N,N-dimethylformamide.

Yield: 36%

$R_f$ value: 0.7 (silica gel; dichloromethane/ethanol=8:2+1% acetic acid)

$C_{27}H_{23}Cl_2N_7O$ (532.43)

Mass spectrum: $(M-H)^-$=530/532/534 (chlorine isotope)

EXAMPLE 79

6-chloro-4-[(1S)-1-(5-chloro-1H-benzimidazol-2-yl)-ethylamino]-7-[(2R/S)-2-aminomethyl-thiazolidinyl-carbonyl]-quinazoline

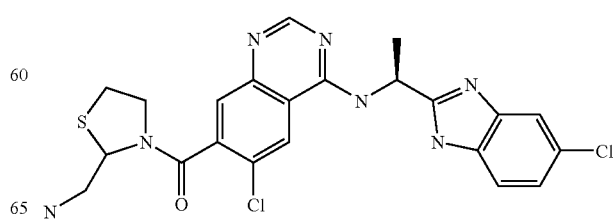

Prepared analogously to Example 8c from 6-chloro-4-[(1S)-1-(5-chloro-1H-benzimidazol-2-yl)-ethylamino]-7-[(2R/S)-2-(tert.-butyloxycarbonyl-aminomethyl)-thiazolidinyl-carbonyl]-quinazoline and trifluoroacetic acid.

Yield: 87%

$R_f$ value: 0.10 (silica gel; dichloromethane/ethanol=8:2+1% acetic acid)

$C_{22}H_{21}Cl_2N_7OS$ (502.43)

Mass spectrum: $(M+H)^+$=502/504/506 (chlorine isotope)

EXAMPLE 80

6-chloro-4-[(1S)-1-(5-chloro-1H-benzimidazol-2-yl)-3-methanesulphonyl-propylamino]-7-[(2R)-2-(methanesulphonyl-aminomethyl)-pyrrolidin-1-yl-carbonyl]-quinazoline

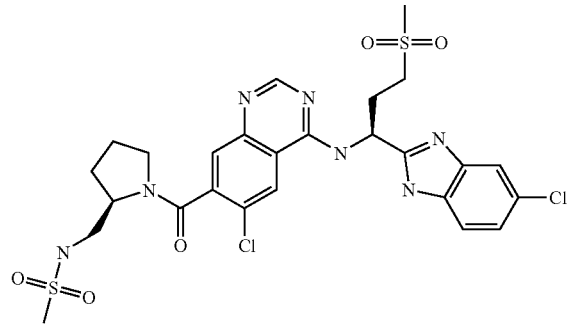

50 mg (62 μmol) 6-chloro-4-[(1S)-1-(5-chloro-1H-benzimidazol-2-yl)-3-methylsulphanyl-propylamino]-7-[(2R)-2-aminomethyl-pyrrolidin-1-yl-carbonyl]-quinazoline-ditrifluoroacetate are dissolved in 5 ml of tetrahydrofuran and at 0° C. combined with 32.5 μl (0.25 mmol) triethylamine and 5.3 μl (68 μmol) methanesulphonic acid chloride. The mixture is stirred at ambient temperature overnight, then water is added and the resulting mixture is extracted with dichloromethane. The organic phase is dried over sodium sulphate and evaporated down.

Yield: 25%

$R_f$ value: 0.75 (silica gel; dichloromethane/ethanol=8:2+2% ammonia solution)

$C_{26}H_{29}Cl_2N_7O_5S_2$ (654.60)

Mass spectrum: $(M-H)^-$=652/654/656 (chlorine isotope)

EXAMPLE 81

6-chloro-4-[(1S)-3-(benzyloxycarbonyl-amino)-1-(5-chloro-1H-benzimidazol-2-yl)-propyl-amino]-7-(2,5-dihydropyrrol-1-yl-carbonyl)-quinazoline

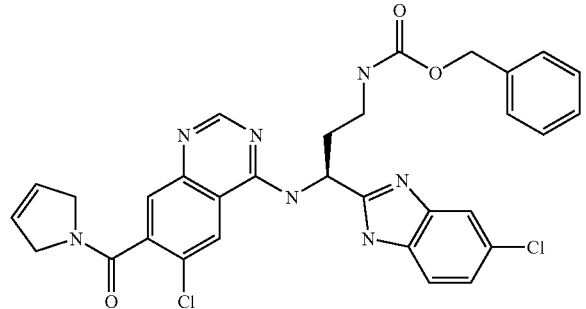

Prepared analogously to Example 2d from 4,6-dichloro-7-(2,5-dihydropyrrol-1-yl-carbonyl)-quinazoline, (S)-3-(benzyloxycarbonyl-amino)-1-(5-chloro-1H-benzimidazol-2-yl)-propylamine and triethylamine in N,N-dimethylformamide.

Yield: 70%

$R_f$ value: 0.45 (silica gel; dichloromethane/ethanol=9:1)

$C_{31}H_{27}Cl_2N_7O_3$ (616.51)

Mass spectrum: $(M+H)^+$=616/618/620 (chlorine isotope)

EXAMPLE 82

7-(2-acetaminomethyl-thiazolidin-1-yl-carbonyl)-6-chloro-4-[(1S)-1-(5-chloro-1H-benzimidazol-2-yl)-ethylamino]-quinazoline

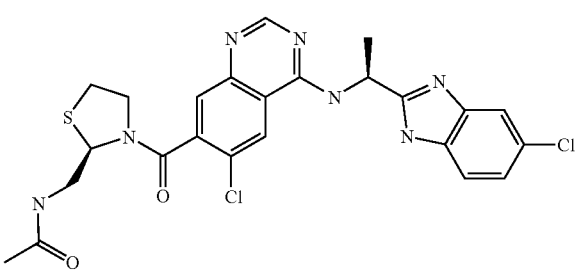

52 mg (0.1 mmol) 7-(2-aminomethyl-thiazolidin-1-yl-carbonyl)-6-chloro-4-[(1S)-1-(5-chloro-1H-benzimidazol-2-yl)-ethylamino]-quinazoline-trifluoroacetate are dissolved in 2.5 ml acetic acid and combined with 11.2 mg (0.11 mmol) acetic anhydride. The mixture is stirred for one day at ambient temperature, the solvent is distilled off and the residue is triturated with ethyl acetate and diethyl ether.

Yield: 87%

$R_f$ value: 0.65 (silica gel; dichloromethane/ethanol=8:2+1% acetic acid)

$C_{24}H_{23}Cl_2N_7O_2S$ (544.47)

Mass spectrum: $(M+H)^+$=544/546/548 (chlorine isotope)

EXAMPLE 83

6-chloro-4-{1-(5-chloro-1H-benzimidazol-2-yl)-3-[(1,2,3,4-tetrahydroisoquinolin-1-yl)-carbonyl-propyl-amino]}-7-(pyrrolidin-1-yl-carbonyl)-quinazoline

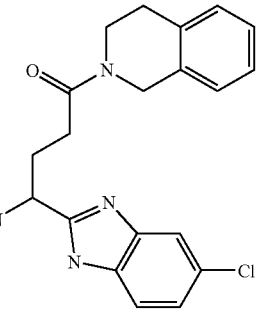

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 1,2,3,4-tetrahydroisoquinoline with TBTU in acetonitrile/tetrahydrofuran and subsequent reaction with trifluoroacetic acid.
Yield: 42% retention time: 2.81 minutes
$C_{33}H_{31}Cl_2N_7O_2$ (628.56)
Mass spectrum: $(M+H)^+=628/630/632$ (chlorine isotope)

EXAMPLE 84

6-chloro-4-[1-(5-chloro-1H-benzimidazol-2-yl)-3-(benzylamino-carbonyl)-propyl-amino]-7-(pyrrolidin-1-yl-carbonyl)-quinazoline

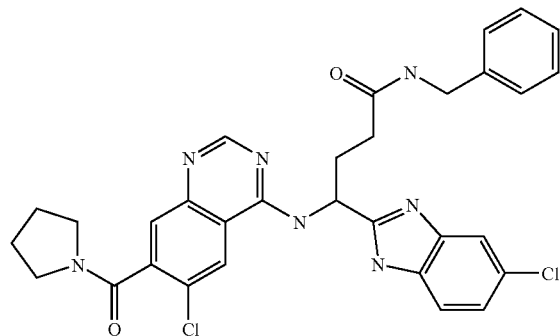

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and benzylamine with TBTU in acetonitrile/tetrahydrofuran and subsequent reaction with trifluoroacetic acid.
Yield: 22%
retention time: 2.63 minutes
$C_{31}H_{29}Cl_2N_7O_2$ (602.52)
Mass spectrum: $(M+H)^+=602/604/606$ (chlorine isotope)

EXAMPLE 85

6-chloro-4-{1-(5-chloro-1H-benzimidazol-2-yl)-3-[(N-methyl-N-phenethyl-amino-carbonyl)-propyl-amino]}-7-(pyrrolidin-1-yl-carbonyl)-quinazoline

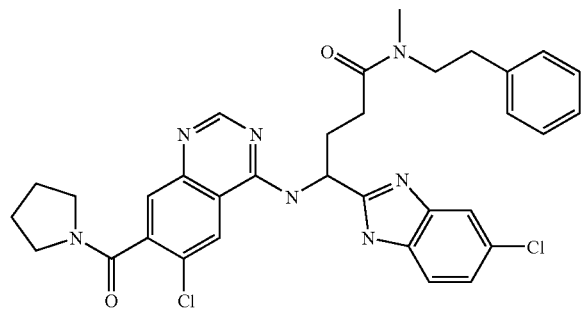

Prepared analogously to Example 61 from 6-chloro-4-[1-(1-tert.-butyloxycarbonyl-5-choro-1H-benzimidazol-2-yl)-3-hydroxycarbonylcarbonyl-propyl-amino]-7-(pyrrodlidin-1-yl-carbonyl)-quinazoline and methyl-phenethylamine with TBTU in acetonitrile/tetrahydrofuran and subsequent reaction with trifluoroacetic acid.
Yield: 26%
retention time: 2.77 minutes
$C_{33}H_{33}Cl_2N_7O_2$ (630.58)
Mass spectrum: $(M+H)^+=630/632/634$ (chlorine isotope)

EXAMPLE 86

6-chloro-4-[1-(5-chloro-1H-benzimidazol-2-yl)-3-(hydroxyethylamino-carbonyl)-propyl-amino]-7-(pyrrolidin-1-yl-carbonyl)-quinazoline

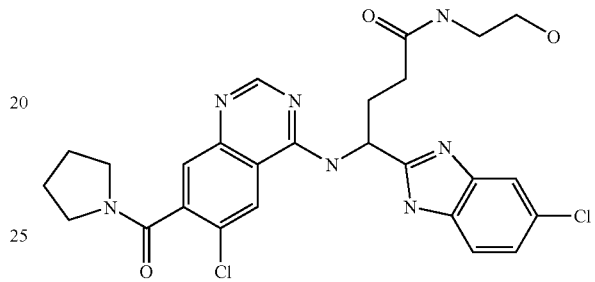

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and aminoethanol with TBTU in acetonitrile/tetrahydrofuran and subsequent reaction with trifluoroacetic acid.
Yield: 70%
retention time: 2.29 minutes
$C_{26}H_{27}Cl_2N_7O_3$ (556.45)
Mass spectrum: $(M+H)^+=556/558/560$ (chlorine isotope)

EXAMPLE 87

6-chloro-4-{1-(5-chloro-1H-benzimidazol-2-yl)-3-[(C-pyridin-3-yl-methylamino-carbonyl)-propyl-amino]}-7-(pyrrolidin-1-yl-carbonyl)-quinazoline

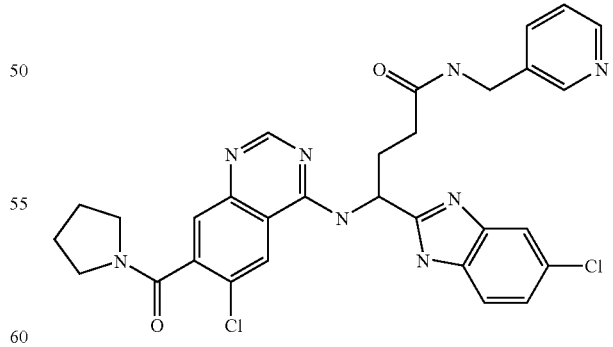

Prepared analogously to Example 61 from 6-chloro-4-[1-(1-teff.-butyloxycarbonyl-5-chloro-1H-benzimidazol-2-yl)-3-hydroxycarbonyl-propyl-amino]-7-(pyrrolidin-1-yl-carbonyl)-quinazoline and C-pyridin-3-yl-methylamine with TBTU in acetonitrile/tetrahydrofuran and subsequent reaction with trifluoroacetic acid.

Yield: 77%
retention time: 2.34 minutes
$C_{30}H_{28}Cl_2N_8O_2$ (603.51)
Mass spectrum: (M+H)⁺=603/605/607 (chlorine isotope)

EXAMPLE 88

6-chloro-4-{1-(5-chloro-1H-benzimidazol-2-yl)-3-[(1-oxa-3,8-diaza-spiro[4.5]decan-2-on-8-yl)-carbonyl]-propyl-amino}-7-(pyrrolidin-1-yl-carbonyl)-quinazoline

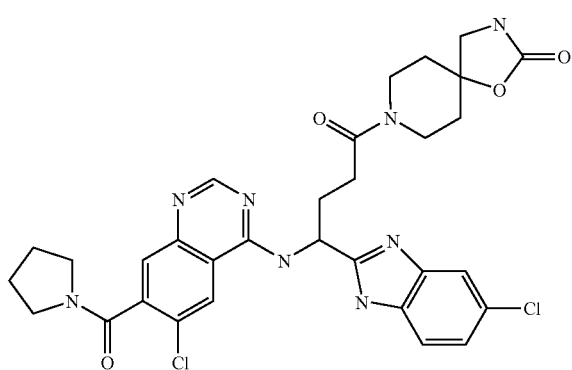

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 1-oxa-3,8-diaza-spiro[4.5]decan-2-one with TBTU in acetonitrile/tetrahydrofuran and subsequent reaction with trifluoroacetic acid.
Yield: 74%
retention time: 2.35 minutes
$C_{31}H_{32}Cl_2N_8O_4$ (651.55)
Mass spectrum: (M+H)⁺=651/653/655 (chlorine isotope)

EXAMPLE 89

6-chloro-4-[1-(5-chloro-1H-benzimidazol-2-yl)-3-(morpholin-4-yl-carbonyl)-propyl-amino]-7-(pyrrolidin-1-yl-carbonyl)-quinazoline

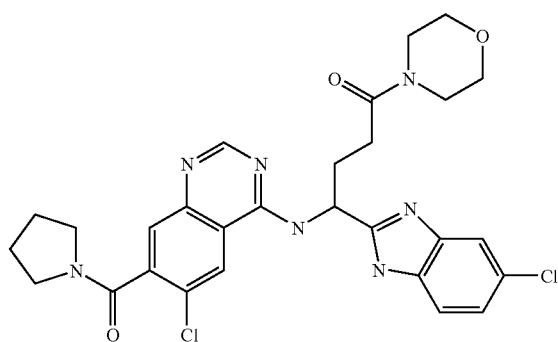

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and morpholine with TBTU in acetonitrile/tetrahydrofuran and subsequent reaction with trifluoroacetic acid.
Yield: 66%
retention time: 2.42 minutes
$C_{28}H_{29}Cl_2N_7O_3$ (582.49)
Mass spectrum: (M+H)⁺=582/584/586 (chlorine isotope)

EXAMPLE 90

6-chloro-4-[1-(5-chloro-1H-benzimidazol-2-yl)-3-(C-cyclohexyl-methylamino-carbonyl)-propyl-amino]-7-(pyrrolidin-1-yl-carbonyl)-quinazoline

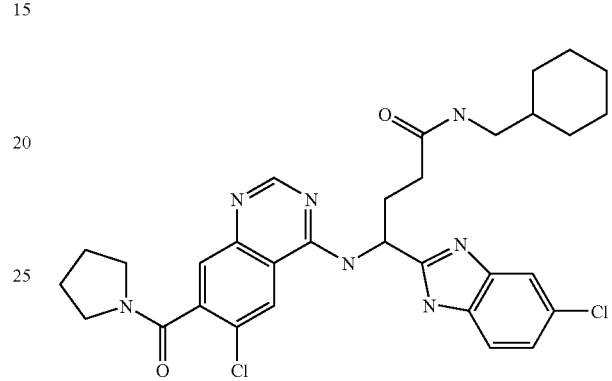

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-cyclohexyl-methylamine with TBTU in acetonitrile/tetrahydrofuran and subsequent reaction with trifluoroacetic acid.
Yield: 41%
retention time: 2.86 minutes
$C_{31}H_{35}Cl_2N_7O_2$ (608.57)
Mass spectrum: (M+H)⁺=608/610/612 (chlorine isotope)

EXAMPLE 91

6-chloro-4-[1-(5-chloro-1H-benzimidazol-2-yl)-3-(methoxyethylamino-carbonyl)-propyl-amino]-7-(pyrrolidin-1-yl-carbonyl)-quinazoline

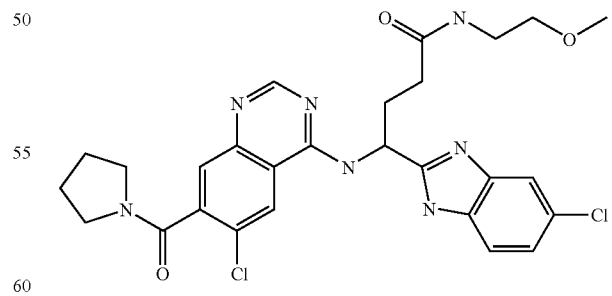

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and methoxyethylamine with TBTU in acetonitrile/tetrahydrofuran and subsequent reaction with trifluoroacetic acid.

Yield: 42%
retention time: 2.38 minutes
$C_{27}H_{29}Cl_2N_7O_3$ (570.48)
Mass spectrum: (M+H)$^+$=570/572/574 (chlorine isotope)

EXAMPLE 92

6-chloro-4-[1-(5-chloro-1H-benzimidazol-2-yl)-3-(dimethylaminoethyl-amino-carbonyl)-propyl-amino]-7-(pyrrolidin-1-yl-carbonyl)-quinazoline

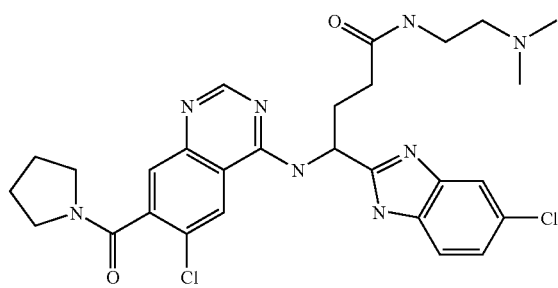

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and dimethylaminoethylamine with TBTU in acetonitrile/tetrahydrofuran and subsequent reaction with trifluoroacetic acid.
Yield: 79%
retention time: 2.33 minutes
$C_{28}H_{32}Cl_2N_8O_2$ (583.52)
Mass spectrum: (M+H)$^+$=583/585/587 (chlorine isotope)

EXAMPLE 93

6-chloro-4-[1-(5-chloro-1H-benzimidazol-2-yl)-3-(cyclopropylamino-carbonyl)-propyl-amino]-7-(pyrrolidin-1-yl-carbonyl)-quinazoline

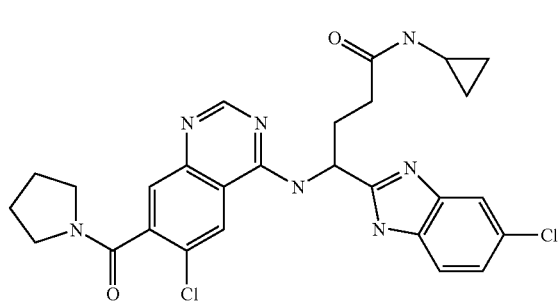

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and cyclopropylamine with TBTU in acetonitrile/tetrahydrofuran and subsequent reaction with trifluoroacetic acid.
Yield: 62%
retention time: 2.42 minutes
$C_{27}H_{27}Cl_2N_7O_2$ (552.46)
Mass spectrum: (M+H)$^+$=552/554/556 (chlorine isotope)

EXAMPLE 94

6-chloro-4-{(1R/S)-1-(5-chloro-1H-benzimidazol-2-yl)-3-[C-(2R/S)-tetrahydrofuran-2-yl-methylamino-carbonyl)-propyl-amino]}-7-(pyrrolidin-1-yl-carbonyl)-quinazoline

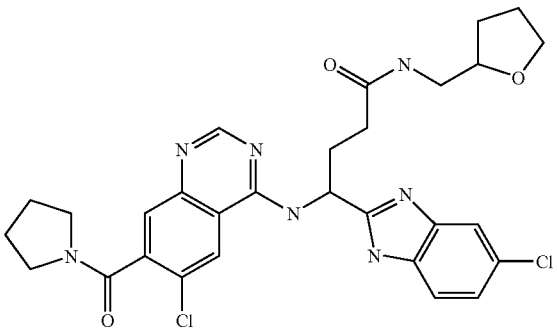

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(tetrahydrofuran-2-yl)-methylamine with TBTU in acetonitrile/tetrahydrofuran and subsequent reaction with trifluoroacetic acid.
Yield: 74%
retention time: 2.44 minutes
$C_{29}H_{31}Cl_2N_7O_3$ (596.52)
Mass spectrum: (M+H)$^+$=596/598/600 (chlorine isotope)

EXAMPLE 95

6-chloro-4-[1-(5-chloro-1H-benzimidazol-2-yl)-3-(dimethylaminopropylamino-carbonyl)-propyl-amino]-7-(pyrrolidin-1-yl-carbonyl)-quinazoline

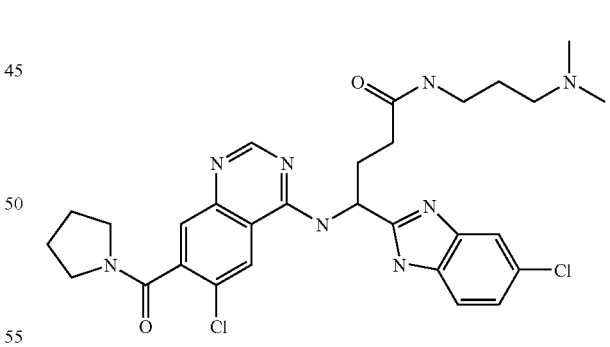

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and dimethylaminopropylamine with TBTU in acetonitrile/tetrahydrofuran and subsequent reaction with trifluoroacetic acid.
Yield: 65%
retention time: 2.33 minutes
$C_{29}H_{34}Cl_2N_8O_2$ (597.55)
Mass spectrum: (M+H)$^+$=597/599/601 (chlorine isotope)

EXAMPLE 96

6-chloro-4-[1-(5-chloro-1H-benzimidazol-2-yl)-3-(aminoethylamino-carbonyl)-propyl-amino]-7-(pyrrolidin-1-yl-carbonyl)-quinazoline

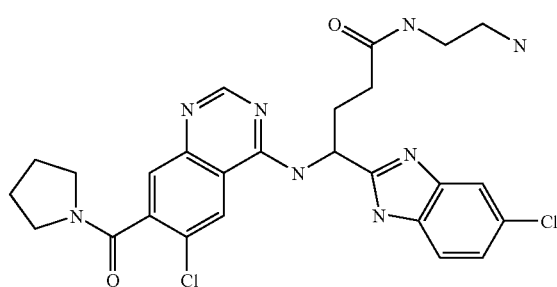

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and N-tert.-butyloxycarbonyl-ethylenediamine with TBTU in acetonitrile/tetrahydrofuran and subsequent reaction with trifluoroacetic acid.

Yield: 71% retention time: 2.31 minutes $C_{26}H_{28}Cl_2N_8O_2$ (555.47)

Mass spectrum: $(M+H)^+$=555/557/559 (chlorine isotope)

EXAMPLE 97

6-chloro-4-[1-(5-chloro-1H-benzimidazol-2-yl)-3-(hydroxycarbonylmethyl-methyl-amino-carbonyl)-propyl-amino]-7-(pyrrolidin-1-yl-carbonyl)-quinazoline

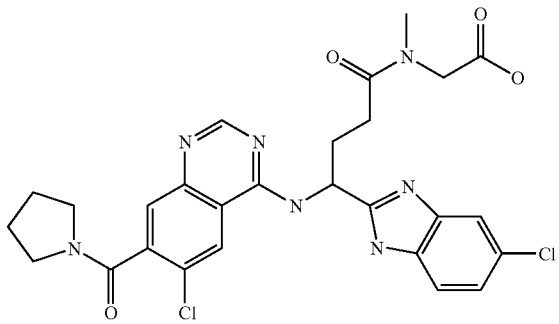

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and tert.-butyl methylamino-acetate with TBTU in acetonitrile/tetrahydrofuran and subsequent reaction with trifluoroacetic acid.

Yield: 57% retention time: 2.35 minutes $C_{27}H_{27}Cl_2N_7O_4$ (584.46)

Mass spectrum: $(M+H)^+$=584/586/588 (chlorine isotope)

EXAMPLE 98

6-chloro-4-{[1-(5-chloro-1H-benzimidazol-2-yl)-3-((3-(pyrrolidin-2-on-1-yl)-propyl-amino-carbonyl)-propyl-amino]}-7-(pyrrolidin-1-yl-carbonyl)-quinazoline

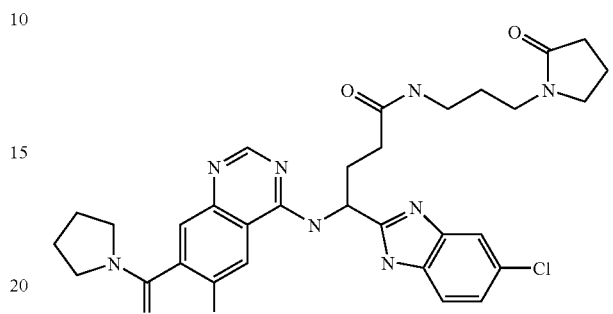

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and (pyrrolidin-2-on-1-yl)-propylamine with TBTU in acetonitrile/tetrahydrofuran and subsequent reaction with trifluoroacetic acid.

Yield: 52% retention time: 2.37 minutes $C_{31}H_{34}Cl_2N_8O_3$ (637.57)

Mass spectrum: $(M+H)^+$=637/639/641 (chlorine isotope)

EXAMPLE 99

6-chloro-4-{1-(5-chloro-1H-benzimidazol-2-yl)-3-[(1-[1,3,5]triazin-2-yl-piperidin-4-ylamino)-carbonyl]-propyl-amino}-7-(pyrrolidin-1-yl-carbonyl)-quinazoline

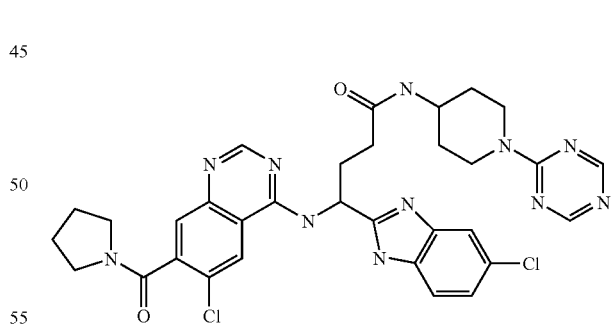

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 1-[1,3,5]triazin-2-yl-piperidin-4-ylamine with TBTU in acetonitrile/tetrahydrofuran and subsequent reaction with trifluoroacetic acid.

Yield: 64% retention time: 2.37 minutes $C_{32}H_{33}Cl_2N_{11}O_2$ (674.59)

Mass spectrum: $(M+H)^+$=674/676/678 (chlorine isotope)

EXAMPLE 100

6-chloro-4-{1-(5-chloro-1H-benzimidazol-2-yl)-3-[(2-imidazol-1-yl-ethylamino)-carbonyl)-propyl-amino]}-7-(pyrrolidin-1-yl-carbonyl)-quinazoline

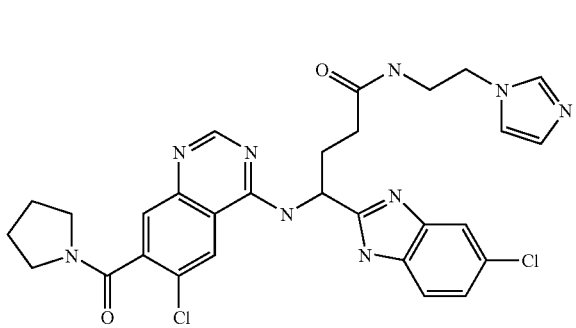

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 2-imidazol-1-yl-ethylamine with TBTU in acetonitrile/tetrahydrofuran and subsequent reaction with trifluoroacetic acid.

Yield: 81% retention time: 2.35 minutes $C_{29}H_{29}Cl_2N_9O_2$ (606.52)

Mass spectrum: $(M+H)^+=606/608/610$ (chlorine isotope)

EXAMPLE 101

6-chloro-4-{1-(5-chloro-1H-benzimidazol-2-yl)-3-[C-(1H-imidazol-2-yl)-methylamino-carbonyl)-propyl-amino]}-7-(pyrrolidin-1-yl-carbonyl)-quinazoline

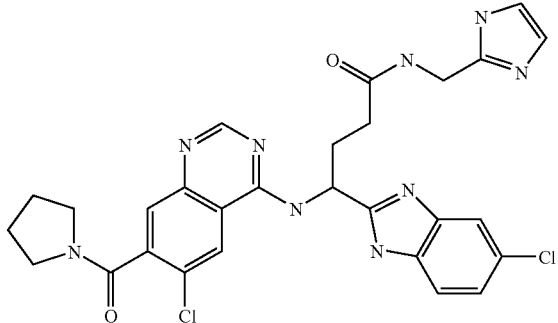

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(1H-imidazol-2-yl)methylamine with TBTU in acetonitrile/tetrahydrofuran and subsequent reaction with trifluoroacetic acid.

Yield: 83% retention time: 2.36 minutes $C_{28}H_{27}Cl_2N_9O_2$ (592.49)

Mass spectrum: $(M+H)^+=592/594/596$ (chlorine isotope)

EXAMPLE 102

6-chloro-4-[1-(5-chloro-1H-benzimidazol-2-yl)-3-(2,2,2-trifluoroethylamino-carbonyl)-propyl-amino]-7-(pyrrolidin-1-yl-carbonyl)-quinazoline

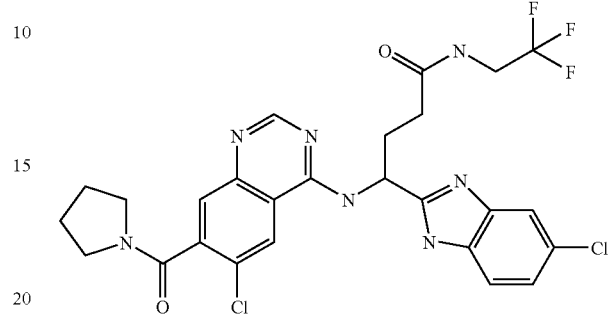

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 2,2,2-trifluoroethylamine with TBTU in acetonitrile/tetrahydrofuran and subsequent reaction with trifluoroacetic acid.

Yield: 57% retention time: 2.57 minutes $C_{26}H_{24}Cl_2F_3N_7O_2$ (594.42)

Mass spectrum: $(M+H)^+=594/596/598$ (chlorine isotope)

EXAMPLE 103

6-chloro-4-{1-(5-chloro-1H-benzimidazol-2-yl)-3-[N-(2-dimethylamino-ethyl)-N-methyl-amino-carbonyl]-propyl-amino}-7-(pyrrolidin-1-yl-carbonyl)-quinazoline

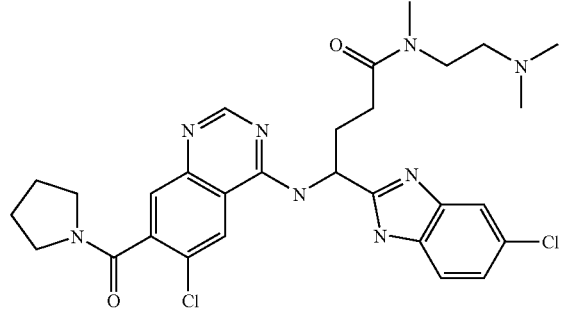

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and N,N,N'-trimethyl-ethyl-1,2-diamine with TBTU in acetonitrile/tetrahydrofuran and subsequent reaction with trifluoroacetic acid.

Yield: 69% retention time: 2.34 minutes $C_{29}H_{34}Cl_2N_8O_2$ (597.55)

Mass spectrum: $(M+H)^+=597/599/601$ (chlorine isotope)

EXAMPLE 104

6-chloro-4-{(1R/S)-1-(5-chloro-1H-benzimidazol-2-yl)-3-[(1R/S)-1-phenyl-ethylamino-carbonyl]-propyl-amino}-7-(pyrrolidin-1-yl-carbonyl)-quinazoline

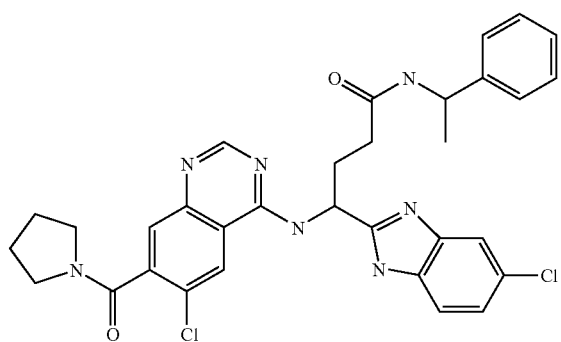

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 1-phenyl-ethylamine with TBTU in acetonitrile/tetrahydrofuran and subsequent reaction with trifluoroacetic acid.

Yield: 52%
retention time: 2.72 minutes
$C_{32}H_{31}Cl_2N_7O_2$ (616.55)
Mass spectrum: $(M+H)^+=616/618/620$ (chlorine isotope)

EXAMPLE 105

6-chloro-4-{1-(5-chloro-1H-benzimidazol-2-yl)-3-[2-(4-methyl-piperazin-1-ylmethyl)-piperidin-1-yl-carbonyl]-propyl-amino}-7-(pyrrolidin-1-yl-carbonyl)-quinazoline

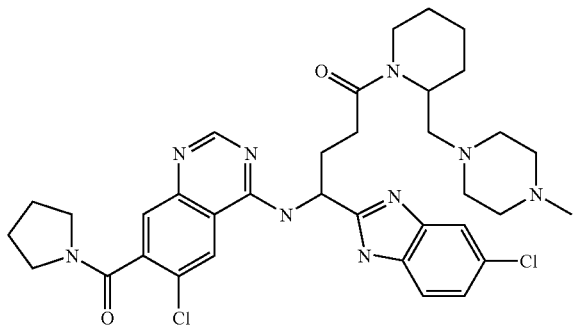

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 2-(4-methyl-piperazin-1-ylmethyl)-piperidine with TBTU in acetonitrile/tetrahydrofuran and subsequent reaction with trifluoroacetic acid.

Yield: 82%
retention time: 2.71 minutes
$C_{35}H_{43}Cl_2N_9O_2$ (692.69)
Mass spectrum: $(M+H)^+=692/694/696$ (chlorine isotope)

EXAMPLE 106

6-chloro-4-[1-(5-chloro-1H-benzimidazol-2-yl)-3-(N-aminocarbonylmethyl-N-methyl-amino-carbonyl)-propyl-amino]-7-(pyrrolidin-1-yl-carbonyl)-quinazoline

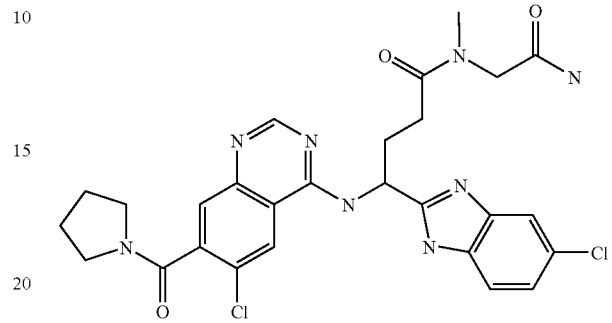

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and methylamino-acetic acid amide with TBTU in acetonitrile/tetrahydrofuran and subsequent reaction with trifluoroacetic acid.

Yield: 82%
retention time: 2.29 minutes
$C_{27}H_{28}Cl_2N_8O_3$ (583.48)
Mass spectrum: $(M+H)^+=583/585/587$ (chlorine isotope)

EXAMPLE 107

6-chloro-4-[1-(5-chloro-1H-benzimidazol-2-yl)-3-(4,5,6,7-tetrahydro-1H-imidazo[4,5-c]pyridin-5-yl-carbonyl)-propyl-amino]-7-(pyrrolidin-1-yl-carbonyl)-quinazoline

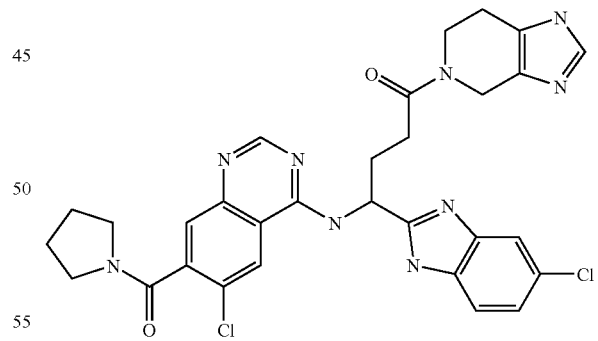

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 4,5,6,7-tetrahydro-1H-imidazo[4,5-c]pyridine with TBTU in acetonitrile/tetrahydrofuran and subsequent reaction with trifluoroacetic acid.

Yield: 72%
retention time: 2.34 minutes
$C_{30}H_{29}Cl_2N_9O_2$ (618.53)
Mass spectrum: $(M+H)^+=618/620/622$ (chlorine isotope)

EXAMPLE 108

6-chloro-4-[1-(5-chloro-1H-benzimidazol-2-yl)-3-(1-oxo-thiomorpholin-4-yl-carbonyl)-propyl-amino]-7-(pyrrolidin-1-yl-carbonyl)-quinazoline

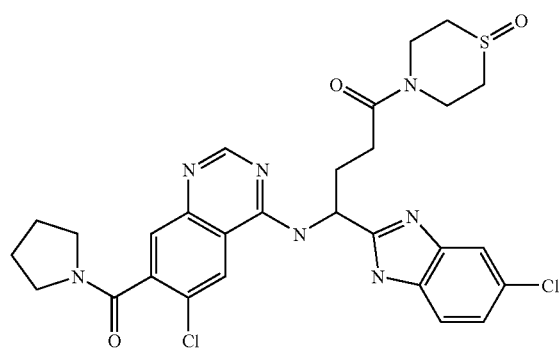

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and thiomorpholine-1-oxide with TBTU in acetonitrile/tetrahydrofuran and subsequent reaction with trifluoroacetic acid.

Yield: 66%
retention time: 2.31 minutes
$C_{28}H_{29}Cl_2N_7O_3S$ (614.56)
Mass spectrum: $(M+H)^+$=614/616/618 (chlorine isotope)

EXAMPLE 109

6-chloro-4-[1-(5-chloro-1H-benzimidazol-2-yl)-3-(N-dimethylaminocarbonylmethyl-N-methyl-amino-carbonyl)-propyl-amino]-7-(pyrrolidin-1-yl-carbonyl)-quinazoline

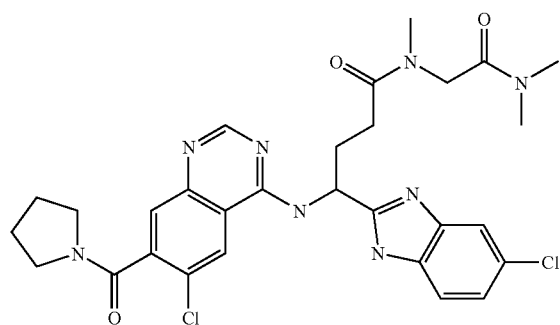

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and methylamino-acetic acid dimethylamide with TBTU in acetonitrile/tetrahydrofuran and subsequent reaction with trifluoroacetic acid.

Yield: 53%
retention time: 2.38 minutes
$C_{29}H_{32}Cl_2N_8O_3$ (611.53)
Mass spectrum: $(M+H)^+$=611/613/615 (chlorine isotope)

EXAMPLE 110

6-chloro-4-[1-(5-chloro-1H-benzimidazol-2-yl)-3-(N-hydroxycarbonylethyl-N-methyl-amino-carbonyl)-propyl-amino]-7-(pyrrolidin-1-yl-carbonyl)-quinazoline

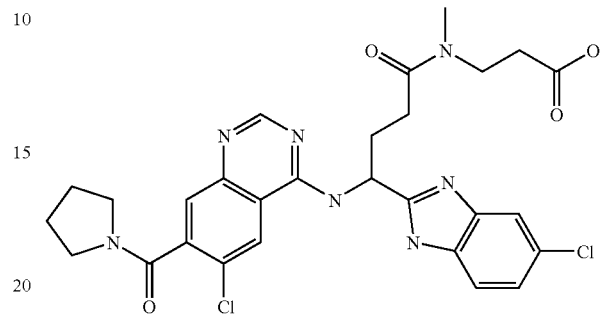

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and tert.-butyl 2-methylamino-propanoate with TBTU in acetonitrile/tetrahydrofuran and subsequent reaction with trifluoroacetic acid.

Yield: 43%
retention time: 2.27 minutes
$C_{28}H_{29}Cl_2N_7O_4$ (598.49)
Mass spectrum: $(M+H)^+$=598/600/602 (chlorine isotope)

EXAMPLE 111

6-chloro-4-{1-(5-chloro-1H-benzimidazol-2-yl)-3-[C-(1-methyl-1H-imidazol-2-yl-methylamino-carbonyl)-propyl-amino]}-7-(pyrrolidin-1-yl-carbonyl)-quinazoline

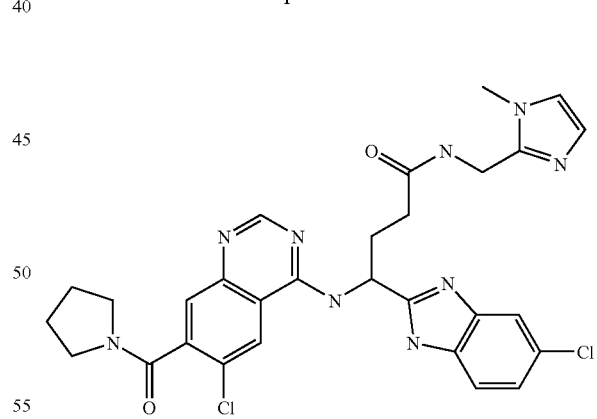

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(1-methyl-1H-imidazol-2-yl) methylamine with TBTU in acetonitrile/tetrahydrofuran and subsequent reaction with trifluoroacetic acid.

Yield: 83%
retention time: 2.35 minutes
$C_{29}H_{29}Cl_2N_9O_2$ (606.52)
Mass spectrum: $(M+H)^+$=606/608/610 (chlorine isotope)

EXAMPLE 112

6-chloro-4-[1-(5-chloro-1H-benzimidazol-2-yl)-3-(N-piperidin-2-yl-aminocarbonyl)-propyl-amino]-7-(pyrrolidin-1-yl-carbonyl)-quinazoline

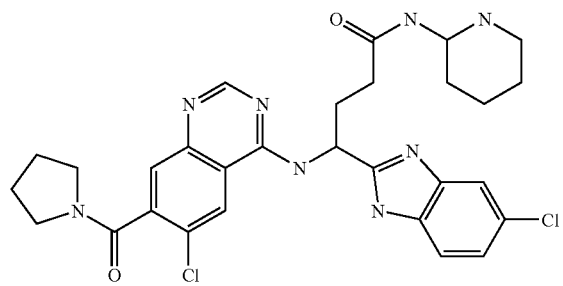

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 2-amino-i-tert.-butyloxycarbonyl-piperidine with TBTU in acetonitrile/tetrahydrofuran and subsequent reaction with trifluoroacetic acid.

Yield: 71% retention time: 2.34 minutes $C_{29}H_{32}Cl_2N_8O_2$ (595.53)

Mass spectrum: $(M+H)^+ = 595/597/599$ (chlorine isotope)

EXAMPLE 113

6-chloro-4-{1-(5-chloro-1H-benzimidazol-2-yl)-3-[C-(tetrahydropyran-4-yl)-methylamino-carbonyl]-propyl-amino}-7-(pyrrolidin-1-yl-carbonyl)-quinazoline

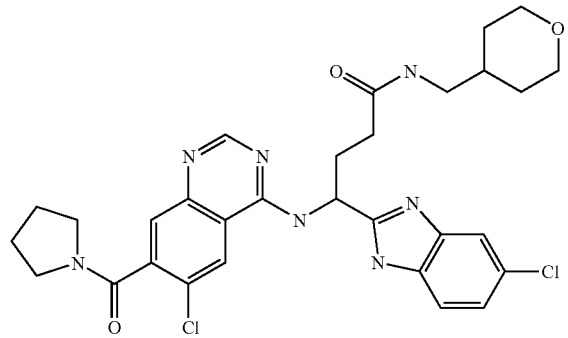

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(tetrahydropyran-4-yl)-methylamine with TBTU in acetonitrile/tetrahydrofuran and subsequent reaction with trifluoroacetic acid.

Yield: 58% retention time: 2.44 minutes $C_{30}H_{33}Cl_2N_7O_3$ (610.54)

Mass spectrum: $(M+H)^+ = 610/612/614$ (chlorine isotope)

EXAMPLE 114

6-chloro-4-[1-(5-chloro-1H-benzimidazol-2-yl)-3-(4-hydroxypiperidin-1-yl-carbonyl)-propyl-amino]-7-(pyrrolidin-1-yl-carbonyl)-quinazoline

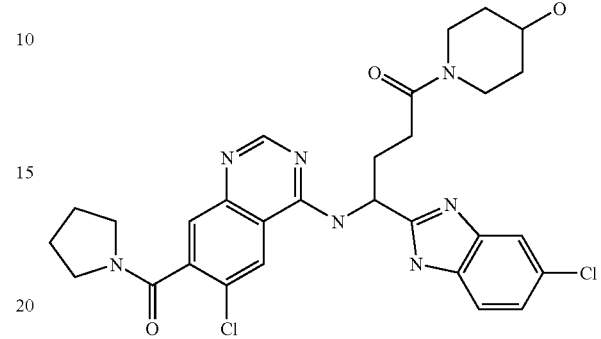

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 4-hydroxypiperidine with TBTU in acetonitrile/tetrahydrofuran and subsequent reaction with trifluoroacetic acid.

Yield: 78% retention time: 2.35 minutes $C_{29}H_{31}Cl_2N_7O_3$ (596.52)

Mass spectrum: $(M+H)^+ = 596/598/600$ (chlorine isotope)

EXAMPLE 115

6-chloro-4-{1-(5-chloro-1H-benzimidazol-2-yl)-3-[C-(pyridin-4-yl)-methylamino-carbonyl]-propyl-amino}-7-(pyrrolidin-1-yl-carbonyl)-quinazoline

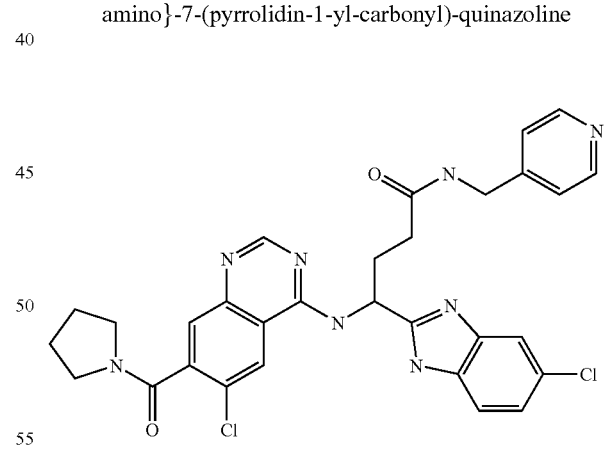

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(pyridin-4-yl)-methylamine with TBTU in acetonitrile/tetrahydrofuran and subsequent reaction with trifluoroacetic acid.

Yield: 88% retention time: 2.33 minutes $C_{30}H_{28}Cl_2N_8O_2$ (603.51)

Mass spectrum: $(M+H)^+ = 603/605/607$ (chlorine isotope)

EXAMPLE 116

6-chloro-4-[1-(5-chloro-1H-benzimidazol-2-yl)-3-(N-methylaminocarbonylmethyl-N-methyl-amino-carbonyl)-propyl-amino]-7-(pyrrolidin-1-yl-carbonyl)-quinazoline

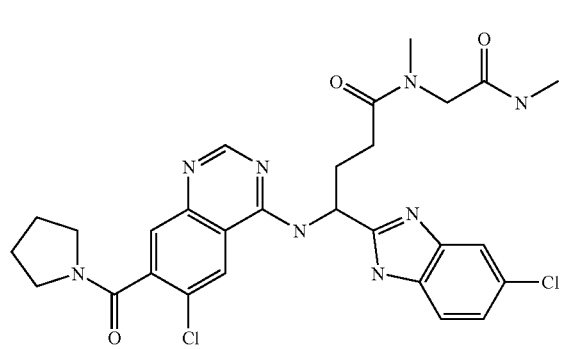

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and methylamino-acetic acid methylamide with TBTU in acetonitrile/tetrahydrofuran and subsequent reaction with trifluoroacetic acid.

Yield: 67%
retention time: 2.29 minutes
$C_{28}H_{30}Cl_2N_8O_3$ (597.50)
Mass spectrum: $(M+H)^+=597/599/601$ (chlorine isotope)

EXAMPLE 117

6-chloro-4-{1-(5-chloro-1H-benzimidazol-2-yl)-3-[N-(2-(1H)-imidazol-4-yl)-ethyl)-N-methyl-amino-carbonyl]-propyl-amino}-7-(pyrrolidin-1-yl-carbonyl)-quinazoline

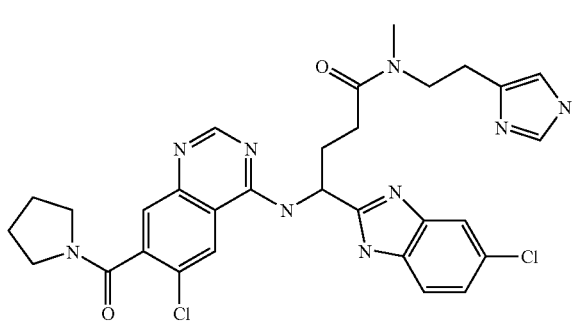

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and [2-(1H-imidazol-4-yl)-ethyl]-methylamine with TBTU in acetonitrile/tetrahydrofuran and subsequent reaction with trifluoroacetic acid.

Yield: 92%
retention time: 2.35 minutes
$C_{29}H_{29}Cl_2N_9O_2$ (606.52)
Mass spectrum: $(M+H)^+=606/608/610$ (chlorine isotope)

EXAMPLE 118

6-chloro-4-[1-(5-chloro-1H-benzimidazol-2-yl)-3-(1-thiazolidin-3-yl-carbonyl)-propyl-amino]-7-(pyrrolidin-1-yl-carbonyl)-quinazoline

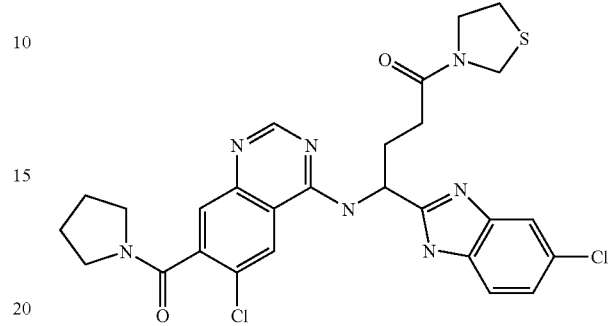

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and thiazolidine with TBTU in acetonitrile/tetrahydrofuran and subsequent reaction with trifluoroacetic acid.

Yield: 24%
retention time: 2.51 minutes
$C_{27}H_{27}Cl_2N_7O_2S$ (584.53)
Mass spectrum: $(M+H)^+=584/586/588$ (chlorine isotope)

EXAMPLE 119

6-chloro-4-[1-(5-chloro-1H-benzimidazol-2-yl)-3-(N-cyclopropyl-N-methyl-amino-carbonyl)-propyl-amino]-7-(pyrrolidin-1-yl-carbonyl)-quinazoline

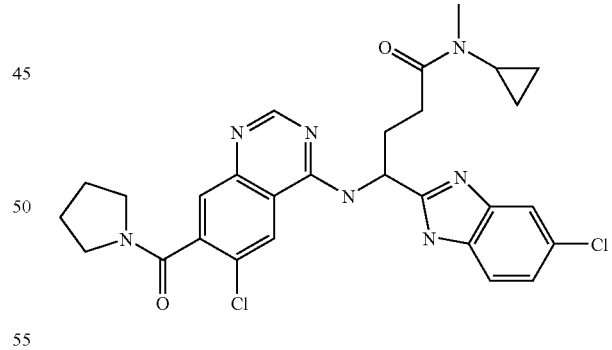

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and cyclopropyl-methylamine with TBTU in acetonitrile/tetrahydrofuran and subsequent reaction with trifluoroacetic acid.

Yield: 62%
retention time: 2.53 minutes
$C_{28}H_{29}Cl_2N_7O_2$ (566.49)
Mass spectrum: $(M+H)^+=566/568/570$ (chlorine isotope)
eb;normal

EXAMPLE 120

6-chloro-4-[1-(5-chloro-1H-benzimidazol-2-yl)-3-(N-cyclopropylmethyl-N-methyl-amino-carbonyl)-propyl-amino]-7-(pyrrolidin-1-yl-carbonyl)-quinazoline

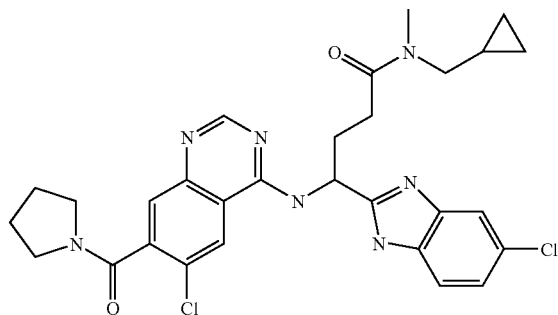

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and cyclopropylmethyl-methylamine with TBTU in acetonitrile/tetrahydrofuran and subsequent reaction with trifluoroacetic acid.

Yield: 72% retention time: 2.63 minutes $C_{29}H_{31}Cl_2N_7O_2$ (580.52)

Mass spectrum: $(M+H)^+$=580/582/584 (chlorine isotope)

EXAMPLE 121

6-chloro-4-[1-(5-chloro-1H-benzimidazol-2-yl)-3-(cyclopentylamino-carbonyl)-propyl-amino]-7-(pyrrolidin-1-yl-carbonyl)-quinazoline

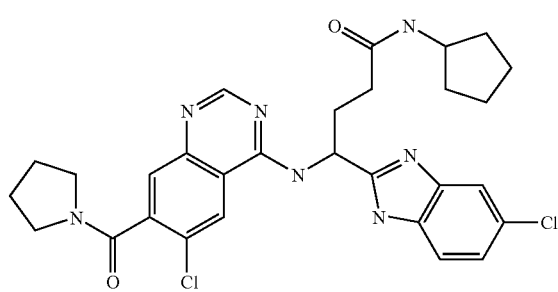

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and cyclopentylamine with TBTU in acetonitrile/tetrahydrofuran and subsequent reaction with trifluoroacetic acid.

Yield: 68% retention time: 2.64 minutes $C_{29}H_{31}Cl_2N_7O_2$ (580.52)

Mass spectrum: $(M+H)^+$=580/582/584 (chlorine isotope)

EXAMPLE 122

6-chloro-4-[1-(5-chloro-1H-benzimidazol-2-yl)-3-(N-piperidin-4-yl-aminocarbonyl)-propyl-amino]-7-(pyrrolidin-1-yl-carbonyl)-quinazoline

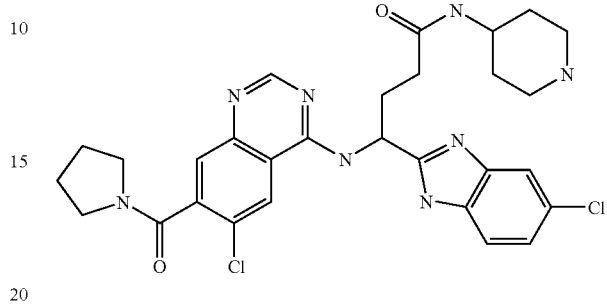

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 4-amino-1-tert.-butyloxycarbonyl-piperidine with TBTU in acetonitrile/tetrahydrofuran and subsequent reaction with trifluoroacetic acid.

Yield: 85% retention time: 2.29 minutes $C_{29}H_{32}Cl_2N_8O_2$ (595.53)

Mass spectrum: $(M+H)^+$=595/597/599 (chlorine isotope)

EXAMPLE 123

6-chloro-4-{1-(5-chloro-1H-benzimidazol-2-yl)-3-[C-(pyridin-2-yl)-methylamino-carbonyl]-propyl-amino}-7-(pyrrolidin-1-yl-carbonyl)-quinazoline

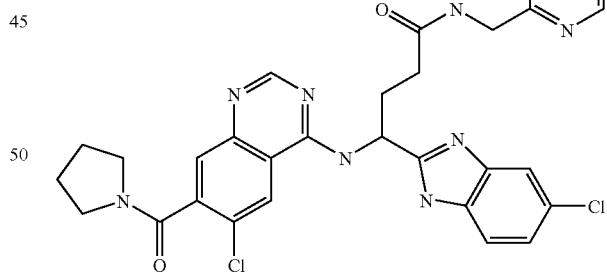

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and C-(pyridin-2-yl)-methylamine with TBTU in acetonitrile/tetrahydrofuran and subsequent reaction with trifluoroacetic acid.

Yield: 69% retention time: 2.35 minutes $C_{30}H_{28}Cl_2N_8O_2$ (603.51)

Mass spectrum: $(M+H)^+$=603/605/607 (chlorine isotope)

EXAMPLE 124

6-chloro-4-[1-(5-chloro-1H-benzimidazol-2-yl)-3-(4-thiazol-2-yl-piperazin-1-yl-carbonyl)-propyl-amino]-7-(pyrrolidin-1-yl-carbonyl)-quinazoline

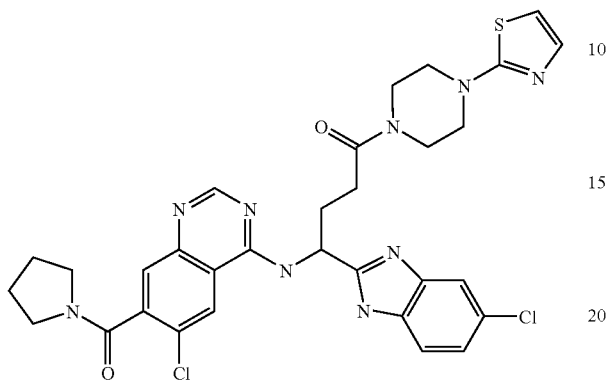

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 1-thiazol-2-yl-piperazine with TBTU in acetonitrile/tetrahydrofuran and subsequent reaction with trifluoroacetic acid.

Yield: 83%
retention time: 2.42 minutes
$C_{31}H_{31}Cl_2N_9O_2S$ (664.62)
Mass spectrum: (M+H)$^+$=664/666/668 (chlorine isotope)

EXAMPLE 125

6-chloro-4-[1-(5-chloro-1H-benzimidazol-2-yl)-3-(piperidin-1-yl-carbonyl)-propyl-amino]-7-(pyrrolidin-1-yl-carbonyl)-quinazoline

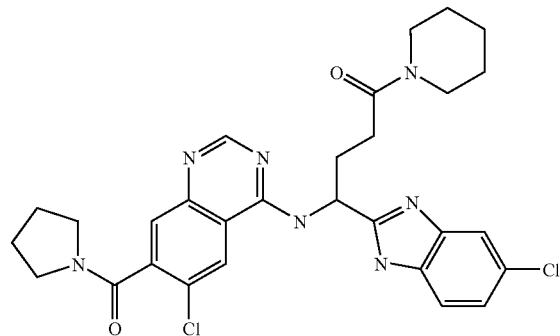

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and piperidine with TBTU in acetonitrile/tetrahydrofuran and subsequent reaction with trifluoroacetic acid.

Yield: 62%
retention time: 2.61 minutes
$C_{29}H_{31}Cl_2N_7O_2$ (580.52)
Mass spectrum: (M+H)$^+$=580/582/584 (chlorine isotope)

EXAMPLE 126

6-chloro-4-[(1S)-1-(5-chloro-1H-benzimidazol-2-yl)-3-amino-propyl-amino]-7-(2,5-dihydropyrrol-1-yl-carbonyl)-quinazoline

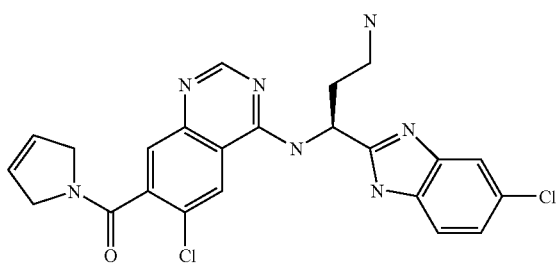

Prepared analogously to Example 15c from 6-chloro-4-[(1S)-3-(benzyloxycarbonyl-amino)-1-(5-chloro-1H-benzimidazol-2-yl)-propyl-amino]-7-(2,5-dihydropyrrol-1-yl-carbonyl)-quinazoline and trimethylsilyl iodide.

Yield: 68%
$R_f$ value: 0.22 (silica gel; dichloromethane/ethanol=8:2+2% ammonia solution)
$C_{23}H_{21}Cl_2N_7O$ (482.38)
Mass spectrum: (M+H)$^+$=482/484/486 (chlorine isotope)

EXAMPLE 127

6-chloro-4-[(1S)-1-(5-chloro-1H-benzimidazol-2-yl)-3-hydroxycarbonyl-propylamino]-7-(pyrrolidin-1-yl-carbonyl)-quinazoline

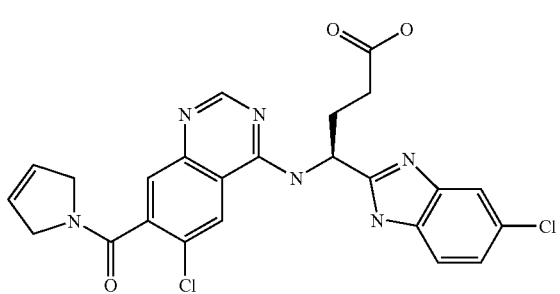

Prepared analogously to Example 15c from 6-chloro-4-[(1S)-1-(5-chloro-1H-benzimidazol-2-yl)-3-benzyloxycarbonyl-propylamino]-7-(pyrrolidin-1-yl-carbonyl)-quinazoline and trimethylsilyl iodide.

Yield: 28%
$R_f$ value: 0.36 (silica gel; dichloromethane/ethanol=8:2)
$C_{24}H_{22}Cl_2N_6O_3$ (513.38)
Mass spectrum: (M+H)$^+$=513/515/517 (chlorine isotope)

EXAMPLE 128

6-chloro-4-[(1S)-1-(5-chloro-1H-benzimidazol-2-yl)-ethylamino]-7-(5,6,7,8-tetrahydro-[1,2,4]triazolo[4,3a]pyridin-4-yl)-quinazoline

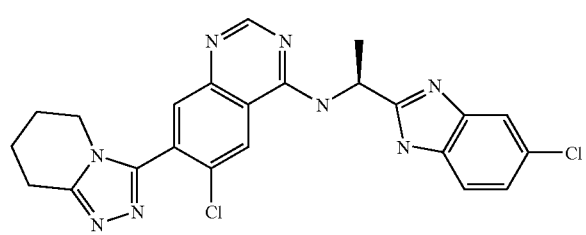

42 mg (60 µmol; 60%) 6-chloro-4-[(1S)-1-(5-chloro-1H-benzimidazol-2-yl)-methylamino]-7-(hydrazino-carbonyl)-quinazoline are placed in 5 ml of ethanol/acetic acid (v/v=2:1), combined with 6.8 mg (60 µmol) of 6-methoxy-2,3,4,5-tetrahydropyridine and stirred for one hour at 70° C. The mixture is poured onto water and the precipitate is suction filtered. The product is dissolved in acetonitrile/water and freeze-dried.

Yield: 26.3 mg (74%)

$C_{23}H_{20}Cl_2N_8$ (479.38)

Mass spectrum: $(M+H)^+$=479/481/483 (chlorine isotope)

EXAMPLE 129

6-chloro-4-[1-(5-chloro-1H-benzimidazol-2-yl)-1-(thiophen-3-yl)-methylamino]-7-(2,5-dihydropyrrol-1-yl-carbonyl)-quinazoline

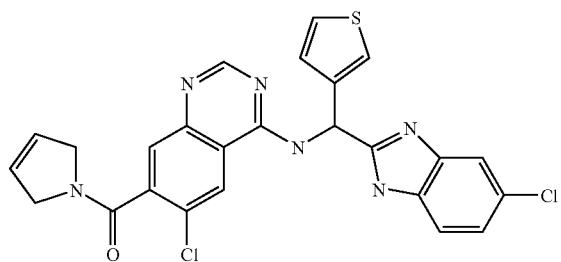

Prepared analogously to Example 2d from 4,6-dichloro-7-(2,5-dihydropyrrol-1-yl-carbonyl)-quinazoline, C-(5-chloro-1H-benzimidazol-2-yl)-C-(thiophen-3-yl)-methylamine-ditrifluoroacetate and triethylamine in N,N-dimethylformamide.

Yield: 14%

$R_f$ value: 0.35 (silica gel; dichloromethane/ethanol=9:1)

$C_{25}H_{18}Cl_2N_6OS$ (521.43)

Mass spectrum: $(M+H)^+$=521/523/525 (chlorine isotope)

EXAMPLE 130

6-chloro-4-[(1S)-1-(5-chloro-1H-benzimidazol-2-yl)-3-(2-oxo-pyrrolidin-1-yl)-propyl-amino]-7-(2,5-dihydropyrrol-1-yl-carbonyl)-quinazoline

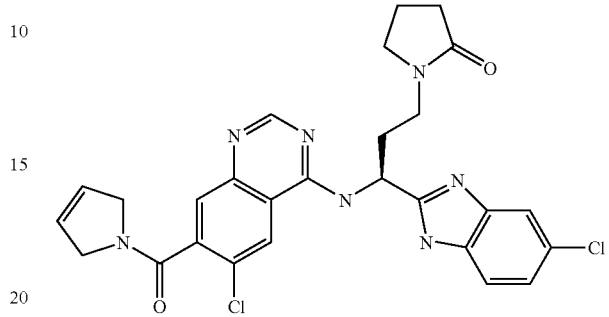

(a) 6-chloro-4-{(1S)-1-(5-chloro-1H-benzimidazol-2-yl)-3-[(3-chloro-propyl-carbonyl)-amino]-propyl-amino}-7-(2,5-dihydropyrrol-1-yl-carbonyl)-quinazoline 300 mg (0.62 mmol) 6-chloro-4-[(1S)-1-(5-chloro-1H-benzimidazol-2-yl)-3-amino-propyl-amino]-7-(2,5-dihydropyrrol-1-yl-carbonyl)-quinazoline are dissolved in 10 ml of tetrahydrofuran and at 0° C. 70 µl (0.62 mmol) of 4-chlorobutanoic acid chloride and 187 µl (1.3 mmol) triethylamine are added. The mixture is heated to ambient temperature, stirred for 18 hours and then evaporated to dryness. The residue is taken up in dichloromethane and extracted twice with water. The organic phase is dried over sodium sulphate and concentrated.

Yield: 260 mg (72%)

$R_f$ value: 0.40 (silica gel; dichloromethane/ethanol=9:1)

(b) 6-chloro-4-[(1S)-1-(5-chloro-1H-benzimidazol-2-yl)-3-(2-oxo-pyrrolidin-1-yl)-propyl-amino]-7-(2,5-dihydropyrrol-1-yl-carbonyl)-quinazoline 260 mg (0.44 mmol) 6-chloro-4-{(1S)-1-(5-chloro-1H-benzimidazol-2-yl)-3-[(3-chloro-propyl-carbonyl)-amino]-propyl-amino}-7-(2,5-dihydropyrrol-1-yl-carbonyl)-quinazoline are dissolved in 5 ml N,N-dimethylformamide and combined with 27 mg (0.56 mmol) sodium hydride (50% dispersion in mineral oil). After two hours a further 20 mg (0.42 mmol) sodium hydride are added and the mixture is stirred for 1.5 hours. Water is added and the mixture is extracted with ethyl acetate. The organic phases are washed twice with water and with saturated saline solution. They are dried over sodium sulphate and evaporated down. The crude product is purified by chromatography (silica gel; eluant: dichloromethane/ethanol 94:6).

Yield: 110 mg (45%)

$R_f$ value: 0.50 (silica gel; dichloromethane/ethanol=9:1)

$C_{27}H_{25}Cl_2N_7O_2$ (550.45)

Mass spectrum: $(M+H)^+$=550/552/554 (chlorine isotope)

EXAMPLE 131

6-chloro-4-[(1S)-1-(5-chloro-1H-benzimidazol-2-yl)-3-(1,1-dioxo-isothiazolidin-2-yl)-propyl-amino]-7-(2,5-dihydropyrrol-1-yl-carbonyl)-quinazoline

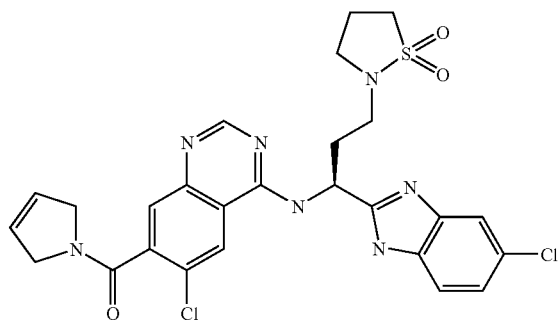

Prepared analogously to Example 130 from 6-chloro-4-[(1S)-1-(5-chloro-1H-benzimidazol-2-yl)-3-amino-propyl-amino]-7-(2,5-dihydropyrrol-1-yl-carbonyl)-quinazoline and 3-chloro-propanesulphonic acid chloride and subsequent cyclisation with sodium hydride in N,N-dimethylformamide.

Yield: 41 % over two steps $R_f$ value: 0.40 (silica gel; dichloromethane/ethanol=9:1)

$C_{26}H_{25}Cl_2N_7O_3S$ (586.50)

Mass spectrum: $(M+H)^+$=586/588/590 (chlorine isotope)

EXAMPLE 132

6-chloro-4-[(1S)-1-(5-chloro-1H-benzimidazol-2-yl)-2-isopropylcarbonyloxy-ethylamino]-7-(2,5-dihydropyrrol-1-yl-carbonyl)-quinazoline

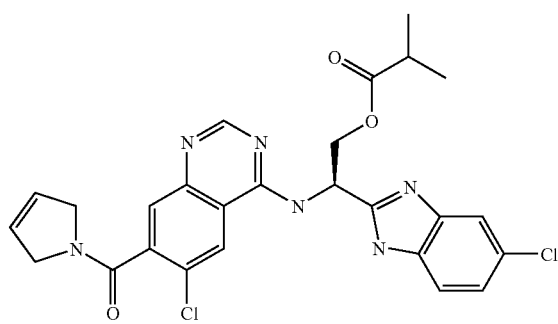

Prepared analogously to Example 37a from 6-chloro-4-[(1S)-1-(5-chloro-1H-benzimidazol-2-yl)-2-hydroxy-ethylamino]-7-(2,5-dihydropyrrol-1-yl-carbonyl)-quinazoline, TBTU, diisopropylethylamine and isobutyric acid in N,N-dimethylformamide/tetrahydrofuran.

Yield: 43%

$R_f$ value: 0.14 (silica gel; dichloromethane/isopropanol=95:5)

$C_{26}H_{24}Cl_2N_6O_3$ (539.42)

Mass spectrum: $(M+H)^+$=539/541/543 (chlorine isotope) $(M-H)^-$=537/539/541 (chlorine isotope)

EXAMPLE 133

6-chloro-4-[(1S)-1-(5-chloro-1H-benzimidazol-2-yl)-4-(hydroxycarbonyl)-butylamino]-7-(2,5-dihydropyrrol-1-yl-carbonyl)-quinazoline

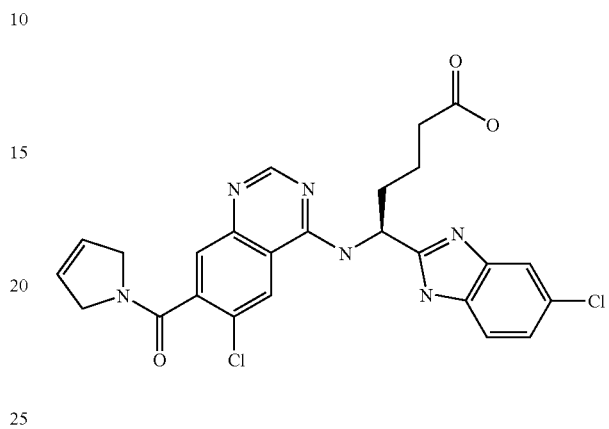

Prepared analogously to Example 8c from 6-chloro-4-[(1S)-1-(5-chloro-1H-benzimidazol-2-yl)-4-(tert.-butyloxycarbonyl)-butylamino]-7-(2,5-dihydropyrrol-1-yl-carbonyl)-quinazoline and trifluoroacetic acid in dichloromethane.

Yield: 33% retention time: 2.30 minutes $C_{25}H_{24}Cl_2N_6O_3$ (527.41)

Mass spectrum: $(M+H)^+$=527/529/531 (chlorine isotope)

EXAMPLE 134

6-chloro-4-[(1S)-1-(5-chloro-1H-benzimidazol-2-yl)-ethylamino]-7-[(2R/S)-2-(pyridin-4-yl)-thiazolidin-3-yl-carbonyl]-quinazoline

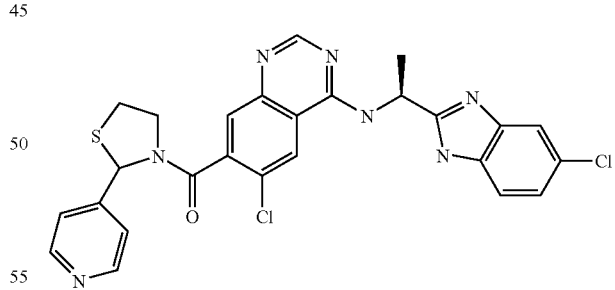

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and 2-(pyridin-4-yl)-thiazolidine in N,N-dimethylformamide.

Yield: 12%

$R_f$ value: 0.55 (silica gel; dichloromethane/ethanol=9:1)

$C_{26}H_{21}Cl_2N_7OS$ (550.47)

Mass spectrum: $(M-H)^-$=548/550/552 (chlorine isotope)

EXAMPLE 135

6-chloro-4-[(1S)-1-(5-chloro-1H-benzimidazol-2-yl)-ethylamino]-7-[(2R/S)-2-(2,2,2-trifluorethyl)-thiazolidin-3-yl-carbonyl]-quinazoline

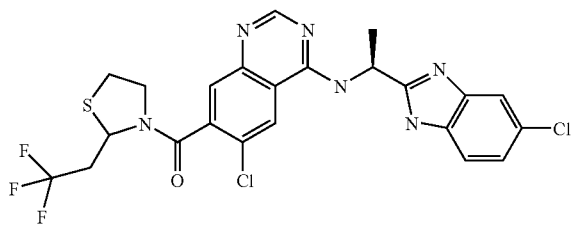

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and 2-(2,2,2-trifluorethyl)-thiazolidine in N,N-dimethylformamide.

Yield: 16%

$R_f$ value: 0.70 (silica gel; dichloromethane/ethanol=9:1)

$C_{23}H_{19}Cl_2F_3N_6OS$ (555.41)

Mass spectrum: $(M+H)^+=555/557/559$ (chlorine isotope)

EXAMPLE 136

6-chloro-4-[(1S)-1-(5-chloro-1H-benzimidazol-2-yl)-3-methanesulphonylamino-propyl-amino]-7-(2,5-dihydropyrrol-1-yl-carbonyl)-quinazoline

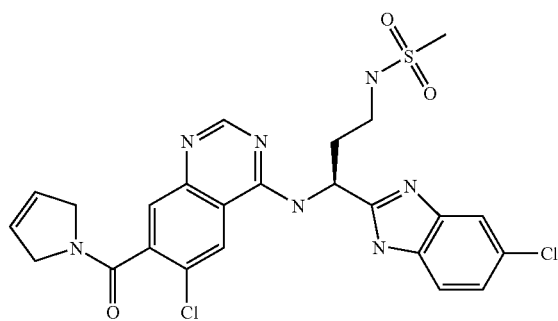

Prepared analogously to Example 80 from 6-chloro-4-[(1S)-1-(5-chloro-1H-benzimidazol-2-yl)-3-amino-propyl-amino]-7-(2,5-dihydropyrrol-1-yl-carbonyl)-quinazoline and methanesulphonic acid chloride in tetrahydrofuran.

Yield: 44%

$R_f$ value: 0.40 (silica gel; dichloromethane/ethanol=9:1)

$C_{24}H_{23}Cl_2N_7O_3S$ (560.46)

Mass spectrum: $(M+H)^+=560/562/564$ (chlorine isotope)

EXAMPLE 137

6-chloro-4-[(1S)-1-(5-chloro-1H-benzimidazol-2-yl)-2-methylsulphanyl-ethylamino]-7-(2,5-dihydro-pyrrol-1-yl-carbonyl)-quinazoline

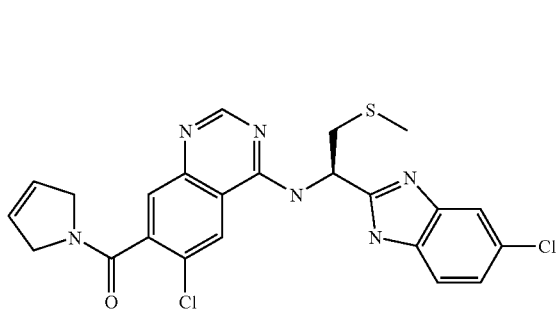

Prepared analogously to Example 2d from 4,6-dichloro-7-(2,5-dihydropyrrol-1-yl-carbonyl)-quinazoline, (S)-1-(5-chloro-1H-benzimidazol-2-yl)-2-methylsulphanyl-ethylamine-ditrifluoroacetate and triethylamine in N,N-dimethylformamide.

Yield: 31%

$R_f$ value: 0.35 (silica gel; dichloromethane/ethanol=9:1)

$C_{23}H_{20}Cl_2N_6OS$ (499.42)

Mass spectrum: $(M+H)^+=499/501/503$ (chlorine isotope)

EXAMPLE 138

4-[(1S)-1-(5-chloro-1H-benzimidazol-2-yl)-ethylamino]-7-(2,5-dihydropyrrol-1-yl-carbonyl)-6-methoxy-quinazoline

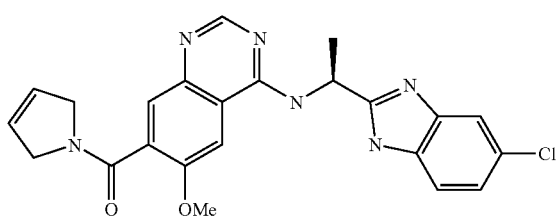

(a) 6-bromo-4-oxo-3,4-dihydro-quinazoline-7-carboxylic acid

Prepared analogously to Example 2a from 6-amino-4-methoxy-terephthalic acid and formamidine-acetate in methylglycol.
Yield: 72%
$R_f$ value: 0.63 (Reversed phase RP8; methanol/5% sodium chloride solution=1:2)
$C_{10}H_8N_2O_4$ (220.19)
Mass spectrum: $(M+H)^+=221$ (bromine isotope)

(b) 4-chloro-7-(2,5-dihydropyrrol-1-yl-carbonyl)-6-methoxy-quinazoline

Prepared analogously to Example 2b or 2c from 6-methoxy-4-oxo-3,4-dihydro-quinazoline-7-carboxylic acid, thionyl chloride, 2,5-dihydropyrrole, sodium hydroxide solution and dichloromethane.
Yield: 39% (over two steps)
$R_f$ value: 0.30 (silica gel; dichloromethane/ethyl acetate=1:1)
$C_{13}H_9BrClN_3O$ (338.593)
Mass spectrum: $(M+H)^+=290/292$ (chlorine, bromine isotope)

(c) 4-[(1S)-1-(5-chloro-1H-benzimidazol-2-yl)-ethylamino]-7-(2,5-dihydropyrrol-1-yl-carbonyl)-6-methoxy-quinazoline Prepared analogously to Example 2d from 4-chloro-7-(2,5-dihydropyrrol-1-yl-carbonyl)-6-methoxy-quinazoline, (S)-1-(5-chloro-1H-benzimidazol-2-yl)-ethylamine-hydrochloride and triethylamine in N,N-dimethylformamide.
Yield: 32%
$R_f$ value: 0.50 (silica gel; dichloromethane/methanol=9:1+1% ammonia solution)
$C_{23}H_{21}ClN_6O_2$ (448.92)
Mass spectrum: $(M+H)^+=449/451$ (chlorine, bromine isotope)

EXAMPLE 139

7-[(2S)-2-(2-aminoethyl)-pyrrolidin-1-yl-carbonyl]-6-chloro-4-[(1R/S)-1-(5-chloro-1H-benzimidazol-2-yl)-ethylamino]-quinazoline

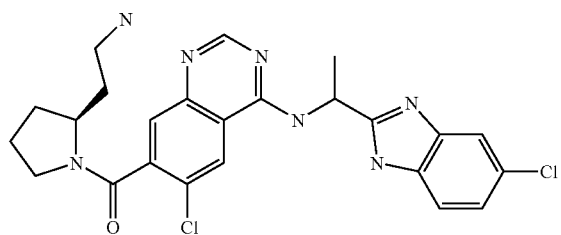

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (2S)-2-(2-tert.-butyloxycarbonyl-aminoethyl)-pyrrolidine in DMSO at ambient temperature and subsequent treatment with trifluoroacetic acid.

HPLC-MS results:
retention time: 3.80 min
$C_{24}H_{25}Cl_2N_7O$ (498.42)
Mass spectrum: $(M+H)^+=499.54$

EXAMPLE 140

6-chloro-4-[(1R/S)-1-(5-chloro-1H-benzimidazol-2-yl)-ethylamino]-7-[(2R/S)-2-ethoxycarbonyl-piperidin-1-yl-carbonyl]-quinazoline

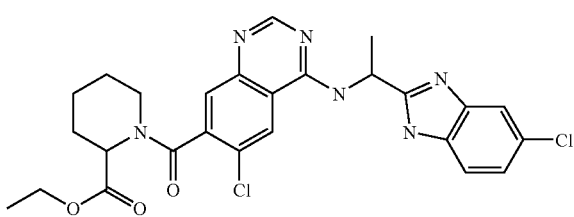

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and ethyl piperidine-2-carboxylate in DMSO at ambient temperature and subsequent treatment with trifluoroacetic acid.

HPLC-MS results:
retention time: 4.43 min
$C_{26}H_{26}Cl_2N_6O_3$ (541.44)
Mass spectrum: $(M+H)^+=542.44$

EXAMPLE 141

6-chloro-4-[1-(5-chloro-1H-benzimidazol-2-yl)-ethylamino]-7-(4,5,6,7-tetrahydro-thieno[3,2-c]pyridin-5-yl-carbonyl)-quinazoline

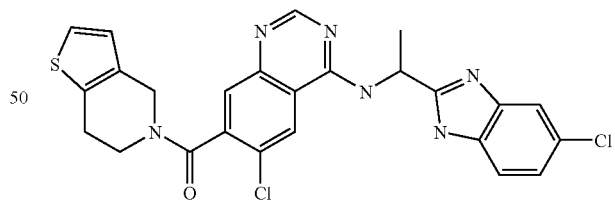

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 4,5,6,7-tetrahydro-thieno[3,2-c]pyridine in DMSO at ambient temperature.

HPLC-MS results:
retention time: 4.43 min
$C_{25}H_{20}Cl_2N_6OS$ (523.45)
Mass spectrum: $(M+H)^+=524.45$

EXAMPLE 142

7-[(2S)-2-benzhydryl-pyrrolidin-1-yl-carbonyl]-6-chloro-4-[(1R/S)-1-(5-chloro-1H-benzimidazol-2-yl)-ethylamino]-quinazoline

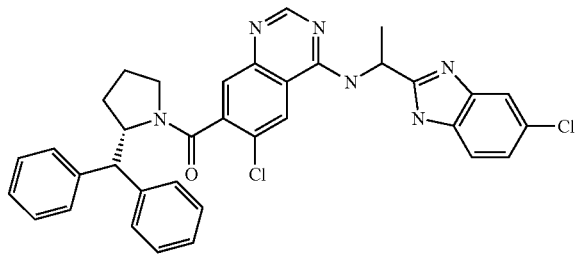

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and (S)-2-benzhydryl-pyrrolidine in DMSO at ambient temperature.
HPLC-MS results:
retention time: 4.86 min
$C_{35}H_{30}Cl_2N_6O$ (621.57)
Mass spectrum: $(M+H)^+=622.57$

EXAMPLE 143

6-chloro-4-[1-(5-chloro-1H-benzimidazol-2-yl)-ethylamino]-7-([1,4]diazepan-1-yl-carbonyl)-quinazoline

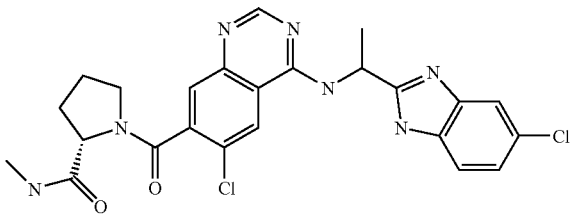

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 1-tert.-butyloxycarbonyl-[1,4]diazepan in DMSO at ambient temperature and subsequent treatment with trifluoroacetic acid.
HPLC-MS results:
retention time: 3.62 min
$C_{23}H_{23}Cl_2N_7O$ (484.39)
Mass spectrum: $(M+H)^+=484.51$

EXAMPLE 144

6-chloro-4-[(1R/S)-1-(5-chloro-1H-benzimidazol-2-yl)-ethylamino]-7-[(2R/S)-2-(2-ethoxycarbonyl-ethyl)-piperidin-1-yl-carbonyl]-quinazoline

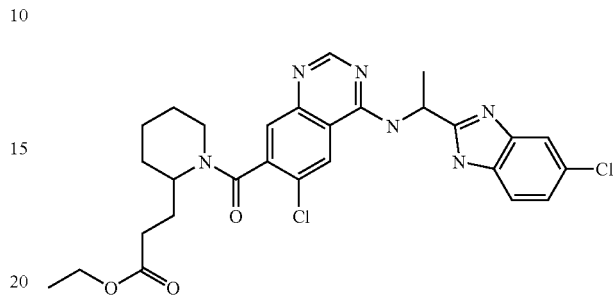

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and ethyl 3-piperidin-2-yl-propionate in DMSO at ambient temperature.
HPLC-MS results:
retention time: 4.48 min
$C_{28}H_{30}Cl_2N_6O_3$ (569.49)
Mass spectrum: $(M+H)^+=570.49$

EXAMPLE 145

6-chloro-4-[(1R/S)-1-(5-chloro-1H-benzimidazol-2-yl)-ethylamino]-7-[(2S)-2-methylaminocarbonyl-pyrrolidin-1-yl-carbonyl]-quinazoline Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and (S)-2-methylaminocarbonyl-pyrrolidine in DMSO at ambient temperature.
HPLC-MS results:
retention time: 3.88 min
$C_{24}H_{23}Cl_2N_7O_2$ (512.40)
Mass spectrum: $(M+H)^+=513.40$

EXAMPLE 146

6-chloro-4-[(1R/S)-1-(5-chloro-1H-benzimidazol-2-yl)-ethylamino]-7-[(3R/S)-3-(3-diethylamino-propyl)-piperidin-1-yl-carbonyl]-quinazoline

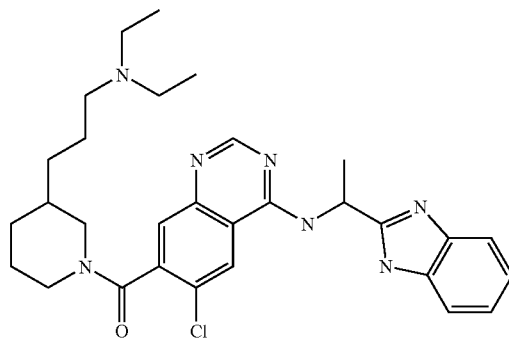

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 3-(3-diethylamino-propyl)-piperidine in DMSO at ambient temperature.
HPLC-MS results:
retention time: 3.97 min
$C_{30}H_{37}Cl_2N_7O$ (582.58)
Mass spectrum: $(M+H)^+=582.02$

EXAMPLE 147

6-chloro-4-[1-(5-chloro-1H-benzimidazol-2-yl)-ethylamino]-7-(4-methyl-piperidin-1-yl-carbonyl)-quinazoline

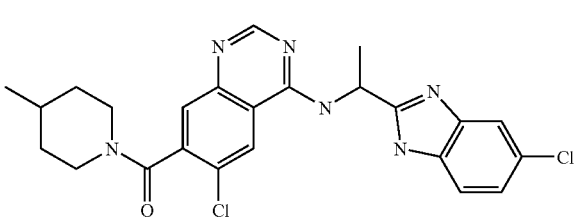

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 4-methyl-piperidine in DMSO at ambient temperature.
HPLC-MS results:
retention time: 4.35 min
$C_{24}H_{24}Cl_2N_6O$ (483.40)
Mass spectrum: $(M+H)^+=484.40$

EXAMPLE 148

6-chloro-4-[(1R/S)-1-(5-chloro-1H-benzimidazol-2-yl)-ethylamino]-7-[(2S)-2-(phenylaminomethyl)-pyrrolidin-1-yl-carbonyl]-quinazoline

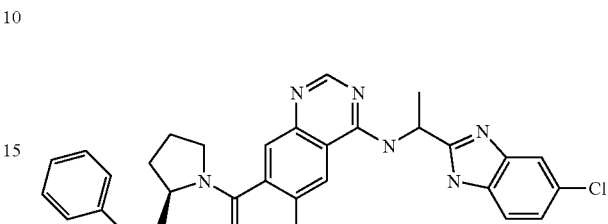

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and (S)-2-(phenylaminomethyl)-pyrrolidine in DMSO at ambient temperature.
HPLC-MS results:
retention time: 4.34 min
$C_{29}H_{27}Cl_2N_7O$ (560.49)
Mass spectrum: $(M+H)^+=561.49$

EXAMPLE 149

6-chloro-4-[(1R/S)-1-(5-chloro-1H-benzimidazol-2-yl)-ethylamino]-7-[(2R/S)-2-benzyl-pyrrolidin-1-yl-carbonyl]-quinazoline

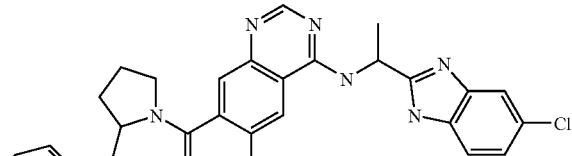

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-benzyl-pyrrolidine in DMSO at ambient temperature.
HPLC-MS results:
retention time: 4.64 min
$C_{29}H_{26}Cl_2N_6O$ (545.47)
Mass spectrum: $(M+H)^+=546.47$

EXAMPLE 150

6-chloro-4-[(1R/S)-1-(5-chloro-1H-benzimidazol-2-yl)-ethylamino]-7-[(3R/S)-3-hydroxy-piperidin-1-yl-carbonyl]-quinazoline

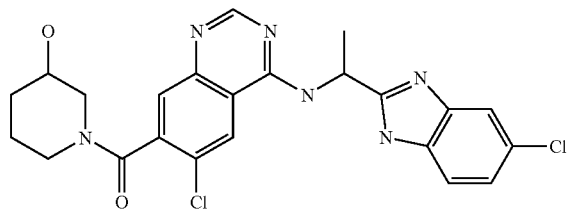

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 3-hydroxy-piperidine in DMSO at ambient temperature.
HPLC-MS results:
retention time: 3.91 min
$C_{23}H_{22}Cl_2N_6O_2$ (485.37)
Mass spectrum: $(M+H)^+$=486.38

EXAMPLE 151

6-chloro-4-[(1R/S)-1-(5-chloro-1H-benzimidazol-2-yl)-ethylamino]-7-[(2S)-2-dimethylaminocarbonyl-pyrrolidin-1-yl-carbonyl]-quinazoline

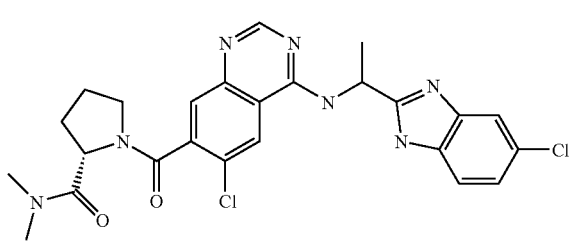

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and (S)-2-dimethylaminocarbonyl-pyrrolidine in DMSO at ambient temperature.
HPLC-MS results:
retention time: 3.97 min
$C_{25}H_{25}Cl_2N_7O_2$ (526.43)
Mass spectrum: $(M+H)^+$=527.43

EXAMPLE 152

6-chloro-4-[1-(5-chloro-1H-benzimidazol-2-yl)-ethylamino]-7-(piperidin-1-yl-carbonyl)-quinazoline

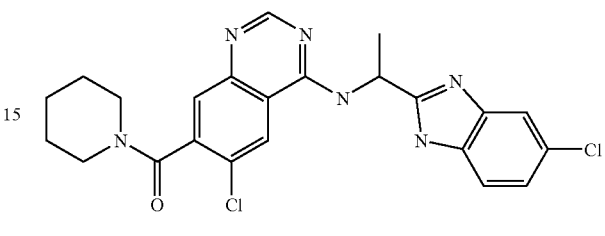

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and piperidine in DMSO at ambient temperature.
HPLC-MS results:
retention time: 4.19 min
$C_{23}H_{22}Cl_2N_6O$ (469.37)
Mass spectrum: $(M+H)^+$=470.38

EXAMPLE 153

6-chloro-4-[1-(5-chloro-1H-benzimidazol-2-yl)-ethylamino]-7-(4-oxo-piperidin-1-yl-carbonyl)-quinazoline

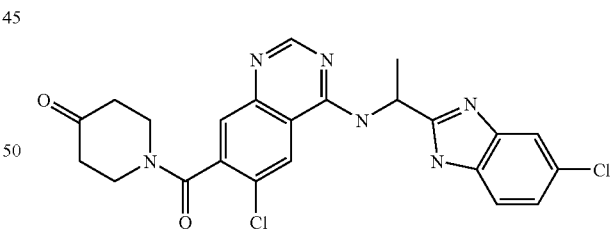

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 4-oxo-piperidine in DMSO at ambient temperature.
HPLC-MS results:
retention time: 3.87 min
$C_{23}H_{20}Cl_2N_6O_2$ (483.36)
Mass spectrum: $(M+H)^+$=484.36

EXAMPLE 154

6-chloro-4-[1-(5-chloro-1H-benzimidazol-2-yl)-ethylamino]-7-(4-methylene-piperidin-1-yl-carbonyl)-quinazoline

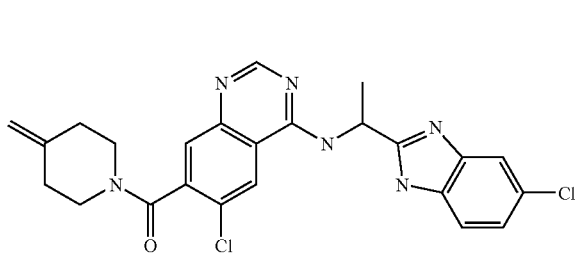

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 4-methylene-piperidine in DMSO at ambient temperature.

HPLC-MS results:

retention time: 4.31 min $C_{24}H_{22}Cl_2N_6O$ (481.39)

Mass spectrum: $(M+H)^+=482.39$

EXAMPLE 155

6-chloro-4-[(1R/S)-1-(5-chloro-1H-benzimidazol-2-yl)-ethylamino]-7-[(2R/S)-2-methyl-piperidin-1-yl-carbonyl]-quinazoline

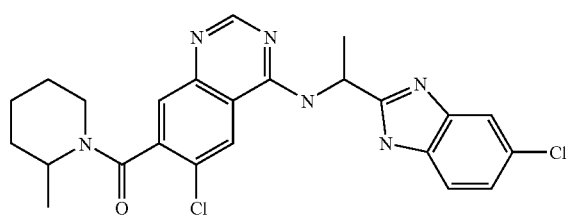

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-methyl-piperidine in DMSO at ambient temperature.

HPLC-MS results:

retention time: 4.31 min $C_{24}H_{24}Cl_2N_6O$ (483.40)

Mass spectrum: $(M+H)^+=484.4$

EXAMPLE 156

6-chloro-4-[(1R/S)-1-(5-chloro-1H-benzimidazol-2-yl)-ethylamino]-7-[(2R/S)-2-benzyloxycarbonyl-pyrrolidin-1-yl-carbonyl]-quinazoline

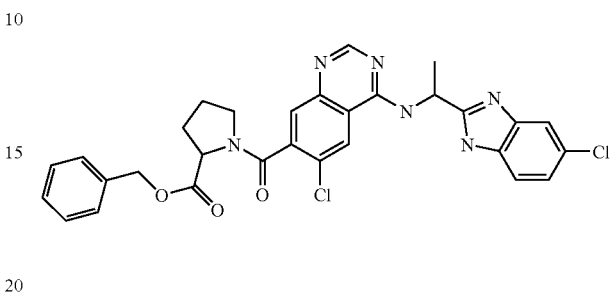

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-benzyloxycarbonyl-pyrrolidine in DMSO at ambient temperature.

HPLC-MS results:

retention time: 4.59 min $C_{30}H_{26}Cl_2N_6O_3$ (589.48)

Mass spectrum: $(M+H)^+=590.48$

EXAMPLE 157

6-chloro-4-[1-(5-chloro-1H-benzimidazol-2-yl)-ethylamino]-7-[N-(3-amino-propyl)-N-ethyl-aminocarbonyl]-quinazoline

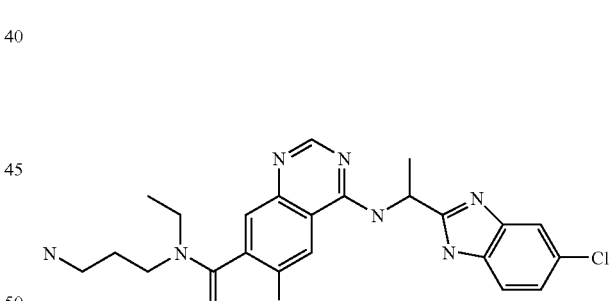

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-(3-tert.-butyloxycarbonylamino-propyl)-ethylamine in DMSO at ambient temperature and subsequent treatment with trifluoroacetic acid.

HPLC-MS results:

retention time: 3.77 min $C_{23}H_{25}Cl_2N_7O$ (486.41)

Mass spectrum: $(M+H)^+=487.52$

EXAMPLE 158

6-chloro-4-[1-(5-chloro-1H-benzimidazol-2-yl)-ethylamino]-7-(N-cyclopropyl-N-methylamino-carbonyl)-quinazoline

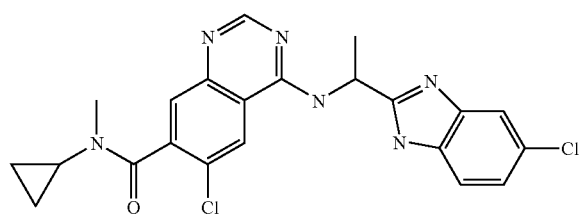

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-cyclopropyl-methylamine in DMSO at ambient temperature.

HPLC-MS results:
retention time: 4.09 min
$C_{22}H_{20}Cl_2N_6O$ (455.35)
Mass spectrum: $(M+H)^+=456.35$

EXAMPLE 159

6-chloro-4-[1-(5-chloro-1H-benzimidazol-2-yl)-ethylamino]-7-(2-oxo-piperazin-4-yl-carbonyl)-quinazoline

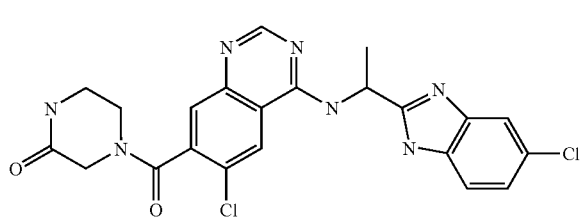

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and piperazinone in DMSO at ambient temperature.

HPLC-MS results:
retention time: 3.77 min
$C_{22}H_{19}Cl_2N_7O_2$ (484.35)
Mass spectrum: $(M+H)^+=483.82$

EXAMPLE 160

6-chloro-4-[(1R/S)-1-(5-chloro-1H-benzimidazol-2-yl)-ethylamino]-7-[(2S)-2-methoxymethyl-pyrrolidin-1-yl-carbonyl]-quinazoline

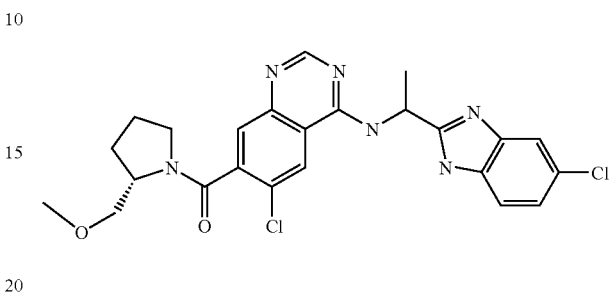

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (S)-2-methoxymethyl-pyrrolidine in DMSO at ambient temperature.

HPLC-MS results:
retention time: 4.16 min
$C_{24}H_{24}Cl_2N_6O_2$ (499.40)
Mass spectrum: $(M+H)^+=500.40$

EXAMPLE 161

6-chloro-4-[(1R/S)-1-(5-chloro-1H-benzimidazol-2-yl)-ethylamino]-7-[(2R)-2-(phenylaminomethyl)-pyrrolidin-1-yl-carbonyl]-quinazoline

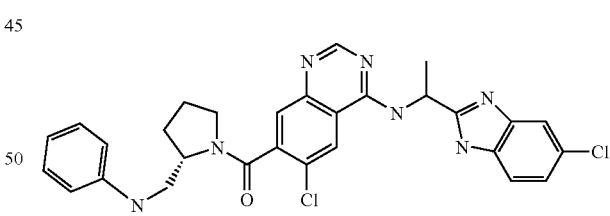

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (R)-2-(phenylaminomethyl)-pyrrolidine in DMSO at ambient temperature.

HPLC-MS results:
retention time: 4.34 min
$C_{29}H_{27}Cl_2N_7O$ (560.49)
Mass spectrum: $(M+H)^+=561.49$

EXAMPLE 162

6-chloro-4-[(1R/S)-1-(5-chloro-1H-benzimidazol-2-yl)-ethylamino]-7-{1-[(3R/S)-3-(1H-benzimidazol-2-yl)-piperidin-1-yl]-carbonyl}-quinazoline

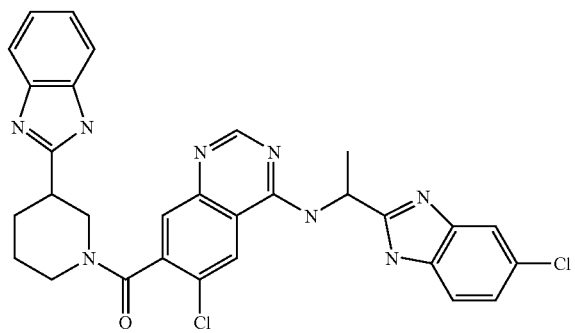

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-piperidin-3-yl-1H-benzimidazole in DMSO at ambient temperature.
HPLC-MS results:
retention time: 4.01 min
$C_{30}H_{26}Cl_2N_8O$ (585.50)
Mass spectrum: $(M+H)^+=584.98$

EXAMPLE 163

6-chloro-4-[(1R/S)-1-(5-chloro-1H-benzimidazol-2-yl)-ethylamino]-7-[(3R/S)-3-dimethylamino-pyrrolidin-1-yl-carbonyl]-quinazoline

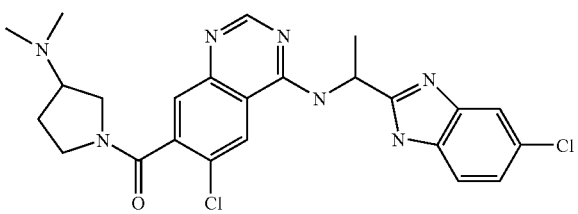

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 3-dimethylamino-pyrrolidine in DMSO at ambient temperature.
HPLC-MS results:
retention time: 3.69 min
$C_{24}H_{25}Cl_2N_7O$ (498.42)
Mass spectrum: $(M+H)^+=499.42$

EXAMPLE 164

6-chloro-4-[1-(5-chloro-1H-benzimidazol-2-yl)-ethylamino]-7-[(2,5-dimethyl-2,5-dihydro-1H-pyrrol-1-yl)-carbonyl]-quinazoline

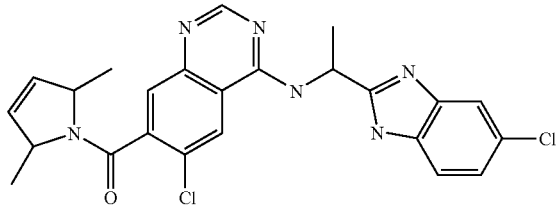

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2,5-dimethyl-2,5-dihydro-1H-pyrrole in DMSO at ambient temperature.
HPLC-MS results:
retention time: 4.27 min
$C_{24}H_{22}Cl_2N_6O$ (481.39)
Mass spectrum: $(M+H)^+=482.39$

EXAMPLE 165

6-chloro-4-[(1R/S)-1-(5-chloro-1H-benzimidazol-2-yl)-ethylamino]-7-[(2R/S)-2-isopropyl-pyrrolidin-1-yl-carbonyl]-quinazoline

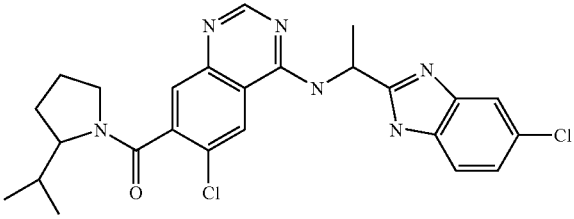

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-isopropyl-pyrrolidine in DMSO at ambient temperature.
HPLC-MS results:
retention time: 4.44 min
$C_{25}H_{26}Cl_2N_6O$ (497.43)
Mass spectrum: $(M+H)^+=498.43$

EXAMPLE 166

6-chloro-4-[(1R/S)-1-(5-chloro-1H-benzimidazol-2-yl)-ethylamino]-7-[(2R/S)-2-aminomethyl-piperidin-1-yl-carbonyl]-quinazoline

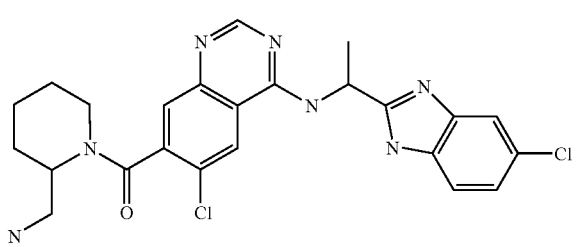

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-(tert.-butyloxycarbonyl-aminomethyl)-piperidine in DMSO at ambient temperature and subsequent treatment with trifluoroacetic acid.
HPLC-MS results:
retention time: 3.82 min
$C_{24}H_{25}Cl_2N_7O$ (498.42)
Mass spectrum: $(M+H)^+=499.54$

EXAMPLE 167

6-chloro-4-[(1R/S)-1-(5-chloro-1H-benzimidazol-2-yl)-ethylamino]-7-[(3R/S)-3-aminomethyl-piperidin-1-yl-carbonyl]-quinazoline

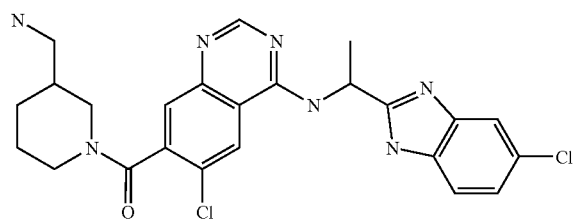

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 3-(tert.-butyloxycarbonyl-aminomethyl)-piperidine in DMSO at ambient temperature and subsequent treatment with trifluoroacetic acid.
HPLC-MS results:
retention time: 3.72 min
$C_{24}H_{25}Cl_2N_7O$ (498.42)
Mass spectrum: $(M+H)^+=499.54$

EXAMPLE 168

6-chloro-4-[(1R/S)-1-(5-chloro-1H-benzimidazol-2-yl)-ethylamino]-7-[(2R)-2-ethoxycarbonyl-pyrrolidin-1-yl-carbonyl]-quinazoline

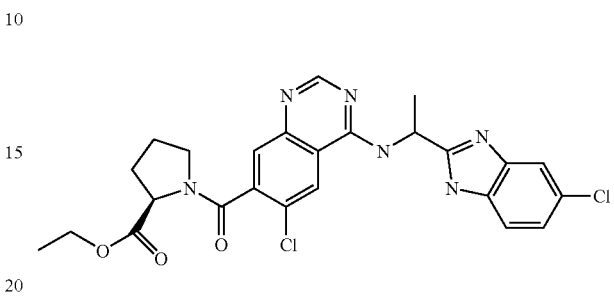

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and (R)-2-ethyloxycarbonyl-pyrrolidine in DMSO at ambient temperature.
HPLC-MS results:
retention time: 4.24 min
$C_{25}H_{24}Cl_2N_6O_3$ (527.41)
Mass spectrum: $(M+H)^+=528.41$

EXAMPLE 169

6-chloro-4-[1-(5-chloro-1H-benzimidazol-2-yl)-ethylamino]-7-[3-(dimethylamino-methyl)-piperidin-1-yl-carbonyl]-quinazoline

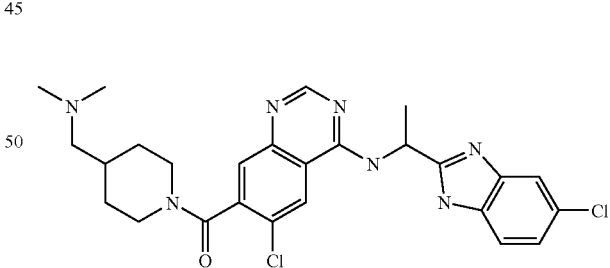

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 3-(dimethylamino-methyl)-piperidine.
HPLC-MS results:
retention time: 3.74 min
$C_{26}H_{29}Cl_2N_7O$ (526.47)
Mass spectrum: $(M+H)^+=527.47$

EXAMPLE 170

6-chloro-4-[(1R/S)-1-(5-chloro-1H-benzimidazol-2-yl)-ethylamino]-7-[(2R/S)-2-phenyl-ethyl)-pyrrolidin-1-yl-carbonyl]-quinazoline

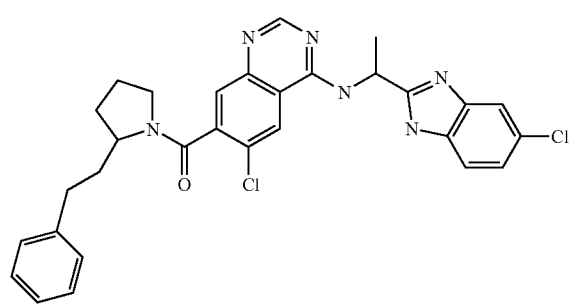

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-phenethyl-pyrrolidine in DMSO at ambient temperature.
HPLC-MS results:
retention time: 4.53 min
$C_{30}H_{28}Cl_2N_6O$ (559.50)
Mass spectrum: $(M+H)^+$=560.5

EXAMPLE 171

6-chloro-4-[(1R/S)-1-(5-chloro-1H-benzimidazol-2-yl)-ethylamino]-7-[(2R/S)-2-(pyridin-2-yl)-pyrrolidin-1-yl-carbonyl]-quinazoline

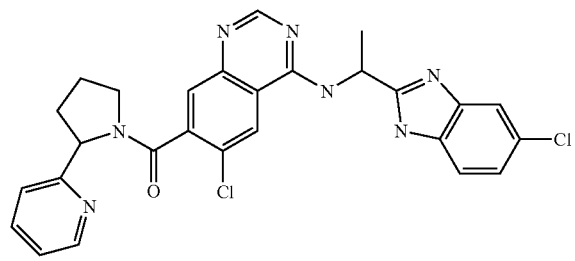

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-(pyridin-2-yl)-pyrrolidine in DMSO at ambient temperature.
HPLC-MS results:
retention time: 3.88 min
$C_{27}H_{23}Cl_2N_7O$ (532.43)
Mass spectrum: $(M+H)^+$=533.44

EXAMPLE 172

6-chloro-4-[(1R/S)-1-(5-chloro-1H-benzimidazol-2-yl)-ethylamino]-7-[(2R/S)-2-amino-ethyl)-piperidin-1-yl-carbonyl]-quinazoline

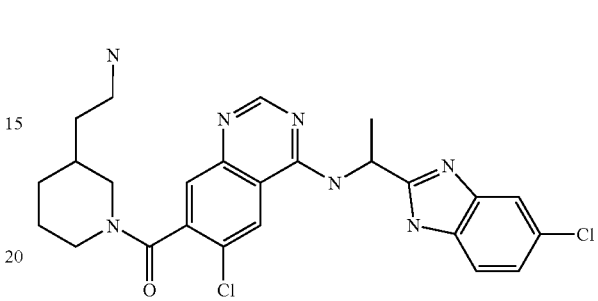

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-(2-tert.-butyloxycarbonylamino-ethyl)-piperidine in DMSO at ambient temperature.
HPLC-MS results:
retention time: 3.76 min
$C_{25}H_{27}Cl_2N_7O$ (512.44)
Mass spectrum: $(M+H)^+$=513.56

EXAMPLE 173

6-chloro-4-[1-(5-chloro-1H-benzimidazol-2-yl)-ethylamino]-7-(4-acetyl-piperazin-1-yl-carbonyl)-quinazoline Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 4-acetyl-piperazine in DMSO at ambient temperature.
HPLC-MS results:
retention time: 3.87 min
$C_{24}H_{23}Cl_2N_7O_2$ (512.40)
Mass spectrum: $(M+H)^+$=513.4

EXAMPLE 174

6-chloro-4-[1-(5-chloro-1H-benzimidazol-2-yl)-ethylamino]-7-[N-(2-amino-ethyl)-N-ethyl-amino-carbonyl]-quinazoline

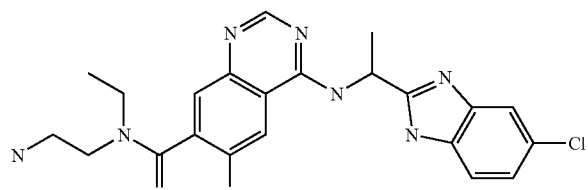

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and N-(2-tert.-butyloxycarbonylamino-ethyl)-ethylamine in DMSO at ambient temperature and subsequent treatment with trifluoroacetic acid.
HPLC-MS results:
retention time: 3.75 min
$C_{22}H_{23}Cl_2N_7O$ (472.38)
Mass spectrum: $(M+H)^+=473.5$

EXAMPLE 175

6-chloro-4-[(1R/S)-1-(5-chloro-1H-benzimidazol-2-yl)-ethylamino]-7-[(2R/S)-2-(pyridin-3-yl)-piperidin-1-yl-carbonyl]-quinazoline

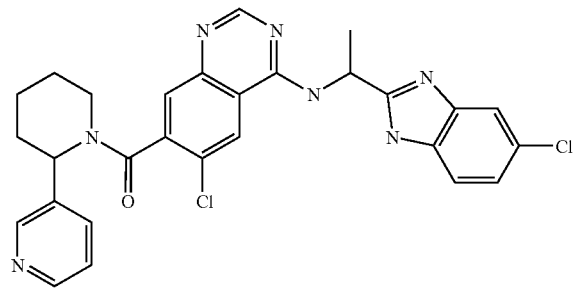

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-(pyridin-3-yl)-piperidine in DMSO at ambient temperature.
HPLC-MS results:
retention time: 3.92 min
$C_{28}H_{25}Cl_2N_7O$ (546.46)
Mass spectrum: $(M+H)^+=547.46$

EXAMPLE 176

6-chloro-4-[(1R/S)-1-(5-chloro-1H-benzimidazol-2-yl)-ethylamino]-7-[(2R/S), (5R/S)-2,5-dimethyl-pyrrolidin-1-yl-carbonyl]-quinazoline

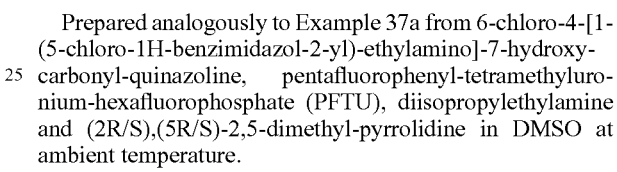

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and (2R/S),(5R/S)-2,5-dimethyl-pyrrolidine in DMSO at ambient temperature.
HPLC-MS results:
retention time: 4.28 min
$C_{24}H_{24}Cl_2N_6O$ (483.40)
Mass spectrum: $(M+H)^+=484.4$

EXAMPLE 177

6-chloro-4-[1-(5-chloro-1H-benzimidazol-2-yl)-ethylamino]-7-(4-aminocarbonyl-piperidin-1-yl-carbonyl)-quinazoline

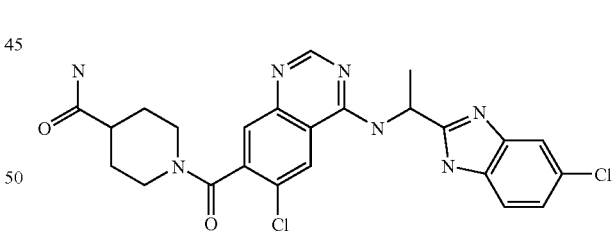

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and piperidine-4-carboxylic acid amide in DMSO at ambient temperature.
HPLC-MS results:
retention time: 3.78 min
$C_{24}H_{23}Cl_2N_7O_2$ (512.40)
Mass spectrum: $(M+H)^+=513.4$

EXAMPLE 178

6-chloro-4-[1-(5-chloro-1H-benzimidazol-2-yl)-ethylamino]-7-(4-hydroxy-piperidin-1-yl-carbonyl)-quinazoline

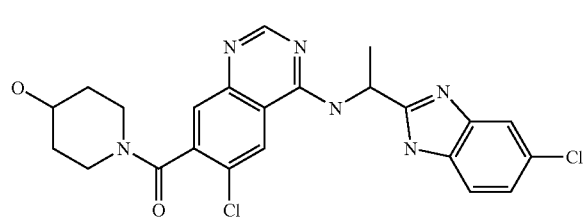

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 4-hydroxypiperidine in DMSO at ambient temperature.

HPLC-MS results:
retention time: 3.83 min
$C_{23}H_{22}Cl_2N_6O_2$ (485.37)
Mass spectrum: $(M+H)^+=486.38$

EXAMPLE 179

6-chloro-4-[(1R/S)-1-(5-chloro-1H-benzimidazol-2-yl)-ethylamino]-7-[(2R/S)-2-ethoxycarbonyl-piperidin-1-yl-carbonyl]-quinazoline

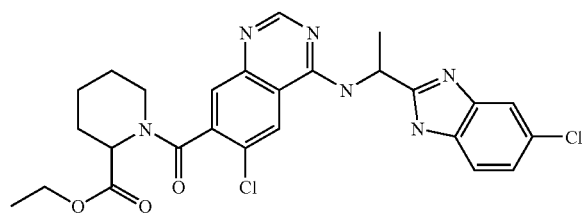

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and ethyl piperidine-2-carboxylate in DMSO at ambient temperature.

HPLC-MS results:
retention time: 4.30 min
$C_{25}H_{24}Cl_2N_6O_3$ (527.41)
Mass spectrum: $(M+H)^+=528.41$

EXAMPLE 180

6-chloro-4-[1-(5-chloro-1H-benzimidazol-2-yl)-ethylamino]-7-[1-(1,4,6,7-tetrahydro-pyrazolo[4,3]pyridin-5-yl)-carbonyl]-quinazoline

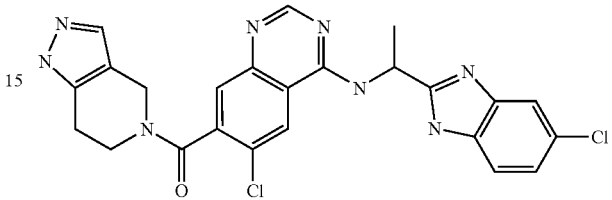

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 4,5,6,7-tetrahydro-1H-pyrazolo[4,3-c]pyridine in DMSO at ambient temperature.

HPLC-MS results:
retention time: 3.89 min
$C_{24}H_{20}Cl_2N_8O$ (507.38)
Mass spectrum: $(M+H)^+=508.4$

EXAMPLE 181

6-chloro-4-[(1R/S)-1-(5-chloro-1H-benzimidazol-2-yl)-ethylamino]-7-(2R, 5S-dimethoxymethyl-pyrrolidin-1-yl-carbonyl)-quinazoline

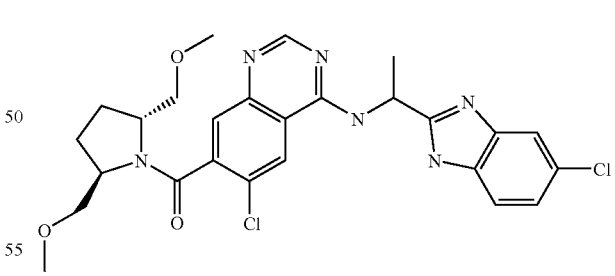

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2R,5S-dimethoxymethyl-pyrrolidine in DMSO at ambient temperature.

HPLC-MS results:
retention time: 4.23 min
$C_{26}H_{28}Cl_2N_6O_3$ (543.45)
Mass spectrum: $(M+H)^+=544.46$

EXAMPLE 182

6-chloro-4-[(1R/S)-1-(5-chloro-1H-benzimidazol-2-yl)-ethylamino]-7-[(2R/S)-2-methoxycarbonyl-pyrrolidin-1-yl-carbonyl]-quinazoline

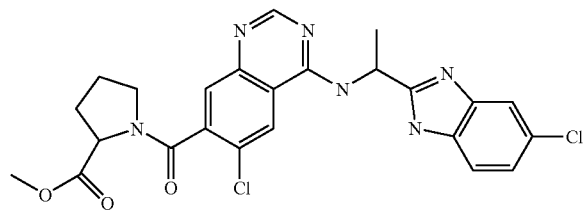

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-methoxycarbonyl-pyrrolidine in DMSO at ambient temperature.
HPLC-MS results:
retention time: 4.11 min
$C_{24}H_{22}Cl_2N_6O_3$ (513.38)
Mass spectrum: $(M+H)^+=514.39$

EXAMPLE 183

6-chloro-4-[1-(5-chloro-1H-benzimidazol-2-yl)-ethylamino]-7-(pyrazolidin-1-yl-carbonyl)-quinazoline

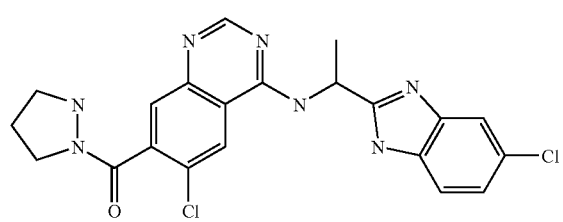

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-tert.-butyloxycarbonyl-pyrazolidine in DMSO at ambient temperature.
HPLC-MS results:
retention time: 3.85 min
$C_{21}H_{19}Cl_2N_7O$ (456.34)
Mass spectrum: $(M+H)^+=457.45$

EXAMPLE 184

6-chloro-4-[1-(5-chloro-1H-benzimidazol-2-yl)-ethylamino]-7-(1-oxo-thiomorpholin-4-yl-carbonyl)-quinazoline

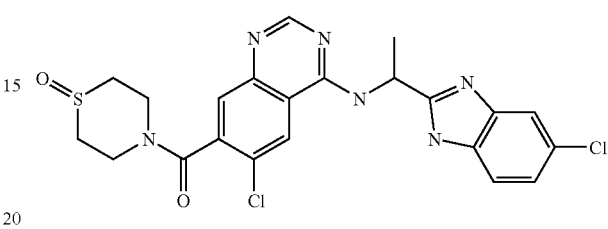

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and thiomorpholine-1-oxide in DMSO at ambient temperature.
HPLC-MS results:
retention time: 3.76 min
$C_{22}H_{20}Cl_2N_6O_2S$ (503.41)
Mass spectrum: $(M+H)^+=504.42$

EXAMPLE 185

6-chloro-4-[(1R/S)-1-(5-chloro-1H-benzimidazol-2-yl)-ethylamino]-7-{(2R/S)-2-[(N-butyl-N-ethyl-amino)-methyl]-piperidin-1-yl-carbonyl}-quinazoline

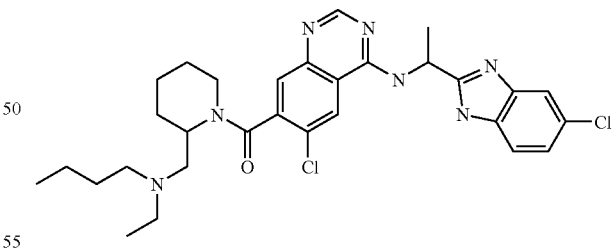

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-butyl-N-ethyl-C-(piperidin-2-yl)-methylamine in DMSO at ambient temperature.
HPLC-MS results:
retention time: 4.11 min
$C_{30}H_{37}Cl_2N_7O$ (582.58)
Mass spectrum: $(M+H)^+=583.58$

EXAMPLE 186

6-chloro-4-[1-(5-chloro-1H-benzimidazol-2-yl)-ethylamino]-7-[N-ethyl-N-(piperidin-4-yl)-aminocarbonyl]-quinazoline

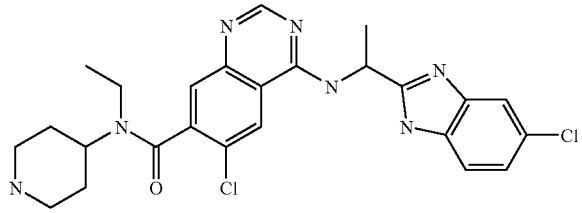

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (1-tert.-butxyloxycarbonyl-piperidin-4-yl)-ethyl-amine in DMSO at ambient temperature and subsequent treatment with trifluoroacetic acid.
HPLC-MS results:
retention time: 3.77 min
$C_{25}H_{27}Cl_2N_7O$ (512.44)
Mass spectrum: $(M+H)^+=513.56$

EXAMPLE 187

6-chloro-4-[(1R/S)-1-(5-chloro-1H-benzimidazol-2-yl)-ethylamino]-7-[(2S)-2-ethoxycarbonyl-pyrrolidin-1-yl-carbonyl]-quinazoline

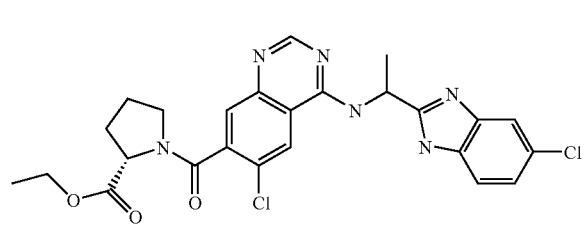

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (2S)-2-(ethoxycarbonyl)-pyrrolidine in DMSO at ambient temperature.
HPLC-MS results:
retention time: 4.22 min
$C_{25}H_{24}Cl_2N_6O_3$ (527.41)
Mass spectrum: $(M+H)^+=528.41$

EXAMPLE 188

6-chloro-4-[1-(5-chloro-1H-benzimidazol-2-yl)-ethylamino]-7-(4-formyl-piperazin-1-yl-carbonyl)-quinazoline

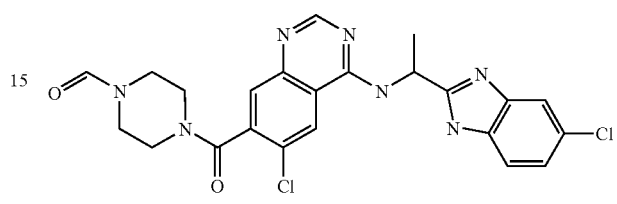

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 4-formyl-piperazine in DMSO at ambient temperature.
HPLC-MS results:
retention time: 3.85 min
$C_{23}H_{21}Cl_2N_7O_2$ (498.37)
Mass spectrum: $(M+H)^+=499.38$

EXAMPLE 189

6-chloro-4-[(1R/S)-1-(5-chloro-1H-benzimidazol-2-yl)-ethylamino]-7-[(2R/S)-2-(2-dimethylamino-ethyl)-piperidin-1-yl-carbonyl]-quinazoline

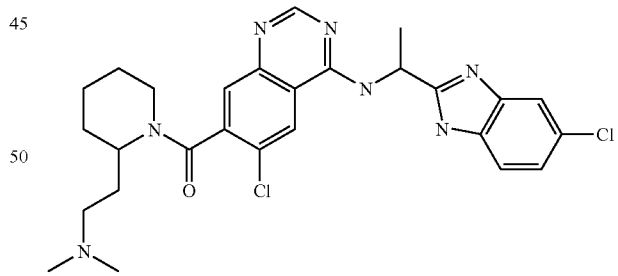

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-(2-dimethylamino-ethyl)-piperidine in DMSO at ambient temperature.
HPLC-MS results:
retention time: 3.90 min
$C_{27}H_{31}Cl_2N_7O$ (540.50)
Mass spectrum: $(M+H)^+=541.5$

EXAMPLE 190

6-chloro-4-[(1R/S)-1-(5-chloro-1H-benzimidazol-2-yl)-ethylamino]-7-[(2R/S)-2-(2-diethylamino-ethyl)-piperidin-1-yl-carbonyl]-quinazoline

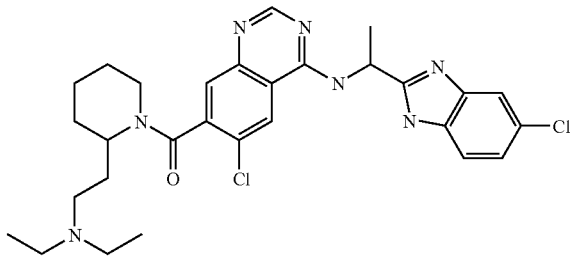

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-(2-diethylamino-ethyl)-piperidine in DMSO at ambient temperature.

HPLC-MS results:
retention time: 3.95 min
$C_{29}H_{35}Cl_2N_7O$ (568.55)
Mass spectrum: $(M+H)^+$=569.55

EXAMPLE 191

6-chloro-4-[1-(5-chloro-1H-benzimidazol-2-yl)-ethylamino]-7-(1,4,6,7-tetrahydro-imidazo[4,5-c]pyridin-5-yl-carbonyl)-quinazoline

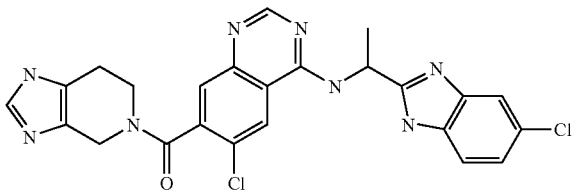

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 4,5,6,7-tetrahydro-1H-imidazo[4,5-c]pyridine in DMSO at ambient temperature.

HPLC-MS results:
retention time: 3.70 min
$C_{24}H_{20}Cl_2N_8O$ (507.38)
Mass spectrum: $(M+H)^+$=508.39

EXAMPLE 192

6-chloro-4-[1-(5-chloro-1H-benzimidazol-2-yl)-ethylamino]-7-(3,6-dihydro-2H-pyridin-1-yl-carbonyl)-quinazoline

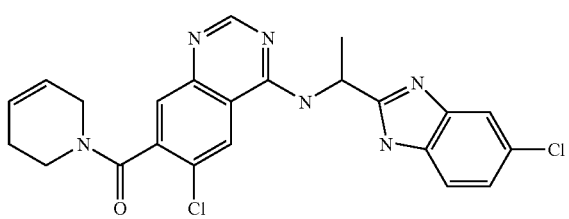

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 1,2,3,6-tetrahydropyridine in DMSO at ambient temperature.

HPLC-MS results:
retention time: 4.19 min
$C_{23}H_{20}Cl_2N_6O$ (467.36)
Mass spectrum: $(M+H)^+$=468.36

EXAMPLE 193

6-chloro-4-[(1R/S)-1-(5-chloro-1H-benzimidazol-2-yl)-ethylamino]-7-{(2R/S)-2-[(N-butyl-N-methyl-amino)-methyl]-piperidin-1-yl-carbonyl}-quinazoline

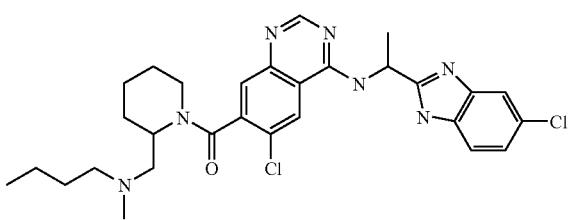

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and N-butyl-N-methyl-C-(piperidin-2-yl)-methylamine in DMSO at ambient temperature.

HPLC-MS results:
retention time: 4.08 min
$C_{29}H_{35}Cl_2N_7O$ (568.55)
Mass spectrum: $(M+H)^+$=569.55

EXAMPLE 194

6-chloro-4-[(1R/S)-1-(5-chloro-1H-benzimidazol-2-yl)-ethylamino]-7-[(2R/S)-2-methyl-morpholin-4-yl-carbonyl]-quinazoline

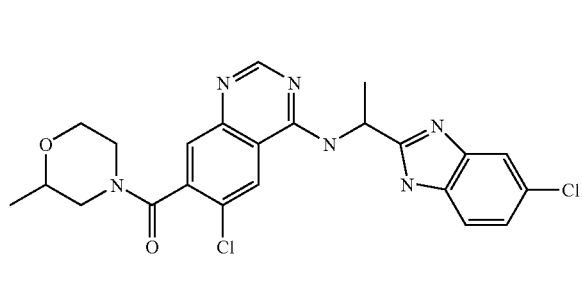

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-methyl-morpholine in DMSO at ambient temperature.

HPLC-MS results:
retention time: 4.08 min
$C_{23}H_{22}Cl_2N_6O_2$ (485.37)
Mass spectrum: $(M+H)^+=486.38$

EXAMPLE 195

6-chloro-4-[1-(5-chloro-1H-benzimidazol-2-yl)-ethylamino]-7-(thiomorpholin-4-yl-carbonyl)-quinazoline

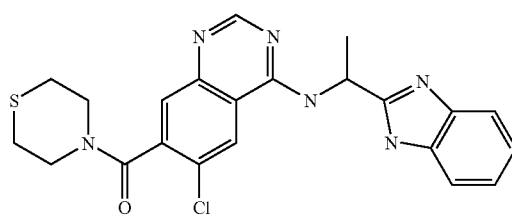

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and thiomorpholine in DMSO at ambient temperature.

HPLC-MS results:
retention time: 4.19 min
$C_{22}H_{20}Cl_2N_6OS$ (487.41)
Mass spectrum: $(M+H)^+=488.42$

EXAMPLE 196

6-chloro-4-[(1R/S)-1-(5-chloro-1H-benzimidazol-2-yl)-ethylamino]-7-[(2R/S)-2-(2-amino-ethyl)-piperidin-1-yl-carbonyl]-quinazoline

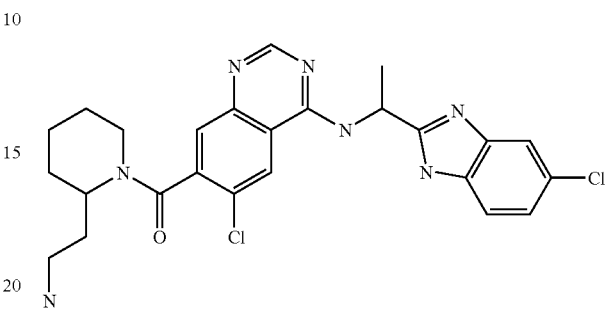

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-(2-tert.-butyloxycarbonylamino-ethyl)-piperidine in DMSO at ambient temperature and subsequent treatment with trifluoroacetic acid.

HPLC-MS results:
retention time: 3.86 min
$C_{25}H_{27}Cl_2N_7O$ (512.44)
Mass spectrum: $(M+H)^+=513.56$

EXAMPLE 197

6-chloro-4-[(1R/S)-1-(5-chloro-1H-benzimidazol-2-yl)-ethylamino]-7-[(2R/S)-2-ethyl-piperidin-1-yl-carbonyl]-quinazoline

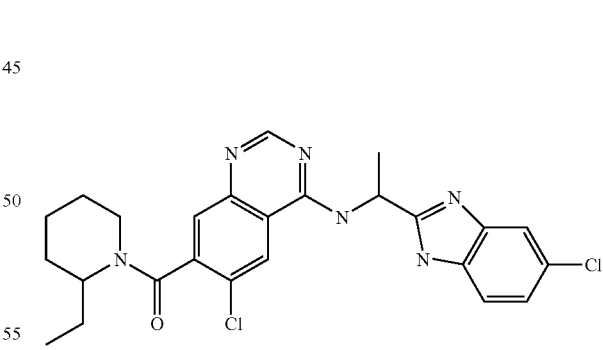

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 2-ethyl-piperidine in DMSO at ambient temperature.

HPLC-MS results:
retention time: 4.47 min
$C_{25}H_{26}Cl_2N_6O$ (497.43)
Mass spectrum: $(M+H)^+=498.43$

EXAMPLE 198

6-chloro-4-[(1R/S)-1-(5-chloro-1H-benzimidazol-2-yl)-ethylamino]-7-[(3R/S)-3-amino-pyrrolidin-1-yl-carbonyl]-quinazoline

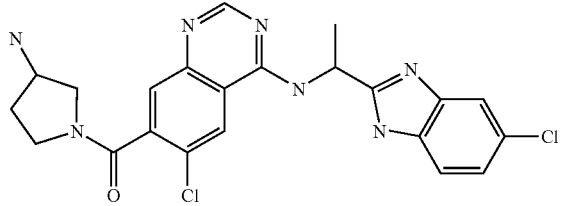

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 3-tert.-butyloxycarbonylamino-pyrrolidine in DMSO at ambient temperature and subsequent treatment with trifluoroacetic acid.

HPLC-MS results:
retention time: 3.59 min
$C_{22}H_{21}Cl_2N_7O$ (470.36)
Mass spectrum: $(M+H)^+=469.84$

EXAMPLE 199

6-chloro-4-[1-(5-chloro-1H-benzimidazol-2-yl)-ethylamino]-7-(4-trifluoromethyl-piperidin-1-yl-carbonyl)-quinazoline

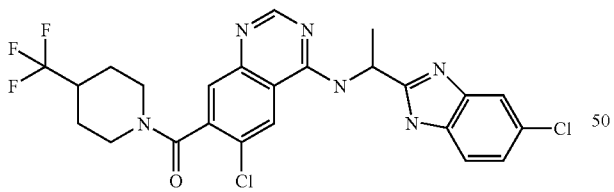

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 4-trifluoromethyl-piperidine in DMSO at ambient temperature.

HPLC-MS results:
retention time: 4.42 min
$C_{24}H_{21}Cl_2F_3N_6O$ (537.37)
Mass spectrum: $(M+H)^+=538.37$

EXAMPLE 200

6-chloro-4-[(1R/S)-1-(5-chloro-1H-benzimidazol-2-yl)-ethylamino]-7-{(3R/S)-3-[4-(pyrrolidin-1-yl)-butyl]-pyrrolidin-1-yl-carbonyl}-quinazoline

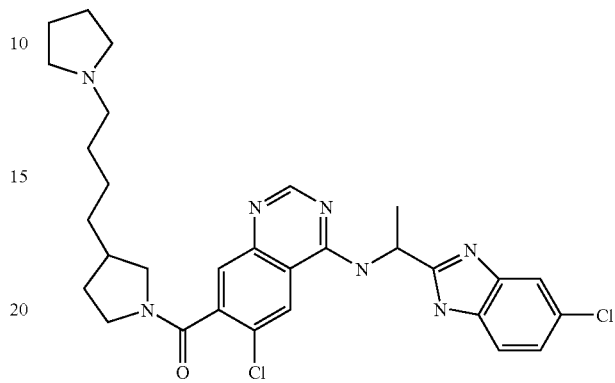

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 3-[4-(pyrrolidin-1-yl)-butyl]-pyrrolidine in DMSO at ambient temperature.

HPLC-MS results:
retention time: 4.05 min
$C_{31}H_{37}Cl_2N_7O$ (594.59)
Mass spectrum: $(M+H)^+=595.59$

EXAMPLE 201

6-chloro-4-[(1R/S)-1-(5-chloro-1H-benzimidazol-2-yl)-ethylamino]-7-{(2R/S)-2-[(N-methyl-N-(pyridin-2-ylmethyl)-amino)-methyl]-piperidin-1-yl-carbonyl}-quinazoline

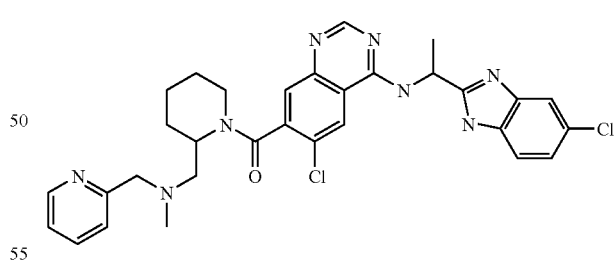

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-methyl-N-(piperidin-2-ylmethyl)-pyridin-2-ylmethyl-amine in DMSO at ambient temperature.

HPLC-MS results:
retention time: 4.03 min
$C_{31}H_{32}Cl_2N_8O$ (603.56)
Mass spectrum: $(M+H)^+=604.56$

EXAMPLE 202

6-chloro-4-[1-(5-chloro-1H-benzimidazol-2-yl)-ethylamino]-7-(4-hydroxy-piperazin-1-yl-carbonyl)-quinazoline

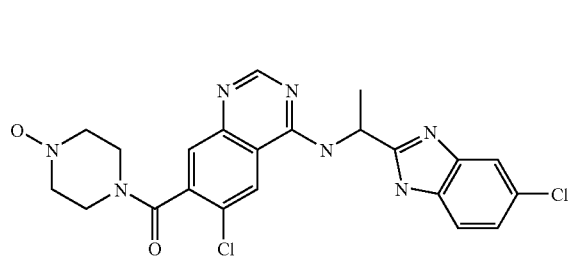

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 4-hydroxy-piperazine in DMSO at ambient temperature.
HPLC-MS results:
retention time: 3.73 min
$C_{22}H_{21}Cl_2N_7O_2$ (486.36)
Mass spectrum: $(M+H)^+ = 487.36$

EXAMPLE 203

6-chloro-4-[(1R/S)-1-(5-chloro-1H-benzimidazol-2-yl)-ethylamino]-7-[(3R/S)-3-(pyrrolidin-1-ylmethyl)-piperidin-1-yl-carbonyl]-quinazoline

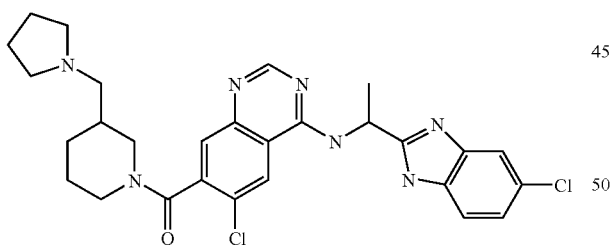

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and 3-(pyrrolidin-1-ylmethyl)-piperidine in DMSO at ambient temperature.
HPLC-MS results:
retention time: 3.81 min
$C_{28}H_{31}Cl_2N_7O$ (552.51)
Mass spectrum: $(M+H)^+ = 553.51$

EXAMPLE 204

6-chloro-4-[(1R/S)-1-(5-chloro-1H-benzimidazol-2-yl)-ethylamino]-7-[(2R/S)-2-diethylaminomethyl-piperidin-1-yl-carbonyl]-quinazoline

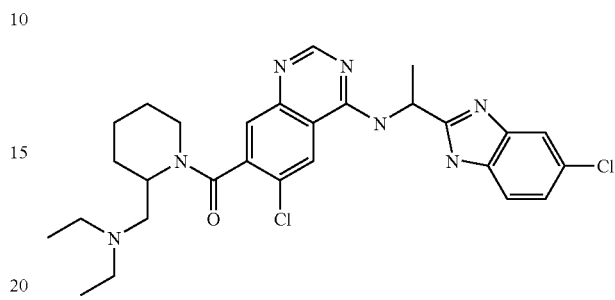

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and N,N-diethyl-N-(piperidin-2-ylmethyl)-amine in DMSO at ambient temperature.
HPLC-MS results:
retention time: 3.94 min
$C_{28}H_{33}Cl_2N_7O$ (554.52)
Mass spectrum: $(M+H)^+ = 555.53$

EXAMPLE 205

6-chloro-4-[(1R/S)-1-(5-chloro-1H-benzimidazol-2-yl)-ethylamino]-7-[(2R/S)-2-(4-diethylamino-butyl)-piperidin-1-yl-carbonyl]-quinazoline

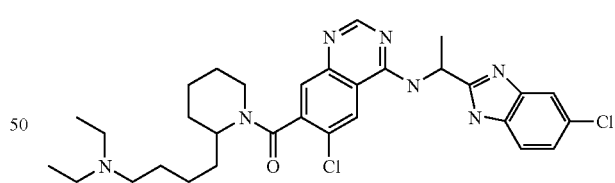

Prepared analogously to Example 37a from 6-chloro-4-[1-(5-chloro-1H-benzimidazol-2-yl)-ethylamino]-7-hydroxy-carbonyl-quinazoline, pentafluorophenyl-tetramethyluronium-hexafluorophosphate (PFTU), diisopropylethylamine and diethyl-(4-piperidin-2-yl-butyl)-amine in DMSO at ambient temperature and subsequent treatment with trifluoroacetic acid.
HPLC-MS results:
retention time: 4.10 min
$C_{31}H_{39}Cl_2N_7O$ (596.60)
Mass spectrum: $(M+H)^+ = 597.61$

EXAMPLE 206

6-chloro-4-[(1R/S)-1-(5-chloro-1H-benzimidazol-2-yl)-ethylamino]-7-[(2R)-2-hydroxymethyl-pyrrolidin-1-yl-carbonyl]-quinazoline

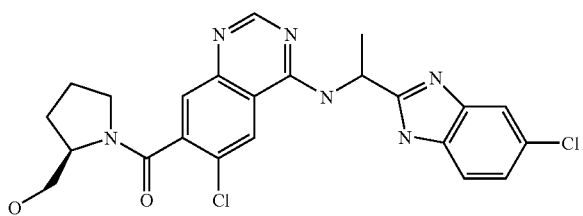

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (2R)-2-hydroxymethyl-pyrrolidine in DMSO at ambient temperature.

HPLC-MS results:
retention time: 3.96 min
$C_{23}H_{22}Cl_2N_6O_2$ (485.37)
Mass spectrum: $(M+H)^+ = 486.38$

EXAMPLE 207

6-chloro-4-[(1R/S)-1-(5-chloro-1H-benzimidazol-2-yl)-ethylamino]-7-[(2R/S)-2-(N-ethyl-N-methyl-aminomethyl)-piperidin-1-yl-carbonyl]-quinazoline

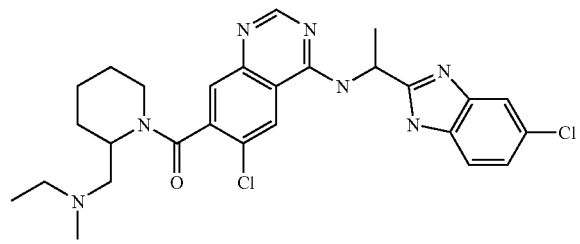

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-ethyl-N-methyl-N-(piperidin-2-ylmethyl)-amine in DMSO at ambient temperature.

HPLC-MS results:
retention time: 3.93 min
$C_{27}H_{31}Cl_2N_7O$ (540.50)
Mass spectrum: $(M+H)^+ = 540.04$

EXAMPLE 208

6-chloro-4-[(1R/S)-1-(5-chloro-1H-benzimidazol-2-yl)-ethylamino]-7-[(2R)-2-aminocarbonyl-pyrrolidin-1-yl-carbonyl]-quinazoline

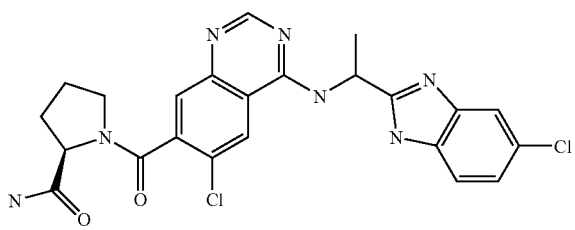

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (2R)-2-(aminocarbonyl)-pyrrolidine in DMSO at ambient temperature.

HPLC-MS results:
retention time: 3.83 min
$C_{23}H_{21}Cl_2N_7O_2$ (498.37)
Mass spectrum: $(M+H)^+ = 499.38$

EXAMPLE 209

6-chloro-4-[(1R/S)-1-(5-chloro-1H-benzimidazol-2-yl)-ethylamino]-7-[(2S)-2-hydroxymethyl-pyrrolidin-1-yl-carbonyl]-quinazoline

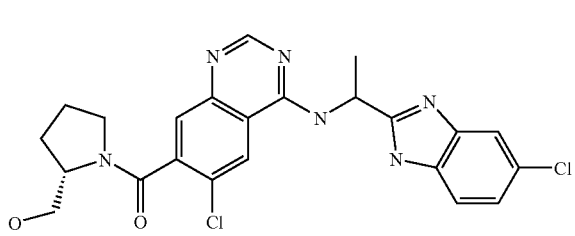

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (2S)-2-hydroxymethyl-pyrrolidine in DMSO at ambient temperature.

HPLC-MS results:
retention time: 3.95 min
$C_{23}H_{22}Cl_2N_6O_2$ (485.37)
Mass spectrum: $(M+H)^+ = 486.38$

EXAMPLE 210

6-chloro-4-[(1R/S)-1-(5-chloro-1H-benzimidazol-2-yl)-ethylamino]-7-[(2R/S)-2-(4-methyl-piperazin-1-ylmethyl)-piperidin-1-yl-carbonyl]-quinazoline

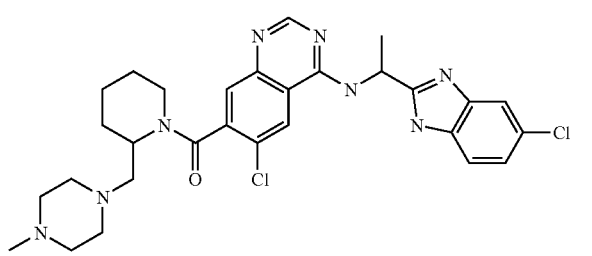

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 1-methyl-4-(piperidin-2-ylmethyl)-piperazine in DMSO at ambient temperature.

HPLC-MS results:
retention time: 3.92 min
$C_{29}H_{34}Cl_2N_8O$ (581.55)
Mass spectrum: $(M+H)^+$=582.55

EXAMPLE 211

6-chloro-4-[(1R/S)-1-(5-chloro-1H-benzimidazol-2-yl)-ethylamino]-7-[(2R)-2-methoxymethyl-pyrrolidin-1-yl-carbonyl]-quinazoline

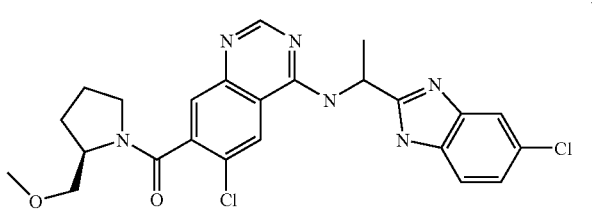

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and (2R)-2-methoxymethyl-pyrrolidine in DMSO at ambient temperature.

HPLC-MS results:
retention time: 4.16 min
$C_{24}H_{24}Cl_2N_6O_2$ (499.40)
Mass spectrum: $(M+H)^+$=500.40

EXAMPLE 212

6-chloro-4-[(1R/S)-1-(5-chloro-1H-benzimidazol-2-yl)-ethylamino]-7-[(2R/S)-2-(3-dimethylamino-propyl)-piperidin-1-yl-carbonyl]-quinazoline

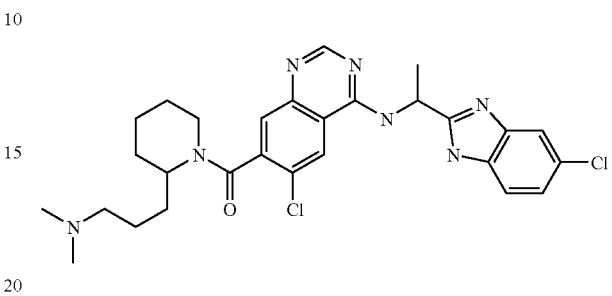

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N,N-dimethyl-N-(3-piperidin-2-yl-propyl)-amine in DMSO at ambient temperature and subsequent treatment with trifluoroacetic acid.

HPLC-MS results:
retention time: 3.96 min
$C_{28}H_{33}Cl_2N_7O$ (554.52)
Mass spectrum: $(M+H)^+$=555.53

EXAMPLE 213

6-chloro-4-[(1R/S)-1-(5-chloro-1H-benzimidazol-2-yl)-ethylamino]-7-[(2R/S)-2-diethylaminocarbonyl-piperidin-1-yl-carbonyl]-quinazoline

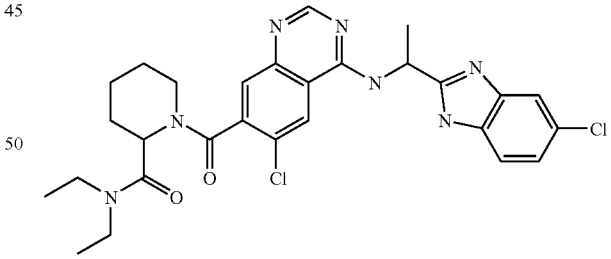

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-diethylaminocarbonyl-piperidine in DMSO at ambient temperature.

HPLC-MS results:
retention time: 4.40 min
$C_{28}H_{31}Cl_2N_7O_2$ (568.51)
Mass spectrum: $(M+H)^+$=569.51

EXAMPLE 214

6-chloro-4-[(1R/S)-1-(5-chloro-1H-benzimidazol-2-yl)-ethylamino]-7-{(2R/S)-2-[(N-cyclohexyl-N-methyl-amino)-methyl]-piperidin-1-yl-carbonyl}-quinazoline

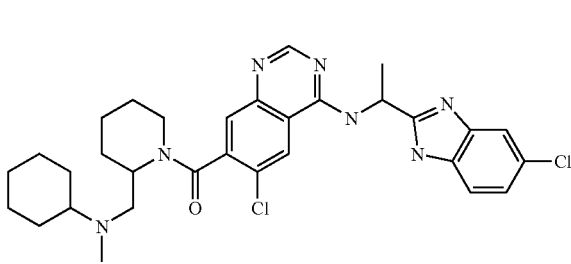

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and N-cyclohexyl-N-methyl-piperidin-2-ylmethyl-amine in DMSO at ambient temperature.
HPLC-MS results:
retention time: 4.13 min
$C_{31}H_{37}Cl_2N_7O$ (594.59)
Mass spectrum: $(M+H)^+=595.59$

EXAMPLE 215

6-chloro-4-[(1R/S)-1-(5-chloro-1H-benzimidazol-2-yl)-ethylamino]-7-[(2R/S)-2-piperidin-1-ylmethyl-piperidin-1-yl-carbonyl]-quinazoline

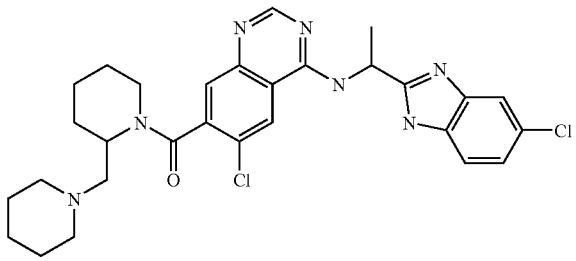

Prepared analogously to Example 37a from 6-chloro-4-[1-(5-chloro-1H-benzimidazol-2-yl)-ethylamino]-7-hydroxycarbonyl-quinazoline, pentafluorophenyl-tetramethyluronium-hexafluorophosphate (PFTU), diisopropylethylamine and 2-(piperidin-1-ylmethyl)-piperidine in DMSO at ambient temperature.
HPLC-MS results:
retention time: 3.96 min
$C_{29}H_{33}Cl_2N_7O$ (566.53)
Mass spectrum: $(M+H)^+=567.54$

EXAMPLE 216

4-[(1S)-1-(5-chloro-1H-benzimidazol-2-yl)-3-(methylsulphanyl)-propylamino]-6-methoxy-7-(2,5-dihydropyrrol-1-yl-carbonyl)-quinazoline

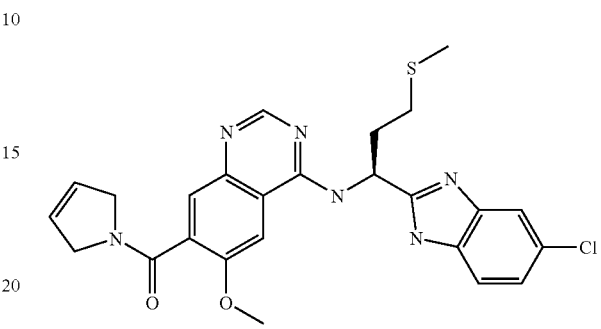

Prepared analogously to Example 2d from 4-chloro-6-methoxy-7-(2,5-dihydropyrrol-1-yl-carbonyl)-quinazoline, (S)-1-(5-chloro-1H-benzimidazol-2-yl)-3-methylsulphanyl-propylamine-ditrifluoroacetate and triethylamine in N,N-dimethylformamide.
Yield: 19%
$R_f$ value: 0.50 (silica gel; dichloromethane/methanol=8:2+1% ammonia solution)
$C_{25}H_{25}ClN_6O_2S$ (509.03)
Mass spectrum: $(M+H)^+=509/511$ (chlorine isotope) $(M-H)^-=507/509$ (chlorine isotope)

EXAMPLE 217

4-[(1S)-1-(5-chloro-1H-benzimidazol-2-yl)-2-methoxy-ethylamino]-6-methoxy-7-(2,5-dihydropyrrol-1-yl-carbonyl)-quinazoline Prepared analogously to Example 2d from 4-chloro-6-methoxy-7-(2,5-dihydropyrrol-1-yl-carbonyl)-quinazoline, (S)-1-(5-chloro-1H-benzimidazol-2-yl)-2-methoxy-ethylamine-trifluoroacetate and triethylamine in N,N-dimethylformamide.
Yield: 9%
$R_f$ value: 0.45 (silica gel; ethyl acetate/ethanol=9:1+1% ammonia solution)
$C_{24}H_{23}ClN_6O_3$ (478.94)
Mass spectrum: $(M+H)^+=479/481$ (chlorine isotope) $(M-H)^-=477/479$ (chlorine isotope)

EXAMPLE 218

6-chloro-4-[(1S)-1-(5-chloro-1H-benzimidazol-2-yl)-ethylamino]-7-[(2R/S)-2-(1-methyl-1H-pyrazol-4-yl)-thiazolidinyl-carbonyl]-quinazoline

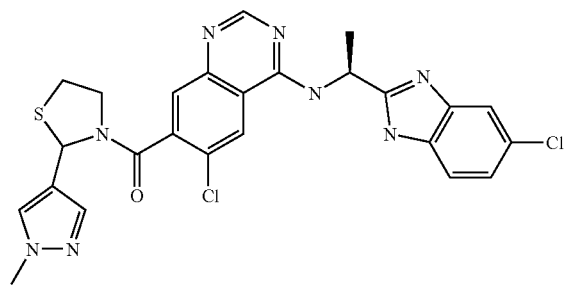

Prepared analogously to Example 37a from 6-chloro-4-[(1S)-1-(5-chloro-1H-benzimidazol-2-yl)-ethylamino]-7-hydroxycarbonyl-quinazoline, TBTU, N-methylmorpholine and 2-(1-methyl-1H-pyrazol-4-yl)-thiazolidine in N,N-dimethylformamide.

Yield: 7%

$R_f$ value: 0.65 (silica gel; dichloromethane/ethanol=9:1)

$C_{25}H_{22}Cl_2N_8OS$ (553.48)

Mass spectrum: $(M+H)^+=553/555/557$

EXAMPLE 219

6-chloro-4-[(1S)-1-(5-chloro-1H-benzimidazol-2-yl)-2-methoxy-ethylamino]-7-(thiazolidinyl-carbonyl)-quinazoline

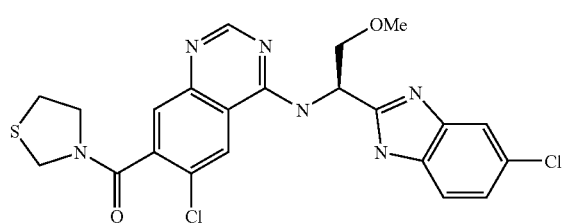

Prepared analogously to Example 37a from 6-chloro-4-[(1S)-1-(5-chloro-1H-benzimidazol-2-yl)-2-methoxy-ethylamino]-7-hydroxycarbonyl-quinazoline, TBTU, N-methylmorpholine and thiazolidine in N,N-dimethylformamide.

Yield: 38%

$R_f$ value: 0.53 (silica gel; dichloromethane/ethanol=9:1)

$C_{22}H_{20}Cl_2N_6O_2S$ (503.41)

Mass spectrum: $(M-H)^-=501/503/505$

EXAMPLE 220

4-[(1S)-1-(5-chloro-1H-benzimidazol-2-yl)-2-methoxy-ethylamino]-6-methyl-7-(2,5-dihydropyrrol-1-yl-carbonyl)-quinazoline

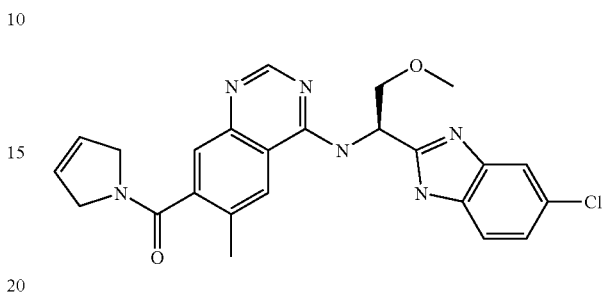

Prepared analogously to Example 2d from 4-chloro-6-methyl-7-(2,5-dihydropyrrol-1-yl-carbonyl)-quinazoline, (S)-1-(5-chloro-1H-benzimidazol-2-yl)-2-methoxy-ethylamine-ditrifluoroacetate and triethylamine in N,N-dimethylformamide.

Yield: 30%

$R_f$ value: 0.40 (silica gel; ethyl acetate/ethanol=9:1+1% ammonia solution)

$C_{24}H_{23}ClN_6O_2$ (462.94)

Mass spectrum: $(M+H)^+=463/465$ (chlorine isotope)

EXAMPLE 221

4-[(1S)-1-(5-chloro-1H-benzimidazol-2-yl)-2-methoxy-ethylamino]-6-methyl-7-(thiazolidinyl-carbonyl)-quinazoline

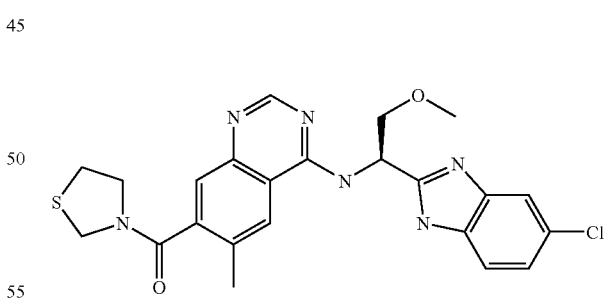

Prepared analogously to Example 2d from 4-chloro-6-methyl-7-(thiazolidinyl-carbonyl)-quinazoline, (S)-1-(5-chloro-1H-benzimidazol-2-yl)-2-methoxy-ethylamine-ditrifluoroacetate and triethylamine in N,N-dimethylformamide.

Yield: 35%

$R_f$ value: 0.55 (silica gel; ethyl acetate/ethanol=9:1+1% ammonia solution)

$C_{23}H_{23}ClN_6O_2S$ (483.00)

Mass spectrum: $(M+H)^+=483/485$ (chlorine isotope)

EXAMPLE 222

6-bromo-4-[(1S)-1-(5-chloro-1H-benzimidazol-2-yl)-2-methoxy-ethylamino]-7-(2,5-dihydropyrrol-1-yl-carbonyl)-quinazoline

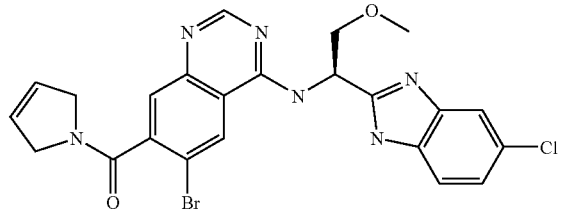

Prepared analogously to Example 2d from 6-bromo-4-chloro-7-(2,5-dihydropyrrol-1-yl-carbonyl)-quinazoline, (S)-1-(5-chloro-1H-benzimidazol-2-yl)-2-methoxy-ethylamine-ditrifluoroacetate and triethylamine in N,N-dimethylformamide.

Yield: 91%

$R_f$ value: 0.57 (silica gel; ethyl acetate/ethanol=9:1+1% ammonia solution)

$C_{23}H_{20}BrClN_6O_2$ (527.81)

Mass spectrum: $(M+H)^+$=527/529/531 (bromine, chlorine isotope)

EXAMPLE 223

6-bromo-4-[(1S)-1-(5-chloro-1H-benzimidazol-2-yl)-2-methoxy-ethylamino]-7-(thiazolidinyl-carbonyl)-quinazoline

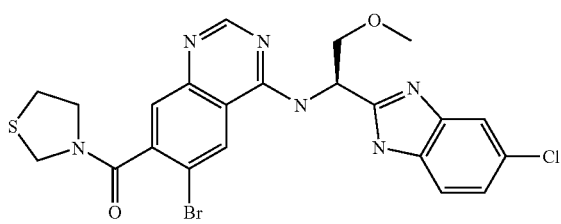

Prepared analogously to Example 2d from 6-bromo-4-chloro-7-(thiazolidinyl-carbonyl)-quinazoline, (S)-1-(5-chloro-1H-benzimidazol-2-yl)-2-methoxy-ethylamine-ditrifluoroacetate and triethylamine in N,N-dimethylformamide.

Yield: 27%

$R_f$ value: 0.67 (silica gel; ethyl acetate/ethanol=9:1+1% ammonia solution)

$C_{22}H_{20}BrClN_6O_2S$ (547.87)

Mass spectrum: $(M+H)^+$=547/549/551 (chlorine isotope)

EXAMPLE 224

6-chloro-4-[(1S)-1-(5-chloro-1H-benzimidazol-2-yl)-ethylamino]-7-(6,7,8,9-tetrahydro-[1,2,4]triazolo[4,3-a]pyridin-4-yl)-quinazoline

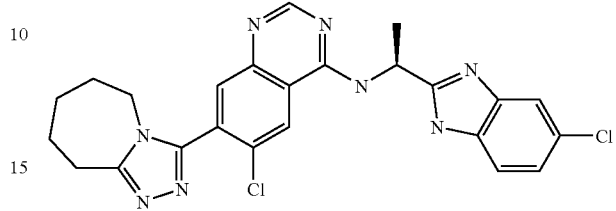

Prepared analogously to Example 128 from 6-chloro-4-[(1S)-1-(5-chloro-1H-benzimidazol-2-yl)-methylamino]-7-(hydrazino-carbonyl)-quinazoline and 7-methoxy-3,4,5,6-tetrahydro-2H-azepine in ethanol/glacial acetic acid.

Yield: 23%

$C_{24}H_{22}Cl_2N_8$ (493.40)

Mass spectrum: $(M+H)^+$=493/495/497 (chlorine isotope)

EXAMPLE 225

6-chloro-4-[(1S)-1-(5-chloro-1-methyl-1H-benzimidazol-2-yl)-3-methylsulphonylamino-propylamino]-7-(2,5-dihydropyrrolyl-carbonyl)-quinazoline

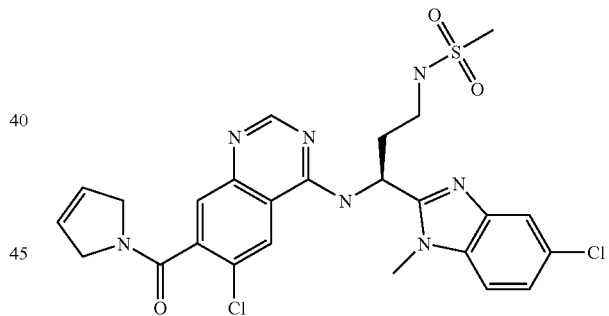

80 mg (0.14 mmol) 6-chloro-4-[(1S)-1-(5-chloro-1H-benzimidazol-2-yl)-3-methyl-sulphonylamino-propylamino]-7-(2,5-dihydropyrrolyl-carbonyl)-quinazoline are dissolved in 5 ml N,N-dimethylformamide, combined with 20 mg (0.14 mmol) potassium carbonate and while cooling with ice 9 µl methyl iodide are added dropwise. The reaction mixture is warmed up to ambient temperature and stirred for four hours.

The mixture is combined with water and extracted three times with ethyl acetate. The combined organic phases are dried over sodium sulphate and concentrated. The crude product is purified by chromatography (silica gel; eluant: dichloromethane/ethanol 95:5).

Yield: 60 mg (73%; 1:1 mixture of the regioisomers 5- and 6-chlorobenzimidazole)

$R_f$ value: 0.50 (silica gel; dichloromethane/ethanol=9:1)

$C_{25}H_{25}Cl_2N_7O_3S$ (574.49)

Mass spectrum: $(M-H)^-$=57.2/574/576 (chlorine isotope)

EXAMPLE 226

6-chloro-4-[(1S)-1-(5-chloro-1H-benzimidazol-2-yl)-2-benzyloxy-ethylamino]-7-(2,5-dihydropyrrol-1-yl-carbonyl)-quinazoline

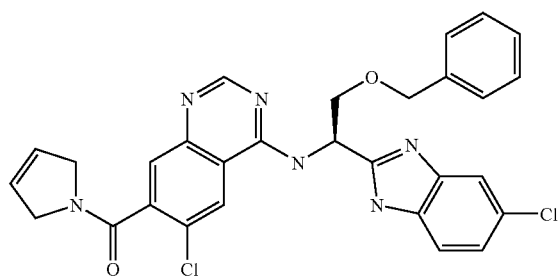

Prepared analogously to Example 2d from 4,6-dichloro-7-(2,5-dihydropyrrol-1-yl-carbonyl)-quinazoline, (S)-1-(5-chloro-1H-benzimidazol-2-yl)-2-benzyloxy-ethylamine and triethylamine in N,N-dimethylformamide.

Yield: 33%

$R_f$ value: 0.65 (silica gel; dichloromethane/ethanol=9:1+1% ammonia solution)

$C_{29}H_{24}Cl_2N_6O_2$ (559.46)

Mass spectrum: $(M+H)^+$=559/561/563 (chlorine isotope)

EXAMPLE 227

6-chloro-4-{1-(5-chloro-1H-benzimidazol-2-yl)-3-[2-(pyridin-4-yl-amino)-ethylamino-carbonyl]-propylamino}-7-(pyrrolidin-1-yl-carbonyl)-quinazoline

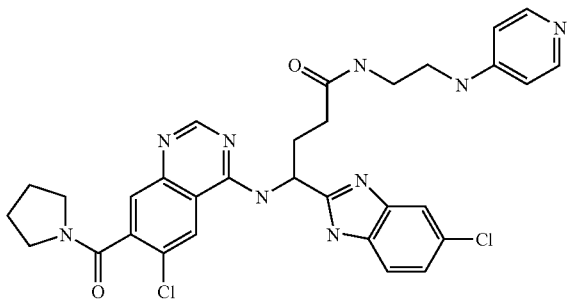

Prepared analogously to Example 61 from 6-chloro-4-[1-(1-tert.-butyloxycarbonyl-5-chloro-1H-benzimidazol-2-yl)-3-hydroxycarbonyl-propyl-amino]-7-(pyrrolidin-1-yl-carbonyl)-quinazoline and 2-(pyridin-4-yl-amino)-ethylamine with TBTU in acetonitrile/tetrahydrofuran and subsequent reaction with trifluoroacetic acid.

Yield: 74% retention time: 2.37 minutes $C_{31}H_{31}Cl_2N_9O_2$ (632.55)

Mass spectrum: $(M+H)^+$=632/634/636 (chlorine isotope)

EXAMPLE 228

4-[(1S)-1-(5-bromo-1H-benzimidazol-2-yl)-2-methoxy-ethylamino]-6-chloro-7-(2,5-dihydropyrrolyl-carbonyl)-quinazoline

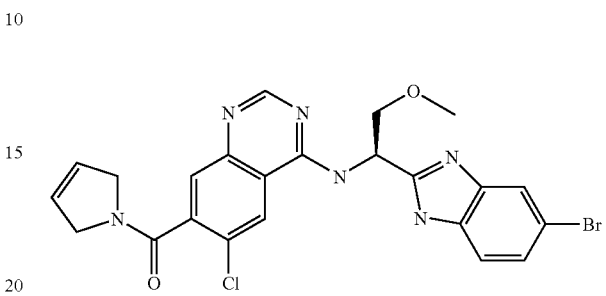

Prepared analogously to Example 2d from 4,6-dichloro-7-(2,5-dihydropyrrolyl-carbonyl)-quinazoline, (S)-1-(5-bromo-1H-benzimidazol-2-yl)-2-methoxy-ethylamine and triethylamine in N,N-dimethylformamide.

Yield: 7%

$R_f$ value: 0.46 (silica gel; dichloromethane/ethanol=9:1)

$C_{23}H_{20}BrClN_6O_2$ (527.81)

Mass spectrum: $(M+H)^+$=527/529/530 (bromine, chlorine isotope)

EXAMPLE 229

4-[(1S)-1-(5-bromo-1H-benzimidazol-2-yl)-ethylamino]-6-chloro-7-(2,5-dihydropyrrolyl-carbonyl)-quinazoline

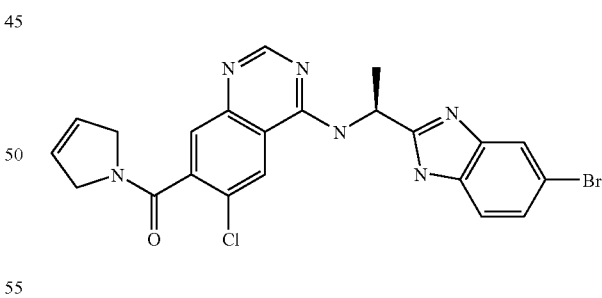

Prepared analogously to Example 2d from 4,6-dichloro-7-(2,5-dihydropyrrolyl-carbonyl)-quinazoline, (S)-1-(5-bromo-1H-benzimidazol-2-yl)-ethylamine and triethylamine in N,N-dimethylformamide.

Yield: 18%

$R_f$ value: 0.40 (silica gel; dichloromethane/ethanol=9:1)

$C_{22}H_{18}BrClN_6O$ (497.78)

Mass spectrum: $(M+H)^+$=497/499/501 (bromine, chlorine isotope)

EXAMPLE 230

6-bromo-4-[(1S)-1-(5-chloro-1H-benzimidazol-2-yl)-but-3-yn-1-yl-amino]-7-(2,5-dihydropyrrol-1-yl-carbonyl)-quinazoline

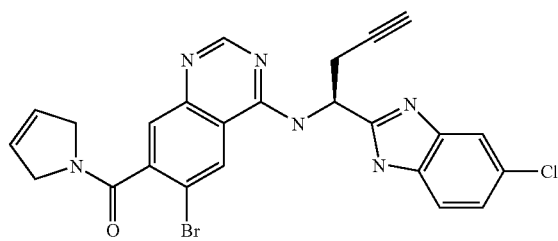

Prepared analogously to Example 2d from 6-bromo-4-chloro-7-(2,5-dihydropyrrol-1-yl-carbonyl)-quinazoline, (S)-1-(5-chloro-1H-benzimidazol-2-yl)-but-3-yn-1-ylamine-ditrifluoroacetate and triethylamine in N,N-dimethylformamide.

Yield: 12%

$R_f$ value: 0.45 (silica gel; ethyl acetate+1% ammonia solution)

$C_{24}H_{18}BrClN_6O$ (521.81)

Mass spectrum: $(M+H)^+=521/523/525$ (bromine, chlorine isotope)

EXAMPLE 231

4-[(1S,2R)-1-(5-chloro-1H-benzimidazol-2-yl)-2-methoxy-propylamino]-6-chloro-7-(2,5-dihydropyrrolyl-carbonyl)-quinazoline

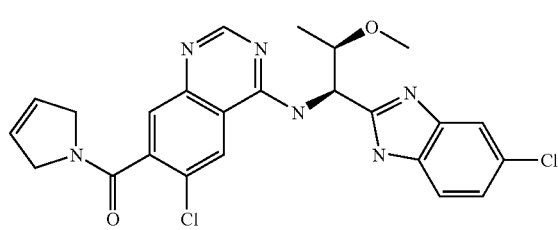

Prepared analogously to Example 2d from 4,6-dichloro-7-(2,5-dihydropyrrolyl-carbonyl)-quinazoline, (1S,2R)-1-(5-bromo-1H-benzimidazol-2-yl)-2-methoxy-propylamine and triethylamine in N,N-dimethylformamide.

Yield: 16%

$R_f$ value: 0.57 (silica gel; dichloromethane/ethanol=9:1)

$C_{24}H_{22}Cl_2N_6O_2$ (497.39)

Mass spectrum: $(M+H)^+=497/499/501$ (chlorine isotope)

EXAMPLE 232

4-[(1S,2S)-1-(5-chloro-1H-benzimidazol-2-yl)-2-tert.-butyloxy-propylamino]-6-chloro-7-(2,5-dihydropyrrolyl-carbonyl)-quinazoline

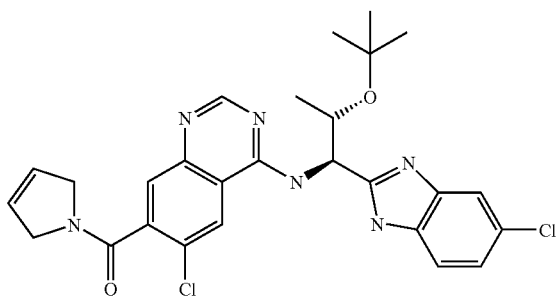

Prepared analogously to Example 2d from 4,6-dichloro-7-(2,5-dihydropyrrolyl-carbonyl)-quinazoline, (1S,2S)-1-(5-bromo-1H-benzimidazol-2-yl)-2-tert.-butyloxy-propylamine and triethylamine in N,N-dimethylformamide.

Yield: 18%

$R_f$ value: 0.36 (silica gel; dichloromethane/ethanol=9:1)

$C_{27}H_{28}Cl_2N_6O_2$ (539.47)

Mass spectrum: $(M+H)^+=539/541/543$ (chlorine isotope)

EXAMPLE 233

4-[(1S,2S)-1-(5-chloro-1H-benzimidazol-2-yl)-2-hydroxy-propylamino]-6-chloro-7-(2,5-dihydropyrrolyl-carbonyl)-quinazoline

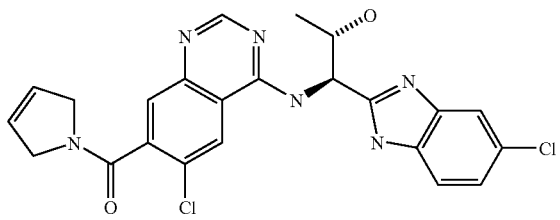

Prepared analogously to Example 8c from 4-[(1S,2S)-1-(5-chloro-1H-benzimidazol-2-yl)-2-tert.-butyloxy-propylamino]-6-chloro-7-(2,5-dihydropyrrolyl-carbonyl)-quinazoline and trifluoroacetic acid.

Yield: quantitative $R_f$ value: 0.20 (silica gel; dichloromethane/ethanol=9:1)

$C_{23}H_{20}Cl_2N_6O_2$ (483.36)

Mass spectrum: $(M+H)^+=483/485/487$ (chlorine isotope)

EXAMPLE 234

6-chloro-4-[1-(benzo[b]thiophen-2-yl)-ethylamino]-7-(pyrrolidin-1-yl-carbonyl)-quinazoline

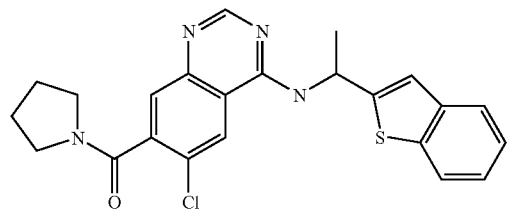

Prepared analogously to Example 2d from 4,6-dichloro-7-(pyrrolidin-1-yl-carbonyl)-quinazoline, 1-benzo[b]thiophen-2-yl-ethylamine and triethylamine in N,N-dimethylformamide.

Yield: 28%

$R_f$ value: 0.50 (silica gel; dichloromethane/ethanol=9:1)
$C_{23}H_{21}ClN_4OS$ (436.97)

Mass spectrum: $(M+H)^+$=437/439 (chlorine isotope)

EXAMPLE 235

6-chloro-4-[(1R/S)-1-(5-chloro-1H-imidazo[4,5-b]pyridin-2-yl)-ethylamino]-7-[(2S)-2-(N-tert.-butyloxycarbonyl-aminomethyl)-pyrrolidin-1-yl-carbonyl]-quinazoline

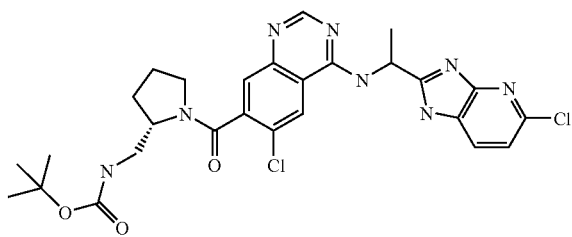

Prepared analogously to Example 2d from 4,6-dichloro-7-[(2S)-2-(N-tert.-butyloxycarbonyl-aminomethyl)-pyrrolidin-1-yl-carbonyl]-quinazoline, 1-(5-chloro-1H-imidazo[4,5-b]pyridin-2-yl)-ethylamine-hydrochloride and triethylamine in N,N-dimethylformamide.

Yield: 20%

$R_f$ value: 0.60 (silica gel; dichloromethane/ethanol=9:1)
$C_{27}H_{30}Cl_2N_8O_3$ (585.50)

Mass spectrum: $(M+H)^+$=585/587/589 (chlorine isotope)

EXAMPLE 236

6-chloro-4-[(1R/S)-1-(5-chloro-1H-imidazo[4,5-b]pyridin-2-yl)-ethylamino]-7-[(2S)-2-aminomethyl-pyrrolidin-1-yl-carbonyl]-quinazoline

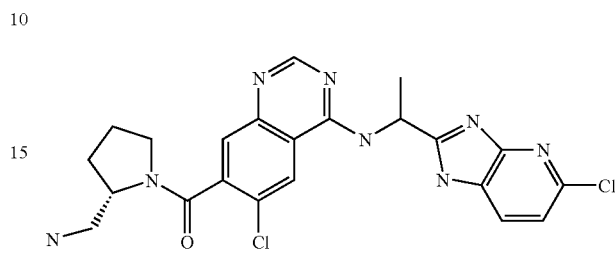

Prepared analogously to Example 8c from 6-chloro-4-[(1R/S)-1-(5-chloro-1H-imidazo[4,5-b]pyridin-2-yl)-ethylamino]-7-[(2S)-2-(N-tert.-butyloxycarbonyl-aminomethyl)-pyrrolidin-1-yl-carbonyl]-quinazoline and trifluoroacetic acid.

Yield: 55%

$R_f$ value: 0.10 (silica gel; dichloromethane/ethanol=8:2+1% acetic acid) $C_{22}H_{22}Cl_2N_8O$ (485.38)

Mass spectrum: $(M+H)^+$=485/487/489 (chlorine isotope)

EXAMPLE 237

6-chloro-4-[1-(5-chloro-benzothiazol-2-yl)-ethylamino]-7-(pyrrolidin-1-yl-carbonyl)-quinazoline

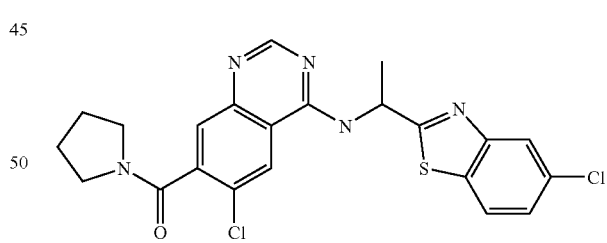

Prepared analogously to Example 2d from 4,6-dichloro-7-(pyrrolidin-1-yl-carbonyl)-quinazoline, 1-(5-chloro-benzothiazol-2-yl)-ethylamine and triethylamine in N,N-dimethylformamide.

Yield: 17%

$R_f$ value: 0.43 (silica gel; dichloromethane/ethanol=9:1)
$C_{22}H_{17}Cl_2N_5OS$ (470.38)

Mass spectrum: $(M+H)^+$=470/472/474 (chlorine isotope)

EXAMPLE 238

6-bromo-4-[1-(5-chloro-1H-indol-2-yl)-methylamino]-7-(2,5-dihydropyrrol-1-yl-carbonyl)-quinazoline

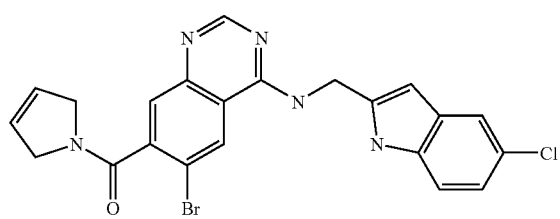

Prepared analogously to Example 2d from 6-bromo-4-chloro-7-(2,5-dihydropyrrol-1-yl-carbonyl)-quinazoline, 1-(5-chloro-1H-indol-2-yl)-methylamine and triethylamine in N,N-dimethylformamide.

Yield: 58%

$R_f$ value: 0.40 (silica gel; ethyl acetate+1% ammonia solution)

$C_{22}H_{17}BrClN_5O$ (482.77)

Mass spectrum: $(M+H)^+=482/484/486$ (bromine, chlorine isotope)

The Examples that follow describe the preparation of pharmaceutical formulations which contain as active substance any desired compound of general formula (I):

EXAMPLE I

Dry ampoule containing 75 mg of active substance per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

EXAMPLE II

Dry ampoule containing 35 mg of active substance per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

EXAMPLE III

Tablet containing 50 mg of active substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE IV

Tablet containing 350 mg of active substance

Composition:

| | |
|---|---|
| (1) Active substance | 350.0 mg |
| (2) Lactose | 136.0 mg |
| (3) Maize starch | >80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE V

Capsules containing 50 mg of active substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE VI

Capsules containing 350 mg of active substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE VII

Suppositories containing 100 mg of active substance 1 suppository contains:

| Active substance | 100.0 mg |
|---|---|
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:

1. A substituted nitrogen-containing heterobicyclic compound of formula

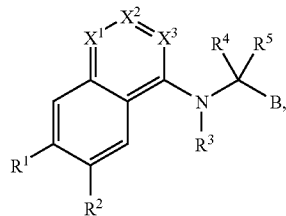

(I)

wherein

R$^1$ denotes a 2,5-dihydro-1H-pyrrol-1-yl-carbonyl, pyrrolidin-1-yl-carbonyl, 2-(aminomethyl)-pyrrolidin-1-yl-carbonyl, 2-(N-tert.-butyloxycarbonylaminomethyl)-pyrrolidin-1-yl-carbonyl, 3-oxo-piperazin-1-yl-carbonyl, morpholin-4-yl-carbonyl, carboxy, 3-aminomethyl-pyrrolidin-1-yl-carbonyl, thiazolidin-3-yl-carbonyl, 3-aminomethyl-pyrrolidin-1-yl-carbonyl, pyrazolidin-3-on-1-yl-carbonyl, pyrrolidin-2-ylmethylamino-carbonyl, 1-tert.-butyloxycarbonyl-pyrrolidin-2-yl-methylamino-carbonyl, 2-(acetylamino-methyl)-pyrrolidin-1-yl-carbonyl, 2-(pyrrolidin-1-yl-methyl)-pyrrolidin-1-yl-carbonyl, 2-(tert.-butyloxycarbonyl-aminomethyl)-thiazolidin-1-yl-carbonyl, 2-(pyridin-4-yl)-pyrrolidin-1-yl-carbonyl, 2-aminomethyl-thiazolidinyl-carbonyl, 2-(methane-sulphonyl-aminomethyl)-pyrrolidin-1-yl-carbonyl, 2-acetaminomethyl-thiazolidin-1-yl-carbonyl, 5,6,7,8-tetrahydro -[1,2,4]triazolo[4,3a]pyridin-4-yl, 2-(pyridin-4-yl)-thiazolidin-3-yl-carbonyl, 2-(2,2,2-trifluor-ethyl)-thiazolidin-3-yl-carbonyl, 2-(2-aminoethyl)-pyrrolidin-1-yl-carbonyl, 2-ethoxycarbonyl-piperidin-1-yl-carbonyl, 4,5,6,7-tetrahydro-thieno[3,2-c]pyridin-5-yl-carbonyl, 2-benzhydryl-pyrrolidin-1-yl-carbonyl, [1,4]diazepan-1-yl-carbonyl, 2-(2-ethoxycarbonyl-ethyl)-piperidin-1-yl-carbonyl, 2-methylaminocarbonyl-pyrrolidin-1-yl-carbonyl, 3-(3-diethylamino-propyl)-piperidin-1-yl-carbonyl, 4-methyl-piperidin-1-yl-carbonyl, 2-(phenylaminomethyl)-pyrrolidin-1-yl-carbonyl, 2-benzyl-pyrrolidin-1-yl-carbonyl, 3-hydroxy-piperidin-1-yl-carbonyl, 2-dimethylaminocarbonyl-pyrrolidin-1-yl-carbonyl, piperidin-1-yl-carbonyl, 4-oxo-piperidin-1-yl-carbonyl, 4-methylene-piperidin-1-yl-carbonyl, 2-methyl-piperidin-1-yl-carbonyl, 2-benzyloxycarbonyl-pyrrolidin-1-yl-carbonyl, N-(3-amino-propyl)-N-ethyl-amino-carbonyl, N-cyclopropyl-N-methylamino-carbonyl, 2-methoxymethyl-pyrrolidin-1-yl-carbonyl, 3-(1H-benzimidazol-2-yl)-piperidin-1-yl]-carbonyl, 3-dimethylamino-pyrrolidin-1-yl-carbonyl, 2,5-dimethyl-2,5-dihydro-1H-pyrrol-1-yl)-carbonyl, 2-isopropyl-pyrrolidin-1-yl-carbonyl, 2-aminomethyl-piperidin-1-yl-carbonyl], 3-aminomethyl-piperidin-1-yl-carbonyl, 2-ethoxycarbonyl-pyrrolidin-1-yl-carbonyl, 3-(dimethylamino-methyl)-piperidin-1-yl-carbonyl, 2-(2-phenyl-ethyl)-pyrrolidin-1-yl-carbonyl, 2-(pyridin-2-yl)-pyrrolidin-1-yl-carbonyl, 2-(2-amino-ethyl)-piperidin-1-yl-carbonyl, 4-acetyl-piperazin-1-yl-carbonyl, N-(2-amino-ethyl)-N-ethyl-amino-carbonyl, 2-(pyridin-3-yl)-piperidin-1-yl-carbonyl, 2,5-dimethyl-pyrrolidin-1-yl-carbonyl, 4-aminocarbonyl-piperidin-1-yl-carbonyl, 4-hydroxy-piperidin-1-yl-carbonyl, 2-ethoxycarbonyl-piperidin-1-yl-carbonyl, 1-(1,4,6,7-tetrahydro-pyrazolo[4,3]pyridin-5-yl)-carbonyl, 2,5-dimethoxymethyl-pyrrolidin-1-yl-carbonyl, 2-methoxycarbonyl-pyrrolidin-1-yl-carbonyl, pyrazolidin-1-yl-carbonyl, 1-oxo-thiomorpholin-4-yl-carbonyl, 2-[(N-butyl-N-ethyl-amino)-methyl]-piperidin-1-yl-carbonyl, N-ethyl-N-(piperidin-4-yl)-aminocarbonyl, 4-formyl-piperazin-1-yl-carbonyl, 2-(2-dimethylamino-ethyl)-piperidin-1-yl-carbonyl, 2-(2-diethylamino-ethyl)-piperidin-1-yl-carbonyl, 1,4,6,7-tetrahydro-imidazo[4,5-c]pyridin-5-yl-carbonyl, 3,6-dihydro-2H-pyridin-1-yl-carbonyl, 2-[(N-butyl-N-methyl-amino)-methyl]-piperidin-1-yl-carbonyl, 2-methyl-morpholin-4-yl-carbonyl, thiomorpholin-4-yl-carbonyl, 2-(2-amino-ethyl)-piperidin-1-yl-carbonyl, 2-ethyl-piperidin-1-yl-carbonyl, 3 -amino-pyrrolidin-1-yl-carbonyl, 4-trifluoromethyl-piperidin-1-yl-carbonyl, 3-[4-(pyrrolidin-1-yl)-butyl]-pyrrolidin-1-yl-carbonyl, 2-[(N-methyl-N-(pyridin-2-ylmethyl)-amino)-methyl]-piperidin-1-yl-carbonyl, 4-hydroxy-piperazin-1-yl-carbonyl, 3-(pyrrolidin-1-ylmethyl)-piperidin-1-yl-carbonyl, 2-diethylaminomethyl-piperidin-1-yl-carbonyl, 2-(4-diethylamino-butyl)-piperidin-1-yl-carbonyl, 2-hydroxymethyl-pyrrolidin-1-yl-carbonyl, 2-(N-ethyl-N-methyl-aminomethyl)-piperidin-1-yl-carbonyl, 2-aminocarbonyl-pyrrolidin-1-yl-carbonyl, 2-(4-methyl-piperazin-1-ylmethyl)-piperidin-1-yl-carbonyl, 2-methoxymethyl-pyrrolidin- 1-yl-carbonyl, 2-(3-dimethylamino-propyl)-piperidin-1-yl-carbonyl, 2-diethylaminocarbonyl-piperidin-1-yl-carbonyl, 2-[(N-cyclohexyl-N-methyl-amino)-methyl]-piperidin-1-yl-carbonyl, 2-piperidin-1-ylmethyl-piperidin-1-yl-carbonyl, 2-(1-methyl-1H-pyrazol-4-yl)-thiazolidinyl-carbonyl or 6,7,8,9-tetrahydro-[1,2,4]triazolo[4,3-a]pyridin-4-yl- group, $R^2$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, nitro, amino, $C_{1-3}$-alkoxy, a mono-, di- or trifluoromethoxy group, $R^3$ denotes a hydrogen atom or a $C_{1-3}$-alkyl group, $R^4$ denotes a hydrogen atom, a methyl, propyl, 2-methyl-suiphanyl-ethyl, 2-methylsuiphonyl-ethyl, hydroxymethyl, 2-carboxyethyl, 2-benzyloxycarbonyl-ethyl, 2-methoxy-ethyl, 2-methylsulphinyl-ethyl, tert.-butyloxycarbonylmethoxy-methyl, 2-ethoxycarbonyl-ethyl, carboxymethoxy-methyl, o-chlorophenyl, p-chlorophenyl, methoxymethyl, 2-diethyl-aminocarbonyl-ethyl, 2-propargyloxycarbonyl-ethyl, 2-(pyrrolidin-1-yl-carbonyl)-ethyl, 2-[N-methyl-N-piperidin-4-yl-amino]-carbonyl-ethyl, 2-[4-methyl-piperazin-1-yl]-carbonyl-ethyl, 2-(C-piperidin-4-yl-methylamino)-carbonyl-ethyl, 2-(N-benzyl-N-methyl-amino)-carbonyl-ethyl, 3-tert.-butyloxycarbonyl-propyl, 2-benzyloxycarbonylamino-ethyl, 2-[(1,2,3,4-tetrahydroisoquinolin-1-yl)-carbonyl-ethyl, 2-(benzylamino-carbonyl)-ethyl, 2-[(N-methyl-N-phenethyl-amino-carbonyl)-ethyl, 2-(hydroxyethylamino-carbonyl)-ethyl, 2-[(C-pyridin-3-yl-methylamino-carbonyl)-propyl, 2-[(1-oxa-3,8-diaza-spiro[4.5]decan-2-on-8-yl)-carbonyl]-ethyl, 2-(morpholin-4-yl-carbonyl)-ethyl, 2-(C-cyclohexyl-methylamino-carbonyl)-ethyl, 2-(methoxyethylamino-carbonyl)-ethyl, 2-(dimethylaminoethyl-amino-carbonyl)-ethyl, 2-(cyclopropylamino-carbonyl)-ethyl, 2-[C-2-tetrahydrofuran-2-yl-methylamino-carbonyl)-ethyl, 2-(dimethylaminopropylamino-carbonyl)-ethyl, 2-(aminoethylamino-carbonyl)-ethyl, 2-(hydroxycarbonylmethyl-methyl-amino-carbonyl)-ethyl, 2-((3-(pyrrolidin-2-on-1-yl)-propyl)-amino-carbonyl)-ethyl, 2-[(1-[1,3,5]triazin-2-yl-piperidin-4-ylamino)-carbonyl]-ethyl, 2-[(2-imidazol-1-yl-ethylamino)-carbonyl)-ethyl, 2-[C-(1H-imidazol-2-yl)-methylamino-carbonyl)-ethyl, 2-(2,2,2-trifluoroethylamino-carbonyl)-ethyl, 2-[N-(2-dimethylamino-ethyl)-N-methyl-amino-carbonyl]-ethyl, 2-[1-phenyl-ethylamino-carbonyl]-ethyl, 2-[2-(4-methyl-piperazin-1-ylmethyl)-piperidin-1-yl-carbonyl]-ethyl, 2-(N-aminocarbonylmethyl-N-methyl-amino-carbonyl)-ethyl, 2-(4,5,6,7-tetrahydro-1H-imidazo[4,5-c]pyridin-5-yl-carbonyl)-ethyl, 2-(1-oxo-thiomorpholin-4-yl-carbonyl)-ethyl, 2-(N-dimethylaminocarbonylmethyl-N-methyl-amino-carbonyl)-ethyl, 2-(N-hydroxycarbonylethyl-N-methyl-amino-carbonyl)-ethyl, 2-[C-(1-methyl-1H-imidazol-2-yl)-methylamino-carbonyl)-ethyl, 2-(N-piperidin-2-yl-aminocarbonyl)-ethyl, 2-[C-(tetrahydropyran-4-yl)-methylamino-carbonyl]-ethyl, 2-(4-hydroxypiperidin-1-yl-carbonyl)-ethyl, 2-[C-(pyridin-4-yl)-methylamino-carbonyl]-ethyl, 2-(N-methylaminocarbonylmethyl-N-methyl-amino-carbonyl)-ethyl, 2-[N-(2-(1H)-imidazol-4-yl)-ethyl-N-methyl-amino-carbonyl]-ethyl, 2-(1-thiazolidin-3-yl-carbonyl)-ethyl, 2-(N-cyclopropyl-N-methyl-amino-carbonyl)-ethyl, 2-(cyclopentylamino-carbonyl)-ethyl, 2-(N-piperidin-4-yl-aminocarbonyl)-ethyl, 2-[C-(pyridin-2-yl)-methylamino-carbonyl]-ethyl, 2-(4-thiazol-2-yl-piperazin-1-yl-carbonyl)-ethyl, 2-(piperidin-1-yl-carbonyl)-ethyl, 2-amino-ethyl, thiophen-3-yl, 2-(2-oxo-pyrrolidin-1-yl)-ethyl, 2-(1,1-dioxo-isothiazolidin-2-yl)-ethyl, isopropylcarbonyloxy-methyl, 3-carboxy-propyl, 2-methylsulphonylamino-ethyl, methylsulphanyl-methyl, benzyloxy-methyl, 2-[2-(pyridin-4-yl-amino)-ethylamino-carbonyl]-ethyl, but-3-yn-1-yl, 1-methoxy-ethyl, 1-tert.-butyloxy-ethyl or 1-hydroxy-ethyl group, $R^5$ denotes a hydrogen atom or a $C_{1-3}$-alkyl group or $R^4$ and $R^5$ together with the carbon atom to which they are bound denote a $C_{3-7}$-cycloalky group, wherein
one of the methylene groups of the $C_{3-7}$-cycloalkyl group may be replaced by an imino, $C_{1-3}$-alkylimino, acylimino or suiphonylimino group, B denotes a benzimidazole of the formula

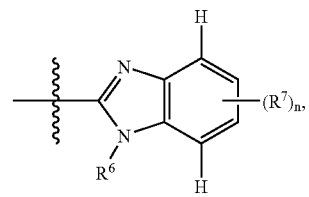

wherein
n denotes the number 1 or 2,
$R^6$ denotes a hydrogen atom or a $C_{1-3}$-alkyl, hydroxy, amino, $C_{1-3}$-alkylamino group,
$R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy or cyano group, and
$X^1$ and $X^3$ are N,
$X^2$ is a CH group optionally substituted by a $C_{1-3}$-alkyl group,
unless otherwise stated the alkyl and alkoxy groups contained in the above definitions which have more than two carbon atoms may be straight-chain or branched and the alkyl groups in the above-mentioned dialkylated groups may be identical or different,
and the hydrogen atoms of the methyl or ethyl groups contained in the above-mentioned definitions may be wholly or partly replaced by fluorine atoms,
the tautomer, the diastereomer, the enantiomer, mixtures thereof and the salt thereof.

2. The compound of formula I according to claim 1 selected from the following compounds, or a tautomer, stereoisomer or salt thereof:

(2) 6-chloro-4-[C-(5-chloro-1H-benzimidazol-2-yl)-methylamino]-7-(pyrrolidin-1-yl-carbonyl)-quinazoline, (3) 4-[C-(5-chloro-1H-benzimidazol-2-yl)methylamino]-7-(pyrrolidin-1-yl-carbonyl)-quinazoline, (4) 6-chloro-4-[1-(5-chloro-1H-benzimidazol-2-yl)-ethylamino]-7-(2,5-dihydropyrrol-1-yl-carbonyl)-quinazoline, (5) 6-chloro-4-[1-(5-chloro-1H-benzimidazol-2-yl)-ethylamino]-7-(2-tert.-butyloxycarbonyl-aminomethyl-pyrrolidin-1-yl-carbonyl)-quinazoline, (6) 6-chloro-4-[1-(5-chloro-1H-benzimidazol-2-yl)-ethylamino]-7-(2-aminomethyl-pyrrolidin-1-yl-carbonyl)-quinazoline, (7) 6-chloro-4-[1-(5-chloro-1H-benzimidazol-2-yl)-ethylamino]-7-(morpholin-4-yl-carbonyl)-quinazoline, (8) 6-chloro-4-[1-(S)-(5-chloro-1H-benzimidazol-2-yl)-ethylamino]-7-(piperazin-3-on-1-yl-carbonyl)-quinazoline,
(9) 6-chloro-4-[1-(S)-(5-chloro-1H-benzimidazol-2-yl)-ethylamino]-7-(2,5-dihydropyrrol-1-yl-carbonyl)-quinazoline,
(10) 6-chloro-4-[1-(S)-(5-chloro-1H-benzimidazol-2-yl)-ethylamino]-7-(pyrrolidin-1-yl-carbonyl)-quinazoline,
(18) 6-chloro-4-[(1S)-1-(5-chloro-1H-benzimidazol-2-yl)-ethylamino]-7-[(2R)-2-tert.-butyloxycarbonyl-aminomethyl-pyrrolidin-1-yl-carbonyl]-quinazoline,
(19) 6-chloro-4-[(1S)-1-(5-chloro-1H-benzimidazol-2-yl)-ethylamino]-7-[(2R)-2-amino-methyl-pyrrolidin-1-yl-carbonyl]-quinazoline,
(20) 6-chloro-4-[(1S)-1-(5-chloro-1H-benzimidazol-2-yl)-2-hydroxy-ethylamino]-7-(2,5-dihydropyrrol-1-yl-carbonyl)-quinazoline,
(21) 6-chloro-4-[(1S)-1-(5-chloro-1H-benzimidazol-2-yl)-2-hydroxy-ethylamino]-7-[(2R)-2-tert.-butyloxycarbonyl-aminomethyl-pyrrolidin-1-yl-carbonyl]-quinazoline,
(22) 6-chloro-4-[(1S)-1-(5-chloro-1H-benzimidazol-2-yl)-2-hydroxy-ethylamino]-7-[(2R)-2-aminomethyl-pyrrolidin-1-yl-carbonyl]-quinazoline,
(23) 6-chloro-4-[(1S)-1-(5-chloro-1H-benzimidazol-2-yl)-ethylamino]-7-[(2S)-2-tert.-butyloxycarbonyl-aminomethyl-pyrrolidin-1-yl-carbonyl]-quinazoline,
(24) 6-chloro-4-[(1S)-1-(5-chloro-1H-benzimidazol-2-yl)-ethylamino]-7-[(2S)-2-aminomethyl-pyrrolidin-1-yl-carbonyl]-quinazoline,
(25) 6-chloro-4-[1-(5-chloro-1H-benzimidazol-2-yl)-3-hydroxycarbonylpropylamino]-7-(pyrrolidin-1-yl-carbonyl)-quinazoline,
(26) 6-chloro-4-[1-(5-chloro-1H-benzimidazol-2-yl)-3-benzyloxycarbonylpropylamino]-7-(pyrrolidin-1-yl-carbonyl)-quinazoline,
(27) 6-chloro-4-[(1S)-1-(5-chloro-1H-benzimidazol-2-yl)-3-methylsulphanyl-propylamino]-7-[(2R)-2-tert.-butyloxycarbonyl-aminomethyl-pyrrolidin-1-yl-carbonyl]-quinazoline,
(28) 6-chloro-4-[(1S)-1-(5-chloro-1H-benzimidazol-2-yl)-3-methylsulphanyl-propylamino]-7-(pyrrolidin-1-yl-carbonyl)-quinazoline,
(29) 6-chloro-4-[(1S)-1-(5-chloro-1H-benzimidazol-2-yl)-3-methoxy-propylamino]-7-(2,5-dihydropyrrol-1-yl-carbonyl)-quinazoline,
(30) 6-chloro-4-[(1S)-1-(5-chloro-1H-benzimidazol-2-yl)-3-methanesulphonyl-propylamino]-7-(pyrrolidin-1-yl-carbonyl)-quinazoline,
(31) 6-chloro-4-[(1S)-1-(5-chloro-1H-benzimidazol-2-yl)-3-methylsulphanyl-propylamino]-7-[(2R)-2-aminomethyl-pyrrolidin-1-yl-carbonyl]-quinazoline,
(32) 6-chloro-4-[(1S)-1-(5-chloro-1H-benzimidazol-2-yl)-3-methanesulphinyl-propylamino]-7-(pyrrolidin-1-yl-carbonyl)-quinazoline,
(33) 6-chloro-4-[(1S)-1-(5-chloro-1H-benzimidazol-2-yl)-3-benzyloxycarbonylpropylamino]-7-(pyrrolidin-1-yl-carbonyl)-quinazoline,
(34) 6-chloro-4-[(1S)-1-(5-chloro-1H-benzimidazol-2-yl)-2-hydroxy-ethylamino]-7-(piperazin-3-on-1-yl-carbonyl)-quinazoline,
(35) 6-chloro-4-[(1S)-1-(5-chloro-1H-benzimidazol-2-yl)-3-methanesulphinyl-propylamino]-7-[(2R)-2-tert.-butyloxycarbonyl-aminomethyl-pyrrolidin-1-yl-carbonyl]-quinazoline,
(36) 6-chloro-4-[(1S)-1-(5-chloro-1H-benzimidazol-2-yl)-ethylamino]-7-hydroxycarbonyl-quinazoline,
(37) 6-chloro-4-[(1S)-1-(5-chloro-1H-benzimidazol-2-yl)-ethylamino]-7-[(3-aminomethyl-pyrrolidin-1-yl-carbonyl]-quinazoline,
(38) 6-chloro-4-[(1S)-1-(5-chloro-1H-benzimidazol-2-yl)-3-benzyloxycarbonylpropylamino]-7-[(2S)-2-tert.-butyloxycarbonyl-aminomethyl-pyrrolidin-1-yl-carbonyl]-quinazoline,
(39) 6-chloro-4-[(1S)-1-(5-chloro-1H-benzimidazol-2-yl)-3-hydroxycarbonylpropyl-amino]-7-[(2S)-2-tert.-butyloxycarbonyl-aminomethyl-pyrrolidin-1-yl-carbonyl]-quinazoline,
(40) 6-chloro-4-[(1S)-1-(5-chloro-1H-benzimidazol-2-yl)-3-hydroxycarbonylpropyl-amino]-7-[(2S)-2-aminomethyl-pyrrolidin-1-yl-carbonyl]-quinazoline,
(41) 6-chloro-4-[(1S)-1-(5-chloro-1H-benzimidazol-2-yl)-3-methanesulphonyl-propylamino]-7-[(2R)-2-tert.-butyloxycarbonyl-aminomethyl-pyrrolidin-1-yl-carbonyl]-quinazoline,
(42) 6-chloro-4-[(1S)-1-(5-chloro-1H-benzimidazol-2-yl)-3-methanesulphonyl-propylamino]-7-[(2R)-2-aminomethyl-pyrrolidin-1-yl-carbonyl]-quinazoline,
(43) 6-chloro-4-[(1S)-1-(5-chloro-1H-benzimidazol-2-yl)-ethylamino]-7-(thiazolidin-3-yl-carbonyl)-quinazoline,
(44) 6-chloro-4-[(1S)-1-(5-chloro-1H-benzimidazol-2-yl)-2-(tert.-butyloxycarbonyl-methoxy)-ethylamino]-7-(pyrrolidin-1-yl-carbonyl)-quinazoline,
(45) 6-chloro-4-[(1S)-1-(5-chloro-1H-benzimidazol-2-yl)-3-ethoxycarbonylpropylamino]-7-(pyrrolidin-1-yl-carbonyl)-quinazoline,
(46) 4-[(1S)-1-(5-chloro-1H-benzimidazol-2-yl)-ethylamino]-6-methyl-7-(pyrrolidin-1-yl-carbonyl)-quinazoline,
(47) 4-[(1S)-1-(5-chloro-1H-benzimidazol-2-yl)-ethylamino]-6-methyl-7-(pyrrolidin-1-yl-carbonyl)-quinazoline,
(48) 6-chloro-4-[(1S)-1-(5-chloro-1H-benzimidazol-2-yl)-ethylamino]-7-[(3S)-3-aminomethyl-pyrrolidin-1-yl-carbonyl]-quinazoline,
(49) 6-chloro-4-[(1S)-1-(5-chloro-1H-benzimidazol-2-yl)-2-(hydroxycarbonylmethoxy)-ethylamino]-7-(pyrrolidin-1-yl-carbonyl)-quinazoline,
(50) 6-chloro-4-[(1S)-1-(5-chloro-1H-benzimidazol-2-yl)-3-methanesulphinyl-propylamino]-7-[(2R)-2-aminomethyl-pyrrolidin-1-yl-carbonyl]-quinazoline,
(51) 4-[(1S)-1-(5-chloro-1H-benzimidazol-2-yl)-3-methylsulphanyl-propylamino]-6-methyl-7-(2,5-dihydropyrrol-1-yl-carbonyl)-quinazoline,
(52) 6-bromo-4-[(1S)-1-(5-chloro-1H-benzimidazol-2-yl)-ethylamino]-7-(2,5-dihydropyrrol-1-yl-carbonyl)-quinazoline,
(53) 6-chloro-4-[(1S)-1-(5-chloro-1H-benzimidazol-2-yl)-3-ethoxycarbonylpropyl-amino]-7-(2,5-dihydropyrrol-1-yl-carbonyl)-quinazoline,
(54) 6-chloro-4-[(1S)-1-(5-chloro-1H-benzimidazol-2-yl)-ethylamino]-7-(pyrazolidin-3-on-1-yl-carbonyl)-quinazoline,
(55) 6-chloro-4-[(1S)-1-(5-chloro-1H-benzimidazol-2-yl)-3-methylsulphanyl-propylamino]-7-(2,5-dihydropyrrol-1-yl-carbonyl)-quinazoline,
(56) 6-chloro-4-[1-(5-chloro-1H-benzimidazol-2-yl)-1-(2-chloro-phenyl)-methylamino]-7-(pyrrolidin-1-yl-carbonyl)-quinazoline,
(57) 6-chloro-4-[1-(5-chloro-1H-benzimidazol-2-yl)-1-(3-chloro-phenyl)-methylamino]-7-(pyrrolidin-1-yl-carbonyl)-quinazoline,

(58) 6-chloro-4-[(1S)-1-(5-chloro-1H-benzimidazol-2-yl)-butylamino]-7-(2,5-dihdropyrrol-1-yl-carbonyl)-quinazoline,
(59) 6-chloro-4-[(1S)-1-(5-chloro-1H-benzimidazol-2-yl)-3-methylsulphanyl-propylamino]-7-(2,5-dihydropyrrol-1-yl-carbonyl)-quinazoline,
(60) 6-chloro-4-[(1S)-1-(5-chloro-1H-benzimidazol-2-yl)-2-methoxy-ethylamino]-7-(2,5-dihydropyrrol-1-yl-carbonyl)-quinazoline,
(61) 6-chloro-4-[1-(5-chloro-1H-benzimidazol-2-yl)-3-diethylaminocarbonyl-propyl-amino]-7-(pyrrolidin-1-yl-carbonyl)-quinazoline,
(62) 6-chloro-4-[(1S)-1-(5-chloro-1H-benzimidazol-2-yl)-3-(pyrrolidin-1-ylcarbonyl)-propylamino]-7-[(2R)-pyrrolidin-2-ylmethylamino-carbonyl]-quinazoline,
(63) 6-chloro-4-[1-(5-chloro-1H-benzimidazol-2-yl)-3-[N-methyl-N-piperidin-4-yl-amino]-carbonyl-propyl-amino]-7-(pyrrolidin-1-yl-carbonyl)-quinazoline,
(64) 6-chloro-4-[1-(5-chloro-1H-benzimidazol-2-yl)-3-[4-methyl-piperazin-1-yl]-carbonyl-propyl-amino]-7-(pyrrolidin-1-yl-carbonyl)-quinazoline,
(65) 6-chloro-4-[1-(5-chloro-1H-benzimidazol-2-yl)-3-(C-piperidin-4-yl-methylamino)-carbonyl-propyl-amino]-7-(pyrrolidin-1-yl-carbonyl)-quinazoline,
(66) 6-chloro-4-[1-(5-chloro-1H-benzimidazol-2-yl)-3-(N-benzyl-N-methyl-amino)-carbonyl-propyl-amino]-7-(pyrrolidin-1-yl-carbonyl)-quinazoline,
(67) 6-chloro-4-[(1S)-1-(5-chloro-1H-benzimidazol-2-yl)-3-methanesulphonyl-propylamino]-1-oxy-7-[(2R)-2-tert.-butyloxycarbonyl-aminomethyl-pyrrolidin-1-yl-carbonyl]-quinazoline,
(68) 4-[(1S)-1-(5-chloro-1H-benzimidazol-2-yl)-3-allyloxycarbonylpropyl-amino]-6-methyl-7-(2,5-dihydropyrrol-1-yl-carbonyl)-quinazoline,
(69) 6-bromo-4-[(1S)-1-(5-chloro-1H-benzimidazol-2-yl)-3-allyloxycarbonylpropyl-amino]-7-(2,5-dihydropyrrol-1-yl-carbonyl)-quinazoline,
(70) 6-chloro-4-[(1S)-1-(5-chloro-1H-benzimidazol-2-yl)-2-methoxy-ethylamino]-7-(pyrrolidin-1-yl-carbonyl)-quinazoline,
(71) 6-chloro-4-[(1S)-1-(5-chloro-1H-benzimidazol-2-yl)-4-(tert.-butyloxycarbonyl)-butyl-amino]-7-(pyrrolidin-1-yl-carbonyl)-quinazoline,
(72) 6-chloro-4-[(1S)-1-(5-chloro-1H-benzimidazol-2-yl)-4-(tert.-butyloxycarbonyl)-butyl-amino]-7-(2,5-dihydropyrrol-1-yl-carbonyl)-quinazoline,
(73) 6-chloro-4-[(1S)-1-(5-chloro-1H-benzimidazol-2-yl)-3-benzyloxycarbonyl-propylamino]-7-[(2R)-(1-tert.-butyloxycarbonyl-pyrrolidin-2-yl-methylamino)-carbonyl]-quinazoline,
(74) 6-chloro-4-[(1S)-1-(5-chloro-1H-benzimidazol-2-yl)-3-methanesulphonyl-propylamino]-1-oxy-7-[(2R)-2-aminomethyl-pyrrolidin-1-yl-carbonyl]-quinazoline,
(75) 6-chloro-4-[(1S)-1-(5-chloro-1H-benzimidazol-2-yl)-ethylamino]-7-[(2R)-2-(acetylamino-methyl)-pyrrolidin-1-yl-carbonyl]-quinazoline,
(76) 6-chloro-4-[(1S)-1-(5-chloro-1H-benzimidazol-2-yl)-ethylamino]-7-[(2S)-2-(pyrrolidin-1-yl-methyl)-pyrrolidin-1-yl-carbonyl]-quinazoline,
(77) 6-chloro-4-[(1S)-1-(5-chloro-1H-benzimidazol-2-yl)-ethylamino]-7-[(2R/S)-2-(tert.-butyloxycarbonyl-aminomethyl)-thiazolidin-1-yl-carbonyl]-quinazoline,
(78) 6-chloro-4-[(1S)-1-(5-chloro-1H-benzimidazol-2-yl)-ethylamino]-7-[(2R/S)-2-(pyridin-4-yl)-pyrrolidin-1-yl-carbonyl]-quinazoline,
(79) 6-chloro-4-[(1S)-1-(5-chloro-1H-benzimidazol-2-yl)-ethylamino]-7-[(2R/S)-2-aminomethyl-thiazolidinyl-carbonyl]-quinazoline,
(80) 6-chloro-4-[(1S)-1-(5-chloro-1H-benzimidazol-2-yl)-3-methanesulphonyl-propylamino]-7-[(2R)-2-(methanesulphonyl-aminomethyl)-pyrrolidin-1-yl-carbonyl]-quinazoline,
(81) 6-chloro-4-[(1S)-3-(benzyloxycarbonyl-amino)-1-(5-chloro-1H-benzimidazol-2-yl)-propyl-amino]-7-(2,5-dihydropyrrol-1-yl-carbonyl)-quinazoline,
(82) 7-(2-acetaminomethyl-thiazolidin-1-yl-carbonyl)-6-chloro-4-[(1S)-1-(5-chloro-1H-benzimidazol-2-yl)-ethylamino]-quinazoline,
(83) 6-chloro-4-{1-(5-chloro-1H-benzimidazol-2-yl)-3-[(1,2,3,4-tetrahydroisoquinolin-1-yl)-carbonyl-propyl-amino]}-7-(pyrrolidin-1-yl-carbonyl)-quinazoline,
(84) 6-chloro-4-[1-(5-chloro-1H-benzimidazol-2-yl)-3-(benzylamino-carbonyl)-propyl-amino]-7-(pyrrolidin-1-yl-carbonyl)-quinazoline,
(85) 6-chloro-4-{1-(5-chloro-1H-benzimidazol-2-yl)-3-[(N-methyl-N-phenethyl-amino-carbonyl)-propyl-amino]}-7-(pyrrolidin-1-yl-carbonyl)-quinazoline,
(86) 6-chloro-4-[1-(5-chloro-1H-benzimidazol-2-yl)-3-(hydroxyethylamino-carbonyl)-propyl-amino]-7-(pyrrolidin-1-yl-carbonyl)-quinazoline,
(87) 6-chloro-4-{1-(5-chloro-1H-benzimidazol-2-yl)-3-[(C-pyridin-3-yl-methylamino-carbonyl)-propyl-amino]}-7-(pyrrolidin-1-yl-carbonyl)-quinazoline,
(88) 6-chloro-4-{1-(5-chloro-1H-benzimidazol-2-yl)-3-[(1-oxa-3,8-diaza-spiro[4.5]decan-2-on-8-yl)-carbonyl]-propyl-amino}-7-(pyrrolidin-1-yl-carbonyl)-quinazoline,
(89) 6-chloro-4-[1-(5-chloro-1H-benzimidazol-2-yl)-3-(morpholin-4-yl-carbonyl)-propyl-amino]-7-(pyrrolidin-1-yl-carbonyl)-quinazoline,
(90) 6-chloro-4-[1-(5-chloro-1H-benzimidazol-2-yl)-3-(C-cyclohexyl-methylamino-carbonyl)-propyl-amino]-7-(pyrrolidin-1-yl-carbonyl)-quinazoline,
(91) 6-chloro-4-[1-(5-chloro-1H-benzimidazol-2-yl)-3-(methoxyethylamino-carbonyl)-propyl-amino]-7-(pyrrolidin-1-yl-carbonyl)-quinazoline,
(92) 6-chloro-4-[1-(5-chloro-1H-benzimidazol-2-yl)-3-(dimethylaminoethyl-amino-carbonyl)-propyl-amino]-7-(pyrrolidin-1-yl-carbonyl)-quinazoline,
(93) 6-chloro-4-[1-(5-chloro-1H-benzimidazol-2-yl)-3-(cyclopropylamino-carbonyl)-propyl-amino]-7-(pyrrolidin-1-yl-carbonyl)-quinazoline,
(94) 6-chloro-4-{(1R/S)-1-(5-chloro-1H-benzimidazol-2-yl)-3-[C-(2R/S)-tetrahydrofuran-2-yl-methylamino-carbonyl)-propyl-amino]}-7-(pyrrolidin-1-yl-carbonyl)-quinazoline,
(95) 6-chloro-4-[1-(5-chloro-1H-benzimidazol-2-yl)-3-(dimethylaminopropylamino-carbonyl)-propyl-amino]-7-(pyrrolidin-1-yl-carbonyl)-quinazoline,
(96) 6-chloro-4-[1-(5-chloro-1H-benzimidazol-2-yl)-3-(aminoethylamino-carbonyl)-propyl-amino]-7-(pyrrolidin-1 -yl-carbonyl)-quinazoline,
(97) 6-chloro-4-[1-(5-chloro-1H-benzimidazol-2-yl)-3-(hydroxycarbonylmethyl-methyl-amino-carbonyl)-propyl-amino]-7-(pyrrolidin-1-yl-carbonyl)-quinazoline,
(98) 6-chloro-4-{[1-(5-chloro-1H-benzimidazol-2-yl)-3-((3-(pyrrolidin-2-on-1yl)-propyl)-amino-carbonyl)-propyl-amino]}-7-(pyrrolidin-1-yl-carbonyl)-quinazoline,

(99) 6-chloro-4-{1-(5-chloro-1H-benzimidazol-2-yl)-3-[(1-[1,3,5]triazin-2-yl-piperidin-4-ylamino)-carbonyl]-propyl-amino}-7-(pyrrolidin-1-yl-carbonyl)-quinazoline, (100) 6-chloro-4-{1-(5-chloro-1H-benzimidazol-2-yl)-3-[(2-imidazol-1-yl-ethylamino)-carbonyl)-propyl-amino]}-7-(pyrrolidin-1-yl-carbonyl)-quinazoline, (101) 6-chloro-4-{1-(5-chloro-1H-benzimidazol-2-yl)-3-[C-(1H-imidazol-2-yl)-methylamino-carbonyl)-propyl-amino]}-7-(pyrrolidin-1-yl-carbonyl)-quinazoline, (102) 6-chloro-4-[1-(5-chloro-1H-benzimidazol-2-yl)-3-(2,2,2-trifluoroethylamino-carbonyl)-propyl-amino]-7-(pyrrolidin-1-yl-carbonyl)-quinazoline, (103) 6-chloro-4-{1-(5-chloro-1H-benzimidazol-2-yl)-3-[N-(2-dimethylamino-ethyl)-N-methyl-amino-carbonyl]-propyl-amino}-7-(pyrrolidin-1-yl-carbonyl)-quinazoline, (104) 6-chloro-4-{(1R/S)-1-(5-chloro-1H-benzimidazol-2-yl)-3-[(1R/S)-1-phenyl-ethylamino-carbonyl]-propyl-amino}-7-(pyrrolidin-1-yl-carbonyl)-quinazoline, (105) 6-chloro-4-{1-(5-chloro-1H-benzimidazol-2-yl)-3-[2-(4-methyl-piperazin-1-ylmethyl)-piperidin-1-yl-carbonyl]-propyl-amino}-7-(pyrrolidin-1-yl-carbonyl)-quinazoline, (106) 6-chloro-4-[1-(5-chloro-1H-benzimidazol-2-yl)-3-(N-aminocarbonylmethyl-N-methyl-amino-carbonyl)-propyl-amino]-7-(pyrrolidin-1-yl-carbonyl)-quinazoline, (107) 6-chloro-4-[1-(5-chloro-1H-benzimidazol-2-yl)-3-(4,5,6,7-tetrahydro-1H-imidazo[4,5-c]pyridin-5-yl-carbonyl)-propyl-amino]-7-(pyrrolidin-1-yl-carbonyl)-quinazoline, (108) 6-chloro-4-[1-(5-chloro-1H-benzimidazol-2-yl)-3-(1-oxo-thiomorpholin-4-yl-carbonyl)-propyl-amino]-7-(pyrrolidin-1-yl-carbonyl)-quinazoline, (109) 6-chloro-4-[1-(5-chloro-1H-benzimidazol-2-yl)-3-(N-dimethylaminocarbonylmethyl-N-methyl-aminocarbonyl)-propyl-amino]-7-(pyrrolidin-1-yl-carbonyl)-quinazoline, (110) 6-chloro-4-[1-(5-chloro-1H-benzimidazol-2-yl)-3-(N-hydroxycarbonylethyl-N-methyl-amino-carbonyl)-propyl-amino]-7-(pyrrolidin-1-yl-carbonyl)-quinazoline, (111) 6-chloro-4-{1-(5-chloro-1H-benzimidazol-2-yl)-3-[C-(1-methyl-1H-imidazol-2-yl)-methylamino-carbonyl)-propyl-amino]}-7-(pyrrolidin-1-yl-carbonyl)-quinazoline, (112) 6-chloro-4-[1-(5-chloro-1H-benzimidazol-2-yl)-3-(N-piperidin-2-yl-aminocarbonyl)-propyl-amino]-7-(pyrrolidin-1-yl-carbonyl)-quinazoline, (113) 6-chloro-4-{1-(5-chloro-1H-benzimidazol-2-yl)-3-[C-(tetrahydropyran-4-yl)-methylamino-carbonyl]-propyl-amino}-7-(pyrrolidin-1-yl-carbonyl)-quinazoline, (114) 6-chloro-4-[1-(5-chloro-1H-benzimidazol-2-yl)-3-(4-hydroxypiperidin-1-yl-carbonyl)-propyl-amino]-7-(pyrrolidin-1-yl-carbonyl)-quinazoline, (115) 6-chloro-4-{1-(5-chloro-1H-benzimidazol-2-yl)-3-[C-(pyridin-4-yl)-methylamino-carbonyl]-propyl-amino}-7-(pyrrolidin-1-yl-carbonyl)-quinazoline, (116) 6-chloro-4-[1-(5-chloro-1H-benzimidazol-2-yl)-3-(N-methylaminocarbonylmethyl-N-methyl-amino-carbonyl)-propyl-amino]-7-(pyrrolidin-1-yl-carbonyl)-quinazoline, (117) 6-chloro-4-{1-(5-chloro-1H-benzimidazol-2-yl)-3-[N-(2-(1H)-imidazol-4-yl)-ethyl)-N-methyl-aminocarbonyl]-propyl-amino}-7-(pyrrolidin-1-yl-carbonyl)-quinazoline, (118) 6-chloro-4-[1-(5-chloro-1H-benzimidazol-2-yl)-3-(1-thiazolidin-3-yl-carbonyl)-propyl-amino]-7-(pyrrolidin-1-yl-carbonyl)-quinazoline, (119) 6-chloro-4-[1-(5-chloro-1H-benzimidazol-2-yl)-3-(N-cyclopropyl-N-methyl-amino-carbonyl)-propyl-amino]-7-(pyrrolidin-1-yl-carbonyl)-quinazoline, (120) 6-chloro-4-[1-(5-chloro-1H-benzimidazol-2-yl)-3-(N-cyclopropylmethyl-N-methyl-amino-carbonyl)-propyl-amino]-7-(pyrrolidin-1-yl-carbonyl)-quinazoline, (121) 6-chloro-4-[1-(5-chloro-1H-benzimidazol-2-yl)-3-(cyclopentylamino-carbonyl)-propyl-amino]-7-(pyrrolidin-1-yl-carbonyl)-quinazoline, (122) 6-chloro-4-[1-(5-chloro-1H-benzimidazol-2-yl)-3-(N-piperidin-4-yl-aminocarbonyl)-propyl-amino]-7-(pyrrolidin-1-yl-carbonyl)-quinazoline, (123) 6-chloro-4-{1-(5-chloro-1H-benzimidazol-2-yl)-3-[C-(pyridin-2-yl)-methylamino-carbonyl]-propyl-amino}-7-(pyrrolidin-1-yl-carbonyl)-quinazoline, (124) 6-chloro-4-[1-(5-chloro-1H-benzimidazol-2-yl)-3-(4-thiazol-2-yl-piperazin-1-yl-carbonyl)-propyl-amino]-7-(pyrrolidin-1-yl-carbonyl)-quinazoline, (125) 6-chloro-4-[1-(5-chloro-1H-benzimidazol-2-yl)-3-(piperidin-1-yl-carbonyl)-propyl-amino]-7-(pyrrolidin-1-yl-carbonyl)-quinazoline, (126) 6-chloro-4-[(1S)-1-(5-chloro-1H-benzimidazol-2-yl)-3-amino-propyl-amino]-7-(2,5-dihydropyrrol-1-yl-carbonyl)-quinazoline, (127) 6-chloro-4-[(1S)-1-(5-chloro-1H-benzimidazol-2-yl)-3-hydroxycarbonyl-propylamino]-7-(pyrrolidin-1-yl-carbonyl)-quinazoline, (128) 6-chloro-4-[(1S)-1-(5-chloro-1H-benzimidazol-2-yl)-ethylamino]-7-(5,6,7,8-tetrahydro-[1,2,4]triazolo[4,3a]pyridin-4-yl)-quinazoline, (129) 6-chloro-4-[1-(5-chloro-1H-benzimidazol-2-yl)-1-(thiophen-3-yl)-methylamino]-7-(2,5-dihydropyrrol-1-yl-carbonyl)-quinazoline, (130) 6-chloro-4-[(1S)-1-(5-chloro-1H-benzimidazol-2-yl)-3-(2-oxo-pyrrolidin-1-yl)-propyl-amino]-7-(2,5-dihydropyrrol-1-yl-carbonyl)-quinazoline, (131) 6-chloro-4-[(1S)-1-(5-chloro-1H-benzimidazol-2-yl)-3-(1,1-dioxo-isothiazolidin-2-yl)-propyl-amino]-7-(2,5-dihydropyrrol-1-yl-carbonyl)-quinazoline, (132) 6-chloro-4-[(1S)-1-(5-chloro-1H-benzimidazol-2-yl)-2-isopropylcarbonyloxy-ethylamino]-7-(2,5-dihydropyrrol-1-yl-carbonyl)-quinazoline, (133) 6-chloro-4-[(1S)-1-(5-chloro-1H-benzimidazol-2-yl)-4-(hydroxycarbonyl)-butylamino]-7-(2,5-dihydropyrrol-1-yl-carbonyl)-quinazoline, (134) 6-chloro-4-[(1S)-1-(5-chloro-1H-benzimidazol-2-yl)-ethylamino]-7-[(2R/S)-2-(pyridin-4-yl)-thiazolidin-3-yl-carbonyl]-quinazoline, (135) 6-chloro-4-[(1S)-1-(5-chloro-1H-benzimidazol-2-yl)-ethylamino]-7-[(2R/S)-2-(2,2,2-trifluorethyl)-thiazolidin-3-yl-carbonyl]-quinazoline, (136) 6-chloro-4-[(1S)-1-(5-chloro-1H-benzimidazol-2-yl)-3-methanesulphonylamino-propyl-amino]-7-(2,5-dihydropyrrol-1-yl-carbonyl)-quinazoline, (137) 6-chloro-4-[(1S)-1-(5-chloro-1H-benzimidazol-2-yl)-2-methylsulphanyl-ethylamino]-7-(2, 5-dihydropyrrol-1-yl-carbonyl)-quinazoline, (138) 4-[(1S)-1-(5-chloro-1H-benzimidazol-2-yl)-ethylamino]-7-(2,5-dihydropyrrol-1-yl-carbonyl)-6-methoxy-quinazoline,
(139) 7-[(2S)-2-(2-aminoethyl)-pyrrolidin-1-yl-carbonyl]-6-chloro-4-[(1R/S)-1-(5-chloro-1H-benzimidazol-2-yl)-ethylamino]-quinazoline,
(140) 6-chloro-4-[(1R/S)-1-(5-chloro-1H-benzimidazol-2-yl)-ethylamino]-7-[(2R/S)-2-ethoxycarbonyl-piperidin-1-yl-carbonyl]-quinazoline,
(141) 6-chloro-4-[1-(5-chloro-1H-benzimidazol-2-yl)-ethylamino]-7-(4,5,6,7-tetrahydro-thieno[3,2-c]pyridin-5-yl-carbonyl)-quinazoline,
(142) 7-[(2S)-2-benzhydryl-pyrrolidin-1-yl-carbonyl]-6-chloro-4-[(1R/S)-1-(5-chloro-1H-benzimidazol-2-yl)-ethylamino]-quinazoline,
(143) 6-chloro-4-[1-(5-chloro-1H-benzimidazol-2-yl)-ethylamino]-7-([1,4]diazepan-1-yl-carbonyl)-quinazoline,
(144) 6-chloro-4-[(1R/S)-1-(5-chloro-1H-benzimidazol-2-yl)-ethylamino]-7-[(2R/S)-2-(2-ethoxycarbonyl-ethyl)-piperidin-1-yl-carbonyl]-quinazoline,
(145) 6-chloro-4-[(1R/S)-1-(5-chloro-1H-benzimidazol-2-yl)-ethylamino]-7-[(2S)-2-methylaminocarbonyl-pyrrolidin-1-yl-carbonyl]-quinazoline,
(146) 6-chloro-4-[(1R/S)-1-(5-chloro-1H-benzimidazol-2-yl)-ethylamino]-7-[(3R/S)-3-(3-diethylamino-propyl)-piperidin-1-yl-carbonyl]-quinazoline,
(147) 6-chloro-4-[1-(5-chloro-1H-benzimidazol-2-yl)-ethylamino]-7-(4-methyl-piperidin-1-yl-carbonyl)-quinazoline,
(148) 6-chloro-4-[(1R/S)-1-(5-chloro-1H-benzimidazol-2-yl)-ethylamino]-7-[(2S)-2-(phenylaminomethyl)-pyrrolidin-1-yl-carbonyl]-quinazoline,
(149) 6-chloro-4-[(1R/S)-1-(5-chloro-1H-benzimidazol-2-yl)-ethylamino]-7-[(2R/S)-2-benzyl-pyrrolidin-1-yl-carbonyl]-quinazoline,
(150) 6-chloro-4-[(1R/S)-1-(5-chloro-1H-benzimidazol-2-yl)-ethylamino]-7-[(3R/S)-3-hydroxy-piperidin-1-yl-carbonyl]-quinazoline,
(151) 6-chloro-4-[(1R/S)-1-(5-chloro-1H-benzimidazol-2-yl)-ethylamino]-7-[(2S)-2-dimethylaminocarbonyl-pyrrolidin-1-yl-carbonyl]-quinazoline,
(152) 6-chloro-4-[1-(5-chloro-1H-benzimidazol-2-yl)-ethylamino]-7-(piperidin-1-yl-carbonyl)-quinazoline,
(153) 6-chloro-4-[1-(5-chloro-1H-benzimidazol-2-yl)-ethylamino]-7-(4-oxo-piperidin-1-yl-carbonyl)-quinazoline,
(154) 6-chloro-4-[1-(5-chloro-1H-benzimidazol-2-yl)-ethylamino]-7-(4-methylene-piperidin-1-yl-carbonyl)-quinazoline,
(155) 6-chloro-4-[(1R/S)-1-(5-chloro-1H-benzimidazol-2-yl)-ethylamino]-7-[(2R/S)-2-methyl-piperidin-1-yl-carbonyl]-quinazoline,
(156) 6-chloro-4-[(1R/S)-1-(5-chloro-1H-benzimidazol-2-yl)-ethylamino]-7-[(2R/S)-2-benzyloxycarbonyl-pyrrolidin-1-yl-carbonyl]-quinazoline,
(157) 6-chloro-4-[1-(5-chloro-1H-benzimidazol-2-yl)-ethylamino]-7-[N-(3-amino-propyl)-N-ethyl-amino-carbonyl]-quinazoline,
(158) 6-chloro-4-[1-(5-chloro-1H-benzimidazol-2-yl)-ethylamino]-7-(N-cyclopropyl-N-methylamino-carbonyl)-quinazoline,
(159) 6-chloro-4-[1-(5-chloro-1H-benzimidazol-2-yl)-ethylamino]-7-(2-oxo-piperazin-4-yl-carbonyl)-quinazoline,
(160) 6-chloro-4-[(1R/S)-1-(5-chloro-1H-benzimidazol-2-yl)-ethylamino]-7-[(2S)-2-methoxymethyl-pyrrolidin-1-yl-carbonyl]-quinazoline,
(161) 6-chloro-4-[(1R/S)-1-(5-chloro-1H-benzimidazol-2-yl)-ethylamino]-7-[(2)-2-(phenylaminomethyl)-pyrrolidin-1-yl-carbonyl]-quinazoline,
(162) 6-chloro-4-[(1R/S)-1-(5-chloro-1H-benzimidazol-2-yl)-ethylamino]-7-{1-[(3R/S)-3-(1H-benzimidazol-2-yl)-piperidin-1-yl]-carbonyl}-quinazoline,
(163) 6-chloro-4-[(1R/S)-1-(5-chloro-1H-benzimidazol-2-yl)-ethylamino]-7-[(3R/S)-3-dimethylamino-pyrrolidin-1-yl-carbonyl]-quinazoline,
(164) 6-chloro-4-[1-(5-chloro-1H-benzimidazol-2-yl)-ethylamino]-7-[(2,5-dimethyl-2,5-dihydro-1H-pyrrol-1-yl)-carbonyl]-quinazoline,
(165) 6-chloro-4-[(1R/S)-1-(5-chloro-1H-benzimidazol-2-yl)-ethylamino]-7-[(2R/S)-2-isopropyl-pyrrolidin-1-yl-carbonyl]-quinazoline,
(166) 6-chloro-4-[(1R/S)-1-(5-chloro-1H-benzimidazol-2-yl)-ethylamino]-7-[(2R/S)-2-aminomethyl-piperidin-1-yl-carbonyl]-quinazoline,
(167) 6-chloro-4-[(1R/S)-1-(5-chloro-1H-benzimidazol-2-yl)-ethylamino]-7-[(3R/S)-3-aminomethyl-piperidin-1-yl-carbonyl]-quinazoline,
(168) 6-chloro-4-[(1R/S)-1-(5-chloro-1H-benzimidazol-2-yl)-ethylamino]-7-[(2R)-2-ethoxycarbonyl-pyrrolidin-1-yl-carbonyl]-quinazoline,
(169) 6-chloro-4-[1-(5-chloro-1H-benzimidazol-2-yl)-ethylamino]-7-[3-(dimethylamino-methyl)-piperidin-1-yl-carbonyl]-quinazoline,
(170) 6-chloro-4-[(1R/S)-1-(5-chloro-1H-benzimidazol-2-yl)-ethylamino]-7-[(2R/S)-2-(2-phenyl-ethyl)-pyrrolidin-1-yl-carbonyl]-quinazoline,
(171) 6-chloro-4-[(1R/S)-1-(5-chloro-1H-benzimidazol-2-yl)-ethylamino]-7-[(2R/S)-2-(pyridin-2-yl)-pyrrolidin-1-yl-carbonyl]-quinazoline,
(172) 6-chloro-4-[(1R/S)-1-(5-chloro-1H-benzimidazol-2-yl)-ethylamino]-7-[(2R/S)-2-(2-amino-ethyl)-piperidin-1-yl-carbonyl]-quinazoline,
(173) 6-chloro-4-[1 -(5-chloro-1H-benzimidazol-2-yl)-ethylamino]-7-(4-acetyl-piperazin-1-yl-carbonyl)-quinazoline,
(174) 6-chloro-4-[1-(5-chloro-1H-benzimidazol-2-yl)-ethylamino]-7-[N-(2-amino-ethyl)-N-ethyl-amino-carbonyl]-quinazoline,
(175) 6-chloro-4-[(1R/S)-1-(5-chloro-1H-benzimidazol-2-yl)-ethylamino]-7-[(2R/S)-2-(pyridin-3-yl)-piperidin-1-yl-carbonyl]-quinazoline,
(176) 6-chloro-4-[(1R/S)-1-(5-chloro-1H-benzimidazol-2-yl)-ethylamino]-7-[(2R/S),(5R/S)-2,5-dimethyl-pyrrolidin-1-yl-carbonyl]-quinazoline,
(177) 6-chloro-4-[1-(5-chloro-1H-benzimidazol-2-yl)-ethylamino]-7-(4-aminocarbonyl-piperidin-1-yl-carbonyl)-quinazoline,
(178) 6-chloro-4-[1-(5-chloro-1H-benzimidazol-2-yl)-ethylamino]-7-(4-hydroxy-piperidin-1-yl-carbonyl)-quinazoline,
(179) 6-chloro-4-[(1R/S)-1-(5-chloro-1H-benzimidazol-2-yl)-ethylamino]-7-[(2R/S)-2-ethoxycarbonyl-piperidin-1-yl-carbonyl]-quinazoline,
(180) 6-chloro-4-[1-(5-chloro-1H-benzimidazol-2-yl)-ethylamino]-7-[1-(1,4,6,7-tetrahydro-pyrazolo[4,3]pyridin-5-yl)-carbonyl]-quinazoline,
(181) 6-chloro-4-[(1R/S)-1-(5-chloro-1H-benzimidazol-2-yl)-ethylamino]-7-(2R, 5S-dimethoxymethyl-pyrrolidin-1-yl-carbonyl)-quinazoline, (182) 6-chloro-4-[(1R/S)-1-(5-chloro-1H-benzimidazol-2-yl)-ethylamino]-7-[(2R/S)-2-methoxycarbonyl-pyrolidin-1-yl-carbonyl]-quinazoline,
(183) 6-chloro-4-[1-(5-chloro-1H-benzimidazol-2-yl)-ethylamino]-7-(pyrazolidin-1-yl-carbonyl)-quinazoline,
(184) 6-chloro-4-[1-(5-chloro-1H-benzimidazol-2-yl)-ethylamino]-7-(1-oxo-thiomorpholin-4-yl-carbonyl)-quinazoline,
(185) 6-chloro-4-[(1R/S)-1-(5-chloro-1H-benzimidazol-2-yl)-ethylamino]-7-{(2R/S)-2-[(N-butyl-N-ethyl-amino)-methyl]-piperidin-1-yl-carbonyl}-quinazoline,
(186) 6-chloro-4-[1-(5-chloro-1H-benzimidazol-2-yl)-ethylamino]-7-[N-ethyl-N-(piperidin-4-yl)-aminocarbonyl]-quinazoline,
(187) 6-chloro-4-[(1R/S)-1-(5-chloro-1H-benzimidazol-2-yl)-ethylamino]-7-[(2S)-2-ethoxycarbonyl-pyrrolidin-1-yl-carbonyl]-quinazoline,
(188) 6-chloro-4-[1-(5-chloro-1H-benzimidazol-2-yl)-ethylamino]-7-(4-formyl-piperazin-1-yl-carbonyl)-quinazoline,
(189) 6-chloro-4-[(1R/S)-1-(5-chloro-1H-benzimidazol-2-yl)-ethylamino]-7-[(2R/S)-2-(2-dimethylamino-ethyl)-piperidin-1-yl-carbonyl]-quinazoline,
(190) 6-chloro-4-[(1R/S)-1-(5-chloro-1H-benzimidazol-2-yl)-ethylamino]-7-[(2R/S)-2-(2-diethylamino-ethyl)-piperidin-1-yl-carbonyl]-quinazoline,
(191) 6-chloro-4-[1-(5-chloro-1H-benzimidazol-2-yl)-ethylamino]-7-(1,4,6,7-tetrahydro-imidazo[4,5-c]pyridin-5-yl-carbonyl)-quinazoline,
(192) 6-chloro-4-[1-(5-chloro-1H-benzimidazol-2-yl)-ethylamino]-7-(3,6-dihydro-2H-pyridin-1-yl-carbonyl)-quinazoline,
(193) 6-chloro-4-[(1R/S)-1-(5-chloro-1H-benzimidazol-2-yl)-ethylamino]-7-{(2R/S)-2-[(N-butyl-N-methyl-amino)-methyl]-piperidin-1-yl-carbonyl}-quinazoline,
(194) 6-chloro-4-[(1R/S)-1-(5-chloro-1H-benzimidazol-2-yl)-ethylamino]-7-[(2R/S)-2-methyl-morpholin-4-yl-carbonyl]-quinazoline,
(195) 6-chloro-4-[1-(5-chloro-1H-benzimidazol-2-yl)-ethylamino]-7-(thiomorpholin-4-yl-carbonyl)-quinazoline,
(196) 6-chloro-4-[(1R/S)-1-(5-chloro-1H-benzimidazol-2-yl)-ethylamino]-7-[(2R/S)-2-(2-amino-ethyl)-piperidin-1-yl-carbonyl]-quinazoline,
(197) 6-chloro-4-[(1R/S)-1-(5-chloro-1H-benzimidazol-2-yl)-ethylamino]-7-[(2R/S)-2-ethyl-piperidin-1-yl-carbonyl]-quinazoline,
(198) 6-chloro-4-[(1R/S)-1-(5-chloro-1H-benzimidazol-2-yl)-ethylamino]-7-[(3R/S)-3-amino-pyrrolidin-1-yl-carbonyl]-quinazoline,
(199) 6-chloro-4-[1-(5-chloro-1H-benzimidazol-2-yl)-ethylamino]-7-(4-trifluoromethyl-piperidin-1-yl-carbonyl)-quinazoline,
(200) 6-chloro-4-[(1R/S)-1-(5-chloro-1H-benzimidazol-2-yl)-ethylamino]-7-{(3R/S)--[4-(pyrrolidin-1-yl)-butyl]-pyrrolidin-1-yl-carbonyl}-quinazoline,
(201) 6-chloro-4-[(1R/S)-1-(5-chloro-1H-benzimidazol-2-yl)-ethylamino]-7-{(2R/S)-2-[(N-methyl-N-(pyridin-2-ylmethyl)-amino)-methyl]-piperidin-1-yl-carbonyl}-quinazoline,
(202) 6-chloro-4-[1-(5-chloro-1H-benzimidazol-2-yl)-ethylamino]-7-(4-hydroxy-piperazin-1-yl-carbonyl)-quinazoline,
(203) 6-chloro-4-[(1R/S)-1-(5-chloro-1H-benzimidazol-2-yl)-ethylamino]-7-[(3R/S)-3-(pyrrolidin-1-ylmethyl)-piperidin-1-yl-carbonyl]-quinazoline,
(204) 6-chloro-4-[(1R/S)-1-(5-chloro-1H-benzimidazol-2-yl)-ethylamino]-7-[(2R/S)-2-diethylaminomethyl-piperidin-1-yl-carbonyl]-quinazoline,
(205) 6-chloro-4-[(1R/S)-1-(5-chloro-1H-benzimidazol-2-yl)-ethylamino]-7-[(2R/S)-2-(4-diethylamino-butyl)-piperidin-1-yl-carbonyl]-quinazoline,
(206) 6-chloro-4-[(1R/S)-1-(5-chloro-1H-benzimidazol-2-yl)-ethylamino]-7-[(2R)-2-hydroxymethyl-pyrrolidin-1-yl-carbonyl]-quinazoline,
(207) 6-chloro-4-[(1R/S)-1-(5-chloro-1H-benzimidazol-2-yl)-ethylamino]-7-[(2R/S)-2-(N-ethyl-N-methyl-aminomethyl)-piperidin-1-yl-carbonyl]-quinazoline,
(208) 6-chloro-4-[(1R/S)-1-(5-chloro-1H-benzimidazol-2-yl)-ethylamino]-7-[(2R)-2-aminocarbonyl-pyrrolidin-1-yl-carbonyl]-quinazoline,
(209) 6-chloro-4-[(1R/S)-1-(5-chloro-1H-benzimidazol-2-yl)-ethylamino]-7-[(2S)-2-hydroxymethyl-pyrrolidin-1-yl-carbonyl]-quinazoline,
(210) 6-chloro-4-[(1R/S)-1-(5-chloro-1H-benzimidazol-2-yl)-ethylamino]-7-[(2R/S)-2-(4-methyl-piperazin-1-ylmethyl)-piperidin-1-yl-carbonyl]-quinazoline,
(211) 6-chloro-4-[(1R/S)-1-(5-chloro-1H-benzimidazol-2-yl)-ethylamino]-7-[(2R)2-methoxymethyl-pyrrolidin-1-yl-carbonyl]-quinazoline,
(212) 6-chloro-4-[(1R/S)-1-(5-chloro-1H-benzimidazol-2-yl)-ethylamino]-7-[(2R/S)-2-(3-dimethylamino-propyl)-piperidin-1-yl-carbonyl]-quinazoline,
(213) 6-chloro-4-[(1R/S)-1-(5-chloro-1H-benzimidazol-2-yl)-ethylamino]-7-[(2R/S)-2-diethylaminocarbonyl-piperidin-1-yl-carbonyl]-quinazoline,
(214) 6-chloro-4-[(1R/S)-1-(5-chloro-1H-benzimidazol-2-yl)-ethylamino]-7-{(2R/S)-2-[(N-cyclohexyl-N-methyl-amino)-methyl]-piperidin-1-yl-carbonyl}-quinazoline, (215) 6-chloro-4-[(1R/S)-1-(5-chloro-1H-benzimidazol-2-yl)-ethylamino]-7-[(2R/S)-2-piperidin-1-ylmethyl-piperidin-1-yl-carbonyl]-quinazoline,
(216) 4-[(1S)-1-(5-chloro-1H-benzimidazol-2-yl)-3-(methylsulphanyl)-propylamino]-6-methoxy-7-(2,5-dihydropyrrol-1-yl-carbonyl)-quinazoline,
(217) 4-[(1S)-1-(5-chloro-1H-benzimidazol-2-yl)-2-methoxy-ethylamino]-6-methoxy-7-(2,5-dihydropyrrol-1-yl-carbonyl)-quinazoline,
(218) 6-chloro-4-[(1S)-1-(5-chloro-1H-benzimidazol-2-yl)-ethylamino]-7-[(2R/S)-2-(1-methyl-1H-pyrazol-4-yl)-thiazolidinyl-carbonyl]-quinazoline,
(219) 6-chloro-4-[(1S)-1-(5-chloro-1H-benzimidazol-2-yl)-2-methoxy-ethylamino]-7-(thiazolidinyl-carbonyl)-quinazoline,
(220) 4-[(1S)-1-(5-chloro-1H-benzimidazol-2-yl)-2-methoxy-ethylamino]-6-methyl-7-(2,5-dihydropyrrol-1-yl-carbonyl)-quinazoline,
(221) 4-[(1S)-1-(5-chloro-1H-benzimidazol-2-yl)-2-methoxy-ethylamino]-6-methyl-7-(thiazolidinyl-carbonyl)-quinazoline,
(222) 6-bromo-4-[(1S)-1-(5-chloro-1H-benzimidazol-2-yl)-2-methoxy-ethylamino]-7-(2,5-dihydropyrrol-1-yl-carbonyl)-quinazoline,
(223) 6-bromo-4-[(1S)-1-(5-chloro-H-benzimidazol-2-yl)-2-methoxy-ethylamino]-7-(thiazolidinyl-carbonyl)-quinazoline,
(224) 6-chloro-4-[(1S)-1-(5-chloro-1H-benzimidazol-2-yl)-ethylamino]-7-(6,7,8,9-tetrahydro-[1,2,4]triazolo[4,3-a]pyridin-4-yl)-quinazoline,
(225) 6-chloro-4-[(1S)-1-(5-chloro-1-methyl-1H-benzimidazol-2-yl)-3-methylsulphonylamino-propylamino]-7-(2,5-dihydropyrrolyl-carbonyl)-quinazoline, (226) 6-chloro-4-[(1S)-1-(5-chloro-1H-benzimidazol-2-yl)-2-benzyloxy-ethylamino]-7-(2,5-dihydropyrrol-1-yl-carbonyl)- quinazoline, (227) 6-chloro-4-{1-(5-chloro-1H-benzimidazol-2-yl)-3-[2-(pyridin-4-yl-amino)-ethylamino-carbonyl]-propylamino}-7- (pyrrolidin-1-yl-carbonyl)-quinazoline, (228) 4-[(1S)-1-(5-bromo-1H-benzimidazol-2-yl)-2-methoxy-ethylamino]-6-chloro-7-(2,5-dihydropyrrolyl-carbonyl)-quinazoline, (229) 4-[(1S)-1-(5-bromo-1H-benzimidazol-2-yl)-ethylamino]-6-chloro-7-(2,5-dihydropyrrolyl-carbonyl)-quinazoline, (230) 6-bromo-4-[(1S)-1-(5-chloro-1H-benzimidazol-2-yl)-but-3-yn-1-yl-amino]-7-(2,5-dihydropyrrol-1-yl-carbonyl)-quinazoline, (231) 4-[(1S,2R)-1-(5-chloro-1H-benzimidazol-2-yl)-2-methoxy-propylamino]-6-chloro-7-(2,5-dihydropyrrolyl-carbonyl)-quinazoline, (232) 4-[(1S,2S)-1-(5-chloro-1H-benzimidazol-2-yl)-2-tert.-butyloxy-propylamino]-6-chloro-7-(2,5-dihydropyrrolyl-carbonyl)-quinazoline, and (233) 4-[(1S,2S)-1-(5-chloro-1H-benzimidazol-2-yl)-2-hydroxy-propylamino]-6-chloro-7-(2,5-dihydropyrrolyl-carbonyl)-quinazoline.

3. A physiologically acceptable salt of the compound according to claim 1.

4. A pharmaceutical composition comprising a compound according to claim 1 together with one or more inert carriers or diluents.

* * * * *